United States Patent
Bamberg et al.

(10) Patent No.: US 7,939,531 B2
(45) Date of Patent: *May 10, 2011

(54) PYRROLOPYRAZINE KINASE INHIBITORS

(75) Inventors: Joe Timothy Bamberg, East Palo Alto, CA (US); Mark Bartlett, Mountain View, CA (US); Daisy Joe DuBois, Palo Alto, CA (US); Todd Richard Elworthy, Los Altos, CA (US); Robert Than Hendricks, San Carlos, CA (US); Johannes Cornelius Hermann, San Francisco, CA (US); Rama K. Kondru, Sunnyvale, CA (US); Remy Lemoine, San Francisco, CA (US); Yan Lou, San Jose, CA (US); Timothy D. Owens, Mountain View, CA (US); Jaehyeon Park, Sunnyvale, CA (US); David Bernard Smith, San Mateo, CA (US); Michael Soth, Milpitas, CA (US); Hanbiao Yang, Sunnyvale, CA (US); Calvin Wesley Yee, Daly City, CA (US)

(73) Assignee: Roche Palo Alto, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/378,978

(22) Filed: Feb. 20, 2009

(65) Prior Publication Data
US 2009/0215750 A1   Aug. 27, 2009

Related U.S. Application Data

(60) Provisional application No. 61/031,035, filed on Feb. 25, 2008, provisional application No. 61/205,724, filed on Jan. 22, 2009.

(51) Int. Cl.
*A61K 31/495* (2006.01)

(52) U.S. Cl. ........ 514/249; 540/599; 544/61; 544/175; 544/373; 546/113; 546/121; 546/176; 546/245; 546/277.4; 546/314; 548/204; 548/236; 548/255; 548/341.5; 548/362.5; 548/376.1; 548/503; 548/530; 548/564; 548/950; 549/58; 549/59; 549/356; 549/505

(58) Field of Classification Search .................. 514/249; 540/599; 544/61, 175, 373; 546/113, 121, 546/176, 245, 277.4, 314; 548/204, 236, 548/255, 341.5, 362.5, 376.1, 503, 530, 564, 548/950; 549/58, 59, 356, 505
See application file for complete search history.

(56) References Cited

U.S. PATENT DOCUMENTS

| | | |
|---|---|---|
| 2006/0148801 A1 | 7/2006 | Hsieh et al. |
| 2007/0049615 A1 | 3/2007 | Ibrahim et al. |

FOREIGN PATENT DOCUMENTS

| | | |
|---|---|---|
| WO | 0147922 A2 | 7/2001 |
| WO | 03000688 A1 | 1/2003 |
| WO | 03082868 A1 | 10/2003 |
| WO | 2008033798 A2 | 3/2008 |
| WO | 2008063888 A2 | 5/2008 |
| WO | 2008079903 A1 | 7/2008 |

*Primary Examiner* — James O Wilson
*Assistant Examiner* — Douglas M Willis
(74) *Attorney, Agent, or Firm* — George W. Johnston; Dennis P. Tramaloni; Jennifer L. Kisko

(57) ABSTRACT

The present invention relates to the use of novel pyrrolopyrazine derivatives of Formula I,

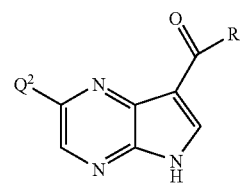

wherein the variables Q and R are defined as described herein, which inhibit JAK and SYK and are useful for the treatment of auto-immune and inflammatory diseases.

32 Claims, No Drawings

PYRROLOPYRAZINE KINASE INHIBITORS

CROSS-REFERENCE TO RELATED APPLICATIONS

This application is entitled to the benefit of U.S. provisional patent application Ser. No. 61/031,035 filed on Feb. 25, 2008 and Ser. No. 61/205,724 filed on Jan. 22, 2009, the disclosures of which are incorporated herein by reference.

FIELD OF THE INVENTION

The present invention relates to the use of novel pyrrolopyrazine derivatives which are JAK and SYK inhibitors and selectively inhibit JAK3 and are useful for the treatment of auto-immune and inflammatory diseases.

BACKGROUND OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

The JAKs (JAnus Kinases) are a family of cytoplasmic protein tyrosine kinases including JAK1, JAK2, JAK3 and TYK2. Each of the JAKs is preferentially associated with the intracytoplasmic portion of discrete cytokine receptors (*Annu. Rev. Immunol.* 16 (1998), pp. 293-322). The JAKs are activated following ligand binding and initiate signaling by phosphorylating cytokine receptors that, per se, are devoid of intrinsic kinase activity. This phosphorylation creates docking sites on the receptors for other molecules known as STAT proteins (signal transducers and activators of transcription) and the phosphorylated JAKs bind various STAT proteins. STAT proteins, or STATs, are DNA binding proteins activated by phosphorylation of tyrosine residues, and function both as signaling molecules and transcription factors and ultimately bind to specific DNA sequences present in the promoters of cytokine-responsive genes (Leonard et al., (2000), J. Allergy Clin. Immunol. 105:877-888).

JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas.

Thus, the JAKs and STATs are components of multiple potentially intertwined signal-transduction pathways (*Oncogene* 19 (2000), pp. 5662-5679), which indicates the difficulty of specifically targeting one element of the JAK-STAT pathway without interfering with other signal transduction pathways.

The JAK kinases, including JAK3, are abundantly expressed in primary leukemic cells from children with acute lymphoblastic leukemia, the most common form of childhood cancer, and studies have correlated STAT activation in certain cells with signals regulating apoptosis (Demoulin et al., (1996), Mol. Cell. Biol. 16:4710-6; Jurlander et al., (1997), Blood. 89:4146-52; Kaneko et al., (1997), Clin. Exp. Immun. 109:185-193; and Nakamura et al., (1996), J. Biol. Chem. 271: 19483-8). They are also known to be important to lymphocyte differentiation, function and survival. JAK3 in particular plays an essential role in the function of lymphocytes, macrophages, and mast cells. Given the importance of this JAK kinase, compounds which modulate the JAK pathway, including those selective for JAK3, can be useful for treating diseases or conditions where the function of lymphocytes, macrophages, or mast cells is involved (Kudlacz et al., (2004) Am. J. Transplant 4:51-57; Changelian (2003) Science 302:875-878). Conditions in which targeting of the JAK pathway or modulation of the JAK kinases, particularly JAK3, are contemplated to be therapeutically useful include, leukemia, lymphoma, transplant rejection (e.g., pancreas islet transplant rejection, bone marrow transplant applications (e.g., graft-versus-host disease), autoimmune diseases (e.g., diabetes), and inflammation (e.g., asthma, allergic reactions). Conditions which can benefit for inhibition of JAK3 are discussed in greater detail below.

However, in contrast to the relatively ubiquitous expression of JAK1, JAK2 and Tyk2, JAK3 has a more restricted and regulated expression. Whereas some JAKs (JAK1, JAK2, Tyk2) are used by a variety of cytokine receptors, JAK3 is used only by cytokines that contain a γc in their receptor. JAK3, therefore, plays a role in cytokine signaling for cytokines which receptor was shown to date to use the common gamma chain; IL-2, IL-4, IL-7, IL-9, IL-15 and IL-21. JAK1 interacts with, among others, the receptors for cytokines IL-2, IL-4, IL-7, IL-9 and IL-21, while JAK2 interacts with, among others, the receptors for IL-9 and TNF-alpha. Upon the binding of certain cytokines to their receptors (e.g., IL-2, IL-4, IL-7, IL-9, IL-15 and IL-21), receptor oligomerization occurs, resulting in the cytoplasmic tails of associated JAK kinases being brought into proximity and facilitating the trans-phosphorylation of tyrosine residues on the JAK kinase. This trans-phosphorylation results in the activation of the JAK kinase.

Animal studies have suggested that JAK3 not only plays a critical role in B and T lymphocyte maturation, but that JAK3 is constitutively required to maintain T cell function. Modulation of immune activity through this novel mechanism can prove useful in the treatment of T cell proliferative disorders such as transplant rejection and autoimmune diseases.

In particular, JAK3 has been implicated in a variety of biological processes. For example, the proliferation and survival of murine mast cells induced by IL-4 and IL-9 have been shown to be dependent on JAK3- and gamma chain-signaling (Suzuki et al., (2000), Blood 96:2172-2180). JAK3 also plays a crucial role in IgE receptor-mediated mast cell degranulation responses (Malaviya et al., (1999), Biochem. Biophys. Res. Commun. 257:807-813), and inhibition of JAK3 kinase has been shown to prevent type I hypersensitivity reactions, including anaphylaxis (Malaviya et al., (1999), J. Biol. Chem. 274:27028-27038). JAK3 inhibition has also been shown to result in immune suppression for allograft rejection (Kirken, (2001), Transpl. Proc. 33:3268-3270). JAK3 kinases have also been implicated in the mechanism involved in early and late stages of rheumatoid arthritis (Muller-Ladner et al., (2000), J. Immunal. 164:3894-3901); familial amyotrophic lateral sclerosis (Trieu et al., (2000), Biochem Biophys. Res. Commun. 267:22-25); leukemia (Sudbeck et al., (1999), Clin. Cancer Res. 5:1569-1582); mycosis fungoides, a form of T-cell lymphoma (Nielsen et al., (1997), Prac. Natl. Acad.

Sci. USA 94:6764-6769); and abnormal cell growth (Yu et al., (1997), J. Immunol. 159:5206-5210; Catlett-Falcone et al., (1999), Immunity 10:105-115).

JAK3 inhibitors are useful therapy as immunosuppressive agents for organ transplants, xeno transplantation, lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable.

Non-hematopoietic expression of JAK3 has also been reported, although the functional significance of this has yet to be clarified (J. Immunol. 168 (2002), pp. 2475-2482). Because bone marrow transplants for SCID are curative (Blood 103 (2004), pp. 2009-2018), it seems unlikely that JAK3 has essential non-redundant functions in other tissues or organs. Hence, in contrast with other targets of immunosuppressive drugs, the restricted distribution of JAK3 is appealing. Agents that act on molecular targets with expression limited to the immune system might lead to an optimal efficacy:toxicity ratio. Targeting JAK3 would, therefore, theoretically offer immune suppression where it is needed (i.e. on cells actively participating in immune responses) without resulting in any effects outside of these cell populations. Although defective immune responses have been described in various STAT$^{-/-}$ strains (J. Investig. Med. 44 (1996), pp. 304-311; Curr. Opin. Cell Biol. 9 (1997), pp. 233-239), the ubiquitous distribution of STATs and the fact that those molecules lack enzymatic activity that could be targeted with small-molecule inhibitors has contributed to their non-selection as key targets for immunosuppression.

SYK (Spleen Tyrosine Kinase) is a non-receptor tyrosine kinase that is essential for B-cell activation through BCR signaling. SYK become activated upon binding to phosphoryated BCR and thus initiates the early singing events following BCR activation. Mice deficient in SYK exhibit an early block in B-cell development (Cheng et al. Nature 378: 303, 1995; Turner et al. Nature 378:298, 1995). Therefore inhibition of SYK enzymatic activity in cells is proposed as a treatment for autoimmune disease through its effects on autoantibody production.

In addition to the role of SYK in BCR signaling and B-cell activation, it also plays a key role in Fc8RI mediated mast cell degranulation and eosinophil activation. Thus, SYK is implicated in allergic disorders including asthma (reviewed in Wong et al. Expert Opin Investig Drugs 13:743, 2004). SYK binds to the phosphorylated gamma chain of Fc8RI via its SH2 domains and is essential for downstream signaling (Taylor et al. Mol. Cell. Biol. 15:4149, 1995). SYK deficient mast cells demonstrate defective degranulation, arachidonic acid and cytokine secretion (Costello et al. Oncogene 13:2595, 1996). This also has been shown for pharmacologic agents that inhibit SYK activity in mast cells (Yamamoto et al. J Pharmacol Exp Ther 306:1174, 2003). Treatment with SYK antisense oligonucleotides inhibits antigen-induced infiltration of eosinophils and neutrophils in an animal model of asthma (Stenton et al. J Immunol 169:1028, 2002). SYK deficient eosinophils also show impaired activation in response to Fc8R stimulation (Lach-Trifilieffe et al. Blood 96:2506, 2000). Therefore, small molecule inhibitors of SYK will be useful for treatment of allergy-induced inflammatory diseases including asthma.

In view of the numerous conditions that are contemplated to benefit by treatment involving modulation of the JAK and/or SYK pathways it is immediately apparent that new compounds that modulate JAK and/or SYK pathways and methods of using these compounds should provide substantial therapeutic benefits to a wide variety of patients. Provided herein are novel pyrrolopyrazine derivatives for use in the treatment of conditions in which targeting of the JAK and/or SYK pathways or inhibition of JAK or SYK kinases, particularly JAK3, and are therapeutically useful for the treatment of auto-immune and inflammatory diseases.

SUMMARY OF THE INVENTION

The novel pyrrolopyrazine derivatives provided herein selectively inhibit JAK3 and are useful for the treatment of auto-immune and inflammatory diseases. The compounds of the invention modulate the JAK and/or SYK pathways and are useful novel pyrrolopyrazine derivatives for the treatment of auto-immune and inflammatory diseases, wherein preferred compounds selectively inhibit JAK3. For example, the compounds of the invention may inhibit JAK3 and SYK, wherein preferred compounds are selective for JAK3 of the JAK kinases and are useful novel pyrrolopyrazine derivatives for the treatment of auto-immune and inflammatory diseases. Furthermore, the compounds of the invention may inhibit JAK3 and JAK2, wherein preferred compounds are selective for JAK3 of the JAK kinases, and are useful novel pyrrolopyrazine derivatives for the treatment of auto-immune and inflammatory diseases. Similarly, the compounds of the invention may inhibit JAK3 and JAK1, wherein preferred compounds are selective for JAK3 of the JAK kinases, and are useful novel pyrrolopyrazine derivatives for the treatment of auto-immune and inflammatory diseases.

The application provides a compound of Formula I

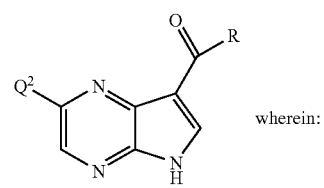

wherein:

R is $R^1$, $R^2$, $R^3$, or $R^4$;

$R^1$ is lower alkyl, lower alkoxy, phenyl, benzyl, heteroaryl, cycloalkyl, heterocycloalkyl, or cycloalkylalkyl, optionally substituted with one or more $R^{1a}$;

$R^{1a}$ is $R^{1b}$ or $R^{1c}$;

$R^{1b}$ is halogen, oxo, hydroxy, or —CN;

$R^{1c}$ is —C(=O)O($R^{1f}$), —C(=O)CH$_2$($R^{1e}$), —S($R^{1f}$), —S(O)$_2$($R^{1f}$), or —S(=O) ($R^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;

$R^{1d}$ is H, halogen, hydroxy, lower alkyl, lower alkoxy, or lower haloalkyl;

$R^{1e}$ is H, lower alkyl, lower alkoxy, —CN, lower haloalkyl, phenyl, heteroaryl, cycloalkyl, or heterocycloalkyl;

$R^{1f}$ is H, lower alkyl, lower haloalkyl, phenyl, heteroaryl, cycloalkyl, or heterocycloalkyl;

$R^2$ is N($R^{2a}$)$_2$;

each $R^{2a}$ is independently H or $R^{2b}$;

each $R^{2b}$ is independently lower alkyl, phenyl, heteroaryl, cycloalkyl, heterocycloalkyl, or heterocycloalkyl alkylene, optionally substituted with one or more $R^{2c}$;

$R^{2c}$ is $R^{2d}$ or $R^{2e}$;

$R^{2d}$ is halogen, oxo, or hydroxy;

$R^{2e}$ is —N($R^{2g}$)$_2$, —C(=O)($R^{2g}$), —C(=O)O ($R^{2g}$), —C(=O)N($R^{2g}$)$_2$, —N($R^{2g}$)C(=O) ($R^{2g}$), —S(=O)$_2$($R^{2g}$), —S(O)$_2$N($R^{2g}$)$_2$, lower alkyl, lower alkoxy, lower haloalkyl, phenyl, heteroaryl, heteroaryloxy, cycloalkyl, or heterocycloalkyl, optionally substituted with one or more $R^{2f}$;

each $R^{2f}$ is independently H, halogen, lower alkyl, lower alkoxy, lower haloalkyl;

each $R^{2g}$ is independently H, lower alkyl, lower alkoxy, lower haloalkyl, or phenyl;

$R^3$ is —C(=O)$R^{3a}$;

$R^{3a}$ is lower alkyl, lower alkoxy, phenyl, or N($R^{3b}$)$_2$;

each $R^{3b}$ is independently H or lower alkyl;

$R^4$ is —O($R^{4a}$);

$R^{4a}$ is H or $R^{4b}$;

$R^{4b}$ is lower alkyl, phenyl, benzyl, lower haloalkyl, cycloalkyl, heterocycloalkyl, heteroaryl, optionally substituted with one or more $R^{4c}$;

$R^{4c}$ is halogen, hydroxy, lower alkyl, lower haloalkyl, or lower alkoxy;

$Q^2$ is cycloalkyl, cycloalkenyl, heterocycloalkyl, or heteroaryl, optionally substituted with one or more $Q^{2a}$;

$Q^{2a}$ is $Q^{2b}$ or $Q^{2c}$;

$Q^{2b}$ is halogen, oxo, hydroxy, —CN, —SCH$_3$, —S(O)$_2$CH$_3$, or —S(=O)CH$_3$;

$Q^{2c}$ is $Q^{2d}$ or $Q^{2e}$;

or two $Q^{2a}$ come together to form a bicyclic ring system, optionally substituted with one or more $Q^{2b}$ or $Q^{2c}$;

$Q^{2d}$ is —O($Q^{2e}$), —S(=O)$_2$($Q^{2e}$), —C(=O)N($Q^{2e}$)$_2$, —S(O)$_2$($Q^{2e}$), —C(=O)($Q^{2e}$), —C(=O)O($Q^{2e}$), —N($Q^{2e}$)$_2$; —N($Q^{2e}$)C(=O)($Q^{2e}$), —N($Q^{2e}$)C(=O)O ($Q^{2e}$), or —N($Q^{2e}$)C(=O)N($Q^{2e}$)$_2$;

each $Q^{2e}$ is independently H or $Q^{2e'}$;

each $Q^{2e'}$ is independently lower alkyl, phenyl, benzyl, lower haloalkyl, cycloalkyl, cycloalkenyl, heterocycloalkyl, or heteroaryl, optionally substituted with one or more $Q^{2f}$;

$Q^{2f}$ is $Q^{2g}$ or $Q^{2h}$;

$Q^{2g}$ is halogen, hydroxy, cyano, oxo, or —C(=O) ($Q^{2h}$);

$Q^{2h}$ is lower alkyl, lower haloalkyl, lower alkoxy, amino, phenyl, benzyl, cycloalkyl, heterocycloalkyl, or heteroaryl, optionally substituted with one or more $Q^{2i}$; and $Q^{2i}$ is halogen, hydroxy, cyano, lower alkyl, lower haloalkyl, or lower alkoxy;

or a pharmaceutically acceptable salt thereof.

In one variation of the above embodiment, R is $R^1$.

In one variation of the above embodiment, $R^1$ is lower alkyl.

In one variation of the above embodiment, $R^1$ is tert-butyl.

In one embodiment of the compound of Formula I, $R^1$ is cycloalkyl.

In one embodiment of the compound of Formula I, $R^1$ is heterocycloalkyl.

In one embodiment of the compound of Formula I, $R^1$ is benzyl.

In one embodiment of the compound of Formula I, $R^1$ is phenyl.

In one embodiment of the compound of Formula I, R is $R^2$ and $R^2$ is NH($R^{2a}$).

In one variation of the above embodiment, $R^{2a}$ is $R^{2b}$.

In one variation of the above embodiment, $R^{2b}$ is lower alkyl.

In one variation of the above embodiment, $R^{2b}$ is isopropyl.

In one embodiment of the compound of Formula I, $R^{2b}$ is heterocycloalkyl.

In one embodiment of the compound of Formula I, $R^{2b}$ is cycloalkyl.

In one embodiment of the compound of Formula I, $R^{2b}$ is heterocycloalkyl alkylene.

In one variation of the above embodiment, $R^{2b}$ is pyrrolidinyl alkylene.

In one variation of the above embodiment, $R^{2b}$ is pyrrolidinyl methylene.

In one variation of any of the above embodiments, $Q^2$ is heterocycloalkyl.

In one variation of the above embodiment, $Q^2$ is heterocycloalkyl, optionally substituted with one or more $Q^{2a}$.

In one variation of the above embodiment, $Q^2$ is pyrrolidine.

In another variation of the above embodiment, $Q^2$ is piperidine.

In one variation of the above embodiment, $Q^2$ is piperazine.

In another variation of the above embodiment, $Q^2$ is pyrrolidine.

In one embodiment of the compound of Formula I, $Q^2$ is heteroaryl, optionally substituted with one or more $Q^{2a}$.

In one variation of the above embodiment, $Q^2$ is pyridine.

In one embodiment of the compound of Formula I, $Q^2$ is heteroaryl, $Q^{2a}$ is $Q^{2c}$ and $Q^{2c}$ is heterocycloalkyl, optionally substituted with one or more $Q^{2d}$.

In one embodiment of the compound of Formula I, $Q^2$ is cycloalkyl.

The application provides a compound Formula I of the group consisting of:

1-[2-(1-Benzenesulfonyl-1H-indol-3-yl)-5H-pyrrolo[2,3-b]pyrazin-7-yl]-2,2-dimethyl-propan-1-one;

1-[2-(1H-Indol-3-yl)-5H-pyrrolo[2,3-b]pyrazin-7-yl]-2,2-dimethyl-propan-1-one;

2-Cyclohex-1-enyl-5H-pyrrolo[2,3-b]pyrazine-7-carboxylic acid isopropylamide;

2-Cyclohexyl-5H-pyrrolo[2,3-b]pyrazine-7-carboxylic acid isopropylamide;

1-{2-[2-(4-Acetyl-piperazin-1-yl)-pyridin-4-yl]-5H-pyrrolo[2,3-b]pyrazin-7-yl}-2,2-dimethyl-propan-1-one;

1-[2-(5-Methoxy-pyridin-3-yl)-5H-pyrrolo[2,3-b]pyrazin-7-yl]-2,2-dimethyl-propan-1-one;

[1-(7-Isopropylcarbamoyl-5H-pyrrolo[2,3-b]pyrazin-2-yl)-piperidin-3-yl]-methyl-carbamic acid tert-butyl ester;

2-(3-Methylamino-piperidin-1-yl)-5H-pyrrolo[2,3-b]pyrazine-7-carboxylic acid isopropylamide; compound with trifluoro-acetic acid;

2,2-Dimethyl-1-(2-pyrrolidin-1-yl-5H-pyrrolo[2,3-b]pyrazin-7-yl)-propan-1-one;

1-[7-(2,2-Dimethyl-propionyl)-2'-pyrrolidin-1-yl-5H-[2,5']bi[pyrrolo[2,3-b]pyrazinyl]-7'-yl]-2,2-dimethyl-propan-1-one;

2,2-Dimethyl-1-[2-(2-pyrrolidin-1-yl-pyridin-4-yl)-5H-pyrrolo[2,3-b]pyrazin-7-yl]-propan-1-one;

1-[2-(1-Cyclopentyl-1H-[1,2,3]triazol-4-yl)-5H-pyrrolo[2,3-b]pyrazin-7-yl]-2,2-dimethyl-propan-1-one;

2,2-Dimethyl-1-[2-(3,4,5,6-tetrahydro-2H-[1,2']bipyridinyl-4'-yl)-5H-pyrrolo[2,3-b]pyrazin-7-yl]-propan-1-one;

1-{2-[2-(3-Dimethylamino-pyrrolidin-1-yl)-pyridin-4-yl]-5H-pyrrolo[2,3-b]pyrazin-7-yl}-2,2-dimethyl-propan-1-one;

2,2-Dimethyl-1-[2-(2-thiomorpholin-4-yl-pyridin-4-yl)-5H-pyrrolo[2,3-b]pyrazin-7-yl]-propan-1-one;

2,2-Dimethyl-1-{2-[2-(2-methyl-pyrrolidin-1-yl)-pyridin-4-yl]-5H-pyrrolo[2,3-b]pyrazin-7-yl}-propan-1-one;
1-[2-(1,3-Dihydro-isoindol-2-yl)-5H-pyrrolo[2,3-b]pyrazin-7-yl]-2,2-dimethyl-propan-1-one;
1-[2-(2,3-Dihydro-indol-1-yl)-5H-pyrrolo[2,3-b]pyrazin-7-yl]-2,2-dimethyl-propan-1-one;
2-[7-(2,2-Dimethyl-propionyl)-5H-pyrrolo[2,3-b]pyrazin-2-yl]-3,4-dihydro-2H-isoquinolin-1-one;
1-[7-(2,2-Dimethyl-propionyl)-5H-pyrrolo[2,3-b]pyrazin-2-yl]-3,4-dihydro-1H-quinolin-2-one;
2-[7-(2,2-Dimethyl-propionyl)-5H-pyrrolo[2,3-b]pyrazin-2-yl]-2,3-dihydro-isoindol-1-one;
1-[7-(2,2-Dimethyl-propionyl)-5H-pyrrolo[2,3-b]pyrazin-2-yl]-piperidin-2-one;
1-[7-(2,2-Dimethyl-propionyl)-5H-pyrrolo[2,3-b]pyrazin-2-yl]-pyrrolidin-2-one;
1-[2-(1H-Indol-3-yl)-5H-pyrrolo[2,3-b]pyrazin-7-yl]-2,2-dimethyl-propan-1-one;
2,2-Dimethyl-1-[2-(6-pyrrolidin-1-yl-pyridin-2-yl)-5H-pyrrolo[2,3-b]pyrazin-7-yl]-propan-1-one;
2,2-Dimethyl-1-[2-(4-pyrrolidin-1-yl-pyridin-2-yl)-5H-pyrrolo[2,3-b]pyrazin-7-yl]-propan-1-one;
2,2-Dimethyl-1-(2-pyridin-2-yl-5H-pyrrolo[2,3-b]pyrazin-7-yl)-propan-1-one;
[1-(7-Isopropylcarbamoyl-5H-pyrrolo[2,3-b]pyrazin-2-yl)-piperidin-3-yl]-methyl-carbamic acid tert-butyl ester;
2-(3-Methylamino-piperidin-1-yl)-5H-pyrrolo[2,3-b]pyrazine-7-carboxylic acid; isopropylamide; compound with trifluoro-acetic acid;
5-[7-(2,2-Dimethyl-propionyl)-5H-pyrrolo[2,3-b]pyrazin-2-yl]-thiophene-3-carboxylic acid (tetrahydro-pyran-4-yl)-amide;
5-[7-(2,2-Dimethyl-propionyl)-5H-pyrrolo[2,3-b]pyrazin-2-yl]-thiophene-2-carboxylic acid cyclopentylamide;
5-[7-(2,2-Dimethyl-propionyl)-5H-pyrrolo[2,3-b]pyrazin-2-yl]-thiophene-2-carboxylic acid (tetrahydro-pyran-4-yl)-amide;
1-(2-Cyclopropyl-5H-pyrrolo[2,3-b]pyrazin-7-yl)-2,2-dimethyl-propan-1-one;
5-[7-(2,2-Dimethyl-propionyl)-5H-pyrrolo[2,3-b]pyrazin-2-yl]-thiophene-3-carboxylic acid;
5-[7-(2,2-Dimethyl-propionyl)-5H-pyrrolo[2,3-b]pyrazin-2-yl]-thiophene-3-carboxylic acid (2-dimethylamino-ethyl)-amide;
1-{2-[2-(3-Methoxy-phenyl)-cyclopent-1-enyl]-5H-pyrrolo[2,3-b]pyrazin-7-yl}-2,2-dimethyl-propan-1-one;
6-{2-[7-(2,2-Dimethyl-propionyl)-5H-pyrrolo[2,3-b]pyrazin-2-yl]-cyclopent-1-enyl}-pyridine-2-carboxylic acid ethyl ester;
2,2-Dimethyl-1-[2-(2-phenyl-cyclopent-1-enyl)-5H-pyrrolo[2,3-b]pyrazin-7-yl]-propan-1-one;
5-{2-[7-(2,2-Dimethyl-propionyl)-5H-pyrrolo[2,3-b]pyrazin-2-yl]-cyclopent-1-enyl}-1H-indole-2-carboxylic acid ethyl ester;
4-[7-(1-Methyl-cyclohexanecarbonyl)-5H-pyrrolo[2,3-b]pyrazin-2-yl]-thiophene-2-carboxylic acid cyanomethyl-methyl-amide;
(1-Methyl-cyclohexyl)-{2-[5-(morpholine-4-carbonyl)-thiophen-3-yl]-5H-pyrrolo[2,3-b]pyrazin-7-yl}-methanone;
1-(2-Furan-3-yl-5H-pyrrolo[2,3-b]pyrazin-7-yl)-2,2-dimethyl-propan-1-one;
4-[7-(1-Methyl-cyclohexanecarbonyl)-5H-pyrrolo[2,3-b]pyrazin-2-yl]-thiophene-2-carboxylic acid (1-ethyl-propyl)-amide;
{2-[5-(4-Hydroxy-4-methyl-piperidine-1-carbonyl)-thiophen-3-yl]-5H-pyrrolo[2,3-b]pyrazin-7-yl}-(1-methyl-cyclohexyl)-methanone;
2,2-Dimethyl-1-[2-(2-pyrrolidin-1-yl-pyridin-4-yl)-5H-pyrrolo[2,3-b]pyrazin-7-yl]-propan-1-one;
2,2-Dimethyl-1-[2-(3,4,5,6-tetrahydro-2H-[1,2']bipyridinyl-4'-yl)-5H-pyrrolo[2,3-b]pyrazin-7-yl]-propan-1-one;
1-{2-[2-(3-Dimethylamino-pyrrolidin-1-yl)-pyridin-4-yl]-5H-pyrrolo[2,3-b]pyrazin-7-yl}-2,2-dimethyl-propan-1-one;
2,2-Dimethyl-1-[2-(2-thiomorpholin-4-yl-pyridin-4-yl)-5H-pyrrolo[2,3-b]pyrazin-7-yl]-propan-1-one;
2,2-Dimethyl-1-{2-[2-(2-methyl-pyrrolidin-1-yl)-pyridin-4-yl]-5H-pyrrolo[2,3-b]pyrazin-7-yl}-propan-1-one;
1-{2-[2-(3-Hydroxy-pyrrolidin-1-yl)-pyridin-4-yl]-5H-pyrrolo[2,3-b]pyrazin-7-yl}-2,2-dimethyl-propan-1-one;
1-{2-[2-(3,3-Difluoro-pyrrolidin-1-yl)-pyridin-4-yl]-5H-pyrrolo[2,3-b]pyrazin-7-yl}-2,2-dimethyl-propan-1-one;
1-[2-(2-Azepan-1-yl-pyridin-4-yl)-5H-pyrrolo[2,3-b]pyrazin-7-yl]-2,2-dimethyl-propan-1-one;
1-{2-[2-((S)-3-Fluoro-pyrrolidin-1-yl)-pyridin-4-yl]-5H-pyrrolo[2,3-b]pyrazin-7-yl}-2,2-dimethyl-propan-1-one;
1-{2-[2-((R)-3-Fluoro-pyrrolidin-1-yl)-pyridin-4-yl]-5H-pyrrolo[2,3-b]pyrazin-7-yl}-2,2-dimethyl-propan-1-one;
1-{2-[2-(1,1-Dioxo-1$\lambda^6$-thiomorpholin-4-yl)-pyridin-4-yl]-5H-pyrrolo[2,3-b]pyrazin-7-yl}-2,2-dimethyl-propan-1-one;
1-[2-(2-Chloro-pyridin-4-yl)-5H-pyrrolo[2,3-b]pyrazin-7-yl]-2,2-dimethyl-propan-1-one 2,2-Dimethyl-1-{2-[2-(1-oxo-1$\lambda^4$-thiomorpholin-4-yl)-pyridin-4-yl]-5H-pyrrolo[2,3-b]pyrazin-7-yl}-propan-1-one;
1-[2-(2-Cyclopent-1-enyl-pyridin-4-yl)-5H-pyrrolo[2,3-b]pyrazin-7-yl]-2,2-dimethyl-propan-1-one;
(1-Methyl-cyclohexyl)-[2-(2-pyrrolidin-1-yl-pyridin-4-yl)-5H-pyrrolo[2,3-b]pyrazin-7-yl]-methanone;
1-[2-(4-Hydroxy-3,4,5,6-tetrahydro-2H-[1,2']bipyridinyl-4'-yl)-5H-pyrrolo[2,3-b]pyrazin-7-yl]-2,2-dimethyl-propan-1-one;
5-[7-(1-Methyl-cyclohexanecarbonyl)-5H-pyrrolo[2,3-b]pyrazin-2-yl]-thiophene-2-carboxylic acid (1-ethyl-propyl)-amide;
{2-[5-(3,3-Difluoro-azetidine-1-carbonyl)-thiophen-2-yl]-5H-pyrrolo[2,3-b]pyrazin-7-yl}-(1-methyl-cyclohexyl)-methanone;
{2-[5-(4-Hydroxy-piperidine-1-carbonyl)-thiophen-2-yl]-5H-pyrrolo[2,3-b]pyrazin-7-yl}-(1-methyl-cyclohexyl)-methanone;
(1-Methyl-cyclohexyl)-{2-[2-(1-oxo-1$\lambda^4$-thiomorpholin-4-yl)-pyridin-4-yl]-5H-pyrrolo[2,3-b]pyrazin-7-yl}-methanone;
{2-[5-(Azetidine-1-carbonyl)-thiophen-2-yl]-5H-pyrrolo[2,3-b]pyrazin-7-yl}-(1-methyl-cyclohexyl)-methanone;
{2-[5-(3-Hydroxy-azetidine-1-carbonyl)-thiophen-2-yl]-5H-pyrrolo[2,3-b]pyrazin-7-yl}-(1-methyl-cyclohexyl)-methanone;
1-{2-[2-((1S,5R,6R)-6-Hydroxymethyl-3-aza-bicyclo[3.1.0]hex-3-yl)-pyridin-4-yl]-5H-pyrrolo[2,3-b]pyrazin-7-yl}-2,2-dimethyl-propan-1-one;
(1-Methyl-cyclohexyl)-{2-[5-(morpholine-4-carbonyl)-thiophen-2-yl]-5H-pyrrolo[2,3-b]pyrazin-7-yl}-methanone;
5-[7-(1-Methyl-cyclohexanecarbonyl)-5H-pyrrolo[2,3-b]pyrazin-2-yl]-thiophene-2-carboxylic acid diethylamide;
5-[7-(1-Methyl-cyclohexanecarbonyl)-5H-pyrrolo[2,3-b]pyrazin-2-yl]-thiophene-2-carboxylic acid cyclopentyl-methyl-amide;

{2-[5-(4-Hydroxy-4-methyl-piperidine-1-carbonyl)-thiophen-2-yl]-5H-pyrrolo[2,3-b]pyrazin-7-yl}-(1-methyl-cyclohexyl)-methanone;

5-[7-(1-Methyl-cyclohexanecarbonyl)-5H-pyrrolo[2,3-b]pyrazin-2-yl]-thiophene-2-carboxylic acid bis-(2-hydroxy-ethyl)-amide;

5-[7-(1-Methyl-cyclohexanecarbonyl)-5H-pyrrolo[2,3-b]pyrazin-2-yl]-thiophene-2-carboxylic acid (2-hydroxy-ethyl)-methyl-amide;

{2-[5-(3-Hydroxy-pyrrolidine-1-carbonyl)-thiophen-2-yl]-5H-pyrrolo[2,3-b]pyrazin-7-yl}-(1-methyl-cyclohexyl)-methanone;

5-[7-(2,2-Dimethyl-propionyl)-5H-pyrrolo[2,3-b]pyrazin-2-yl]-thiophene-2-carboxylic acid cyanomethyl-methyl-amide;

5-[7-(2,2-Dimethyl-propionyl)-5H-pyrrolo[2,3-b]pyrazin-2-yl]-thiophene-2-carboxylic acid bis-(2-hydroxy-ethyl)-amide;

1-{2-[5-(4-Hydroxy-4-methyl-piperidine-1-carbonyl)-thiophen-2-yl]-5H-pyrrolo[2,3-b]pyrazin-7-yl}-2,2-dimethyl-propan-1-one;

1-{2-[5-(Azetidine-1-carbonyl)-thiophen-2-yl]-5H-pyrrolo[2,3-b]pyrazin-7-yl}-2,2-dimethyl-propan-1-one;

2,2-Dimethyl-1-{2-[5-(pyrrolidine-1-carbonyl)-thiophen-2-yl]-5H-pyrrolo[2,3-b]pyrazin-7-yl}-propan-1-one;

2,2-Dimethyl-1-{2-[5-(piperidine-1-carbonyl)-thiophen-2-yl]-5H-pyrrolo[2,3-b]pyrazin-7-yl}-propan-1-one;

3-Dimethylamino-1-{5-[7-(2,2-dimethyl-propionyl)-5H-pyrrolo[2,3-b]pyrazin-2-yl]-thiophene-2-carbonyl}-azetidine-3-carbonitrile;

1-{2-[5-(4-Hydroxy-piperidine-1-carbonyl)-thiophen-2-yl]-5H-pyrrolo[2,3-b]pyrazin-7-yl}-2,2-dimethyl-propan-1-one;

1-{2-[4-(Azetidine-1-carbonyl)-thiophen-2-yl]-5H-pyrrolo[2,3-b]pyrazin-7-yl}-2,2-dimethyl-propan-1-one;

2,2-Dimethyl-1-{2-[4-(pyrrolidine-1-carbonyl)-thiophen-2-yl]-5H-pyrrolo[2,3-b]pyrazin-7-yl}-propan-1-one;

2,2-Dimethyl-1-{2-[4-(piperidine-1-carbonyl)-thiophen-2-yl]-5H-pyrrolo[2,3-b]pyrazin-7-yl}-propan-1-one;

(1-Methyl-cyclohexyl)-{2-[5-(4-methyl-piperazine-1-carbonyl)-thiophen-2-yl]-5H-pyrrolo[2,3-b]pyrazin-7-yl}-methanone;

{2-[5-(4-Dimethylamino-piperidine-1-carbonyl)-thiophen-2-yl]-5H-pyrrolo[2,3-b]pyrazin-7-yl}-(1-methyl-cyclohexyl)-methanone;

1-(2-Cyclopent-1-enyl-5H-pyrrolo[2,3-b]pyrazin-7-yl)-2,2-dimethyl-propan-1-one;

2,2-Dimethyl-1-(2-pyrrolidin-1-yl-5H-pyrrolo[2,3-b]pyrazin-7-yl)-propan-1-one;

1-[7-(2,2-Dimethyl-propionyl)-2'-pyrrolidin-1-yl-5H-[2,5']bi[pyrrolo[2,3-b]pyrazinyl]-7'-yl]-2,2-dimethyl-propan-1-one;

N-{1-[7-(2,2-Dimethyl-propionyl)-5H-pyrrolo[2,3-b]pyrazin-2-yl]-pyrrolidin-3-yl}-acetamide;

2,2-Dimethyl-1-[2-(2-methyl-pyrrolidin-1-yl)-5H-pyrrolo[2,3-b]pyrazin-7-yl]-propan-1-one;

1-[2-(4-Acetyl-piperazin-1-yl)-5H-pyrrolo[2,3-b]pyrazin-7-yl]-2,2-dimethyl-propan-1-one;

2,2-Dimethyl-1-(2-morpholin-4-yl-5H-pyrrolo[2,3-b]pyrazin-7-yl)-propan-1-one;

1-[2-(5-Fluoro-indol-1-yl)-5H-pyrrolo[2,3-b]pyrazin-7-yl]-2,2-dimethyl-propan-1-one;

1-[2-(5-Methoxy-indol-1-yl)-5H-pyrrolo[2,3-b]pyrazin-7-yl]-2,2-dimethyl-propan-1-one;

1-(2-Indol-1-yl-5H-pyrrolo[2,3-b]pyrazin-7-yl)-2,2-dimethyl-propan-1-one;

1-(2-Indazol-1-yl-5H-pyrrolo[2,3-b]pyrazin-7-yl)-2,2-dimethyl-propan-1-one;

1-[2-(3,4-Dihydro-1H-isoquinolin-2-yl)-5H-pyrrolo[2,3-b]pyrazin-7-yl]-2,2-dimethyl-propan-1-one;

2,2-Dimethyl-1-[2-(1,3,4,9-tetrahydro-β-carbolin-2-yl)-5H-pyrrolo[2,3-b]pyrazin-7-yl]-propan-1-one;

2-{1-[7-(2,2-Dimethyl-propionyl)-5H-pyrrolo[2,3-b]pyrazin-2-yl]-1H-indol-3-yl}-acetamide;

2,2-Dimethyl-1-[2-(1,3,4,5-tetrahydro-pyrido[4,3-b]indol-2-yl)-5H-pyrrolo[2,3-b]pyrazin-7-yl]-propan-1-one;

2,2-Dimethyl-1-[2-(3-phenyl-pyrrolidin-1-yl)-5H-pyrrolo[2,3-b]pyrazin-7-yl]-propan-1-one;

1-(2-Imidazol-1-yl-5H-pyrrolo[2,3-b]pyrazin-7-yl)-2,2-dimethyl-propan-1-one;

2,2-Dimethyl-1-[2-(2-methyl-imidazol-1-yl)-5H-pyrrolo[2,3-b]pyrazin-7-yl]-propan-1-one;

2,2-Dimethyl-1-[2-(2-methyl-4,5-dihydro-imidazol-1-yl)-5H-pyrrolo[2,3-b]pyrazin-7-yl]-propan-1-one;

1-[2-(2-Ethyl-imidazol-1-yl)-5H-pyrrolo[2,3-b]pyrazin-7-yl]-2,2-dimethyl-propan-1-one;

2,2-Dimethyl-1-[2-thiophen-2-yl-5H-pyrrolo[2,3-b]pyrazin-7-yl)-propan-1-one;

2,2-Dimethyl-1-[2-(1H-pyrrol-2-yl)-5H-pyrrolo[2,3-b]pyrazin-7-yl]-propan-1-one;

2,2-Dimethyl-1-(2-thiophen-3-yl-5H-pyrrolo[2,3-b]pyrazin-7-yl)-propan-1-one;

2,2-Dimethyl-1-(2-oxazol-5-yl-5H-pyrrolo[2,3-b]pyrazin-7-yl)-propan-1-one;

2,2-Dimethyl-1-[2-(1H-pyrazol-4-yl)-5H-pyrrolo[2,3-b]pyrazin-7-yl]-propan-1-one;

4-[7-(2,2-Dimethyl-propionyl)-5H-pyrrolo[2,3-b]pyrazin-2-yl]-pyrazole-1-carboxylic acid tert-butyl ester;

2,2-Dimethyl-1-(2-pyrazol-1-yl-5H-pyrrolo[2,3-b]pyrazin-7-yl)-propan-1-one;

2,2-Dimethyl-1-[2-(2H-pyrazol-3-yl)-5H-pyrrolo[2,3-b]pyrazin-7-yl]-propan-1-one;

2,2-Dimethyl-1-(2-pyrrol-1-yl-5H-pyrrolo[2,3-b]pyrazin-7-yl)-propan-1-one;

2,2-Dimethyl-1-[2-(1H-pyrrol-3-yl)-5H-pyrrolo[2,3-b]pyrazin-7-yl]-propan-1-one;

2,2-Dimethyl-1-(2-thiazol-5-yl-5H-pyrrolo[2,3-b]pyrazin-7-yl)-propan-1-one;

3-[7-(2,2-Dimethyl-propionyl)-5H-pyrrolo[2,3-b]pyrazin-2-yl]-1H-indole-5-carbonitrile;

1-[2-(5-Fluoro-1H-indol-3-yl)-5H-pyrrolo[2,3-b]pyrazin-7-yl]-2,2-dimethyl-propan-1-one;

[2-(1H-Indol-3-yl)-5H-pyrrolo[2,3-b]pyrazin-7-yl]-(1-methyl-cyclohexyl)-methanone;

1-{2-[1-(2-Hydroxy-1-hydroxymethyl-ethyl)-1H-indol-3-yl]-5H-pyrrolo[2,3-b]pyrazin-7-yl}-2,2-dimethyl-propan-1-one;

1-[2-(1H-Indol-3-yl)-5H-pyrrolo[2,3-b]pyrazin-7-yl]-2,2-dimethyl-propan-1-one;

1-(2-Benzo[b]thiophen-2-yl-5H-pyrrolo[2,3-b]pyrazin-7-yl)-2,2-dimethyl-propan-1-one;

2,2-Dimethyl-1-[2-(5-phenyl-thiophen-2-yl)-5H-pyrrolo[2,3-b]pyrazin-7-yl]-propan-1-one;

2,2-Dimethyl-1-[2-(1-methyl-1H-indol-2-yl)-5H-pyrrolo[2,3-b]pyrazin-7-yl]-propan-1-one;

1-[2-(1H-Indol-2-yl)-5H-pyrrolo[2,3-b]pyrazin-7-yl]-2,2-dimethyl-propan-1-one;

1-[2-(1H-Indol-3-yl)-5-methyl-5H-pyrrolo[2,3-b]pyrazin-7-yl]-2,2-dimethyl-propan-1-one;

2,2-Dimethyl-1-[2-(1-methyl-1H-indol-3-yl)-5H-pyrrolo[2,3-b]pyrazin-7-yl]-propan-1-one;

2,2-Dimethyl-1-[2-(5-phenyl-1H-pyrrol-3-yl)-5H-pyrrolo[2,3-b]pyrazin-7-yl]-propan-1-one;

1-{2-[1-(2-Hydroxy-ethyl)-1H-indol-3-yl]-5H-pyrrolo[2,3-b]pyrazin-7-yl}-2,2-dimethyl-propan-1-one;
1-[2-(6-Fluoro-1H-indol-3-yl)-5H-pyrrolo[2,3-b]pyrazin-7-yl]-2,2-dimethyl-propan-1-one;
1-{2-[1-(2-Methanesulfonyl-ethyl)-1H-indol-3-yl]-5H-pyrrolo[2,3-b]pyrazin-7-yl}-2,2-dimethyl-propan-1-one;
1-[2-(5-Methoxy-1H-indol-3-yl)-5H-pyrrolo[2,3-b]pyrazin-7-yl]-2,2-dimethyl-propan-1-one;
1-[2-(1-Ethyl-1H-indol-3-yl)-5H-pyrrolo[2,3-b]pyrazin-7-yl]-2,2-dimethyl-propan-1-one;
2,2-Dimethyl-1-[2-(5-methyl-1H-indol-3-yl)-5H-pyrrolo[2,3-b]pyrazin-7-yl]-propan-1-one;
2,2-Dimethyl-1-(2-{1-[2-(4-methyl-piperazin-1-yl)-ethyl]-1H-indol-3-yl}-5H-pyrrolo[2,3-b]pyrazin-7-yl)-propan-1-one;
2,2-Dimethyl-1-{2-[1-(2-morpholin-4-yl-ethyl)-1H-indol-3-yl]-5H-pyrrolo[2,3-b]pyrazin-7-yl}-propan-1-one;
1-{2-[1-(3-Hydroxy-2-hydroxymethyl-propyl)-1H-indol-3-yl]-5H-pyrrolo[2,3-b]pyrazin-7-yl}-2,2-dimethyl-propan-1-one;
1-{2-[1-(3-Hydroxy-2-hydroxymethyl-propyl)-1H-pyrrolo[2,3-b]pyridin-3-yl]-5H-pyrrolo[2,3-b]pyrazin-7-yl}-2,2-dimethyl-propan-1-one;
2,2-Dimethyl-1-[2-(6-methyl-1H-indol-3-yl)-5H-pyrrolo[2,3-b]pyrazin-7-yl]-propan-1-one;
1-[2-(6-Methoxy-1H-indol-3-yl)-5H-pyrrolo[2,3-b]pyrazin-7-yl]-2,2-dimethyl-propan-1-one;
1-{2-[1-(2-Amino-ethyl)-1H-indol-3-yl]-5H-pyrrolo[2,3-b]pyrazin-7-yl}-2,2-dimethyl-propan-1-one;
2,2-Dimethyl-1-[2-(6-morpholin-4-yl-pyridin-3-yl)-5H-pyrrolo[2,3-b]pyrazin-7-yl]-propan-1-one;
(1-Methyl-cyclohexyl)-[2-(6-morpholin-4-yl-pyridin-3-yl)-5H-pyrrolo[2,3-b]pyrazin-7-yl]-methanone;
1-[2-(1H-Indol-3-yl)-5H-pyrrolo[2,3-b]pyrazin-7-yl]-2,2-dimethyl-propan-1-one;
1-(2-Imidazo[1,2-a]pyridin-3-yl-5H-pyrrolo[2,3-b]pyrazin-7-yl)-2,2-dimethyl-propan-1-one;
2,2-Dimethyl-1-[2-(1H-pyrrolo[2,3-b]pyridin-3-yl)-5H-pyrrolo[2,3-b]pyrazin-7-yl]-propan-1-one;
2,2-Dimethyl-1-[2-(1H-pyrrolo[3,2-c]pyridin-3-yl)-5H-pyrrolo[2,3-b]pyrazin-7-yl]-propan-1-one;
2,2-Dimethyl-1-[2-(1H-pyrrolo[2,3-c]pyridin-3-yl)-5H-pyrrolo[2,3-b]pyrazin-7-yl]-propan-1-one;
2,2-Dimethyl-1-[2-(1-methyl-1H-pyrrolo[2,3-b]pyridin-3-yl)-5H-pyrrolo[2,3-b]pyrazin-7-yl]-propan-1-one;
2,2-Dimethyl-1-{2-[1-(2-oxo-2-piperazin-1-yl-ethyl)-1H-indol-3-yl]-5H-pyrrolo[2,3-b]pyrazin-7-yl}-propan-1-one;
1-(2-{1-[2-(4-Amino-piperidin-1-yl)-2-oxo-ethyl]-1H-indol-3-yl}-5H-pyrrolo[2,3-b]pyrazin-7-yl)-2,2-dimethyl-propan-1-one;
(1-Methyl-cyclohexyl)-[2-(1-methyl-1H-pyrrolo[2,3-b]pyridin-3-yl)-5H-pyrrolo[2,3-b]pyrazin-7-yl]-methanone;
2,2-Dimethyl-1-(2-{1-[2-(4-methyl-piperazin-1-yl)-2-oxo-ethyl]-1H-indol-3-yl}-5H-pyrrolo[2,3-b]pyrazin-7-yl)-propan-1-one;
(1-Methyl-cyclopentyl)-[2-(1-methyl-1H-pyrrolo[2,3-b]pyridin-3-yl)-5H-pyrrolo[2,3-b]pyrazin-7-yl]-methanone;
1-[2-(5-Methoxy-pyridin-3-yl)-5H-pyrrolo[2,3-b]pyrazin-7-yl]-2,2-dimethyl-propan-1-one;
4-[7-(1-Methyl-cyclohexanecarbonyl)-5H-pyrrolo[2,3-b]pyrazin-2-yl]-thiophene-2-carboxylic acid (1-ethyl-propyl)-amide;
{2-[5-(4-Hydroxy-4-methyl-piperidine-1-carbonyl)-thiophen-3-yl]-5H-pyrrolo[2,3-b]pyrazin-7-yl}-(1-methyl-cyclohexyl)-methanone;
5-[7-(2,2-Dimethyl-propionyl)-5H-pyrrolo[2,3-b]pyrazin-2-yl]-thiophene-2-carboxylic acid (2-hydroxy-ethyl)-methyl-amide;
2-Cyclopropyl-5H-pyrrolo[2,3-b]pyrazine-7-carboxylic acid ((S)-2-hydroxy-1,2-dimethyl-propyl)-amide;
4-[7-(1-Methyl-cyclohexanecarbonyl)-5H-pyrrolo[2,3-b]pyrazin-2-yl]-thiophene-2-carboxylic acid;
4-[7-(1-Methyl-cyclohexanecarbonyl)-5H-pyrrolo[2,3-b]pyrazin-2-yl]-thiophene-2-carboxylic acid (2-amino-2-methyl-propyl)-amide;
{2-[5-(4-Dimethylamino-piperidine-1-carbonyl)-thiophen-3-yl]-5H-pyrrolo[2,3-b]pyrazin-7-yl}-(1-methyl-cyclohexyl)-methanone;
2-Cyclopropyl-5H-pyrrolo[2,3-b]pyrazine-7-carboxylic acid (3-hydroxy-2,2-dimethyl-propyl)-amide;
2-Cyclopropyl-5H-pyrrolo[2,3-b]pyrazine-7-carboxylic acid tert-butylamide;
2-[7-(2,2-Dimethyl-propionyl)-5H-pyrrolo[2,3-b]pyrazin-2-yl]-pyrrole-1-carboxylic acid tert-butyl ester; and
2-Thiophen-2-yl-5H-pyrrolo[2,3-b]pyrazine-7-carboxylic acid (3-hydroxy-2,2-dimethyl-propyl)-amide.

In one aspect, the application provides a method for treating an inflammatory and/or autoimmune condition comprising administering to a patient in need thereof a therapeutically effective amount of the compound of Formula I.

In one variation of the above method, the above method further comprises administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

In one aspect, the application provides a method for treating an inflammatory condition comprising administering to a patient in need thereof a therapeutically effective amount of the compound of Formula I, wherein R is $R^1$.

In one aspect, the application provides a method for inhibiting T-cell proliferative disorder comprising administering to a patient in need thereof a therapeutically effective amount of the compound of Formula I.

In one aspect, the application provides a method for inhibiting T-cell proliferative disorder comprising administering to a patient in need thereof a therapeutically effective amount of the compound of Formula I, wherein R is $R^2$.

In one variation of the above method, the proliferative disorder is cancer.

In one aspect, the application provides a method for treating a B-cell proliferative disorder comprising administering to a patient in need thereof a therapeutically effective amount of the compound of Formula I.

In one aspect, the application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

In one aspect, the application provides a method for preventing or treating all forms of organ rejection, including acute allograft or xenograft rejection and chronic allograft or xenograft rejection, of vascularized or non-vascularized transplants, comprising administering to a patient in need thereof a therapeutically effective amount of the compound of Formula I.

In one aspect, the application provides a method for inhibiting JAK3 activity comprising administering the compound of Formula I, wherein the compound exhibits an $IC_{50}$ of 50 micromolar or less in an in vitro biochemical assay of JAK3 activity.

In one variation of the above method, the compound exhibits an $IC_{50}$ of 100 nanomolar or less in an in vitro biochemical assay of JAK3 activity.

In one variation of the above method, the compound exhibits an $IC_{50}$ of 10 nanomolar or less in an in vitro biochemical assay of JAK3 activity.

In one aspect, the application provides a method for inhibiting SYK activity comprising administering the compound of Formula I, wherein the compound exhibits an $IC_{50}$ of 50 micromolar or less in an in vitro biochemical assay of SYK activity.

In one variation of the above method, the compound exhibits an $IC_{50}$ of 100 nanomolar or less in an in vitro biochemical assay of SYK activity.

In one variation of the above method, the compound exhibits an $IC_{50}$ of 10 nanomolar or less in an in vitro biochemical assay of SYK activity.

In one aspect, the application provides a method for treating an inflammatory condition comprising co-administering to a patient in need thereof an anti-inflammatory compound in combination with a therapeutically effective amount of the compound of Formula I.

In one aspect, the application provides a method for treating an immune disorder comprising co-administering to a patient in need thereof an immunosuppressant compound in combination with a therapeutically effective amount of the compound of Formula I.

The application provides a pharmaceutical composition comprising the compound of Formula I, admixed with at least one pharmaceutically acceptable carrier, excipient or diluent.

In one variation, the above pharmaceutical composition further comprises an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

In one aspect, the application provides a use of the compound of Formula I in the manufacture of a medicament for the treatment of an inflammatory disorder.

In one aspect, the application provides a use of the compound of Formula I in the manufacture of a medicament for the treatment of an autoimmune disorder.

In certain embodiments of formula I, the subject compounds are more specifically of formula II:

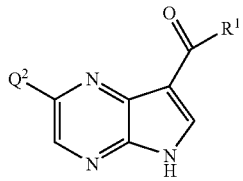

II wherein $R^1$ is lower alkyl, lower alkoxy, phenyl, benzyl, heteroaryl, cycloalkyl, heterocycloalkyl, or cycloalkylalkyl, optionally substituted with one or more $R^{1a}$;
$R^{1a}$ is $R^{1b}$ or $R^{1c}$;
$R^{1b}$ is halogen, oxo, hydroxy, or —CN;
$R^{1c}$ is —C(=O)O($R^{1f}$), —C(=O)$CH_2$($R^{1e}$, —S($R^{1f}$), —S(O)$_2$($R^{1f}$), or —S(=O) ($R^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;
$R^{1d}$ is H, halogen, hydroxy, lower alkyl, lower alkoxy, or lower haloalkyl;
$R^{1e}$ is H, lower alkyl, lower alkoxy, —CN, lower haloalkyl, phenyl, heteroaryl, cycloalkyl, or heterocycloalkyl;
$R^{1f}$ is H, lower alkyl, lower haloalkyl, phenyl, heteroaryl, cycloalkyl, or heterocycloalkyl; and
$Q^2$ is as defined herein.

In certain embodiments of formula II, $R^1$ is lower alkyl, preferably tert-butyl. In certain embodiments of formula I, the subject compounds are more specifically of formula III:

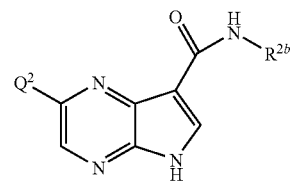

III wherein $R^{2b}$ is independently lower alkyl, phenyl, heteroaryl, cycloalkyl, heterocycloalkyl, or heterocycloalkyl alkylene, optionally substituted with one or more $R^{2c}$;
$R^{2c}$ is $R^{2d}$ or $R^{2e}$;
$R^{2d}$ is halogen, oxo, or hydroxy;
$R^{2e}$ is —N($R^{2g}$)$_2$, —C(=O)($R^{2g}$), —C(=O)O($R^{2g}$), —C(=O)N($R^{2g}$)$_2$, —N($R^{2g}$)C(=O)($R^{2g}$), —S(=O)$_2$($R^{2g}$), —S(O)$_2$ N($R^{2g}$)$_2$, lower alkyl, lower alkoxy, lower haloalkyl, phenyl, heteroaryl, heteroaryloxy, cycloalkyl, or heterocycloalkyl, optionally substituted with one or more $R^{2f}$;
each $R^{2f}$ is independently H, halogen, lower alkyl, lower alkoxy, lower haloalkyl;
each $R^{2g}$ is independently H, lower alkyl, lower alkoxy, lower haloalkyl, or phenyl; and
$Q^2$ is as defined herein.

In certain embodiments of formula III, $R^2$ is lower alkyl optionally substituted with one or more R as defined herein.

In certain embodiments of formula III, $R^2$ is lower alkyl optionally substituted with one or more $R^{2d}$ as defined herein. Preferably $R^{2d}$ is hydroxy.

In certain embodiments of either formulae I, II or III, $Q^2$ is heterocycloalkyl or heteroaryl optionally substituted with one or more $Q^{2a}$ as defined herein.

In certain embodiments of either formulae I, II or III, $Q^2$ is cycloalkyl or cycloalkenyl, preferably cycloalkyl, optionally substituted with one or more $Q^{2a}$ as defined herein.

In certain embodiments of either formulae I, II or III, $Q^2$ is piperidinyl, pyrrolidinyl, isoindolinyl, dihydroisoquinolinyle, piperazinyl, morpholinyl, tetrahydrorcarbonlinyl, imidazolinyl, indolyl, pyridinyl, pyrrolopyrazinyle, triazole, thiophenyl, furanyl, indazolyl, imidazolyl, pyrrolyl, oxazolyl, pyrazolyl, thiazolyl, benzothiophenyl, pyrrolopyridinylor pyrrolopyrazinyl, optionally substituted with one or more $Q^{2a}$ as defined herein.

In certain embodiments of either formulae I, II or III, $Q^2$ is piperidinyl, pyrrolidinyl, isoindolinyl, dihydroisoquinolinyle, piperazinyl, morpholinyl, tetrahydrorcarbonlinyl or imidazolinyl, optionally substituted with one or more $Q^{2a}$ as defined herein.

In certain embodiments of either formulae I, II or III, $Q^2$ is indolyl, pyridinyl, pyrrolopyrazinyle, triazole, thiophenyl, furanyl, indazolyl, imidazolyl, pyrrolyl, oxazolyl, pyrazolyl, thiazolyl, benzothiophenyl, pyrrolopyridinylor pyrrolopyrazinyl, optionally substituted with one or more $Q^{2a}$ as defined herein.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., R, R', or Q) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " ----- " drawn through a bond each refer to the point of attachment of a functional group or other chemical moiety to the rest of the molecule of which it is a part. Thus, for example:

MeC(═O)OR⁴ wherein R⁴ =

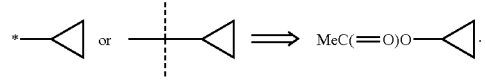

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "come together to form a bicyclic ring system" as used herein means join to form a bicyclic ring system, wherein each ring may be made up of either 4-7 carbon atoms or 4-7 carbon and heteroatoms, and may be saturated or unsaturated.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The definitions described herein may be appended to form chemically-relevant combinations, such as "heteroalkylaryl," "haloalkylheteroaryl," "arylalkylheterocyclyl," "alkylcarbonyl," "alkoxyalkyl," "cycloalkylalkyl" and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term-(ar)alkyl refers to either an unsubstituted alkyl or an aralkyl group. The term (hetero)aryl or (het)aryl refers to either an aryl or a heteroaryl group.

Compounds of formula I may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(═O)—CH-8-C(—OH)═CH—), amide/imidic acid (—C(═O)—NH-8-C(—OH)═N—) and amidine (—C(═NR)—NH-8-C(—NHR)═N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of*

*Therapeutics*, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"-, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl", "aryl alkyl", or "aralkyl" are interpreted similarly except R' is an aryl radical. The terms "heteroaryl alkyl" or "heteroarylalkyl" are interpreted similarly except R' is optionally an aryl or a heteroaryl radical.

The term "haloalkyl" as used herein denotes a unbranched or branched chain alkyl group as defined above wherein 1, 2, 3 or more hydrogen atoms are substituted by a halogen. The term "lower haloalkyl" denotes a straight or branched chain hydrocarbon residue containing 1 to 6 carbon atoms, wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined.

"$C_{1-10}$ alkoxy" as used herein refers to an —O-alkyl wherein alkyl is $C_{1-10}$.

The term "hydroxyalkyl" as used herein denotes an alkyl radical as herein defined wherein one to three hydrogen atoms on different carbon atoms is/are replaced by hydroxyl groups.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkenyl" refers to a partially unsaturated carbocyclic containing 5 to 7 carbon atoms unless otherwise specified and having a carbon-carbon double bond within the ring. For example, $C_{5-6}$ cycloalkenyl refers to a cycloalkenyl group having from 5 to 6 member atoms. In certain embodiments cycloalkenyl groups have one carbon-carbon double bond within the ring. In other embodiments, cycloalkenyl groups have more than one carbon-carbon double bond within the ring. However, cycloalkenyl rings are not aromatic. Cycloalkenyl groups may be optionally substituted with one or more substituent. Examples of cycloalkenyl include, but are not limited to, cyclopentenyl and cyclohexenyl.

The term "halogen" or "halo" as used herein means fluorine, chlorine, bromine, or iodine.

The term "heteroaryl" as used herein means a monocyclic, bicyclic, or tricyclic radical of 5 to 18 ring atoms having at least one aromatic ring containing four to eight atoms per ring, incorporating one or more N, O, or S heteroatoms, the remaining ring atoms being carbon, with the understanding that the attachment point of the heteroaryl radical will be on an aromatic ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, pyrrolyl, pyrazolyl, imidazolyl, indolyl oxazol, isoxazole, thiazole, isothiazole, triazoline, triazolyl, thiophenyl, furanyl, thiadiazole and oxadiaxoline which can optionally be substituted with one or more, preferably one or two substituents selected from hydroxy, cyano, alkyl, alkoxy, thio, lower haloalkoxy, alkylthio, halo, haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, indazolyl, isoquinolinyl, benzofuryl, benzothiophenyl, benzoxazole, benzisoxazole, benzothiazole, pyrrolopyridinyl, pyrrolopyrazinyl and benzisothiazole.

The term "heterocycloalkyl", "heterocyclyl" or "heterocycle" as used herein denotes a monovalent saturated cyclic radical, consisting of one or more rings, preferably one to two rings or three rings, of three to eight atoms per ring, incorporating one or more ring carbon atoms and one or more ring heteroatoms (chosen from N, O or $S(=O)_{0-2}$), wherein the point of attachment can be through either a carbon atom or a heteroatom, and which can optionally be independently substituted with one or more, preferably one or two or three substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, pyrrolidinyl, morpholinyl, piperazinyl, piperidinyl, isoindolinyl, dihydroisoquinolinyle, tetrahydropyranyl, tetrahydrocarbolinyl, imidazolinyl, thiomorpholinyl, quinuclidinyl and imidazolinyl.

The phrase "organ rejection" includes acute allograft or xenograft rejection and chronic allograft or xenograft rejection in the setting of vascularized and/or non-vascularized (e.g. bone marrow, pancreatic islet cells) transplants.

Commonly used abbreviations include: acetyl (Ac), azo-bis-isobutyrylnitrile (AIBN), atmospheres (Atm), 9-borabicyclo[3.3.1]nonane (9-BBN or BBN), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-carboxyanhydride (NCA), N-chlorosuccinimide (NCS), N-methylmorpholine (NMM), N-methylpyrrolidone (NMP), pyridinium chlorochromate (PCC), pyridinium dichromate (PDC), phenyl (Ph), propyl (Pr), iso-propyl (i-Pr), pounds per square inch (psi), pyridine (pyr), room temperature (rt or RT), tert-butyldimethylsilyl or t-$BuMe_2Si$ (TBDMS), triethylamine (TEA or $Et_3N$), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v. 4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts exemplified compounds according to Formula I.

TABLE I

| COMPOUND | SYSTEMATIC NAME | STRUCTURE | MP |
|---|---|---|---|
| I-1 | 1-[2-(1-Benzenesulfonyl-1H-indol-3-yl)-5H-pyrrolo[2,3-b]pyrazin-7-yl]-2,2-dimethyl-propan-1-one | 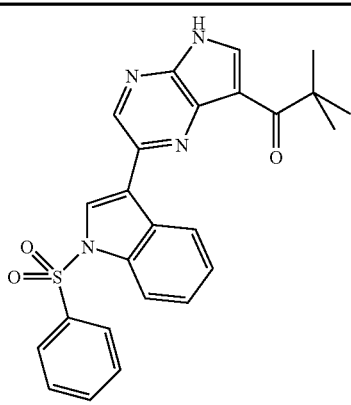 | 267.0-268.0 |

TABLE I-continued

| COMPOUND | SYSTEMATIC NAME | STRUCTURE | MP |
|---|---|---|---|
| I-2 | 1-[2-(1H-Indol-3-yl)-5H-pyrrolo[2,3-b]pyrazin-7-yl]-2,2-dimethyl-propan-1-one | 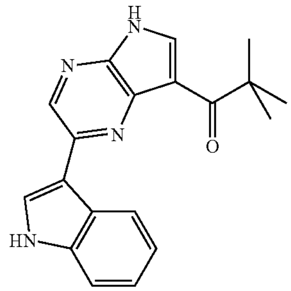 | |
| I-3 | 2-Cyclohex-1-enyl-5H-pyrrolo[2,3-b]pyrazine-7-carboxylic acid isopropylamide | 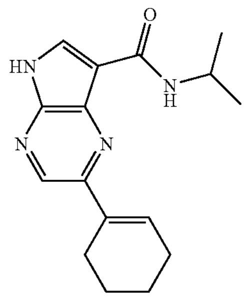 | |
| I-4 | 2-Cyclohexyl-5H-pyrrolo[2,3-b]pyrazine 7-carboxylic acid isopropylamide | 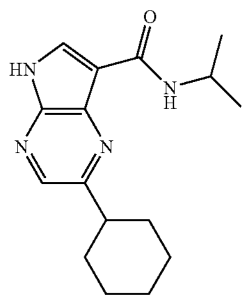 | |
| I-5 | 1-{2-[2-(4-Acetyl-piperazin-1-yl)-pyridin-4-yl]-5H-pyrrolo[2,3-b]pyrazin-7-yl}-2,2-dimethyl-propan-1-one | 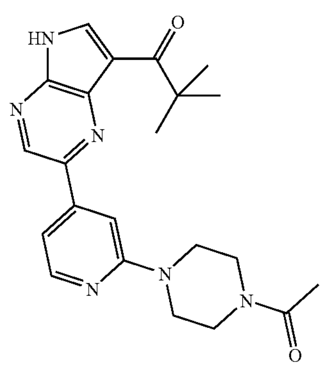 | 257.0-260.0 |
| I-6 | 1-[2-(5-Methoxy-pyridin-3-yl)-5H-pyrrolo[2,3-b]pyrazin-7-yl]-2,2-dimethyl-propan-1-one | 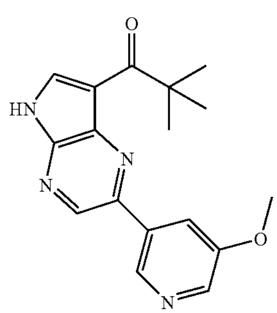 | 215-223.6 |

TABLE I-continued

| COMPOUND | SYSTEMATIC NAME | STRUCTURE | MP |
|---|---|---|---|
| I-7 | [1-(7-Isopropylcarbamoyl-5H-pyrrolo[2,3-b]pyrazin-2-yl)-piperidin-3-yl]-methyl-carbamic acid tert-butyl ester | 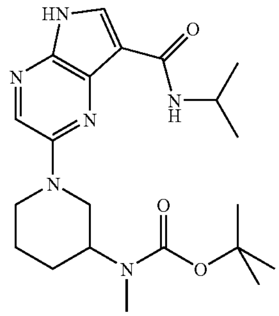 | 251-252 |
| I-8 | 2-(3-Methylamino-piperidin-1-yl)-5H-pyrrolo[2,3-b]pyrazine-7-carboxylic acid isopropylamide; compound with trifluoro-acetic acid | 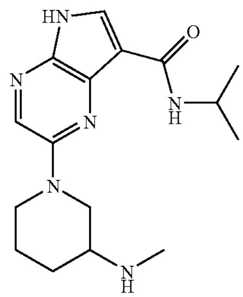 | 54-64 |
| I-9 | 2,2-Dimethyl-1-(2-pyrrolidin-1-yl-5H-pyrrolo[2,3-b]pyrazin-7-yl)-propan-1-one | 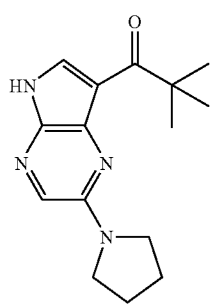 | |
| I-10 | 1-[7-(2,2-Dimethyl-propionyl)-2'-pyrrolidin-1-yl-5H-[2,5']bi[pyrrolo[2,3-b]pyrazinyl]-7'-yl]-2,2-dimethyl-propan-1-one | 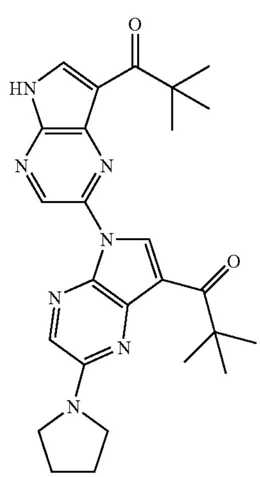 | |

TABLE I-continued

| COMPOUND | SYSTEMATIC NAME | STRUCTURE | MP |
| --- | --- | --- | --- |
| I-11 | 2,2-Dimethyl-1-[2-(2-pyrrolidin-1-yl-pyridin-4-yl)-5H-pyrrolo[2,3-b]pyrazin-7-yl]-propan-1-one | 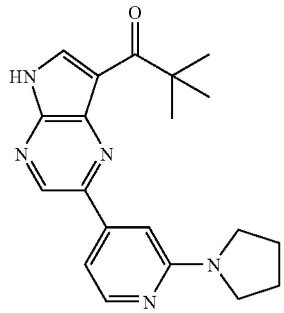 | 275.1-276.4 |
| I-12 | 1-[2-(1-Cyclopentyl-1H-[1,2,3]triazol-4-yl)-5H-pyrrolo[2,3-b]pyrazin-7-yl]-2,2-dimethyl-propan-1-one | 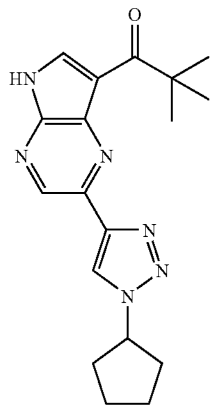 | 193.3-199.3 |
| I-13 | 2,2-Dimethyl-1-[2-(3,4,5,6-tetrahydro-2H-[1,2']bipyridinyl-4'-yl)-5H-pyrrolo[2,3-b]pyrazin-7-yl]-propan-1-one | 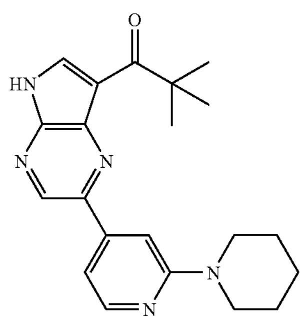 | 250.0-251.0 |
| I-14 | 1-{2-[2-(3-Dimethylamino-pyrrolidin-1-yl)-pyridin-4-yl]-5H-pyrrolo[2,3-b]pyrazin-7-yl}-2,2-dimethyl-propan-1-one | 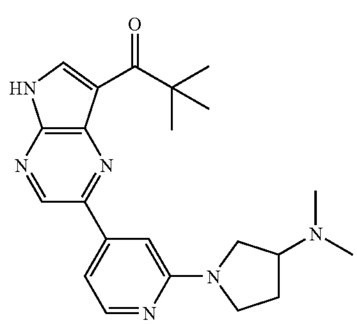 | 226.0-228.0 |

TABLE I-continued
| COMPOUND | SYSTEMATIC NAME | STRUCTURE | MP |
|---|---|---|---|
| I-15 | 2,2-Dimethyl-1-[2-(2-thiomorpholin-4-yl-pyridin-4-yl)-5H-pyrrolo[2,3-b]pyrazin-7-yl]-propan-1-one | 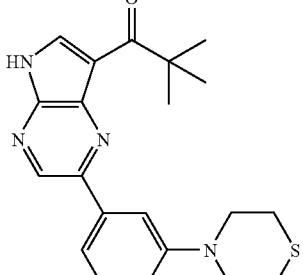 | 287.0-290.0 |
| I-16 | 2,2-Dimethyl-1-{2-[2-(2-methyl-pyrrolidin-1-yl)-pyridin-4-yl]-5H-pyrrolo[2,3-b]pyrazin-7-yl}-propan-1-one | 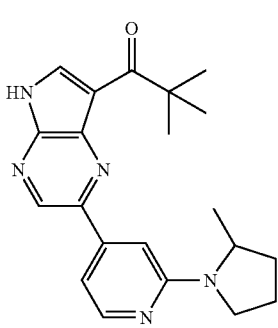 | 220.0-221.0 |
| I-17 | 1-[2-(1,3-Dihydro-isoindol-2-yl)-5H-pyrrolo[2,3-b]pyrazin-7-yl]-2,2-dimethyl-propan-1-one | 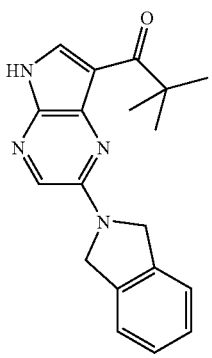 | |
| I-18 | 1-[2-(2,3-Dihydro-indol-1-yl)-5H-pyrrolo[2,3-b]pyrazin-7-yl]-2,2-dimethyl-propan-1-one | 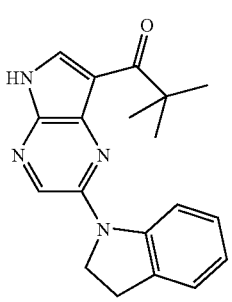 | |

TABLE I-continued
| COMPOUND | SYSTEMATIC NAME | STRUCTURE | MP |
|---|---|---|---|
| I-19 | 2-[7-(2,2-Dimethyl-propionyl)-5H-pyrrolo[2,3-b]pyrazin-2-yl]-3,4-dihydro-2H-isoquinolin-1-one | 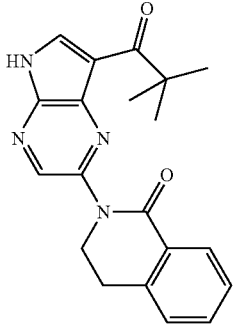 | |
| I-20 | 1-[7-(2,2-Dimethyl-propionyl)-5H-pyrrolo[2,3-b]pyrazin-2-yl]-3,4-dihydro-1H-quinolin-2-one | 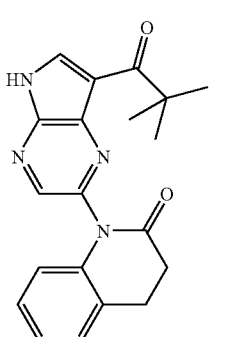 | |
| I-21 | 2-[7-(2,2-Dimethyl-propionyl)-5H-pyrrolo[2,3-b]pyrazin-2-yl]-2,3-dihydro-isoindol-1-one | 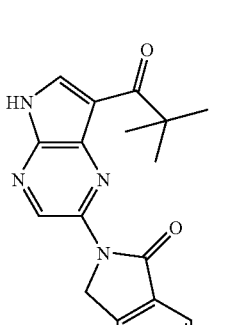 | |
| I-22 | 1-[7-(2,2-Dimethyl-propionyl)-5H-pyrrolo[2,3-b]pyrazin-2-yl]-piperidin-2-one | 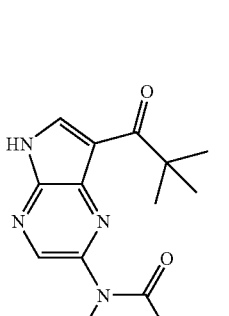 | |

TABLE I-continued

| COMPOUND | SYSTEMATIC NAME | STRUCTURE | MP |
|---|---|---|---|
| I-23 | 1-[7-(2,2-Dimethyl-propionyl)-5H-pyrrolo[2,3-b]pyrazin-2-yl]-pyrrolidin-2-one | 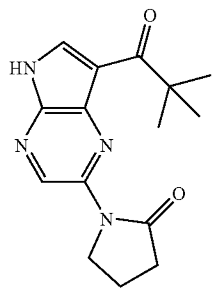 | |
| I-24 | 1-[2-(1H-Indol-3-yl)-5H-pyrrolo[2,3-b]pyrazin-7-yl]-2,2-dimethyl-propan-1-one | 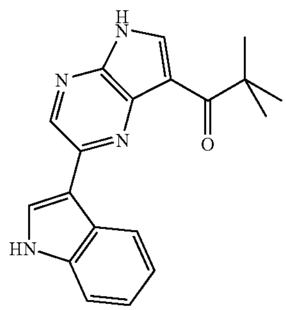 | |
| I-25 | 2,2-Dimethyl-1-[2-(6-pyrrolidin-1-yl-pyridin-2-yl)-5H-pyrrolo[2,3-b]pyrazin-7-yl]-propan-1-one | 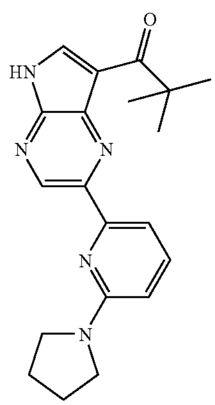 | |
| I-26 | 2,2-Dimethyl-1-[2-(4-pyrrolidin-1-yl-pyridin-2-yl)-5H-pyrrolo[2,3-b]pyrazin-7-yl]-propan-1-one | 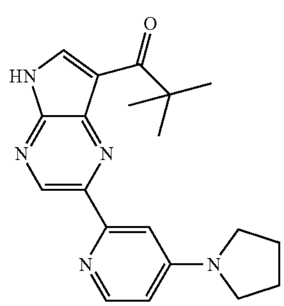 | |
| I-27 | 2,2-Dimethyl-1-(2-pyridin-2-yl-5H-pyrrolo[2,3-b]pyrazin-7-yl)-propan-1-one | 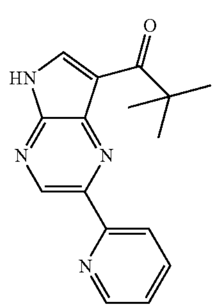 | |

TABLE I-continued

| COMPOUND | SYSTEMATIC NAME | STRUCTURE | MP |
|---|---|---|---|
| I-28 | [1-(7-Isopropylcarbamoyl-5H-pyrrolo[2,3-b]pyrazin-2-yl)-piperidin-3-yl]-methyl-carbamic acid tert-butyl ester | 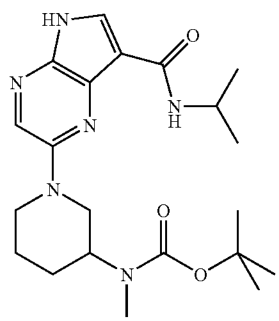 | |
| I-29 | 2-(3-Methylamino-piperidin-1-yl)-5H-pyrrolo[2,3-b]pyrazine-7-carboxylic acid isopropylamide; compound with trifluoro-acetic acid | 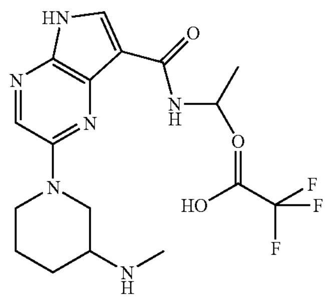 | |
| I-30 | 5-[7-(2,2-Dimethyl-propionyl)-5H-pyrrolo[2,3-b]pyrazin-2-yl]-thiophene-3-carboxylic acid (tetrahydro-pyran-4-yl)-amide | 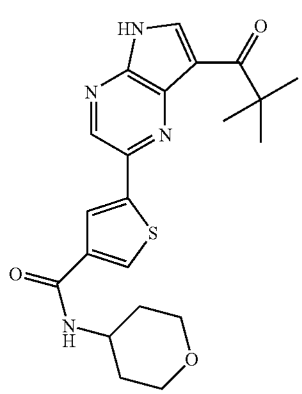 | |
| I-31 | 5-[7-(2,2-Dimethyl-propionyl)-5H-pyrrolo[2,3-b]pyrazin-2-yl]-thiophene-2-carboxylic acid cyclopentylamide | 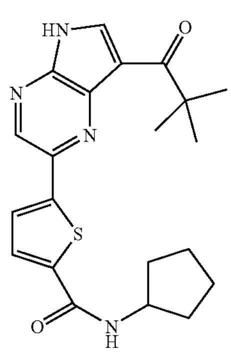 | |

TABLE I-continued

| COMPOUND | SYSTEMATIC NAME | STRUCTURE | MP |
|---|---|---|---|
| I-32 | 5-[7-(2,2-Dimethyl-propionyl)-5H-pyrrolo[2,3-b]pyrazin-2-yl]-thiophene-2-carboxylic acid (tetrahydro-pyran-4-yl)-amide | 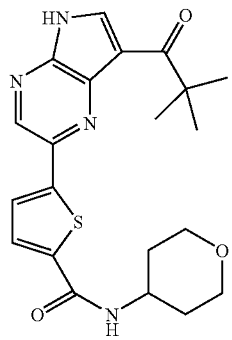 | |
| I-33 | 1-(2-Cyclopropyl-5H-pyrrolo[2,3-b]pyrazin-7-yl)-2,2-dimethyl-propan-1-one | 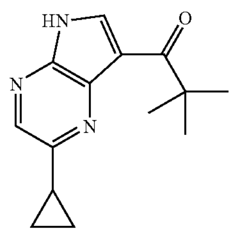 | |
| I-34 | 5-[7-(2,2-Dimethyl-propionyl)-5H-pyrrolo[2,3-b]pyrazin-2-yl]-thiophene-3-carboxylic acid | 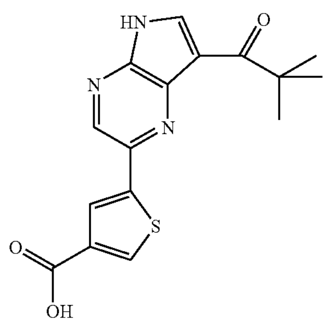 | |
| I-35 | 5-[7-(2,2-Dimethyl-propionyl)-5H-pyrrolo[2,3-b]pyrazin-2-yl]-thiophene-3-carboxylic acid (2-dimethylamino-ethyl)-amide | 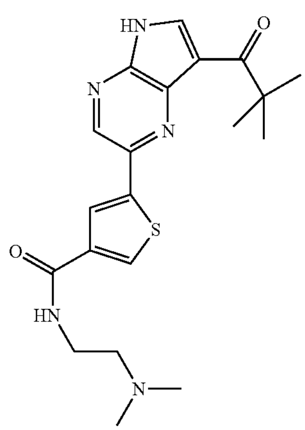 | |
| I-36 | 1-{2-[2-(3-Methoxy-phenyl)-cyclopent-1-enyl]-5H-pyrrolo[2,3-b]pyrazin-7-yl}-2,2-dimethyl-propan-1-one | 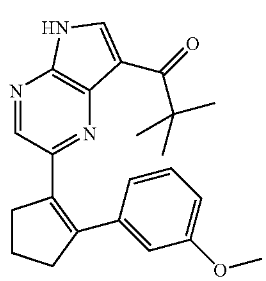 | |

TABLE I-continued

| COMPOUND | SYSTEMATIC NAME | STRUCTURE | MP |
|---|---|---|---|
| I-37 | 6-{2-[7-(2,2-Dimethyl-propionyl)-5H-pyrrolo[2,3-b]pyrazin-2-yl]-cyclopent-1-enyl}-pyridine-2-carboxylic acid ethyl ester | 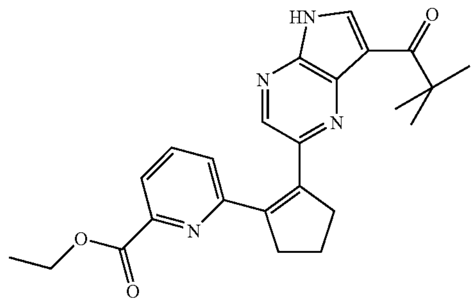 | |
| I-38 | 2,2-Dimethyl-1-[2-(2-phenyl-cyclopent-1-enyl)-5H-pyrrolo[2,3-b]pyrazin-7-yl]-propan-1-one | 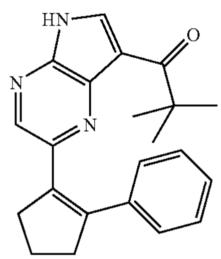 | |
| I-39 | 5-{2-[7-(2,2-Dimethyl-propionyl)-5H-pyrrolo[2,3-b]pyrazin-2-yl]-cyclopent-1-enyl}-1H-indole-2-carboxylic acid ethyl ester | 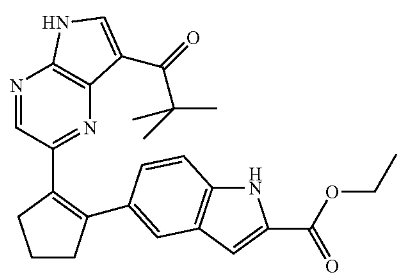 | |
| I-40 | 4-[7-(1-Methyl-cyclohexanecarbonyl)-5H-pyrrolo[2,3-b]pyrazin-2-yl]-thiophene-2-carboxylic acid cyanomethyl-methyl-amide | 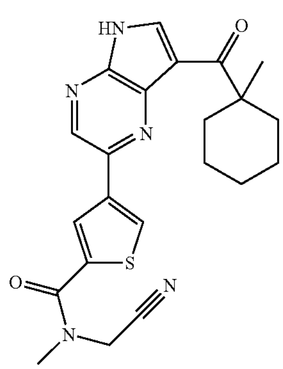 | |

TABLE I-continued

| COMPOUND | SYSTEMATIC NAME | STRUCTURE | MP |
|---|---|---|---|
| I-41 | (1-Methyl-cyclohexyl)-{2-[5-(morpholine-4-carbonyl)-thiophen-3-yl]-5H-pyrrolo[2,3-b]pyrazin-7-yl}-methanone | 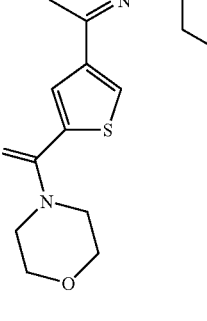 | |
| I-42 | 1-(2-Furan-3-yl-5H-pyrrolo[2,3-b]pyrazin-7-yl)-2,2-dimethyl-propan-1-one | 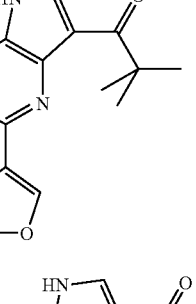 | |
| I-43 | 4-[7-(1-Methyl-cyclohexanecarbonyl)-5H-pyrrolo[2,3-b]pyrazin-2-yl]-thiophene-2-carboxylic acid (1-ethyl-propyl)-amide | 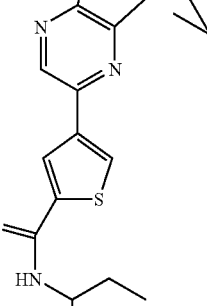 | |
| I-44 | {2-[5-(4-Hydroxy-4-methyl-piperidine-1-carbonyl)-thiophen-3-yl]-5H-pyrrolo[2,3-b]pyrazin-7-yl}-(1-methyl-cyclohexyl)-methanone | 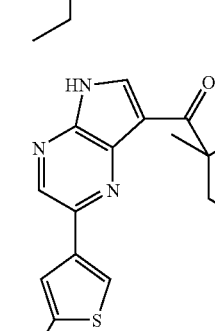 | |

TABLE I-continued

| COMPOUND | SYSTEMATIC NAME | STRUCTURE | MP |
|---|---|---|---|
| I-45 | 2,2-Dimethyl-1-[2-(2-pyrrolidin-1-yl-pyridin-4-yl)-5H-pyrrolo[2,3-b]pyrazin-7-yl]-propan-1-one | 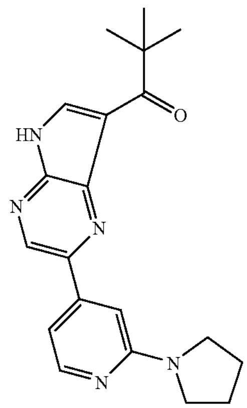 | |
| I-46 | 2,2-Dimethyl-1-[2-(3,4,5,6-tetrahydro-2H-[1,2']bipyridinyl-4'-yl)-5H-pyrrolo[2,3-b]pyrazin-7-yl]-propan-1-one | 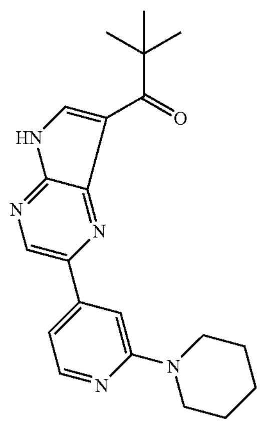 | |
| I-47 | 1-{2-[2-(3-Dimethylamino-pyrrolidin-1-yl)-pyridin-4-yl]-5H-pyrrolo[2,3-b]pyrazin-7-yl}-2,2-dimethyl-propan-1-one | 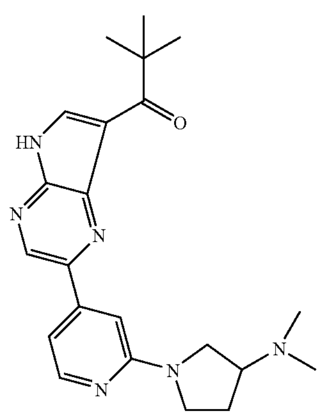 | |
| I-48 | 2,2-Dimethyl-1-[2-(2-thiomorpholin-4-yl-pyridin-4-yl)-5H-pyrrolo[2,3-b]pyrazin-7-yl]-propan-1-one | 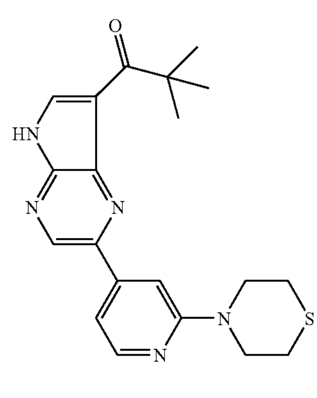 | |

TABLE I-continued

| COMPOUND | SYSTEMATIC NAME | STRUCTURE | MP |
|---|---|---|---|
| I-49 | 2,2-Dimethyl-1-{2-[2-(2-methyl-pyrrolidin-1-yl)-pyridin-4-yl]-5H-pyrrolo[2,3-b]pyrazin-7-yl}-propan-1-one | 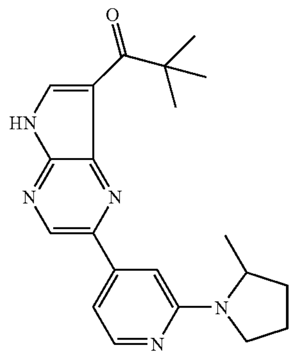 | |
| I-50 | 1-{2-[2-(3-Hydroxy-pyrrolidin-1-yl)-pyridin-4-yl]-5H-pyrrolo[2,3-b]pyrazin-7-yl}-2,2-dimethyl-propan-1-one | 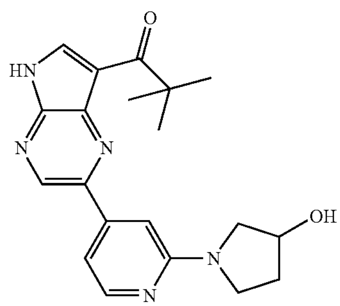 | |
| I-51 | 1-{2-[2-(3,3-Difluoro-pyrrolidin-1-yl)-pyridin-4-yl]-5H-pyrrolo[2,3-b]pyrazin-7-yl}-2,2-dimethyl-propan-1-one | 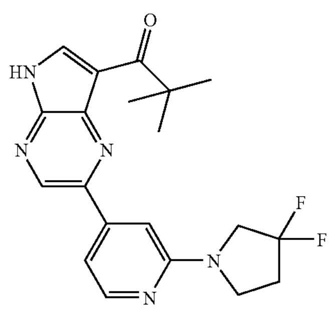 | |
| I-52 | 1-[2-(2-Azepan-1-yl-pyridin-4-yl)-5H-pyrrolo[2,3-b]pyrazin-7-yl]-2,2-dimethyl-propan-1-one | 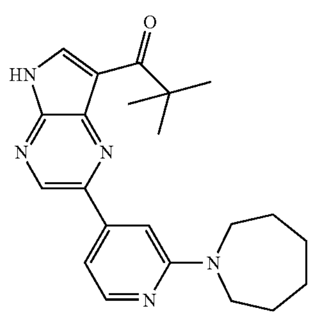 | |
| I-53 | 1-{2-[2-((S)-3-Fluoro-pyrrolidin-1-yl)-pyridin-4-yl]-5H-pyrrolo[2,3-b]pyrazin-7-yl}-2,2-dimethyl-propan-1-one | Chiral | |

TABLE I-continued

| COMPOUND | SYSTEMATIC NAME | STRUCTURE | MP |
|---|---|---|---|
| I-54 | 1-{2-[2-((R)-3-Fluoro-pyrrolidin-1-yl)-pyridin-4-yl]-5H-pyrrolo[2,3-b]pyrazin-7-yl}-2,2-dimethyl-propan-1-one | 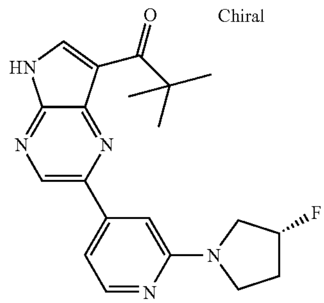 | |
| I-55 | 1-{2-[2-(1,1-Dioxo-1$\lambda^6$-thiomorpholin-4-yl)-pyridin-4-yl]-5H-pyrrolo[2,3-b]pyrazin-7-yl}-2,2-dimethyl-propan-1-one | 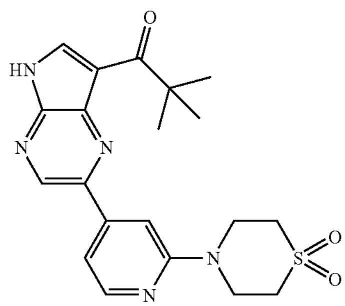 | |
| I-56 | 1-[2-(2-Chloro-pyridin-4-yl)-5H-pyrrolo[2,3-b]pyrazin-7-yl]-2,2-dimethyl-propan-1-one | 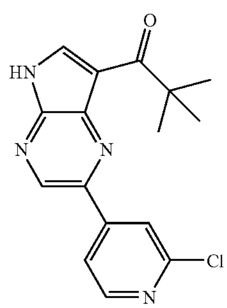 | |
| I-57 | 2,2-Dimethyl-1-{2-[2-(1-oxo-1$\lambda^4$-thiomorpholin-4-yl)-pyridin-4-yl]-5H-pyrrolo[2,3-b]pyrazin-7-yl}-propan-1-one | 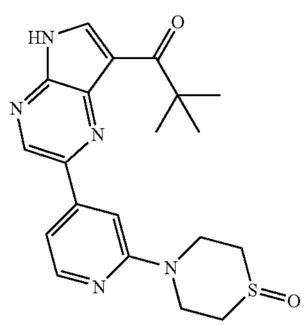 | |
| I-58 | 1-[2-(2-Cyclopent-1-enyl-pyridin-4-yl)-5H-pyrrolo[2,3-b]pyrazin-7-yl]-2,2-dimethyl-propan-1-one | 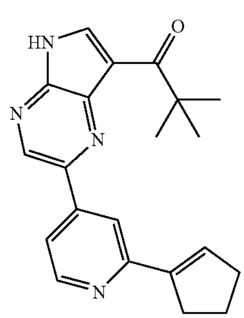 | |

TABLE I-continued

| COMPOUND | SYSTEMATIC NAME | STRUCTURE | MP |
|---|---|---|---|
| I-59 | (1-Methyl-cyclohexyl)-[2-(2-pyrrolidin-1-yl-pyridin-4-yl)-5H-pyrrolo[2,3-b]pyrazin-7-yl]-methanone | 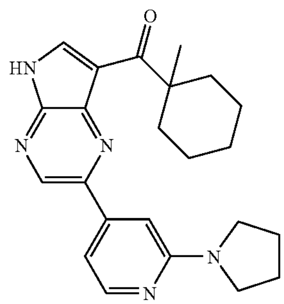 | |
| I-60 | 1-[2-(4-Hydroxy-3,4,5,6-tetrahydro-2H-[1,2']bipyridinyl-4'-yl)-5H-pyrrolo[2,3-b]pyrazin-7-yl]-2,2-dimethyl-propan-1-one | 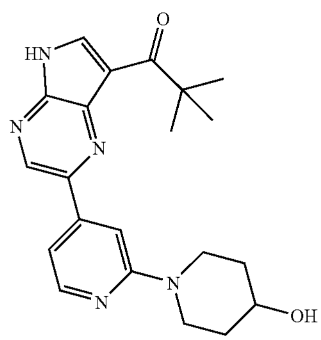 | |
| I-61 | 5-[7-(1-Methyl-cyclohexanecarbonyl)-5H-pyrrolo[2,3-b]pyrazin-2-yl]-thiophene-2-carboxylic acid (1-ethyl-propyl)-amide | 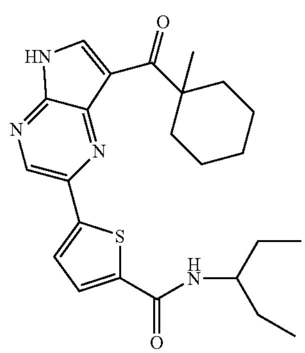 | |
| I-62 | {2-[5-(3,3-Difluoro-azetidine-1-carbonyl)-thiophen-2-yl]-5H-pyrrolo[2,3-b]pyrazin-7-yl}-(1-methyl-cyclohexyl)-methanone | 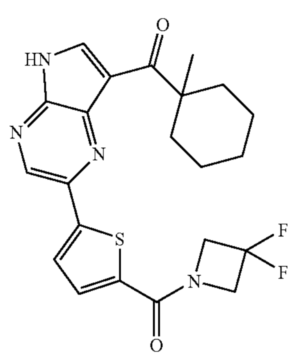 | |

TABLE I-continued

| COMPOUND | SYSTEMATIC NAME | STRUCTURE | MP |
|---|---|---|---|
| I-63 | {2-[5-(4-Hydroxy-piperidine-1-carbonyl)-thiophen-2-yl]-5H-pyrrolo[2,3-b]pyrazin-7-yl}-(1-methyl-cyclohexyl)-methanone | 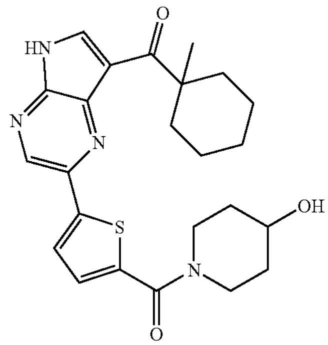 | |
| I-64 | (1-Methyl-cyclohexyl)-{2-[2-(1-oxo-1$\lambda^4$-thiomorpholin-4-yl)-pyridin-4-yl]-5H-pyrrolo[2,3-b]pyrazin-7-yl}-methanone | 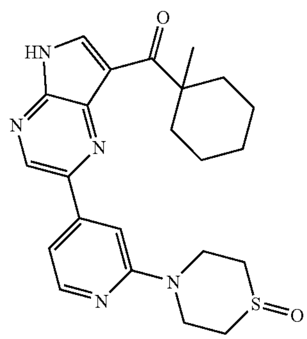 | |
| I-65 | {2-[5-(Azetidine-1-carbonyl)-thiophen-2-yl]-5H-pyrrolo[2,3-b]pyrazin-7-yl}-(1-methyl-cyclohexyl)-methanone | 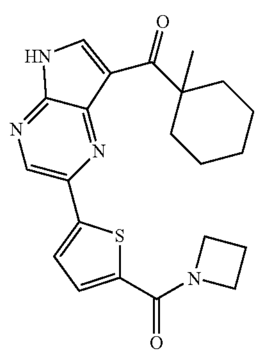 | |
| I-66 | {2-[5-(3-Hydroxy-azetidine-1-carbonyl)-thiophen-2-yl]-5H-pyrrolo[2,3-b]pyrazin-7-yl}-(1-methyl-cyclohexyl)-methanone | 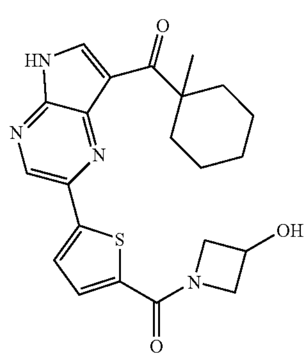 | |

TABLE I-continued

| COMPOUND | SYSTEMATIC NAME | STRUCTURE | MP |
|---|---|---|---|
| I-67 | 1-{2-[2-((1S,5R,6R)-6-Hydroxymethyl-3-aza-bicyclo[3.1.0]hex-3-yl)-pyridin-4-yl]-5H-pyrrolo[2,3-b]pyrazin-7-yl}-2,2-dimethyl-propan-1-one | 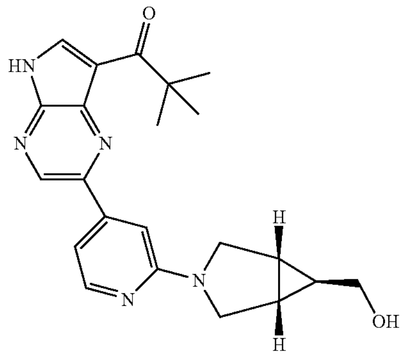 | |
| I-68 | (1-Methyl-cyclohexyl)-{2-[5-(morpholine-4-carbonyl)-thiophen-2-yl]-5H-pyrrolo[2,3-b]pyrazin-7-yl}-methanone | 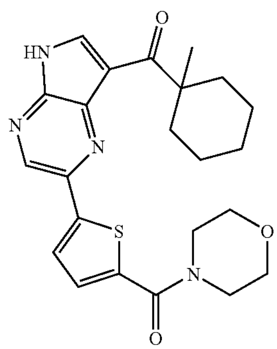 | |
| I-69 | 5-[7-(1-Methyl-cyclohexanecarbonyl)-5H-pyrrolo[2,3-b]pyrazin-2-yl]-thiophene-2-carboxylic acid diethylamide | 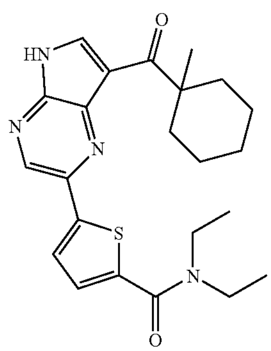 | |
| I-70 | 5-[7-(1-Methyl-cyclohexanecarbonyl)-5H-pyrrolo[2,3-b]pyrazin-2-yl]-thiophene-2-carboxylic acid cyclopentyl-methyl-amide | 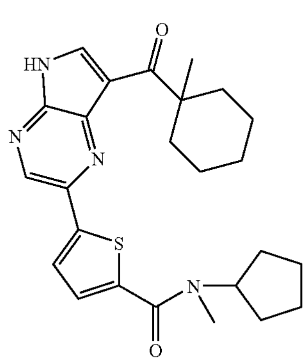 | |

TABLE I-continued

| COMPOUND | SYSTEMATIC NAME | STRUCTURE | MP |
|---|---|---|---|
| I-71 | {2-[5-(4-Hydroxy-4-methyl-piperidine-1-carbonyl)-thiophen-2-yl]-5H-pyrrolo[2,3-b]pyrazin-7-yl}-(1-methyl-cyclohexyl)-methanone | 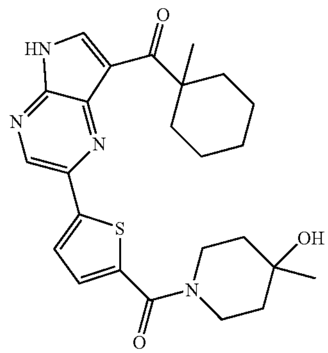 | |
| I-72 | 5-[7-(1-Methyl-cyclohexanecarbonyl)-5H-pyrrolo[2,3-b]pyrazin-2-yl]-thiophene-2-carboxylic acid bis-(2-hydroxy-ethyl)-amide | 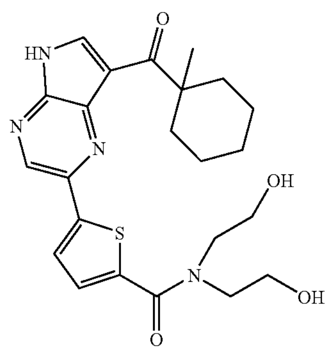 | |
| I-73 | 5-[7-(1-Methyl-cyclohexanecarbonyl)-5H-pyrrolo[2,3-b]pyrazin-2-yl]-thiophene-2-carboxylic acid (2-hydroxy-ethyl)-methyl-amide | 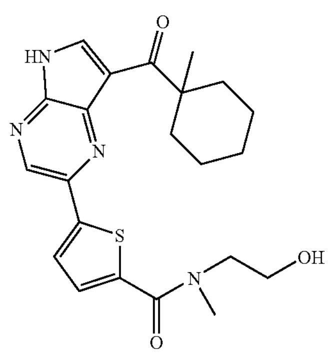 | |
| I-74 | {2-[5-(3-Hydroxy-pyrrolidine-1-carbonyl)-thiophen-2-yl]-5H-pyrrolo[2,3-b]pyrazin-7-yl}-(1-methyl-cyclohexyl)-methanone | 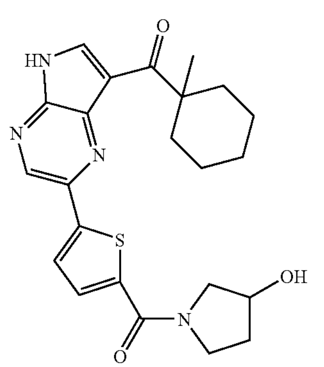 | |

TABLE I-continued

| COMPOUND | SYSTEMATIC NAME | STRUCTURE | MP |
|---|---|---|---|
| I-75 | 5-[7-(2,2-Dimethyl-propionyl)-5H-pyrrolo[2,3-b]pyrazin-2-yl]-thiophene-2-carboxylic acid cyanomethyl-methyl-amide | 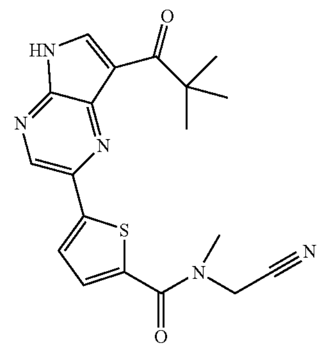 | |
| I-76 | 5-[7-(2,2-Dimethyl-propionyl)-5H-pyrrolo[2,3-b]pyrazin-2-yl]-thiophene-2-carboxylic acid bis-(2-hydroxy-ethyl)-amide | 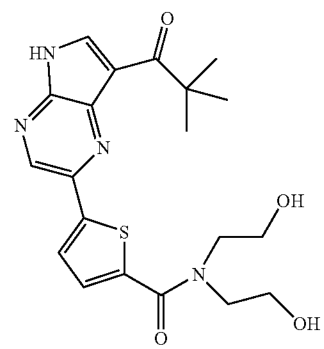 | |
| I-77 | 1-{2-[5-(4-Hydroxy-4-methyl-piperidine-1-carbonyl)-thiophen-2-yl]-5H-pyrrolo[2,3-b]pyrazin-7-yl}-2,2-dimethyl-propan-1-one | 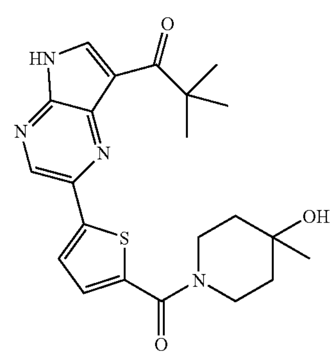 | |
| I-78 | 1-{2-[5-(Azetidine-1-carbonyl)-thiophen-2-yl]-5H-pyrrolo[2,3-b]pyrazin-7-yl}-2,2-dimethyl-propan-1-one | 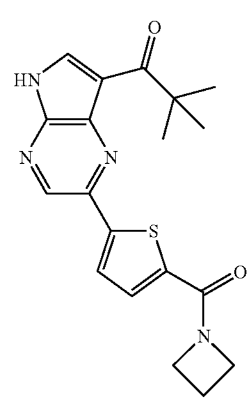 | |

TABLE I-continued

| COMPOUND | SYSTEMATIC NAME | STRUCTURE | MP |
|---|---|---|---|
| I-79 | 2,2-Dimethyl-1-{2-[5-(pyrrolidine-1-carbonyl)-thiophen-2-yl]-5H-pyrrolo[2,3-b]pyrazin-7-yl}-propan-1-one | 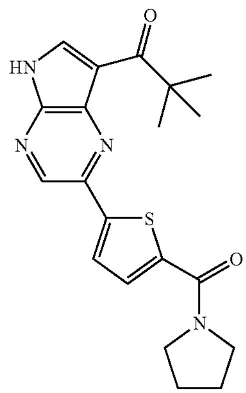 | |
| I-80 | 2,2-Dimethyl-1-{2-[5-(piperidine-1-carbonyl)-thiophen-2-yl]-5H-pyrrolo[2,3-b]pyrazin-7-yl}-propan-1-one | 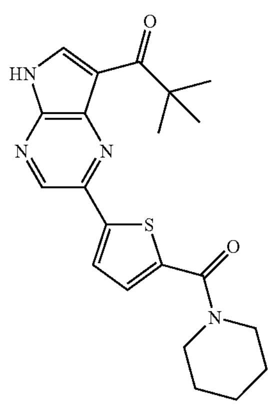 | |
| I-81 | 3-Dimethylamino-1-{5-[7-(2,2-dimethyl-propionyl)-5H-pyrrolo[2,3-b]pyrazin-2-yl]-thiophene-2-carbonyl}-azetidine-3-carbonitrile | 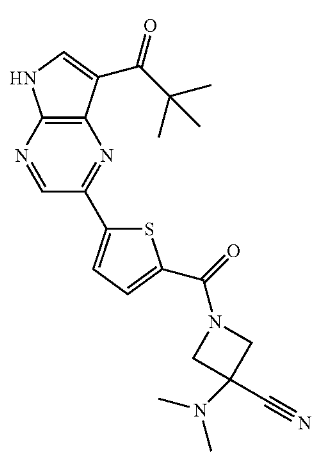 | |

TABLE I-continued

| COMPOUND | SYSTEMATIC NAME | STRUCTURE | MP |
|---|---|---|---|
| I-82 | 1-{2-[5-(4-Hydroxy-piperidine-1-carbonyl)-thiophen-2-yl]-5H-pyrrolo[2,3-b]pyrazin-7-yl}-2,2-dimethyl-propan-1-one | 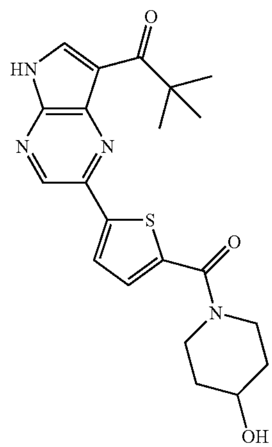 | |
| I-83 | 1-{2-[4-(Azetidine-1-carbonyl)-thiophen-2-yl]-5H-pyrrolo[2,3-b]pyrazin-7-yl}-2,2-dimethyl-propan-1-one | 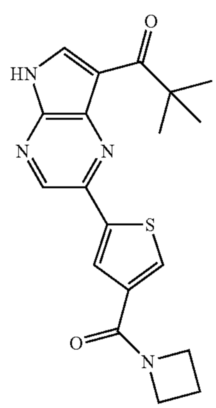 | |
| I-84 | 2,2-Dimethyl-1-{2-[4-(pyrrolidine-1-carbonyl)-thiophen-2-yl]-5H-pyrrolo[2,3-b]pyrazin-7-yl}-propan-1-one | 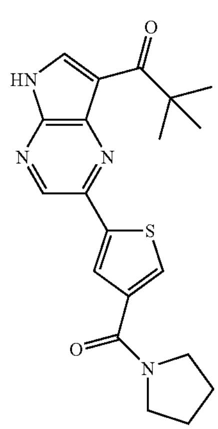 | |

TABLE I-continued

| COMPOUND | SYSTEMATIC NAME | STRUCTURE | MP |
|---|---|---|---|
| I-85 | 2,2-Dimethyl-1-{2-[4-(piperidine-1-carbonyl)-thiophen-2-yl]-5H-pyrrolo[2,3-b]pyrazin-7-yl}-propan-1-one | 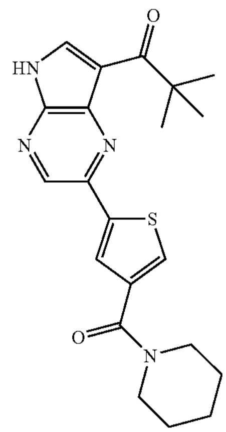 | |
| I-86 | (1-Methyl-cyclohexyl)-{2-[5-(4-methyl-piperazine-1-carbonyl)-thiophen-2-yl]-5H-pyrrolo[2,3-b]pyrazin-7-yl}-methanone | 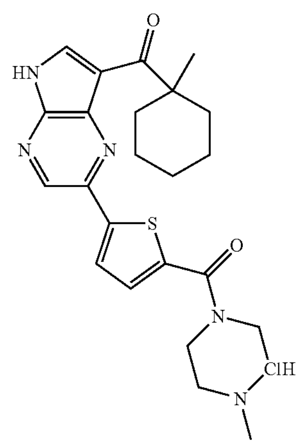 | |
| I-87 | {2-[5-(4-Dimethylamino-piperidine-1-carbonyl)-thiophen-2-yl]-5H-pyrrolo[2,3-b]pyrazin-7-yl}-(1-methyl-cyclohexyl)-methanone | 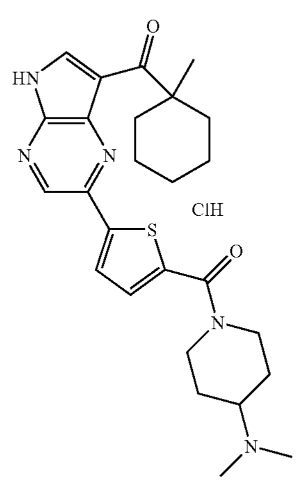 | |

TABLE I-continued

| COMPOUND | SYSTEMATIC NAME | STRUCTURE | MP |
|---|---|---|---|
| I-88 | 1-(2-Cyclopent-1-enyl-5H-pyrrolo[2,3-b]pyrazin-7-yl)-2,2-dimethyl-propan-1-one | 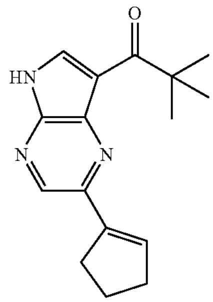 | |
| I-89 | 2,2-Dimethyl-1-(2-pyrrolidin-1-yl-5H-pyrrolo[2,3-b]pyrazin-7-yl)-propan-1-one | 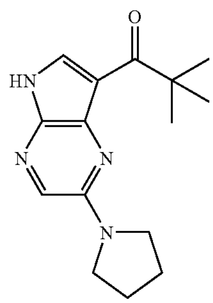 | |
| I-90 | 1-[7-(2,2-Dimethyl-propionyl)-2'-pyrrolidin-1-yl-5H-[2,5']bi[pyrrolo[2,3-b]pyrazinyl]-7'-yl]-2,2-dimethyl-propan-1-one | 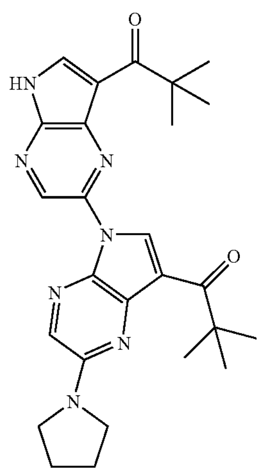 | |
| I-91 | N-{1-[7-(2,2-Dimethyl-propionyl)-5H-pyrrolo[2,3-b]pyrazin-2-yl]-pyrrolidin-3-yl}-acetamide | 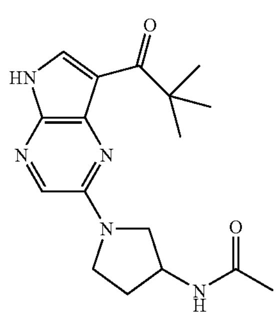 | |

TABLE I-continued

| COMPOUND | SYSTEMATIC NAME | STRUCTURE | MP |
|---|---|---|---|
| I-92 | 2,2-Dimethyl-1-[2-(2-methyl-pyrrolidin-1-yl)-5H-pyrrolo[2,3-b]pyrazin-7-yl]-propan-1-one | 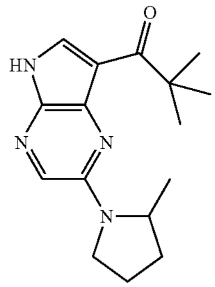 | |
| I-93 | 1-[2-(4-Acetyl-piperazin-1-yl)-5H-pyrrolo[2,3-b]pyrazin-7-yl]-2,2-dimethyl-propan-1-one | 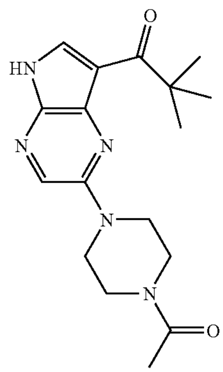 | |
| I-94 | 2,2-Dimethyl-1-(2-morpholin-4-yl-5H-pyrrolo[2,3-b]pyrazin-7-yl)-propan-1-one | 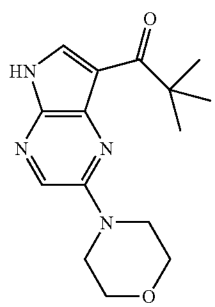 | |
| I-95 | 1-[2-(5-Fluoro-indol-1-yl)-5H-pyrrolo[2,3-b]pyrazin-7-yl]-2,2-dimethyl-propan-1-one | 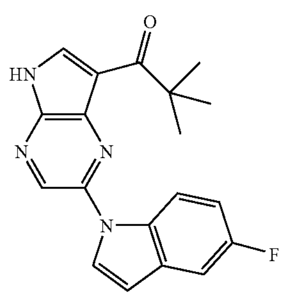 | |
| I-96 | 1-[2-(5-Methoxy-indol-1-yl)-5H-pyrrolo[2,3-b]pyrazin-7-yl]-2,2-dimethyl-propan-1-one | 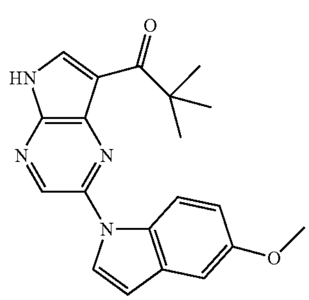 | |

TABLE I-continued

| COMPOUND | SYSTEMATIC NAME | STRUCTURE | MP |
|---|---|---|---|
| I-97 | 1-(2-Indol-1-yl-5H-pyrrolo[2,3-b]pyrazin-7-yl)-2,2-dimethyl-propan-1-one | 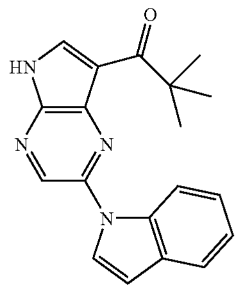 | |
| I-98 | 1-(2-Indazol-1-yl-5H-pyrrolo[2,3-b]pyrazin-7-yl)-2,2-dimethyl-propan-1-one | 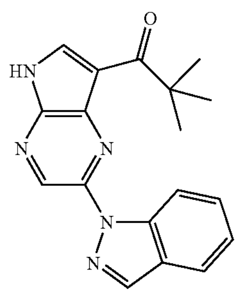 | |
| I-99 | 1-[2-(3,4-Dihydro-1H-isoquinolin-2-yl)-5H-pyrrolo[2,3-b]pyrazin-7-yl]-2,2-dimethyl-propan-1-one | 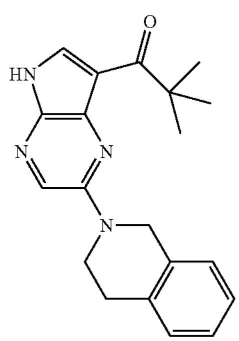 | |
| I-100 | 2,2-Dimethyl-1-[2-(1,3,4,9-tetrahydro-β-carbolin-2-yl)-5H-pyrrolo[2,3-b]pyrazin-7-yl]-propan-1-one | 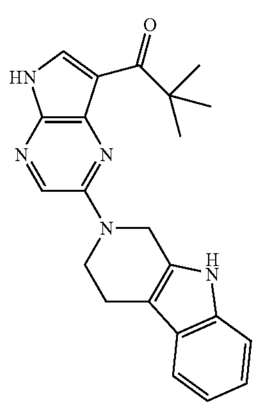 | |

TABLE I-continued

| COMPOUND | SYSTEMATIC NAME | STRUCTURE | MP |
|---|---|---|---|
| I-101 | 2-{1-[7-(2,2-Dimethyl-propionyl)-5H-pyrrolo[2,3-b]pyrazin-2-yl]-1H-indol-3-yl}-acetamide | 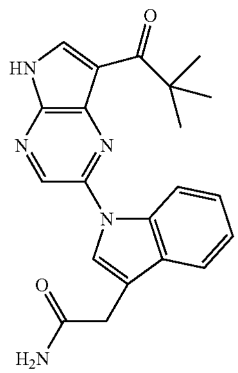 | |
| I-102 | 2,2-Dimethyl-1-[2-(1,3,4,5-tetrahydro-pyrido[4,3-b]indol-2-yl)-5H-pyrrolo[2,3-b]pyrazin-7-yl]-propan-1-one | 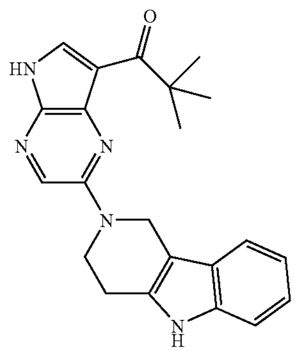 | |
| I-103 | 2,2-Dimethyl-1-[2-(3-phenyl-pyrrolidin-1-yl)-5H-pyrrolo[2,3-b]pyrazin-7-yl]-propan-1-one | 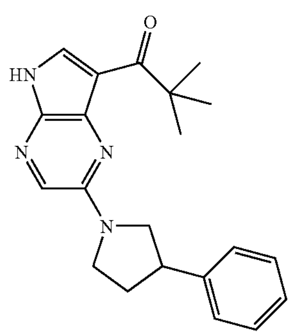 | |
| I-104 | 1-[2-(2-Benzyl-pyrrolidin-1-yl)-5H-pyrrolo[2,3-b]pyrazin-7-yl]-2,2-dimethyl-propan-1-one | 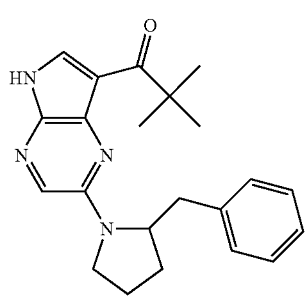 | |
| I-105 | 1-[2-(1-Benzyl-1H-[1,2,3]triazol-4-yl)-5H-pyrrolo[2,3-b]pyrazin-7-yl]-2,2-dimethyl-propan-1-one | 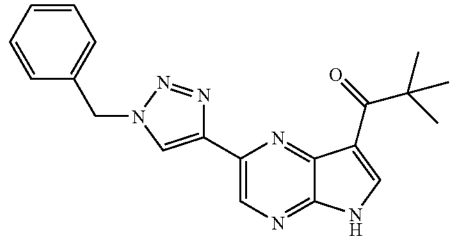 | |

TABLE I-continued

| COMPOUND | SYSTEMATIC NAME | STRUCTURE | MP |
|---|---|---|---|
| I-106 | (1-Methyl-cyclohexyl)-(2-thiophen-2-yl-5H-pyrrolo[2,3-b]pyrazin-7-yl)-methanone | 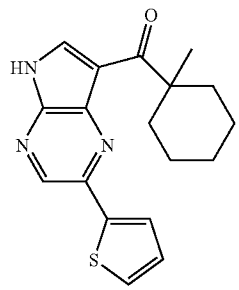 | |
| I-107 | 1-(2-Imidazol-1-yl-5H-pyrrolo[2,3-b]pyrazin-7-yl)-2,2-dimethyl-propan-1-one | 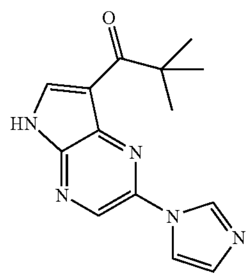 | |
| I-108 | 2,2-Dimethyl-1-[2-(2-methyl-imidazol-1-yl)-5H-pyrrolo[2,3-b]pyrazin-7-yl]-propan-1-one | 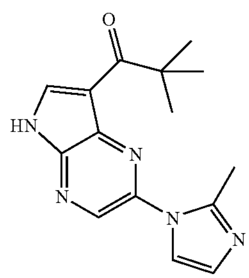 | |
| I-109 | 2,2-Dimethyl-1-[2-(2-methyl-4,5-dihydro-imidazol-1-yl)-5H-pyrrolo[2,3-b]pyrazin-7-yl]-propan-1-one | 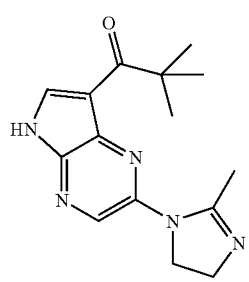 | |
| I-110 | 1-[2-(2-Ethyl-imidazol-1-yl)-5H-pyrrolo[2,3-b]pyrazin-7-yl]-2,2-dimethyl-propan-1-one | 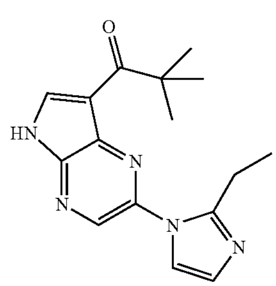 | |

TABLE I-continued

| COMPOUND | SYSTEMATIC NAME | STRUCTURE | MP |
|---|---|---|---|
| I-111 | 2,2-Dimethyl-1-(2-thiophen-2-yl-5H-pyrrolo[2,3-b]pyrazin-7-yl)-propan-1-one | 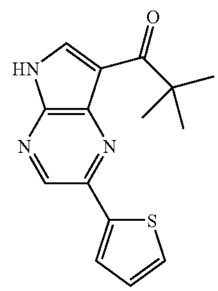 | |
| I-112 | 2,2-Dimethyl-1-[2-(1H-pyrrol-2-yl)-5H-pyrrolo[2,3-b]pyrazin-7-yl]-propan-1-one | 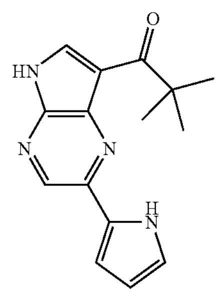 | |
| I-113 | 2,2-Dimethyl-1-(2-thiophen-3-yl-5H-pyrrolo[2,3-b]pyrazin-7-yl)-propan-1-one | 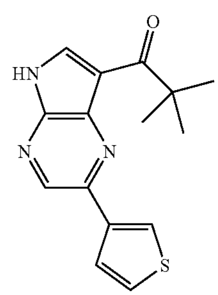 | |
| I-114 | 2,2-Dimethyl-1-(2-oxazol-5-yl-5H-pyrrolo[2,3-b]pyrazin-7-yl)-propan-1-one | 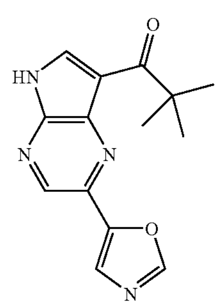 | |
| I-115 | 2,2-Dimethyl-1-[2-(1H-pyrazol-4-yl)-5H-pyrrolo[2,3-b]pyrazin-7-yl]-propan-1-one | 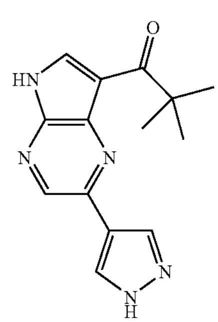 | |

TABLE I-continued

| COMPOUND | SYSTEMATIC NAME | STRUCTURE | MP |
|---|---|---|---|
| I-116 | 4-[7-(2,2-Dimethyl-propionyl)-5H-pyrrolo[2,3-b]pyrazin-2-yl]-pyrazole-1-carboxylic acid tert-butyl ester | 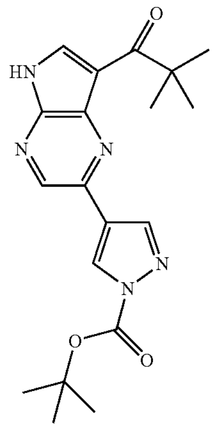 | |
| I-117 | 2,2-Dimethyl-1-(2-pyrazol-1-yl-5H-pyrrolo[2,3-b]pyrazin-7-yl)-propan-1-one | 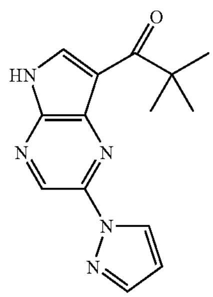 | |
| I-118 | 2,2-Dimethyl-1-[2-(2H-pyrazol-3-yl)-5H-pyrrolo[2,3-b]pyrazin-7-yl]-propan-1-one | 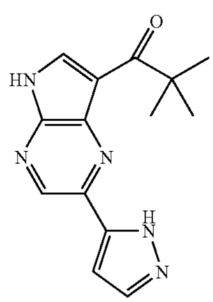 | |
| I-119 | 2,2-Dimethyl-1-(2-pyrrol-1-yl-5H-pyrrolo[2,3-b]pyrazin-7-yl)-propan-1-one | 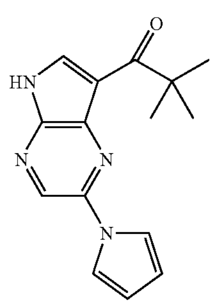 | |

TABLE I-continued

| COMPOUND | SYSTEMATIC NAME | STRUCTURE | MP |
|---|---|---|---|
| I-120 | 2,2-Dimethyl-1-[2-(1H-pyrrol-3-yl)-5H-pyrrolo[2,3-b]pyrazin-7-yl]-propan-1-one | 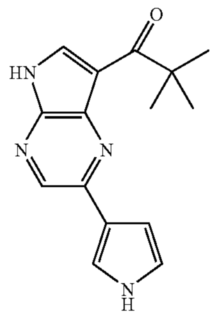 | |
| I-121 | 2,2-Dimethyl-1-(2-thiazol-5-yl-5H-pyrrolo[2,3-b]pyrazin-7-yl)-propan-1-one | 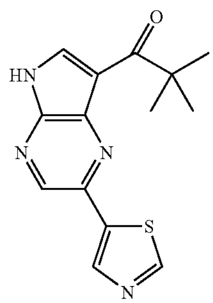 | |
| I-122 | 3-[7-(2,2-Dimethyl-propionyl)-5H-pyrrolo[2,3-b]pyrazin-2-yl]-1H-indole-5-carbonitrile | 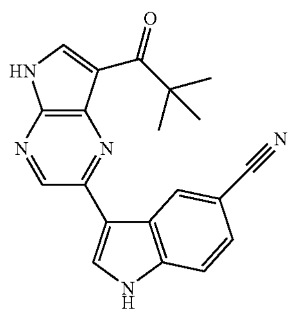 | |
| I-123 | 1-[2-(5-Fluoro-1H-indol-3-yl)-5H-pyrrolo[2,3-b]pyrazin-7-yl]-2,2-dimethyl-propan-1-one | 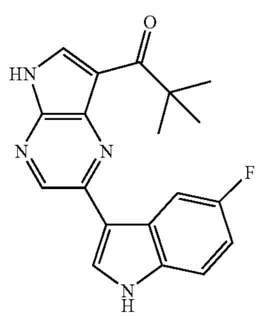 | |
| I-124 | [2-(1H-Indol-3-yl)-5H-pyrrolo[2,3-b]pyrazin-7-yl]-(1-methyl-cyclohexyl)-methanone | 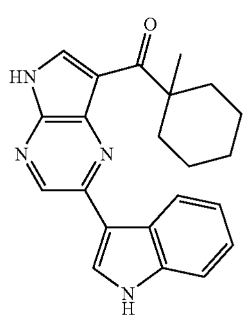 | |

TABLE I-continued

| COMPOUND | SYSTEMATIC NAME | STRUCTURE | MP |
|---|---|---|---|
| I-125 | 1-{2-[1-(2-Hydroxy-1-hydroxymethyl-ethyl)-1H-indol-3-yl]-5H-pyrrolo[2,3-b]pyrazin-7-yl}-2,2-dimethyl-propan-1-one | 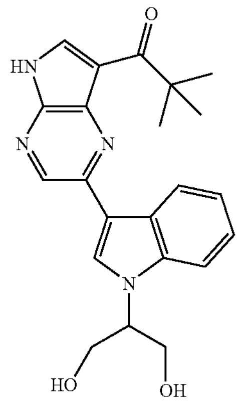 | |
| I-126 | 1-[2-(1H-Indol-3-yl)-5H-pyrrolo[2,3-b]pyrazin-7-yl]-2,2-dimethyl-propan-1-one | 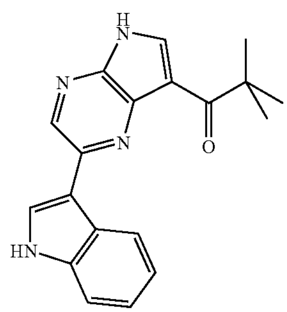 | |
| I-127 | 1-(2-Benzo[b]thiophen-2-yl-5H-pyrrolo[2,3-b]pyrazin-7-yl)-2,2-dimethyl-propan-1-one | 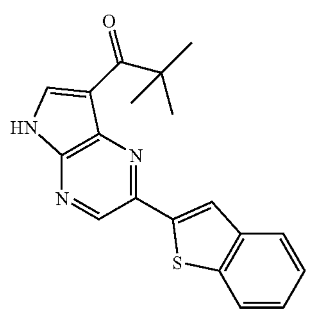 | |
| I-128 | 2,2-Dimethyl-1-[2-(5-phenyl-thiophen-2-yl)-5H-pyrrolo[2,3-b]pyrazin-7-yl]-propan-1-one | 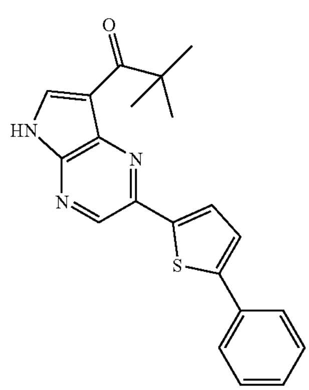 | |

TABLE I-continued

| COMPOUND | SYSTEMATIC NAME | STRUCTURE | MP |
|---|---|---|---|
| I-129 | 2,2-Dimethyl-1-[2-(1-methyl-1H-indol-2-yl)-5H-pyrrolo[2,3-b]pyrazin-7-yl]-propan-1-one | 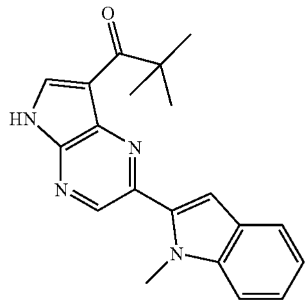 | |
| I-130 | 1-[2-(1H-Indol-2-yl)-5H-pyrrolo[2,3-b]pyraizn-7-yl]-2,2-dimethyl-propan-1-one | 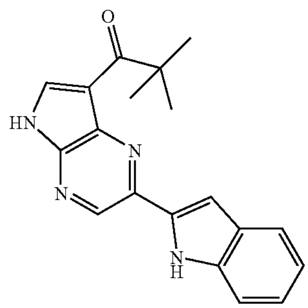 | |
| I-131 | 1-[2-(1H-Indol-3-yl)-5-methyl-5H-pyrrolo[2,3-b]pyrazin-7-yl]-2,2-dimethyl-propan-1-one | 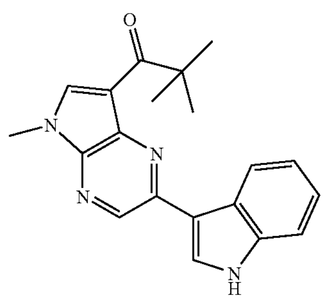 | |
| I-132 | 2,2-Dimethyl-1-[2-(1-methyl-1H-indol-3-yl)-5H-pyrrolo[2,3-b]pyrazin-7-yl]-propan-1-one | 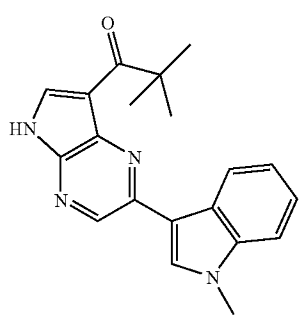 | |
| I-133 | 2,2-Dimethyl-1-[2-(5-phenyl-1H-pyrrol-3-yl)-5H-pyrrolo[2,3-b]pyrazin-7-yl]-propan-1-one | 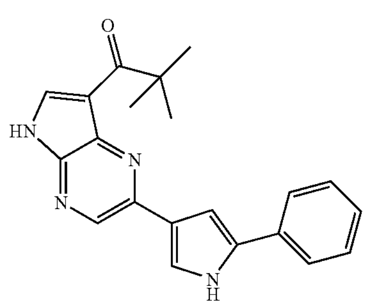 | |

TABLE I-continued

| COMPOUND | SYSTEMATIC NAME | STRUCTURE | MP |
|---|---|---|---|
| I-134 | 1-{2-[1-(2-Hydroxy-ethyl)-1H-indol-3-yl]-5H-pyrrolo[2,3-b]pyrazin-7-yl}-2,2-dimethyl-propan-1-one | 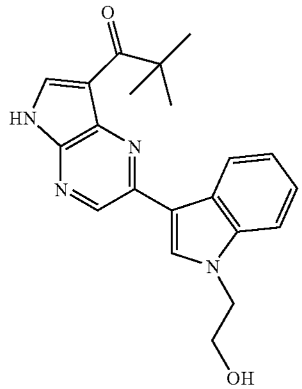 | |
| I-135 | 1-[2-(6-Fluoro-1H-indol-3-yl)-5H-pyrrolo[2,3-b]pyrazin-7-yl]-2,2-dimethyl-propan-1-one | 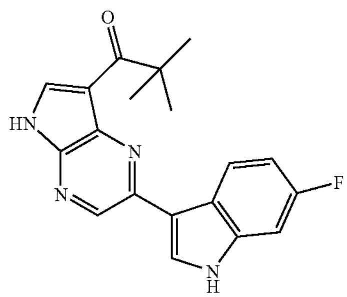 | |
| I-136 | 1-{2-[1-(2-Methanesulfonyl-ethyl)-1H-indol-3-yl]-5H-pyrrolo[2,3-b]pyrazin-7-yl}-2,2-dimethyl-propan-1-one | 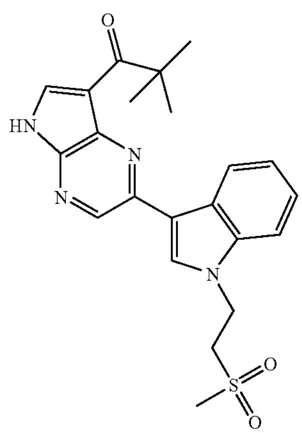 | |
| I-137 | 1-[2-(5-Methoxy-1H-indol-3-yl)-5H-pyrrolo[2,3-b]pyrazin-7-yl]-2,2-dimethyl-propan-1-one | 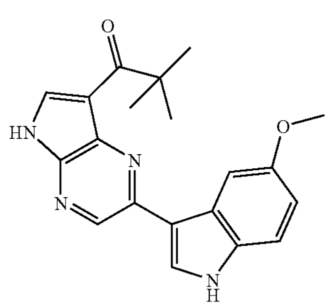 | |

TABLE I-continued

| COMPOUND | SYSTEMATIC NAME | STRUCTURE | MP |
|---|---|---|---|
| I-138 | 1-[2-(1-Ethyl-1H-indol-3-yl)-5H-pyrrolo[2,3-b]pyrazin-7-yl]-2,2-dimethyl-propan-1-one | 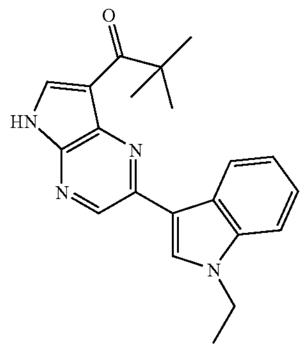 | |
| I-139 | 2,2-Dimethyl-1-[2-(5-methyl-1H-indol-3-yl)-5H-pyrrolo[2,3-b]pyrazin-7-yl]-propan-1-one | 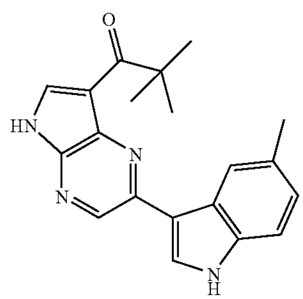 | |
| I-140 | 2,2-Dimethyl-1-(2-{1-[2-(4-methyl-piperazin-1-yl)-ethyl]-1H-indol-3-yl}-5H-pyrrolo[2,3-b]pyrazin-7-yl)-propan-1-one | 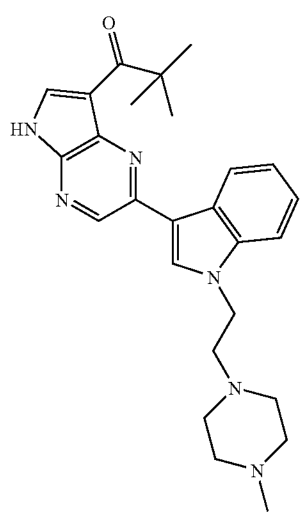 | |

TABLE I-continued

| COMPOUND | SYSTEMATIC NAME | STRUCTURE | MP |
|---|---|---|---|
| I-141 | 2,2-Dimethyl-1-{2-[1-(2-morpholin-4-yl-ethyl)-1H-indol-3-yl]-5H-pyrrolo[2,3-b]pyrazin-7-yl}-propan-1-one | 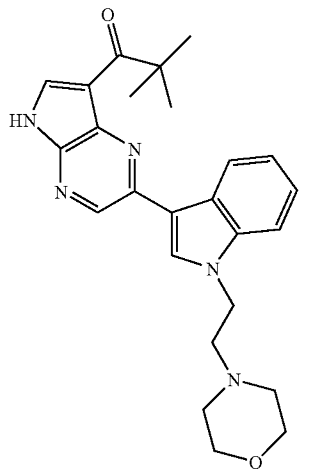 | |
| I-142 | 1-{2-[1-(3-Hydroxy-2-hydroxymethyl-propyl)-1H-indol-3-yl]-5H-pyrrolo[2,3-b]pyrazin-7-yl}-2,2-dimethyl-propan-1-one | 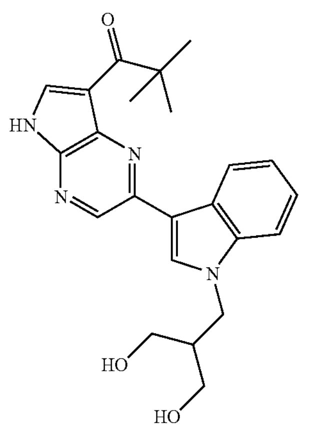 | |
| I-143 | 1-{2-[1-(3-Hydroxy-2-hydroxymethyl-propyl)-1H-pyrrolo[2,3-b]pyridin-3-yl]-5H-pyrrolo[2,3-b]pyrazin-7-yl}-2,2-dimethyl-propan-1-one | 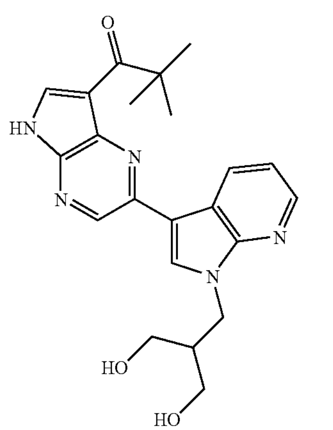 | |
| I-144 | 2,2-Dimethyl-1-[2-(6-methyl-1H-indol-3-yl)-5H-pyrrolo[2,3-b]pyrazin-7-yl]-propan-1-one | 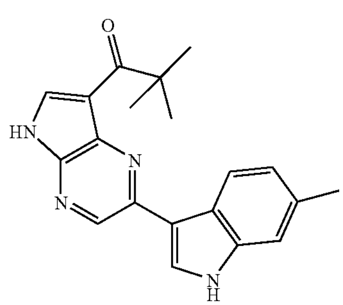 | |

TABLE I-continued

| COMPOUND | SYSTEMATIC NAME | STRUCTURE | MP |
|---|---|---|---|
| I-145 | 1-[2-(6-Methoxy-1H-indol-3-yl)-5H-pyrrolo[2,3-b]pyrazin-7-yl]-2,2-dimethyl-propan-1-one | 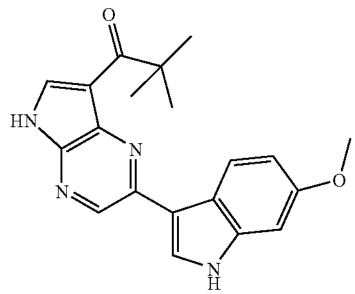 | |
| I-146 | 1-{2-[1-(2-Amino-ethyl)-1H-indol-3-yl]-5H-pyrrolo[2,3-b]pyrazin-7-yl}-2,2-dimethyl-propan-1-one | 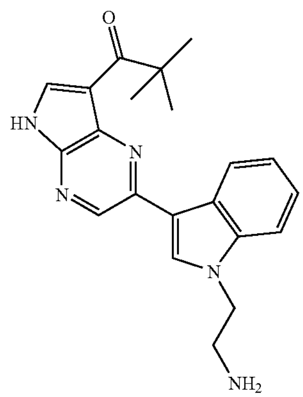 | |
| I-147 | 2,2-Dimethyl-1-[2-(6-morpholin-4-yl-pyridin-3-yl)-5H-pyrrolo[2,3-b]pyrazin-7-yl]-propan-1-one | 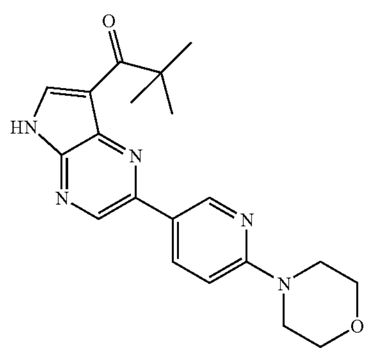 | |
| I-148 | (1-Methyl-cyclohexyl)-[2-(6-morpholin-4-yl-pyridin-3-yl)-5H-pyrrolo[2,3-b]pyrazin-7-yl]-methanone | 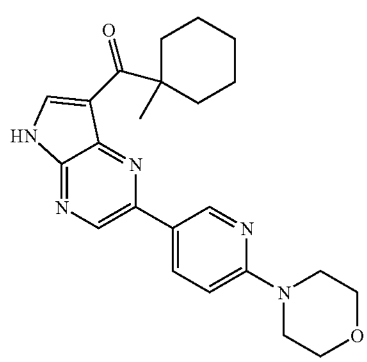 | |

TABLE I-continued

| COMPOUND | SYSTEMATIC NAME | STRUCTURE | MP |
|---|---|---|---|
| I-149 | 1-[2-(1H-Indol-3-yl)-5H-pyrrolo[2,3-b]pyrazin-7-yl]-2,2-dimethyl-propan-1-one | 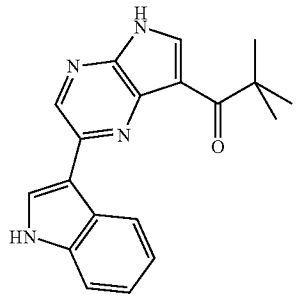 | |
| I-150 | 1-(2-Imidazo[1,2-a]pyridin-3-yl-5H-pyrrolo[2,3-b]pyrazin-7-yl)-2,2-dimethyl-propan-1-one | 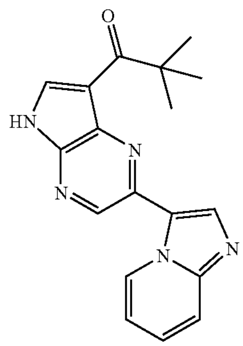 | |
| I-151 | 2,2-Dimethyl-1-[2-(1H-pyrrolo[2,3-b]pyridin-3-yl)-5H-pyrrolo[2,3-b]pyrazin-7-yl]-propan-1-one | 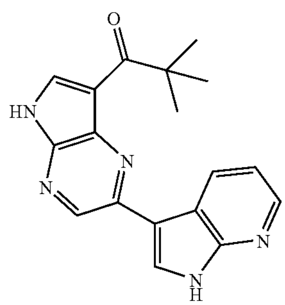 | |
| I-152 | 2,2-Dimethyl-1-[2-(1H-pyrrolo[3,2-c]pyridin-3-yl)-5H-pyrrolo[2,3-b]pyrazin-7-yl]-propan-1-one | 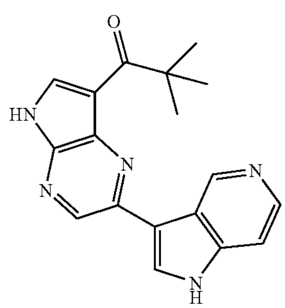 | |
| I-153 | 2,2-Dimethyl-1-[2-(1H-pyrrolo[2,3-c]pyridin-3-yl)-5H-pyrrolo[2,3-b]pyrazin-7-yl]-propan-1-one | 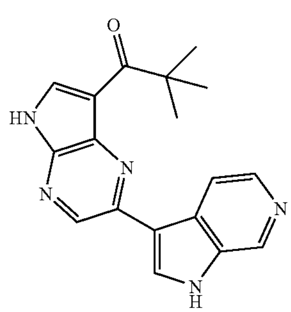 | |

TABLE I-continued

| COMPOUND | SYSTEMATIC NAME | STRUCTURE | MP |
|---|---|---|---|
| I-154 | 2,2-Dimethyl-1-[2-(1-methyl-1H-pyrrolo[2,3-b]pyridin-3-yl)-5H-pyrrolo[2,3-b]pyrazin-7-yl]-propan-1-one | 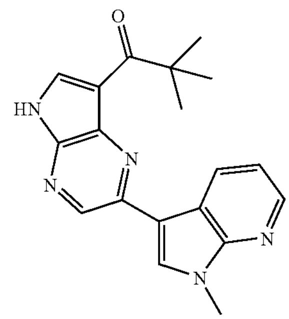 | |
| I-155 | 2,2-Dimethyl-1-{2-[1-(2-oxo-2-piperazin-1-yl-ethyl)-1H-indol-3-yl]-5H-pyrrolo[2,3-b]pyrazin-7-yl}-propan-1-one | 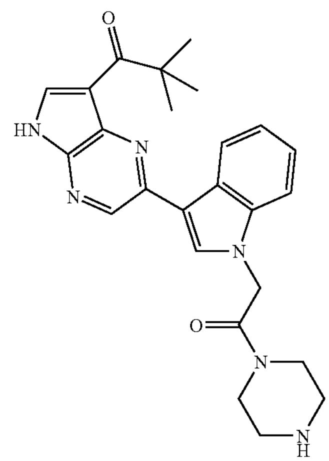 | |
| I-156 | 1-(2-{1-[2-(4-Amino-piperidin-1-yl)-2-oxo-ethyl]-1H-indol-3-yl}-5H-pyrrolo[2,3-b]pyrazin-7-yl)-2,2-dimethyl-propan-1-one | 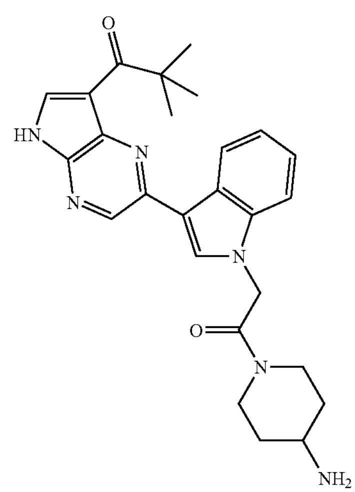 | |
| I-157 | (1-Methyl-cyclohexyl)-[2-(1-methyl-1H-pyrrolo[2,3-b]pyridin-3-yl)-5H-pyrrolo[2,3-b]pyrazin-7-yl]-methanone | 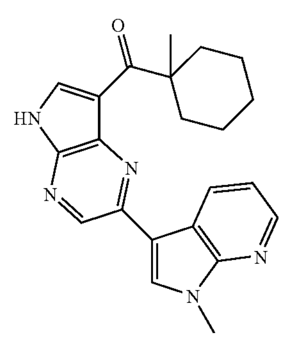 | |

TABLE I-continued

| COMPOUND | SYSTEMATIC NAME | STRUCTURE | MP |
|---|---|---|---|
| I-158 | 2,2-Dimethyl-1-(2-{1-[2-(4-methyl-piperazin-1-yl)-2-oxo-ethyl]-1H-indol-3-yl}-5H pyrrolo[2,3-b]pyraizn-7-yl)-propan-1-one | 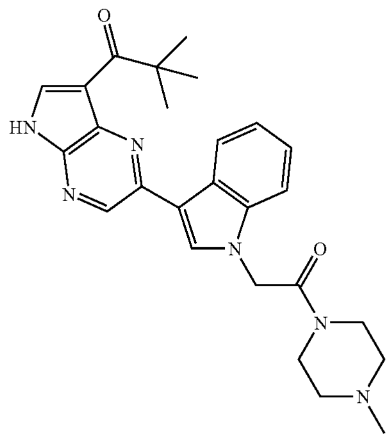 | |
| I-159 | (1-Methyl-cyclopentyl)-[2-(1-methyl-1H-pyrrolo[2,3-b]pyridin-3-yl)-5H-pyrrolo[2,3-b]pyrazin-7-yl]-methanone | 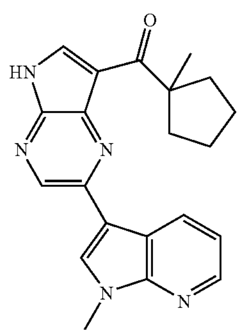 | |
| I-160 | 1-[2-(5-Methoxy-pyridin-3-yl)-5H-pyrrolo[2,3-b]pyrazin-7-yl]-2,2-dimethyl-propan-1-one | 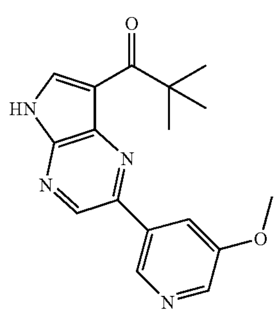 | |
| I-161 | 4-[7-(1-Methyl-cyclohexanecarbonyl)-5H-pyrrolo[2,3-b]pyrazin-2-yl]-thiophene-2-carboxylic acid (1-ethyl-propyl)-amide | 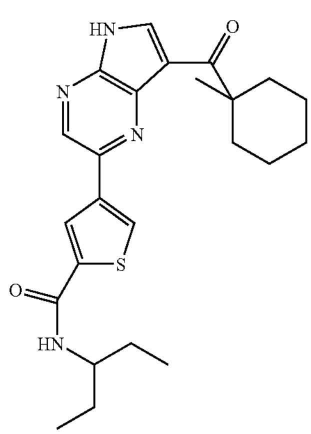 | |

TABLE I-continued

| COMPOUND | SYSTEMATIC NAME | STRUCTURE | MP |
|---|---|---|---|
| I-162 | {2-[5-(4-Hydroxy-4-methyl-piperidine-1-carbonyl)-thiophen-3-yl]-5H-pyrrolo[2,3-b]pyrazin-7-yl}-(1-methyl-cyclohexyl)-methanone | 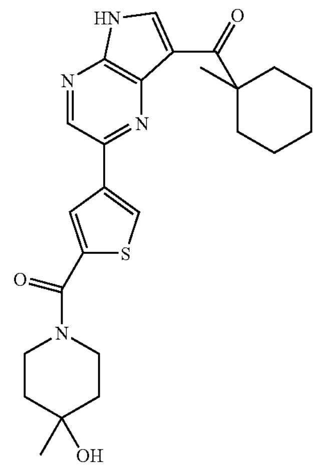 | |
| I-163 | 5-[7-(2,2-Dimethyl-propionyl)-5H-pyrrolo[2,3-b]pyrazin-2-yl]-thiophene-2-carboxylic acid (2-hydroxy-ethyl)-methyl-amide | 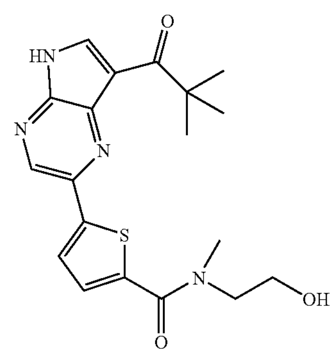 | |
| I-164 | 2-Cyclopropyl-5H-pyrrolo[2,3-b]pyrazine-7-carboxylic acid ((S)-2-hydroxy-1,2-dimethyl-propyl)-amide | Chiral | |
| I-165 | 4-[7-(1-Methyl-cyclohexanecarbonyl)-5H-pyrrolo[2,3-b]pyrazin-2-yl]-thiophene-2-carboxylic acid | 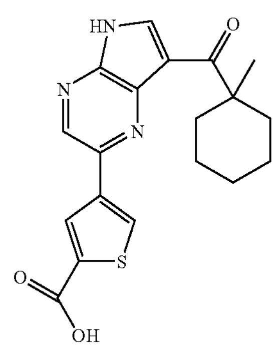 | |

TABLE I-continued

| COMPOUND | SYSTEMATIC NAME | STRUCTURE | MP |
|---|---|---|---|
| I-166 | 4-[7-(1-Methyl-cyclohexanecarbonyl)-5H-pyrrolo[2,3-b]pyrzin-2-yl]-thiophene-2-carboxylic acid (2-amino-2-methyl-propyl)-amide | 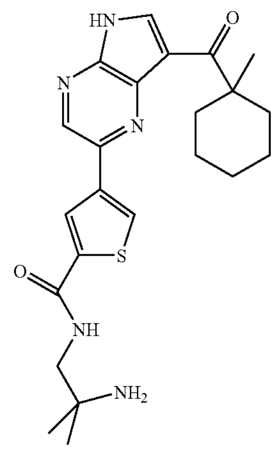 | |
| I-167 | {2-[5-(4-Dimethylamino-piperidine-1-carbonyl)-thiophen-3-yl]-5H-pyrrolo[2,3-b]pyrazin-7-yl}-(1-methyl-cyclohexyl)-methanone | 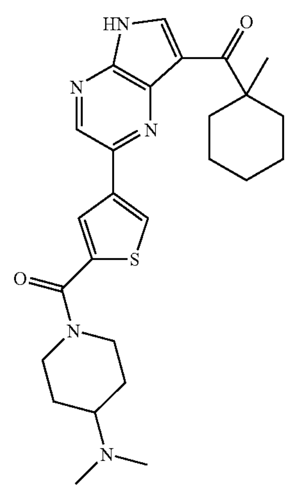 | |
| I-168 | 2-Cyclopropyl-5H-pyrrolo[2,3-b]pyrazine-7-carboxylic acid (3-hydroxy-2,2-dimethyl-propyl)-amide | 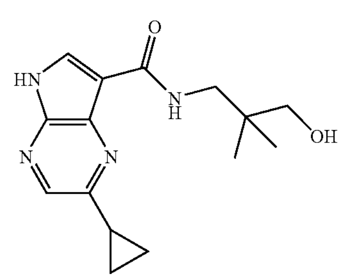 | |
| I-169 | 2-Cyclopropyl-5H-pyrrolo[2,3-b]pyrazine-7-carboxylic acid tert-butylamide | 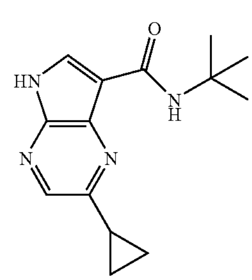 | |

TABLE I-continued

| COMPOUND | SYSTEMATIC NAME | STRUCTURE | MP |
|---|---|---|---|
| I-170 | 2-[7-(2,2-Dimethyl-propionyl)-5H-pyrrolo[2,3-b]pyrazin-2-yl]-pyrrole-1-carboxylic acid tert-butyl ester | 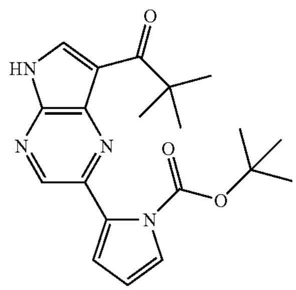 | |
| I-171 | 2-Thiophen-2-yl-5H-pyrrolo[2,3-b]pyrazine-7-carboxylic acid (3-hydroxy-2,2-dimethyl-propyl)-amide | 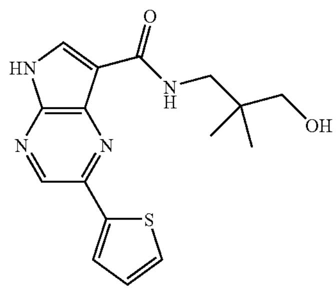 | |

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzene-sulfonic acid, 4-chlorobenzenesulfonic acid, 2-naphthalene-sulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g. gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in *Remington: The Science and Practice ofpharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medications with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLES

Example 1

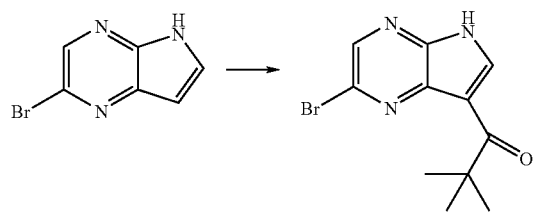

1-(2-Bromo-5H-pyrrolo[2,3-b]pyrazin-7-yl)-2,2-dimethyl-propan-1-one

To a slurry of 5-bromo-4,7-diazaindole (1.97 g, 9.95 mmol) in 40 mL of dichloromethane at 0-5° C. was added diethylaluminum chloride (1.0 M in hexane, 30 mL, 30 mmol). The reaction mixture was stirred at 0-5° C. for 30 min., then pivaloyl chloride (12 mL, 97 mmol) was added. The mixture was heated to reflux and stirred for 15 h, then cooled to 0-5° C. Sat. aq. NaHCO$_3$ (40 mL) was carefully added, and the mixture was then partitioned between 300 mL of a sat. aq. NaCl solution and 300 mL of ethyl acetate. The mixture was filtered through a plug of celite and the layers were separated. The aqueous layer was extracted with 300 mL of ethyl acetate. The combined organic layers were dried over MgSO$_4$, filtered, and concentrated to a residue. Silica gel chromatography (20->60% EtOAc/hexanes) afforded 2.50 g (89%) of 1-(2-bromo-5H-pyrrolo[2,3-b]pyrazin-7-yl)-2,2-dimethyl-propan-1-one as an off-white solid.

Example 2

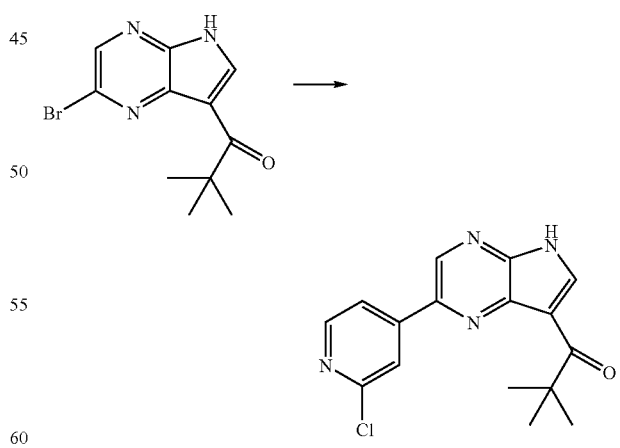

1-[2-(2-Chloro-pyridin-4-yl)-5H-pyrrolo[2,3-b]pyrazin-7-yl]-2,2-dimethyl-propan-1-one A mixture of 1-(2-bromo-5H-pyrrolo[2,3-b]pyrazin-7-yl)-2,2-dimethyl-propan-1-one (0.430 g, 1.53 mmol), 2-chloropyridine-4-boronic acid (0.362 g, 2.30 mmol), potassium carbonate (0.782 g, 5.66 mmol), Pd(dppf)Cl$_2$.CH$_2$Cl$_2$ (0.098 g, 0.12 mmol), 10 mL dioxane and 2.5 mL water was stirred at 160° C. in a microwave for 30 min. The resulting red mixture was partitioned between 80 mL of ethyl acetate and 150 mL of water. The aqueous layer was extracted with two 80 mL portions of ethyl acetate. The combined organic layers were dried over MgSO$_4$, filtered and concentrated to a residue. Silica gel chromatography (0->100% EtOAc/hexanes) afforded 0.155 g (32%) of 1-[2-(2-chloro-pyridin-4-yl)-5H-pyrrolo[2,3-b]pyrazin-7-yl]-2,2-dimethyl-propan-1-one as a red solid.

1-{2-[3-(3-Methoxy-pyrrolidin-1-yl)-phenyl]-5H-pyrrolo[2,3-b]pyrazin-7-yl}-2,2-dimethyl-propan-1-one was prepared according to the above general procedure and was obtained by replacing 2-chloropyridine-4-boronic acid with 3-methoxy-1-[3-(4,4,5,5-tetramethyl-[1,3,2]dioxaborolan-2-yl)-phenyl]-pyrrolidine: m.p. 194-195° C.; MS m/z 379 (M$^{+H}$).

1-{2-[3-(4-Methoxy-benzyloxy)-phenyl]-5H-pyrrolo[2,3-b]pyrazin-7-yl}-2,2-dimethyl-propan-1-one was prepared according to the above general procedure and was obtained by replacing 2-chloropyridine-4-boronic acid with 2-[3-(4-methoxy-benzyloxy)-phenyl]-4,4,5,5-tetramethyl-[1,3,2]dioxaborolane: m.p. >300° C.; MS m/z 416 (M$^{+H}$).

1-(2-Cyclopropyl-5H-pyrrolo[2,3-b]pyrazin-7-yl)-2,2-dimethyl-propan-1-one was prepared according to the above general procedure and was obtained by replacing 2-chloro-pyridine-4-boronic acid with potassium cyclopropyltrifluoroborate, replacing potassium carbonate with potassium phosphate, replacing dioxane with toluene then replacing the palladium (II) salt with tetrakis[triphenylphosphibne]palladium (0): m.p. 266-268° C.; MS m/z 244 (M$^{+H}$).

Example 3

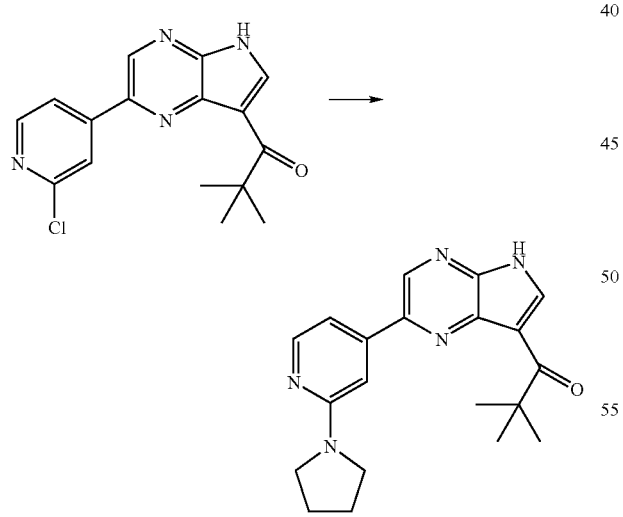

2,2-Dimethyl-1-[2-(2-pyrrolidin-1-yl-pyridin-4-yl)-5H-pyrrolo[2,3-b]pyrazin-7-yl]-propan-1-one A mixture of 1-[2-(2-chloro-pyridin-4-yl)-5H-pyrrolo[2,3-b]pyrazin-7-yl]-2,2-dimethyl-propan-1-one (0.030 g, 0.095 mmol), 0.100 mL of pyrrolidine and 1.5 mL of N-methylpyrollidinone was stirred at 150° C. in a pressure tube for 3 h. The resulting black solution was partitioned between 30 mL of ethyl acetate and 40 mL of water. The organic layer was washed with three 30 mL portions of water, dried over MgSO$_4$, filtered and concentrated to a residue. Silica gel chromatography (0->60% EtOAc/hexanes) afforded 0.020 g (61%) of 2,2-dimethyl-1-[2-(2-pyrrolidin-1-yl-pyridin-4-yl)-5H-pyrrolo[2,3-b]pyrazin-7-yl]-propan-1-one as a yellow solid.

The following compounds were prepared according to the above general procedure:

2,2-Dimethyl-1-[2-(3,4,5,6-tetrahydro-2H-[1,2']bipyridinyl-4'-yl)-5H-pyrrolo[2,3-b]pyrazin-7-yl]-propan-1-one 1-{2-[2-(3-Dimethylamino-pyrrolidin-1-yl)-pyridin-4-yl]-5H-pyrrolo[2,3-b]pyrazin-7-yl}-2,2-dimethyl-propan-1-one 2,2-Dimethyl-1-[2-(2-thiomorpholin-4-yl-pyridin-4-yl)-5H-pyrrolo[2,3-b]pyrazin-7-yl]-propan-1-one 2,2-Dimethyl-1-{2-[2-(2-methyl-pyrrolidin-1-yl)-pyridin-4-yl]-5H-pyrrolo[2,3-b]pyrazin-7-yl}-propan-1-one 1-{2-[2-(3-Hydroxy-pyrrolidin-1-yl)-pyridin-4-yl]-5H-pyrrolo[2,3-b]pyrazin-7-yl}-2,2-dimethyl-propan-1-one 1-{2-[2-(3,3-Difluoro-pyrrolidin-1-yl)-pyridin-4-yl]-5H-pyrrolo[2,3-b]pyrazin-7-yl}-2,2-dimethyl-propan-1-one 1-[2-(2-Azepan-1-yl-pyridin-4-yl)-5H-pyrrolo[2,3-b]pyrazin-7-yl]-2,2-dimethyl-propan-1-one 1-{2-[2-((S)-3-Fluoro-pyrrolidin-1-yl)-pyridin-4-yl]-5H-pyrrolo[2,3-b]pyrazin-7-yl}-2,2-dimethyl-propan-1-one 1-{2-[2-((R)-3-Fluoro-pyrrolidin-1-yl)-pyridin-4-yl]-5H-pyrrolo[2,3-b]pyrazin-7-yl}-2,2-dimethyl-propan-1-one 1-{2-[2-(1,1-Dioxo-1λ6-thiomorpholin-4-yl)-pyridin-4-yl]-5H-pyrrolo[2,3-b]pyrazin-7-yl}-2,2-dimethyl-propan-1-one 2,2-Dimethyl-1-{2-[2-(1-oxo-1λ4-thiomorpholin-4-yl)-pyridin-4-yl]-5H-pyrrolo[2,3-b]pyrazin-7-yl}-propan-1-one Methyl-cyclohexyl)-[2-(2-pyrrolidin-1-yl-pyridin-4-yl)-5H-pyrrolo[2,3-b]pyrazin-7-yl]-methanone 1-[2-(4-Hydroxy-3,4,5,6-tetrahydro-2H-[1,2']bipyridinyl-4'-yl)-5H-pyrrolo[2,3-b]pyrazin-7-yl]-2,2-dimethyl-propan-1-one Methyl-cyclohexyl)-{2-[2-(1-oxo-1λ4-thiomorpholin-4-yl)-pyridin-4-yl]-5H-pyrrolo[2,3-b]pyrazin-7-yl}-methanone 1-{2-[2-((1S,5R,6R)-6-Hydroxymethyl-3-aza-bicyclo[3.1.0]hex-3-yl)-pyridin-4-yl]-5H-pyrrolo[2,3-b]pyrazin-7-yl}-2,2-dimethyl-propan-1-one Example 4

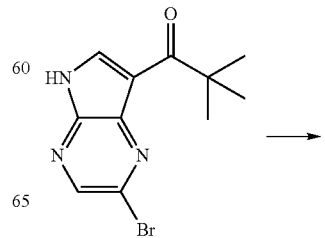

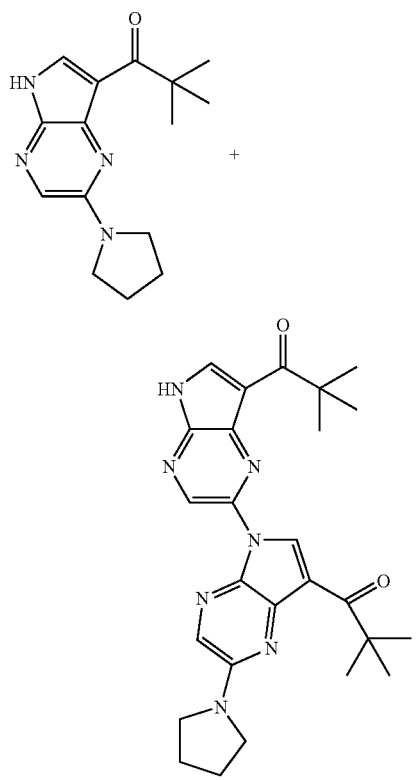

2,2-Dimethyl-1-(2-pyrrolidin-1-yl-5H-pyrrolo[2,3-b]pyrazin-7-yl)-propan-1-one and 1-[7'-(2,2-dimethyl-propionyl)-2'-pyrrolidin-1-yl-5H-[2,5']bi[pyrrolo[2,3-b]pyrazinyl]-7-yl]-2,2-dimethyl-propan-1-one. DMSO (2 mL) was added to a mixture of copper iodide (10 mg; 0.05 mmol), d,l-proline (12 mg; 0.10 mmol), potassium carbonate (108 mg; 0.77 mmol), and 1-(2-Bromo-5H-pyrrolo[2,3-b]pyrazin-7-yl)-2,2-dimethyl-propan-1-one (100 mg; 0.35 mmol). Pyrrolidine (0.6 mL; 7.1 mmol) was added and the resulting mixture was stirred at 110° C. (oil bath) for 24 hrs. TLC analysis (5% MeOH/DCM) shows two more-polar products. The reaction mixture was poured into 50 mL of saturated sodium bicarbonate solution and extracted with EtOAc (2×30 mL). The organic layers were combined, washed with brine, dried over MgSO4, and concentrated to give a yellow oil. Chromatography (SiO$_2$; 1% MeOH/DCM) gives 1-[7'-(2,2-dimethyl-propionyl)-2'-pyrrolidin-1-yl-5H-[2,5']bi[pyrrolo[2,3-b]pyrazinyl]-7-yl]-2,2-dimethyl-propan-1-one (36%; ms=474 [M+H]; $^1$H NMR (DMSO): δ 7.83 (s), 8.64 (s), 8.91 (s), 9.54 (s) ppm) as the upper R$_f$ product and 2,2-dimethyl-1-(2-pyrrolidin-1-yl-5H-pyrrolo[2,3-b]pyrazin-7-yl)-propan-1-one (17%; MS=273 [M+H]; $^1$H NMR (DMSO): δ 7.71 (s), 8.1 (s) ppm) as the lower R$_f$ product.

Example 5

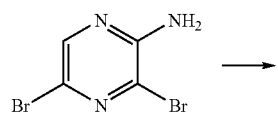

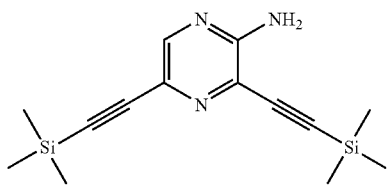

Trimethylsilylacetylene (11.1 mL, 80 mmol) was added to a solution of 2-amino-3,6-dibromopyrazine (5.06 g, 20 mmol), Pd(PPh$_3$)$_2$Cl$_2$ (0.140 g, 0.20 mmol), triethylamine (11.4 mL, 80 mmol) and copper(I) iodide (0.114 g, 0.60 mmol) in 50 mL of tetrahydrofuran at 0-5° C. The reaction mixture was allowed to warm to RT and stirred for 64 h. Additional trimethylsilylacetylene (5.6 mL, 40 mmol), Pd(PPh$_3$)$_2$Cl$_2$ (0.140 g, 0.20 mmol) and copper(I) iodide (0.114 g, 0.60 mmol) were added, and the mixture was stirred at 50° C. for 22 h then allowed to cool to RT. The mixture was diluted with 200 mL of ethyl acetate and 200 mL of hexanes, then sequentially washed with three 200 mL portions of water and 200 mL of a sat. aq. NaHCO$_3$ solution, dried over MgSO$_4$, filtered and concentrated to a residue. Silica gel chromatography (0->25% EtOAc/hexanes) afforded 4.36 g (76%) of 3,5-bis-trimethylsilanylethynyl-pyrazin-2-ylamine as a brown oil.

Example 6

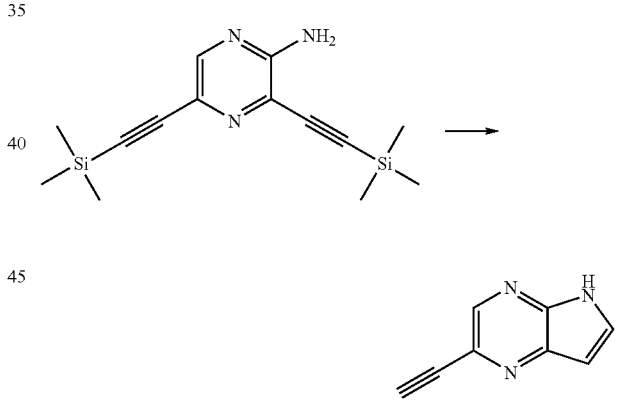

Potassium tert-butoxide (1.0 M in tetrahydrofuran, 45.6 mL, 45.6 mmol) was added dropwise to a solution of 3,5-bis-trimethylsilanylethynyl-pyrazin-2-ylamine (4.36 g, 15.2 mmol) in 60 mL of tetrahydrofuran. The reaction mixture was heated to reflux and stirred for 15 h, allowed to cool to RT, then treated with 100 mL of water. The resulting mixture was diluted with 250 mL of ethyl acetate and filtered through a plug of Celite, rinsing with 200 mL of ethyl acetate and 100 mL of water. The filtrate layers were separated, and the organic layer sequentially wasked with two 200 mL portions of water and 200 mL of a sat. aq. NaCl solution, dried over MgSO$_4$, filtered and concentrated to 0.911 g (42%) of 2-ethynyl-5H-pyrrolo[2,3-b]pyrazine as an impure brown solid that was used without further purification.

Example 7

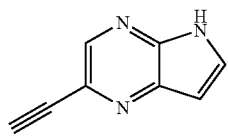

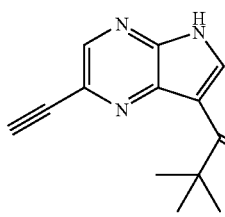

1-(2-ethynyl-5H-pyrrolo[2,3-b]pyrazin-7-yl)-2,2-dimethyl-propan-1-one

Diethylaluminum chloride (1.0 M in hexanes, 19.1 mL, 19.1 mmol) was added to a suspension of impure 2-ethynyl-5H-pyrrolo[2,3-b]pyrazine (0.911 g, 6.36 mmol) in 25 mL of dichloromethane at 0-5° C. The mixture was stirred at 0-5° C. for 30 min., then pivaloyl chloride (7.8 mL, 63.6 mmol) was slowly added. The mixture was heated to reflux and stirred for 6 h then cooled to 0-5° C. Sat. Aq. NaHCO₃ (50 mL) was carefully added, and the resulting mixture was diluted with 100 mL of ethyl acetate and filtered through a plug of Celite, rinsing with ethyl acetate and water. The filtrate layers were separated, and the aqueous layer extracted with 250 mL of ethyl acetate. The combined organic layers were dried over MgSO₄, filtered and concentrated to a residue. Silica gel chromatography (20->60% EtOAc/hexanes) afforded 0.180 g (12%) of 1-(2-ethynyl-5H-pyrrolo[2,3-b]pyrazin-7-yl)-2,2-dimethyl-propan-1-one as a brown solid.

Example 8

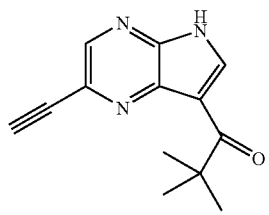

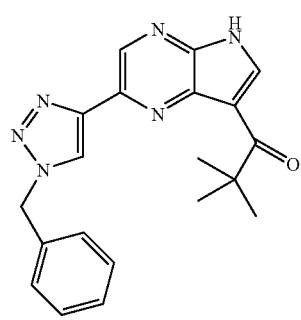

1-[2-(1-benzyl-1H-[1,2,3]triazol-4-yl)-5H-pyrrolo[2,3-b]pyrazin-7-yl]-2,2-dimethyl-propan-1-one A solution of 1-(2-ethynyl-5H-pyrrolo[2,3-b]pyrazin-7-yl)-2,2-dimethyl-propan-1-one (0.100 g, 0.44 mmol), benzyl azide (0.055 mL, 0.44 mmol), CuSO₄ (0.007 g, 0.04 mmol), and L-ascorbic acid (0.078 g, 0.44 mmol) in 3 mL of tert-butanol and 3 mL of water was stirred for 1.5 h, then diluted with 30 mL of water and extracted with 100 mL of ethyl acetate. The organic layer was dried over MgSO₄, filtered and concentrated to a residue. Silica gel chromatography (0->50% EtOAc/hexanes) afforded 0.036 g (23%) of 1-[2-(1-benzyl-1H-[1,2,3]triazol-4-yl)-5H-pyrrolo[2,3-b]pyrazin-7-yl]-2,2-dimethyl-propan-1-one as an off-white solid. MS: 361 M+1, M.P. 235.0-237.0° C.

The following compounds were prepared according to the above general procedure:

1-[2-(1-Cyclopentyl-1H-[1,2,3]triazol-4-yl)-5H-pyrrolo[2,3-b]pyrazin-7-yl]-2,2-dimethyl-propan-1-one 1-[2-(1-Cyclohexyl-1H-[1,2,3]triazol-4-yl)-5H-pyrrolo[2,3-b]pyrazin-7-yl]-2,2-dimethyl-propan-1-one

Example 9

TBAF Deprotection

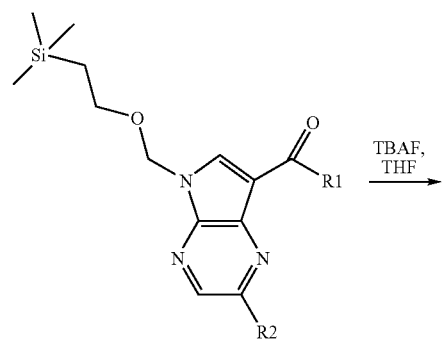

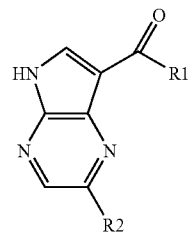

1-[2-(1,3-Dihydro-isoindol-2-yl)-5H-pyrrolo[2,3-b]pyrazin-7-yl]-2,2-dimethyl-propan-1-one To a solution of 1-[2-(1,3-Dihydro-isoindol-2-yl)-5-(2-trimethylsilanyl-ethoxymethyl)-5H-pyrrolo[2,3-b]pyrazin-7-yl]-2,2-dimethyl-propan-1-one (270 mg, 0.599 mmol) in 7 mL of THF was added 5.99 mL (5.99 mmol) of 1.0 M TBAF in THF. Heated the mixture to 85° C. for 2 h. The reaction was quenched with 5 mL acetone and 15 mL of saturated aqueous NaHCO₃ then diluted with ethyl acetate and water and partitioned. The organic phase was washed with brine, dried over MgSO₄, filtered, and concentrated. Recrystallization from dichloromethane afforded 153.3 mg (80% yield) of 1-[2-(1,3-Dihydro-isoindol-2-yl)-H-pyrrolo[2,3-b]pyrazin-7-yl]-2,2-dimethyl-propan-1-one as a white solid.

Prepared above:

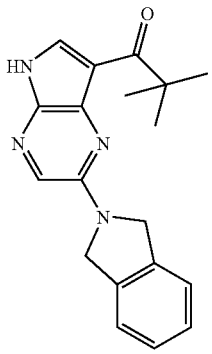

Product isolated as a white solid, 0.1533 g, 80% yield. 1H-NMR (CDCl3, 400 MHz): 12.48 (s, 1H), 8.18 (s, 1H), 7.76 (s, 1H), 7.37 (m, 4H), 4.93 (s, 4H), 1.54 ppm (s, 9H). 13C-NMR (CDCl3, 101 MHz): 200.6, 150.1, 137.6, 136.1, 135.6, 132.1, 127.7, 124.8, 123.2, 113.7, 53.1, 43.2, 26.0 ppm. MP=292-293° C. IR (KBr): 1652, 1559, 1500, 1485, 1465, 1399, 1235, 951 cm-1. MS (E/I): 321 (M+H).

1-[2-(2,3-Dihydro-indol-1-yl)-5H-pyrrolo[2,3-b]pyrazin-7-yl]-2,2-dimethyl-propan-1-one Following above Example:

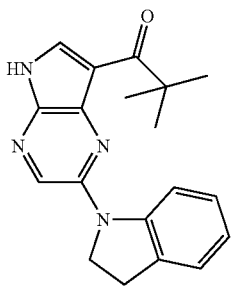

Product isolated as a bright yellow solid, 0.1026 g, 75% yield. 1H-NMR (CDCl3, 400 MHz): 8.28 (s, 1H), 8.14 (s, 1H), 7.3-6.9 (m, 4H), 4.20 (t, 2H), 3.28 (t, 2H), 1.56 ppm (s, 9H). 13C-NMR (CDCl3, 76 MHz): 148.6, 144.5, 136.4, 135.3, 131.4, 127.2, 126.6, 124.9, 120.9, 115.6, 112.4, 50.1, 43.7, 27.8, 26.0 ppm. MP=216-217° C. IR (KBr): 3428, 1641, 1553, 1492, 1455, 1401, 1384, 472, 401 cm-1. MS (E/I): 321(M+H).

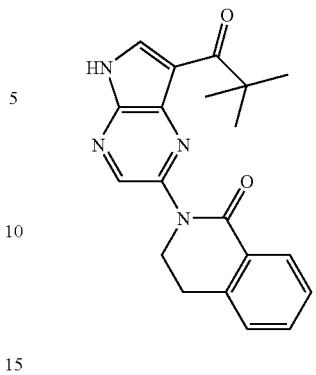

2-[7-(2,2-Dimethyl-propionyl)-5H-pyrrolo[2,3-b]pyrazin-2-yl]-3,4-dihydro-2H-isoquinolin-1-one Product isolated as a yellow foam, 0.0606 g, 29% yield. 1H-NMR (CDCl3, 400 MHz): 10.87 (s, 1H), 9.08 (s, 1H), 8.40 (s, 1H), 8.24 (m, 1H), 7.6-7.2 (m, 3H), 4.40 (t, 2H, J=6.1 Hz), 3.22 (t, 2H, J=6.4 Hz) 1.49 ppm (s, 9H). 13C-NMR (CDCl3, 76 MHz): 201.6, 165.1, 146.9, 139.1, 138.6, 136.6, 135.4, 132.8, 132.6, 129.3, 129.0, 127.3, 127.2, 115.7, 46.2, 43.7, 28.5, 26.1 ppm. MP=113-115° C. IR (KBr): 3427, 2920, 1646, 1384, 1249, 1079, 468, 443, 405 cm-1. MS (E/I): 349 (M+H)

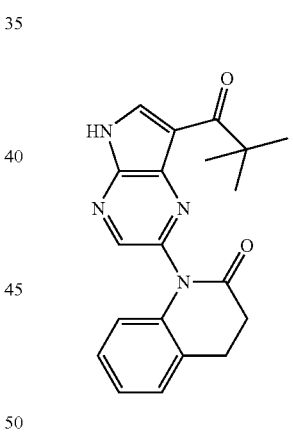

1-[7-(2,2-Dimethyl-propionyl)-5H-pyrrolo[2,3-b]pyrazin-2-yl]-3,4-dihydro-1H-quinolin-2-one Product isolated as a yellow solid, 0.1626 g, 87% yield. 1H-NMR (CDCl3, 400 MHz): 8.31 (s, 1H), 8.29 (s, 1H), 7.25 (m, 1H), 7.01 (m, 2H), 6.35 (m, 1H), 3.14 (t, 2H), 2.91 (t, 2H) 1.35 ppm (s, 9H). 13C-NMR (CDCl3, 76 MHz): 201.3, 171.6, 143.2, 140.7, 140.3, 137.9, 137.8, 135.0, 128.0, 127.2, 125.6, 123.6, 116.9, 115.6, 43.8, 32.2, 26.2, 25.6 ppm. MP=257-259° C. IR (KBr): 3430, 2963, 1695, 1684, 1670, 1653, 1636, 1604, 1495, 1457, 1384, 1364, 1336, 1311 cm-1. MS (E/I): 349 (M+H)

2-[7-(2,2-Dimethyl-propionyl)-5H-pyrrolo[2,3-b]pyrazin-2-yl]-2,3-dihydro-isoindol-1-one

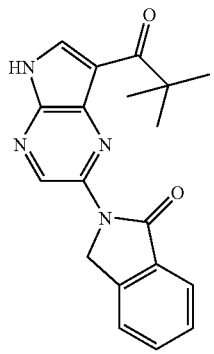

Product isolated as an off-white solid, 0.081 g, 49% yield. 1H-NMR (CDCl3, 400 MHz): 12.95 (s, 1H), 9.5 (s, 1H), 8.5 (s, 1H), 7.9-7.5 (m, 4H), 5.2 (s, 2H), 1.47 ppm (s, 9H). 13C-NMR (CDCl3, 76 MHz): 199.9, 166.6, 144.0, 141.5, 138.7, 138.0, 132.7, 131.9, 131.6, 129.2, 128.2, 123.8, 123.4, 113.7, 49.5, 42.9, 25.8 ppm. MP=287-289° C. IR (KBr): 3427, 1706, 1653, 1494, 1470, 1400, 1374, 1345, 1301, 1245 cm-1. MS (E/I): 335 (M+H)

Example 10

Preparation of Pyrrolopyrazine C-5 Amines

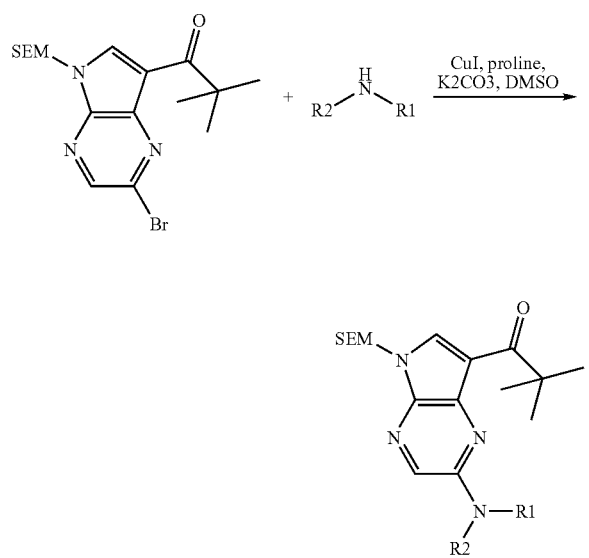

1-[2-(1,3-Dihydro-isoindol-2-yl)-5-(2-trimethylsilanyl-ethoxymethyl)-5H-pyrrolo[2,3-b]pyrazin-7-yl]-2,2-dimethyl-propan-1-one MS (E/I): 451 (M+H)

1-[2-(2,3-Dihydro-indol-1-yl)-5-(2-trimethylsilanyl-ethoxymethyl)-5H-pyrrolo[2,3-b]pyrazin-7-yl]-2,2-dimethyl-propan-1-one MS (E/I): 451 (M+H)

Example 11

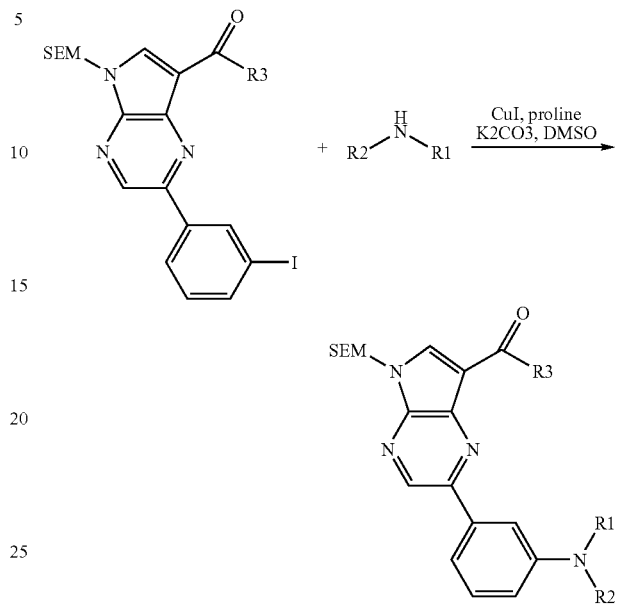

4-{3-[7-(2,2-Dimethyl-propionyl)-5-(2-trimethylsilanyl-ethoxymethyl)-5H-pyrrolo[2,3-b]pyrazin-2-yl]-phenyl}-1,5-dimethyl-piperazin-2-one 1H-NMR (CDCl3, 400 MHz): 8.83 (s, 1H), 8.46 (s, 1H), 7.82 (m, 1H), 7.48 (m, 1H), 6.98 (m, 1H), 5.74 (s, 2H), 4.15 (m, 1H), 3.88 (m, 2H), 3.65 (t, 2H), 3.14 (s, 2H), 3.10 (s, 3H), 1.63 (s, 9H), 1.4 (d, 3H), 0.98 (t, 2H), 0.01 ppm (s, 9H).

3-Methyl-4-{3-[7-(1-methyl-cyclohexanecarbonyl)-5-(2-trimethylsilanyl-ethoxymethyl)-5H-pyrrolo[2,3-b]pyrazin-2-yl]-phenyl}-piperazin-2-one 1H-NMR (CDCl3, 400 MHz): 8.83 (s, 1H), 8.45 (s, 1H), 7.81 (s, 1H), 7.58 (d, 1H), 7.47 (t, 1H), 7.01 (d, 1H), 6.37 (br s, 1H), 5.74 (s, 2H), 4.52 (q, 1H), 3.76 (m, 2H), 3.65 (t, 2H), 3.52 (m, 2H), 2.56 (m, 2H), 1.7-1.4 (m, 11H), 1.54 (d, 3H), 0.97 (t, 2H), 0.01 ppm (s, 9H).

[2-(3-Cyclopentylamino-phenyl)-5-(2-trimethylsilanyl-ethoxymethyl)-5H-pyrrolo[2,3-b]pyrazin-7-yl]-(1-methyl-cyclohexyl)-methanone: MS (E/I): 533 (M+H).

1-[2-(3-Cyclopentylamino-phenyl)-5-(2-trimethylsilanyl-ethoxymethyl)-5H-pyrrolo[2,3-b]pyrazin-7-yl]-2,2-dimethyl-propan-1-one: MS (E/I): 493 (M+H).

1-[2-[3-(2-Hydroxy-cyclopentylamino)-phenyl]-5-(2-trimethylsilanyl-ethoxymethyl)-5H-pyrrolo[2,3-b]pyrazin-7-yl]-2,2-dimethyl-propan-1-one: MS (E/I): 509 (M+H).

2,2-Dimethyl-1-[2-[3-(1-methyl-pyrrolidin-3-ylamino)-phenyl]-5-(2-trimethylsilanyl-ethoxymethyl)-5H-pyrrolo[2,3-b]pyrazin-7-yl]-propan-1-one: MS (E/I): 508 (M+H).

2,2-Dimethyl-1-[2-[3-(tetrahydro-furan-3-ylamino)-phenyl]-5-(2-trimethylsilanyl-ethoxymethyl)-5H-pyrrolo[2,3-b]pyrazin-7-yl]-propan-1-one: MS (E/I): 495 (M+H).

1-[2-[3-(1-Methanesulfonyl-piperidin-4-ylamino)-phenyl]-5-(2-trimethylsilanyl-ethoxymethyl)-5H-pyrrolo[2,3-b]pyrazin-7-yl]-2,2-dimethyl-propan-1-one: MS (E/I): 586 (M+H).

1-[2-[3-((cis)-2-Hydroxy-cyclopentylamino)-phenyl]-5-(2-trimethylsilanyl-ethoxymethyl)-5H-pyrrolo[2,3-b]pyrazin-7-yl]-2,2-dimethyl-propan-1-one: MS (E/I): 509 (M+H).

1-[2-[3-((trans)-2-Hydroxy-cyclopentylamino)-phenyl]-5-(2-trimethylsilanyl-ethoxymethyl)-5H-pyrrolo[2,3-b]pyrazin-7-yl]-2,2-dimethyl-propan-1-one: MS (E/I): 509 (M+H).

Example 12

Preparation of Pyrrolopyrazine C-5 Amides

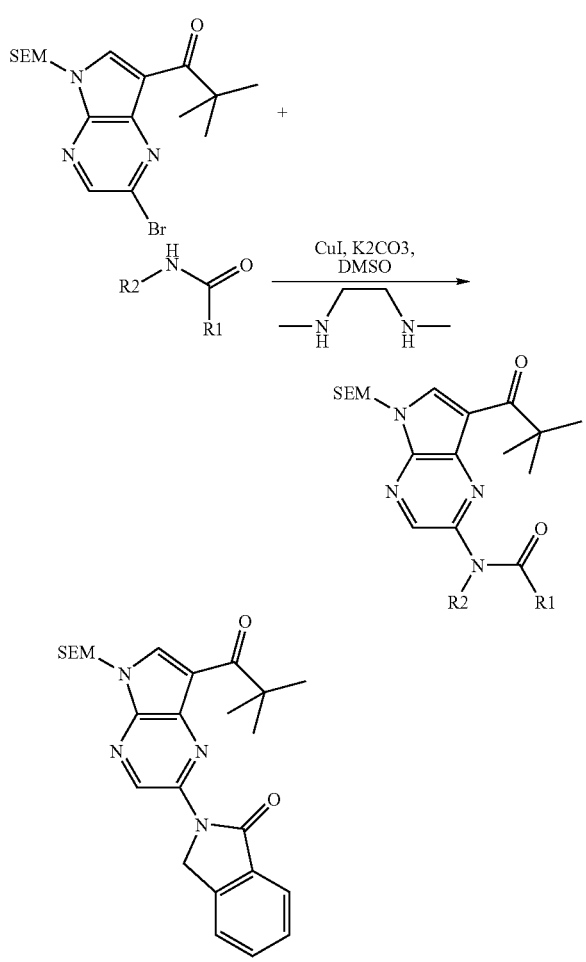

2-[7-(2,2-Dimethyl-propionyl)-5-(2-trimethylsilanyl-ethoxymethyl)-5H-pyrrolo[2,3-b]pyrazin-2-yl]-2,3-dihydro-isoindol-1-one Toluene was added to a mixture of 1-[2-Bromo-5-(2-trimethylsilanyl-ethoxymethyl)-5H-pyrrolo[2,3-b]pyrazin-7-yl]-2,2-dimethyl-propan-1-one (0.250 g, 0.606 mmol), 2,3-Dihydro-isoindol-1-one (0.097 g, 0.727 mmol), copper iodide (11.6 mg, 0.061 mmol), and potassium carbonate (0.168 g, 1.212 mmol) under argon. Dimethyl ethylenediamine (0.013 mL; 0.011 g, 0.121 mmol) was subsequently added and the reaction was stirred for 16 h at 110° C. The reaction was diluted with ethyl acetate and filtered through a silica plug before being concentrated in vacuo. Silica gel chromatography (0->25% EtOAc/hexanes over 30 minutes) afforded 0.2206 g (78% yield) of 2-[7-(2,2-Dimethyl-propionyl)-5-(2-trimethylsilanyl-ethoxymethyl)-5H-pyrrolo[2,3-b]pyrazin-2-yl]-2,3-dihydro-isoindol-1-one. MS (E/I): 465 (M+H)

2-[7-(2,2-Dimethyl-propionyl)-5-(2-trimethylsilanyl-ethoxymethyl)-5H-pyrrolo[2,3-b]pyrazin-2-yl]-3,4-dihydro-2H-isoquinolin-1-one. MS (E/I): 479 (M+H)

1-[7-(2,2-Dimethyl-propionyl)-5-(2-trimethylsilanyl-ethoxymethyl)-5H-pyrrolo[2,3-b]pyrazin-2-yl]-3,4-dihydro-1H-quinolin-2-one. MS (E/I): 479 (M+H)

Example 13

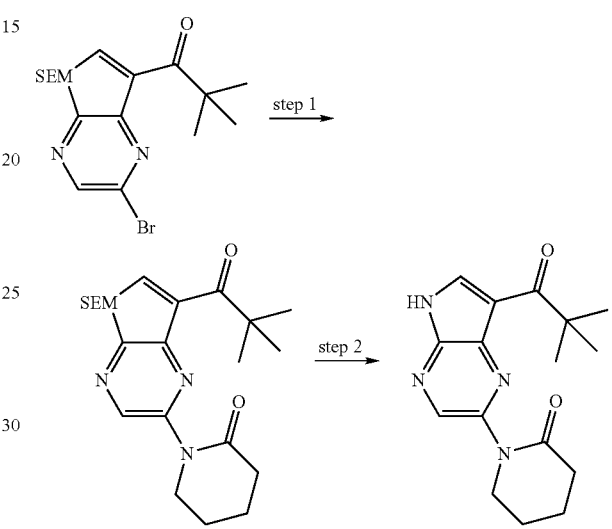

1-[7-(2,2-Dimethyl-propionyl)-5H-pyrrolo[2,3-b]pyrazin-2-yl]-piperidin-2-one. General procedures described in these Examples were followed but in step 2, the deprotection of SEM group was carried out at refluxing temperature of EtOH for 6 h. $^1$H NMR (CDCl$_3$): δ 8.85 (s, 1H), 8.36 (d, J=3 Hz, 2H), 4.08-4.05 (m, 2H), 2.72-2.69 (m, 2H), 2.07-2.02 (m, 4H), 1.49 (s, 9H); MS [M+H]$^+$: 301.

Example 14

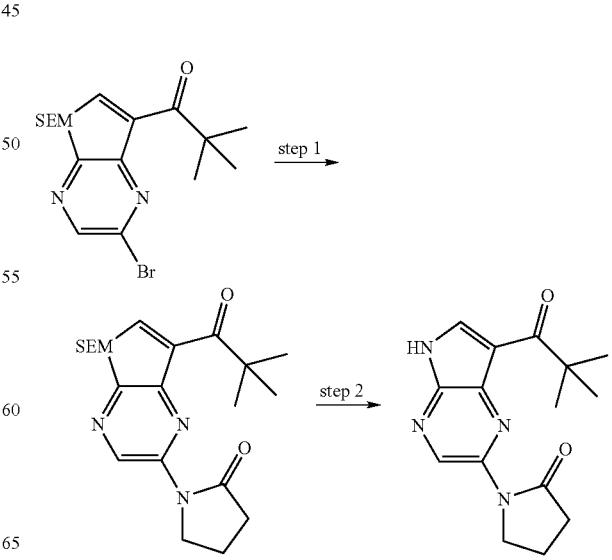

1-[7-(2,2-Dimethyl-propionyl)-5H-pyrrolo[2,3-b]pyrazin-2-yl]-pyrrolidin-2-one. General procedures described in these Examples were followed except in step 2, the deprotection of SEM group was carried out at refluxing temperature of EtOH overnight. $^1$H NMR (CDCl$_3$): δ 11.32 (s, 1H), 9.51 (s, 1H), 8.42 (d, J=3.4 Hz, 1H), 4.22 (t, J=6 Hz, 2H), 2.76 (t, J=12 Hz, 2H), 2.26 (quin, J=7.6 Hz, 2H), 1.49 (s, 9H); MS [M+H]$^+$: 287.

Example 15

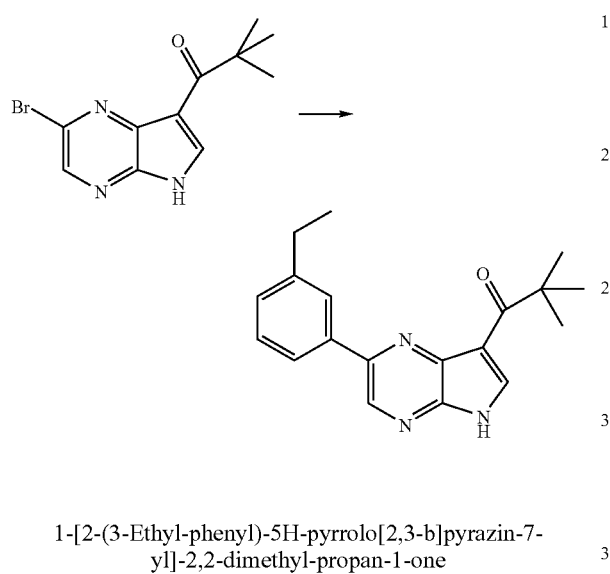

1-[2-(3-Ethyl-phenyl)-5H-pyrrolo[2,3-b]pyrazin-7-yl]-2,2-dimethyl-propan-1-one

A microwave tube was charged with 1-(2-bromo-5H-pyrrolo[2,3-b]pyrazin-7-yl)-2,2-dimethyl-propan-1-one (152 mg, 0.54 mmol), 3-ethylphenylboronic acid (89 mg, 0.59 mmol), [1,1'-bis(diphenylphosphino)ferrocene]dichloro-palladium(II) (35 mg, 0.042 mmol), and K$_2$CO$_3$ (186 mg, 1.34 mmol). Dioxane (4 ml) and water (1 ml) were added, and the tube was microwaved at 150° C. for 45 min. The reaction mixture was filtered through a plug of celite. The filtrate was collected and partitioned between EtOAc/water. The organic layers were collected, dried over MgSO$_4$, filtered, and concentrated giving a dark brown solid. The crude product was purified by silica gel chromatography using 20-50% EtOAc in hexanes as eluant provided 82 mg (50%) of 1-[2-(3-ethyl-phenyl)-5H-pyrrolo[2,3-b]pyrazin-7-yl]-2,2-dimethyl-propan-1-one as a yellow solid. MP 199-200.1° C., M+H=308.

Example 16

(1-Methyl-cyclohexyl)-(2-thiophen-2-yl-5H-pyrrolo[2,3-b]pyrazin-7-yl)-methanone (1-Methyl-cyclohexyl)-(2-thiophen-2-yl-5H-pyrrolo[2,3-b]pyrazin-7-yl)-methanone was prepared starting from (2-bromo-5H-pyrrolo[2,3-b]pyrazin-7-yl)-(1-methyl-cyclohexyl)-methanone and thiophene-2-boronic acid following general procedures described in these Examples. MP 224-225° C., M+H=326.

Example 17

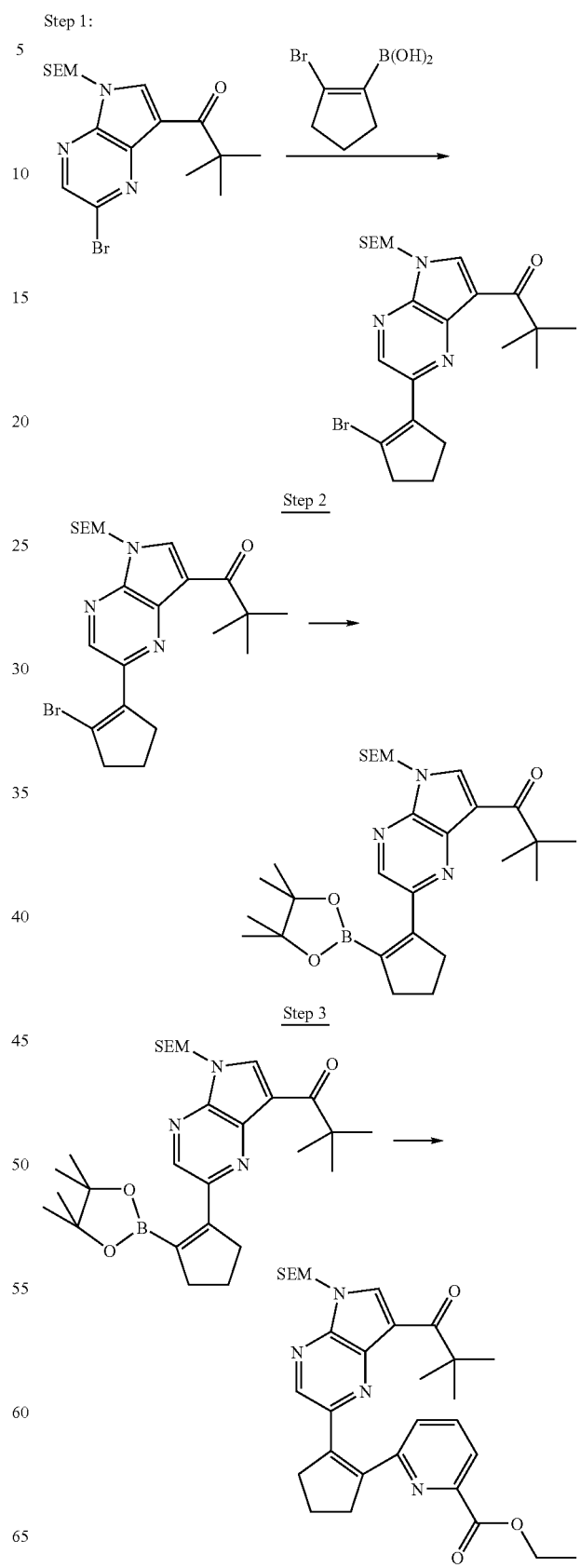

121
-continued
Step 4

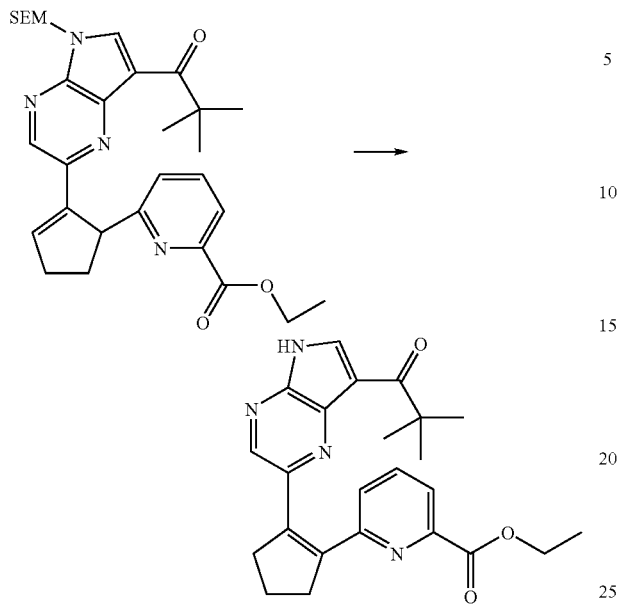

6-{2-[7-(2,2-Dimethyl-propionyl)-5H-pyrrolo[2,3-b]pyrazin-2-yl]-cyclopent-1-enyl}-pyridine-2-carboxylic acid ethyl ester was obtained by the following sequence of reactions.

Step 1: 2-Bromocyclopent-1-enyl 1-boronic acid (3.5 g, 18 mmol, obtained according to WO 2005/037793) was added to a mixture of 1-[2-bromo-5-(2-trimethylsilanyl-ethoxymethyl)-5H-pyrrolo[2,3-b]pyrazin-7-yl]-2,2-dimethyl-propan-1-one (3.30 g, 8.0 mmol), toluene (35 mL), ethanol (15 mL), potassium carbonate (4.2 g, 30 mmol) and tetrakis[triphenylphosphine]palladium (0) (462 mg, 0.40 mmol) under an atmosphere of Argon. The suspension was heated to reflux for 16 hours. It was allowed to cool and partitioned between water (40 mL) and ethyl acetate (4×50 mL). The combined organic layers was stored over anhydrous sodium sulfate. A waxy solid was obtained (1.65 g) following silica gel chromatography (eluant: 5 to 20% EtOAc in hexanes) with spectroscopic properties consistent with the desired alkenylbromide.

Step 2: The alkenyl bromide of step 1 (176 mg, 0.37 mmol) was dissolved in 1,4-dioxane (7 mL) then treated with potassium acetate (110 mg, 1.1 mmol) and palladium (II) (dppf)Cl$_2$ (15 mg, 0.02 mmol) under an Argon atmosphere. Bis(pinacol) diboron (100 mg, 0.39 mmol, CombiBlocks) was added and the mixture was heated to 90° C. for 3 days.

Step 3: At which time, the dark suspension was treated with ethyl 6-chloropyridine 2-carboxylic acid (76 mg, 0.41 mmol, CombiBlocks), potassium carbonate (102 mg, 0.74 mmol) and water (0.2 mL). The mixture was heated to 75° C. for 40 hours. Upon cooling, the mixture was partitioned between dilute aqueous acetic acid and ethyl acetate. The desired pyridine (45 mg) was obtained following silica gel chromatography (eluant: 10 to 30% ethyl acetate-hexanes).

Step 4: The pyridine (41 mg, 0.073 mmol, obtained from step 3) was dissolved in tetrahydrofuran (1.5 mL) and treated with tetrabutylammonium fluoride (0.15 mL, 1 M THF solution) in a sealed tube and heated to 85° C. for 1.5 hours. The title compound was obtained as a foam (5 mg) following silica gel chromatography (eluant: 10 to 80% ethyl acetate-hexanes): m.p. foam; MS m/z 419 (M+H).

122

1-{2-[2-(3-Methoxy-phenyl)-cyclopent-1-enyl]-5H-pyrrolo[2,3-b]pyrazin-7-yl}-2,2-dimethyl-propan-1-one was obtained by replacing bis(pinacol)diboron with 3-methoxyphenylboronic acid in step 2 and omitting step 3: m.p. foam; MS m/z 376 (M$^{+H}$).

2,2-Dimethyl-1-[2-(2-phenyl-cyclopent-1-enyl)-5H-pyrrolo[2,3-b]pyrazin-7-yl]-propan-1-one was obtained by replacing bis(pinacol)diboron with phenylboronic acid in step 2 and omitting step 3: m.p. 207-209° C.; MS m/z 346 (M$^{+H}$).

5-{2-[7-(2,2-Dimethyl-propionyl)-5H-pyrrolo[2,3-b]pyrazin-2-yl]-cyclopent-1-enyl}-1H-indole-2-carboxylic acid ethyl ester was obtained by replacing ethyl 6-chloropyridine 2-carboxylic acid with ethyl 5-bromoindole 2-carboxylic acid in step 3: m.p. 278-280° C.; MS m/z 457 (M$^{+H}$).

Example 18

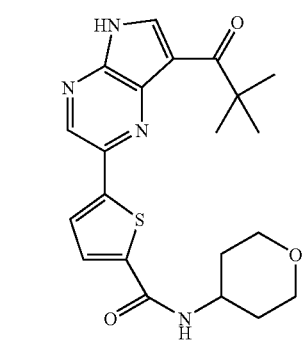

Step 1

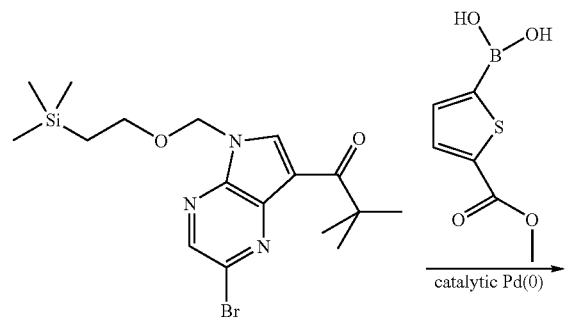

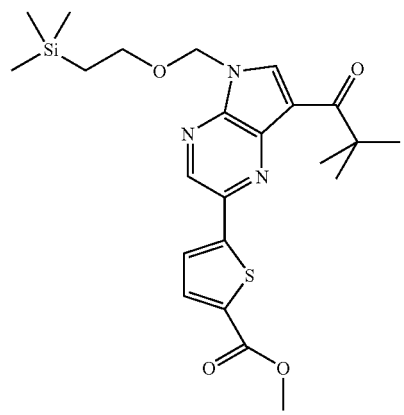

-continued

Step 2

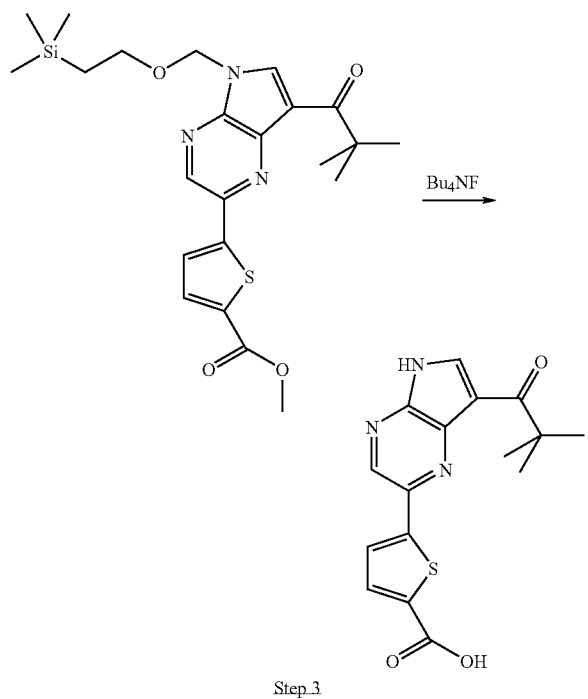

Step 3

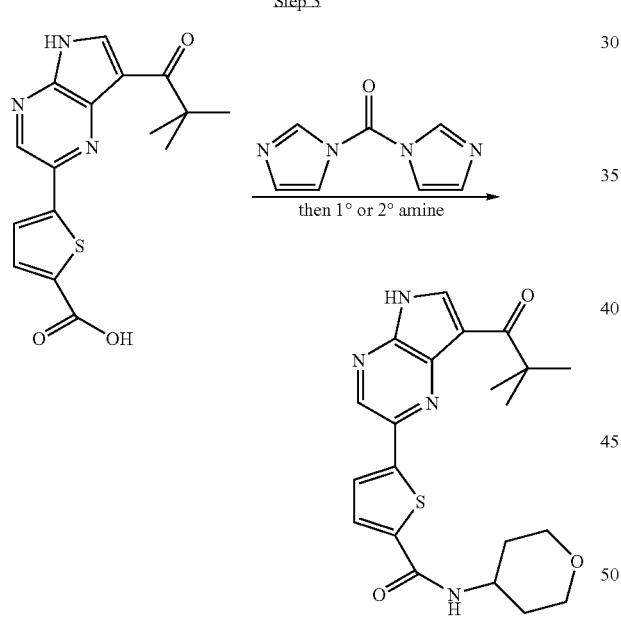

Step 1: 2-Thiopheneboronic acid 5-carboxylic acid methyl ester (390 mg, 2.1 mmol, obtained according from CiVenti Chem) was added to a mixture of 1-[2-bromo-5-(2-trimethylsilanyl-ethoxymethyl)-5H-pyrrolo[2,3-b]pyrazin-7-yl]-2,2-dimethyl-propan-1-one (0.8 g, 1.9 mmol), 1,4-dioxane (12 mL), methanol (2 mL), water (2 mL), cesium carbonate (1.23 g, 3.8 mmol), and Pd(dppf)2 (78 mg, 0.1 mmol) and heated to reflux for 18 hours. A white powder was isolated by silica gel chromatography (eluant: 5 to 40% ethyl acetate) and had spectroscopic properties consistent with the desired ester.

Step 2: The ester (93 mg, 0.2 mmol) was dissolved in tetrahydrofuran (1.5 mL) and tetrabutylammonium fluoride (1 mL, 1 mmol, 1 M THF solution) and the mixture heated to 80° C. in a sealed vessel for 2 hours. The mixture was then treated with aqueous lithium hydroxide (35 mg, 1.5 mmol, 1 M) and stirred 20 hours. The mixture was partitioned between 5% aqueous acetic acid and ethyl acetate (3×30 mL). The combined organic layers were stored over anhydrous sodium sulfate. The desired acid (approx. 150 mg, 0.2 mmol) was obtained as a mixture with tetrabutylammonium salts and used in the next step.

Step 3: The acid (0.2 mmol) was dissolved in N,N-dimethylformamide (3 mL) and vacuum purged with Argon at ambient temperature. Carbonyl diimidazole (35 mg, 0.22 mmol) was added and the bubbling solution was stirred vigorously for 7 minutes. 4-Aminotetrahydropyran (70 mg, 0.69 mmol) was added as a DMF solution (1.5 mL) and the resulting solution was heated to 60° C. After 3.5 hours, the volatiles were removed by vacuum distillation with the pot temperature increased to 70° C. The pot residue was cooled and partitioned between water and ethyl actete (4×25 mL). The combined organic extracts were stored over anhydrous sodium sulfate. 5-[7-(2,2-Dimethyl-propionyl)-5H-pyrrolo[2,3-b]pyrazin-2-yl]-thiophene-2-carboxylic acid (tetrahydro-pyran-4-yl)-amide was obtained as a solid (25 mg) following silica gel chromatography (eluant: 0 to 5% ethanol in ethyl acetate): mp>300° C.; ESMS m/z 413 (M$^{+1}$) for MW of 412.

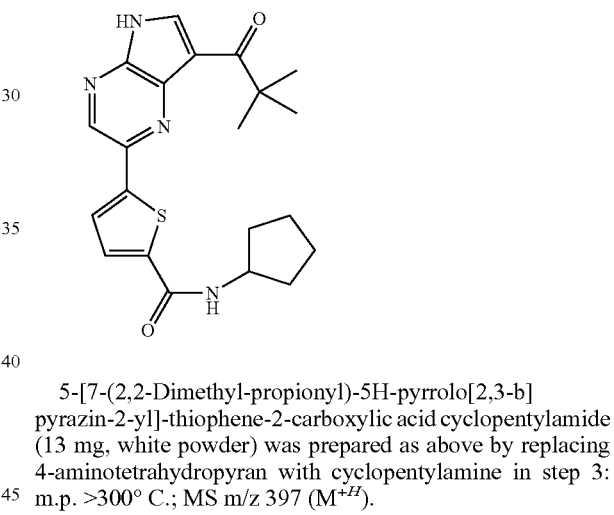

5-[7-(2,2-Dimethyl-propionyl)-5H-pyrrolo[2,3-b]pyrazin-2-yl]-thiophene-2-carboxylic acid cyclopentylamide (13 mg, white powder) was prepared as above by replacing 4-aminotetrahydropyran with cyclopentylamine in step 3: m.p. >300° C.; MS m/z 397 (M$^{+H}$).

Example 19

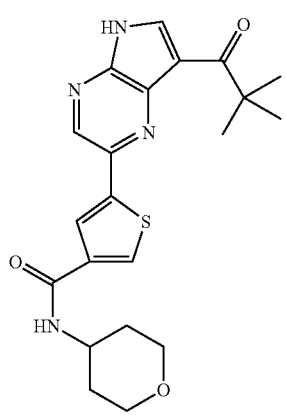

5-[7-(2,2-Dimethyl-propionyl)-5H-pyrrolo[2,3-b]pyrazin-2-yl]-thiophene-3-carboxylic acid (tetrahydro-pyran-4-yl)-amide was prepared by replacing 2-thiopheneboronic acid 5-carboxylic acid methyl ester in step 1 with 5-(4,4,5,5-Tetramethyl-[1,3,2]dioxaborolan-2-yl)-thiophene-3-carboxylic acid ethyl ester, which in-turn was generated from ethyl 2-bromothiophene 4-carboxylate (1.15 g, 4.9 mmol) according to WO 2007/145921, dissolved in anhydrous 1,4-dioxane (25 mL), treated with potassium acetate (1.44 g, 14.7 mmol) and dichloro[1,1'-bis(diphenylphosphino)ferrocene]palladium (II) dichloromethane adduct (Strem, 200 mg, 0.25 mmol) and then vacuum purged with nitrogen. After 3 flushes, bis(pinacol) diboron (Combi-Blocks, 1.31 g, 5.1 mmol) was added and the rust-maroon suspension was heated to 90° C. for 5 hours. The title compound was obtained as powder: m.p. 265-267° C.; MS m/z 413 ($M^{+H}$).

Example 20

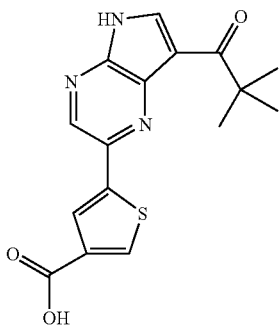

5-[7-(2,2-Dimethyl-propionyl)-5H-pyrrolo[2,3-b]pyrazin-2-yl]-thiophene-3-carboxylic acid was obtained replacing 2-thiopheneboronic acid 5-carboxylic acid methyl ester in step 1 with 5-(4,4,5,5-Tetramethyl-[1,3,2]dioxaborolan-2-yl)-thiophene-3-carboxylic acid ethyl ester, which in-turn was generated from ethyl 2-bromothiophene 4-carboxylate (1.15 g, 4.9 mmol) according to WO 2007/145921, dissolved in anhydrous 1,4-dioxane (25 mL), treated with potassium acetate (1.44 g, 14.7 mmol) and dichloro[1,1'-bis(diphenylphosphino)ferrocene]palladium (II) dichloromethane adduct (Strem, 200 mg, 0.25 mmol) and then vacuum purged with nitrogen. After 3 flushes, bis(pinacol) diboron (Combi-Blocks, 1.31 g, 5.1 mmol) was added and the rust-maroon suspension was heated to 90° C. for 5 hours. Step 3 was not conducted. The title compound was obtained as powder: m.p. >300° C.; MS m/z 330 ($M^{+H}$).

Example 21

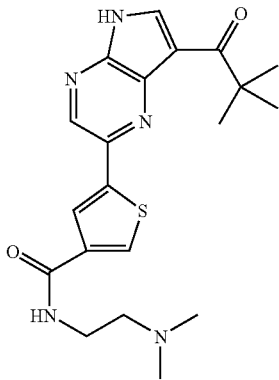

5-[7-(2,2-Dimethyl-propionyl)-5H-pyrrolo[2,3-b]pyrazin-2-yl]-thiophene-3-carboxylic acid (2-dimethylamino-ethyl)-amide was prepared by replacing 2-thiopheneboronic acid 5-carboxylic acid methyl ester in step 1 with 5-(4,4,5,5-Tetramethyl-[1,3,2]dioxaborolan-2-yl)-thiophene-3-carboxylic acid ethyl ester, which in-turn was generated from ethyl 2-bromothiophene 4-carboxylate (1.15 g, 4.9 mmol) according to WO 2007/145921, dissolved in anhydrous 1,4-dioxane (25 mL), treated with potassium acetate (1.44 g, 14.7 mmol) and dichloro[1,1'-bis(diphenylphosphino)ferrocene]palladium (II) dichloromethane adduct (Strem, 200 mg, 0.25 mmol) and then vacuum purged with nitrogen. After 3 flushes, bis(pinacol) diboron (Combi-Blocks, 1.31 g, 5.1 mmol) was added and the rust-maroon suspension was heated to 90° C. for 5 hours. The title compound was obtained as a solid by replacing 4-aminotetrahydropyran with N,N-dimethylethylene diamine in step 3: m.p. 229-231° C.; MS m/z 400 ($M^{+H}$).

Example 22

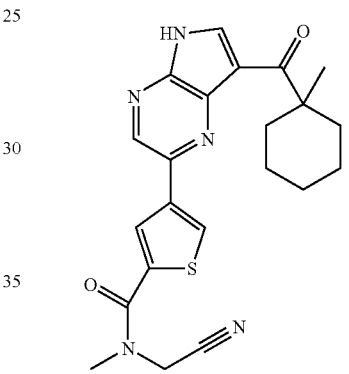

Step 1

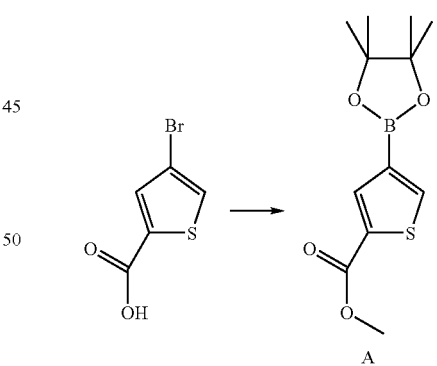

Step 2

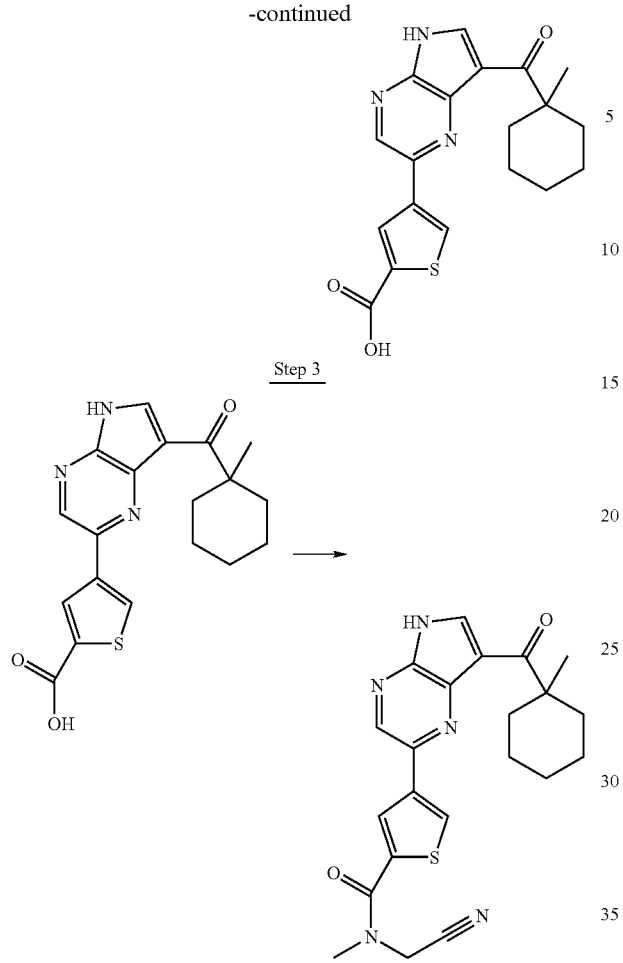

4-[7-(1-Methyl-cyclohexanecarbonyl)-5H-pyrrolo[2,3-b]pyrazin-2-yl]-thiophene-2-carboxylic acid cyanomethyl-methyl-amide was prepared by:

Step 1: 4-bromothiophene 2-carboxlic acid (10 g, 48 mmol, Frontier Chemical) was dissolved in methanol (20 mL) and dichloromethane (100 mL) at ambient temperature. Trimethylsilyl diazomethane (24 mL, 2 M hexane solution from Aldrich) was added over 7 minutes. The solution was stirred for 1.5 hours and quenched with 10% aqueous acetic acid. The mixture was extracted with chloroform and stored over anhydrous sodium sulfate. The desired ester (10.2 g) was obtained following removal of the volatiles as a tan oil. The ester (2.4 g, 11 mmol) was dissolved in anhydrous 1,4-dioxane (100 mL), treated with potassium acetate (2.94 g, 30 mmol) and dichloro[1,1'-bis(diphenylphosphino)ferrocene] palladium (II) dichloromethane adduct (Strem, 409 mg, 0.50 mmol) and then vacuum purged with nitrogen. After 3 flushes, bis(pinacol) diboron (Combi-Blocks, 2.72 g, 10.7 mmol) was added and the rust-maroon mixture was heated to 90° C. for 2.8 hours.

Step 2: The immediate A was used without purification and treated with (2-bromo-5H-pyrrolo[2,3-b]pyrazin-7-yl)-(1-methyl-cyclohexyl)-methanone (3.23 g, 10.0 mmol) and potassium carbonate (2.1 g, 15 mmol, dissolved in 8 mL of water). The mixture heated to reflux for 44 hours. It was cooled and partitioned between 5% aqueous acetic acid and ethyl acetate (4×100 mL). The combined organic extracts were stored over anhydrous sodium sulfate. The desired ester was purified by silica gel chromatography (eluant: 20 to 60% ethyl acetate in hexanes) and obtained as a white powder (1.27 g). The white powder has spectroscopic properties consistent with the desired ester. It (1.27 g, 3.3 mmol) was dissolved in tetrahydrofuran (25 mL) and methanol (1 mL). At ambient temperature, the solution was treated with lithium hydroxide (200 mg, 8.3 mmol, dissolved in 10 mL of water) and stirred for 18 hours. A tan solid formed upon the addition of potassium bisulfate (0.2 M aqueous) which was collected and dried.

Step 3: The acid (150 mg, 0.41 mmol) was dissolved in N,N-dimethylformamide (5 mL) and vacuum purged with Argon at ambient temperature. Carbonyl diimidazole (70 mg, 0.43 mmol) was added and the bubbling solution was stirred vigorously for 10 minutes. Methylamino-acetonitrile hydrochloride salt (65 mg, 0.62 mmol) and diiso-propyl ethylamine (0.2 mL, 1.23 mmol) were added and the resulting solution was heated to 40° C. After 13 hours, the mixture was then heated to 70° C. for 5 hours and then the volatiles were removed by vacuum distillation. The pot residue was cooled and partitioned between water and ethyl acetate (4×25 mL). The combined organic extracts were stored over anhydrous sodium sulfate. The desired amide (19 mg) was purified by silica gel chromatography (eluant: 20 to 100% ethyl acetate in hexanes) and the title compound was obtained as powder: m.p. 191-193° C.; MS m/z 422 ($M^{+H}$).

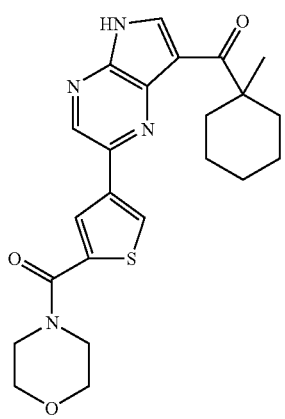

Methyl-cyclohexyl)-{2-[5-(morpholine-4-carbonyl)-thiophen-3-yl]-5H-pyrrolo[2,3-b]pyrazin-7-yl}-methanone was obtained by replacing methylamino-acetonitrile hydrochloride salt with morpholine while heating to 70° C. was omitted in step 3: m.p. 260-262° C.; MS m/z 439 ($M^{+H}$).

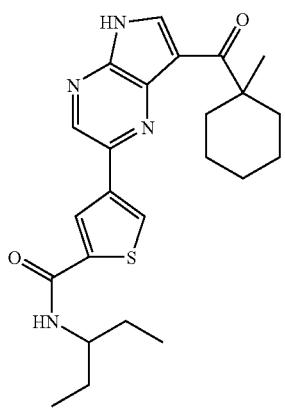

4-[7-(1-Methyl-cyclohexanecarbonyl)-5H-pyrrolo[2,3-b]pyrazin-2-yl]-thiophene-2-carboxylic acid (1-ethyl-propyl)- amide was obtained by replacing methylamino-acetonitrile hydrochloride salt with 3-pentylamine while heating to 70° C. was omitted in step 3: m.p. 273-275° C.; MS m/z 439 ($M^{+H}$).

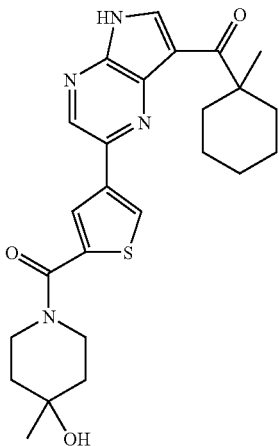

{2-[5-(4-Hydroxy-4-methyl-piperidine-1-carbonyl)-thiophen-3-yl]-5H-pyrrolo[2,3-b]pyrazin-7-yl}-(1-methyl-cyclohexyl)-methanone was obtained by replacing methylamino-acetonitrile hydrochloride salt with 4-hydroxy-4-methylpiperidine hydrochloride salt while heating to 70° C. was omitted in step 3: m.p. 257-259° C.; MS m/z 467 ($M^{+H}$).

Example 23

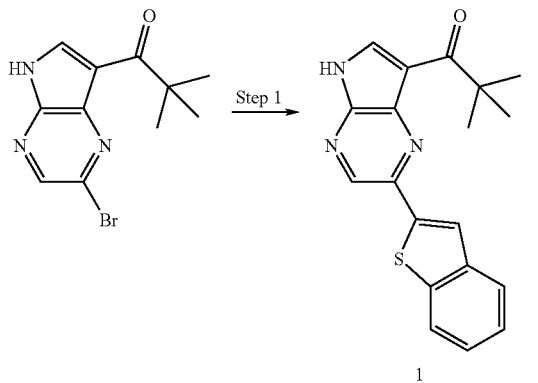

Step 1—A mixture of 1-(2-bromo-5H-pyrrolo[2,3-b]pyrazin-7-yl)-2,2-dimethyl-propan-1-one (0.1 g, 0.354 mmol), benzothiophene-2-boronic acid (0.095 g, 0.532 mmol) and tetrakis(triphenylphsophine)palladium(0) (0.041 g, 35 μmol) in 3.25 mL of 1,4-dioxane and 0.35 mL of 2M aqueous $K_2CO_3$ was stirred at 95° C. overnight before being cooled to RT and evaporated. The residue was adsorbed onto silica and purified by $SiO_2$ chromatography (hexanes/AcOEt 30% EtOAc) to give 0.015 g of 1: 1-(2-benzo[b]thiophen-2-yl-5H-pyrrolo[2,3-b]pyrazin-7-yl)-2,2-dimethyl-propan-1-one (13% yield)

2,2-Dimethyl-1-[2-(5-phenyl-thiophen-2-yl)-5H-pyrrolo[2,3-b]pyrazin-7-yl]-propan-1-one was prepared following the same procedure using 5-phenyl-2-thienyboronic acid (29% yield).

2,2-Dimethyl-1-[2-(1-methyl-1H-indol-2-yl)-5H-pyrrolo[2,3-b]pyrazin-7-yl]-propan-1-one was prepared following the same procedure but using N-methylindole-2-boronic acid (31% yield).

2,2-Dimethyl-1-{2-[1-(toluene-4-sulfonyl)-1H-pyrrolo[2,3-b]pyridin-3-yl]-5H-pyrrolo[2,3-b]pyrazin-7-yl}-propan-1-one was prepared using a similar procedure using 3-(4,4,5,5-tetramethyl-[1,3,2]dioxaborolan-2-yl)-1H-pyrrolo[2,3-b]pyridine as starting material (24% yield). In this reaction 1 equivalent of boronic ester and 2 equivalents of $K_2CO_3$ were used.

2-[7-(2,2-Dimethyl-propionyl)-5H-pyrrolo[2,3-b]pyrazin-2-yl]-indole-1-carboxylic acid tert-butyl ester was prepared following the same procedure but using the commercially available 1-BOC-indole-2-boronic acid as starting material. The product was obtained in 52% yield after $SiO_2$ chromatography (toluene/EtOAc 0-30% EtOAc). It was used in the synthesis of 1-[2-(1H-ndol-2-yl)-5H-pyrrolo[2,3-b]pyrazin-7-yl]-2,2-dimethyl-propan-1-one.

Example 24

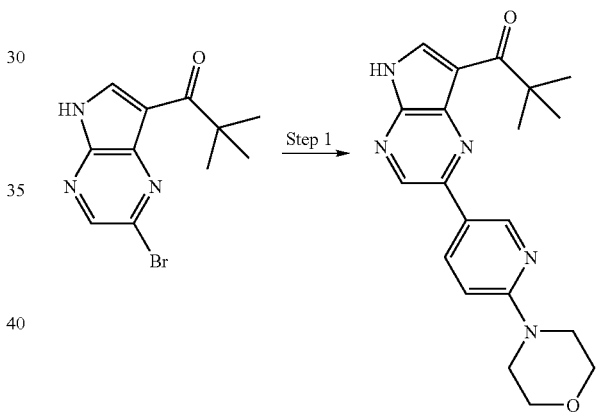

Step 1: A mixture of 1-(2-bromo-5H-pyrrolo[2,3-b]pyrazin-7-yl)-2,2-dimethyl-propan-1-one (0.1 g, 0.354 mmol), commercially available 4-[5-(4,4,5,5-tetramethyl-1,3,2-dioxaborolan-2-yl)-2-pyridinyl]morpholine (0.206 g, 0.709 mmol), $K_2CO_3$ (0.147 g, 1.063 mmol) and tetrakis(triphenylphosphine)palladium(0) (0.041 g, 35 micomol) in 3 mL of MeOH and 1 mL of DCM was degassed by bubbling argon through the mixture. It was then stirred at 110° C. for 25 minutes under microwave irradiation before being cooled to RT. And evaporated. The residue was adsorbed onto $SiO_2$ and purified twice by $SiO_2$ chromatography (hexanes/EtOAc 0-50% EtOAc, followed by DCM/MeOH 0-4% MeOH) to give 0.073 g of 2,2-Dimethyl-1-[2-(6-morpholin-4-yl-pyridin-3-yl)-5H-pyrrolo[2,3-b]pyrazin-7-yl]-propan-1-one (56% yield).

(1-Methyl-cyclohexyl)-[2-(6-morpholin-4-yl-pyridin-3-yl)-5H-pyrrolo[2,3-b]pyrazin-7-yl]-methanone was prepared following the same procedure but using (2-bromo-5H-pyrrolo[2,3-b]pyrazin-7-yl)-(1-methyl-cyclohexyl)-methanone as starting material (29% yield).

Example 25

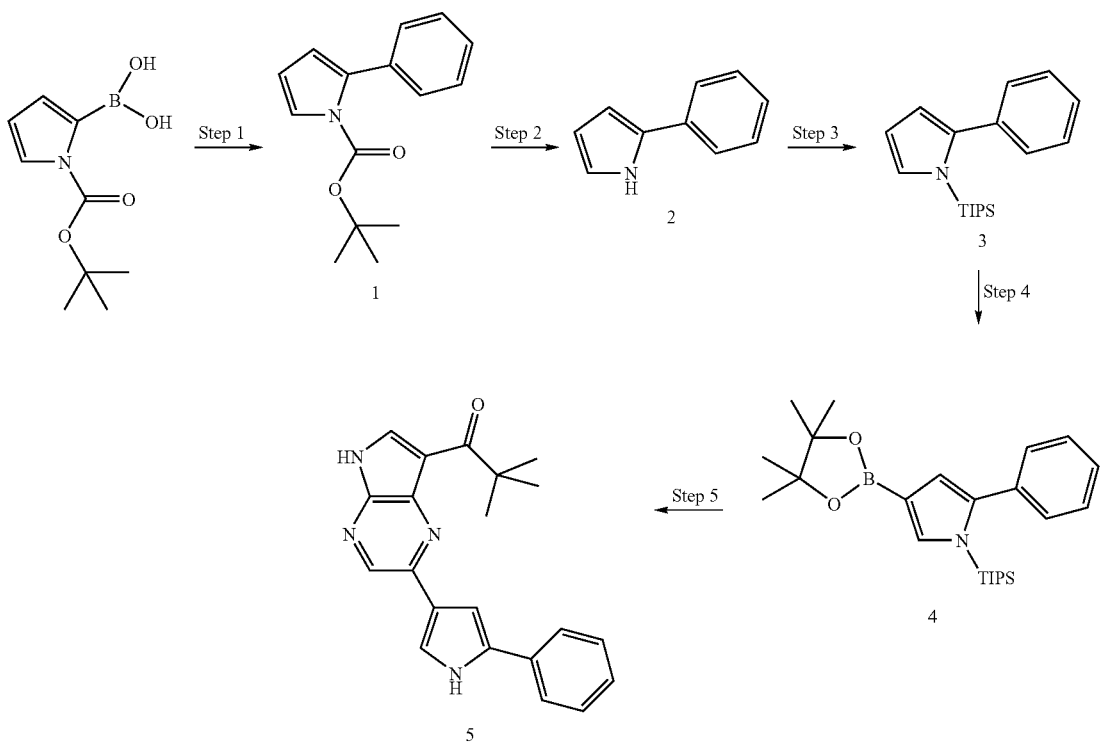

Step 1—A slurry of commercially available N—BOC-pyrrole-2-boronic acid (5 g, 23.69 mmol), tetrakis(triphenylphosphine)palladium(0) (1.37 g. 1.186 mmol) and Na$_2$CO$_3$ (7.5 g, 70.76 mmol) in 200 mL of DME, 100 mL mL and 50 mL H$_2$O was degassed with argon for an hour. Iodobenzene (6 mL, 53.62 mmol) was then added and the resulting mixture was stirred at 90° C. for 2 hours before being cooled to RT and evaporated. The residue was partitioned between DCM and H$_2$O. The aqueous layer was back extracted once with DCM. Combined organic layers were dried over Na$_2$SO$_4$, filtered and evaporated. The residue was purified by SiO$_2$ chromatography (hexanes/DCM 25% DCM) to give 4.8 g of 1 (83% yield).

Step 2—A bi-phasic mixture of 1 (4.7 g, 19.32 mmol) in 20 mL of ethylene glycol was stirred at 180° C. for 30 minutes before being cooled to RT. H$_2$O was added, the precipitate was filtered, rinsed with H$_2$O, and dried under vacuum to give 2.6 g of 2 (94% yield).

Step 3—NaH 60% dispersion in oil (0.8 g, 20 mmol) was added portionwise at 0° C. to a solution of 2 (2.6 g, 18.16 mmol) in 100 mL of DMF. When hydrogen evolution had ceased, triisopropylsilyl chloride (4 mL, 18.69 mmol) was added dropwise and the resulting mixture was allowed to reach RT before being stirred at 40° C. overnight before being cooled to RT, quenched by addition of saturated NH$_4$Cl, and partitioned between H$_2$O and Et$_2$O. The aqueous layer was back extracted three times with Et$_2$O. The combined organic layers were dried (MgSO$_4$), filtered and evaporated. The dark purple residue was purified by SiO$_2$ chromatography (hexanes/DCM 7% DCM) to give 4 g of 3 (74% yield).

Step 4—4,4,5,5-Tetramethyl-1,3,2-dioxaborolane (0.15 mL, 1.002 mmol) was added at RT under argon to a mixture of (1,5cyclo°Ctadiene)(methoxy)iridium(I) dimer (0.033 g, 50 μmol) and 4,4'-di-tert-butyl-2,2'-dipyridyl (0.013 g, 50 micromol) in 0.8 mL of hexanes. The resulting red solution was stirred at RT for 10 minutes before adding 3 (0.3 g, 1.002 mmol) in 0.7 mL of hexanes. Generation of hydrogen was observed. The reaction mixture was stirred at RT overnight before being filtered through SiO$_2$. The filtrate was evaporated and the residue was purified by SiO$_2$ chromatography (toluene/EtOAc 0-5% EtOAc) to give 0.085 g of 4 (20% yield).

Step 5—A mixture of 1-(2-bromo-5H-pyrrolo[2,3-b]pyrazin-7-yl)-2,2-dimethyl-propan-1-one (0.05 g, 0.177 mmol), 4 (0.087 g, 0.204 mmol), tetrakis(triphenylphosphine)palladium(0) (0.02 g, 18 μmol) in 1.5 mL of degassed 1,4-dioxane and 0.27 mL of 2M K$_2$CO$_3$ (5.32 mmol) was stirred at 95° C. overnight before being cooled to RT and evaporated. The residue was subjected to the same reaction conditions with fresh tetrakis(triphenylphosphine)palladium (0) and K$_2$CO$_3$ but stirring at 95° C. over the weekend. The reaction mixture was cooled to RT and evaporated. The residue was purified by SiO$_2$ chromatography (toluene/EtOAc 0-30% EtOAc). The fractions containing the product were evaporated. The residue was taken into MeOH. The suspension was sonicated, the insoluble material was filtered, rinsed with MeOH, and dried under vacuum to give 0.009 g of 5: 2,2-dimethyl-1-[2-(5-phenyl-1H-pyrrol-3-yl)-5H-pyrrolo[2,3-b]pyrazin-7-yl]-propan-1-one (15% yield).

Example 26

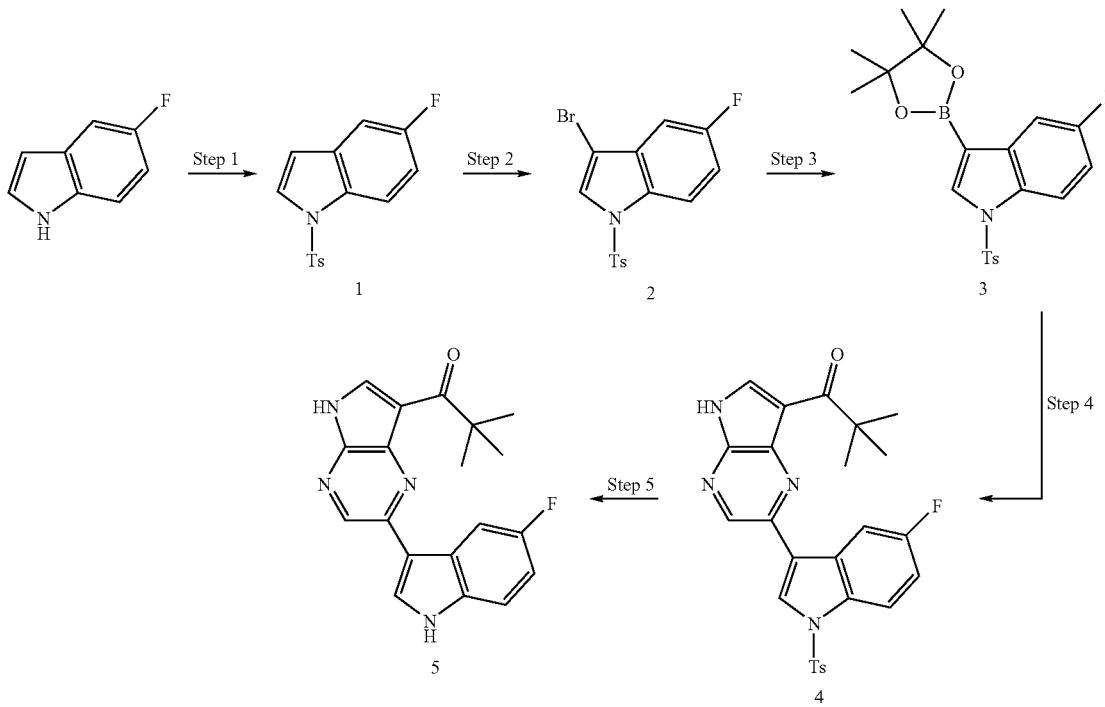

Step 1—To a vigorously stirred solution of commercially available 5-fluoroindole (5 g, 37 mmol) and tetrabutylammonium hydrogensulfate (1.9 g, 5.6 mmol) in 100 mL of toluene, at 0° C. was added 50% aqueous NaOH (100 mL) and p-toluenesulfonyl chloride (10.6 g, 55.6 mmol). The resulting mixture was stirred at 0° C. to RT over the weekend before being partitioned between toluene and H$_2$O. The organic layer was washed with saturated aqueous ammonium chloride, dried over Na$_2$SO$_4$, filtered, and evaporated to give 10 g of 1 (94% yield)

6-Fluoro-1-(toluene-4-sulfonyl)-1H-indole was prepared following the same procedure but using 6-fluoroindole as starting material (98% yield)

Step 2—Copper(II) bromide (9.3 g, 41.64 mmol) was added at RT to a solution of 1 (4 g, 13.83 mmol) in 100 mL of acetonitrile. The reaction mixture was stirred at RT for 24 hours before being quenched by addition of 100 mL of 7M methanolic ammonia, and extracted with EtOAc. The organic layer was dried over Na$_2$SO$_4$, filtered and evaporated to give 4.8 g of 2 (94% yield)

3-Bromo-6-fluoro-1-(toluene-4-sulfonyl)-1H-indole was prepared following the same procedure but using 6-fluoro-1-(toluene-4-sulfonyl)-1H-indole as starting material (98% yield).

3-Bromo-5-methoxy-1-(toluene-4-sulfonyl)-1H-indole was prepared following the same procedure using 5-methoxy-1-(toluene-4-sulfonyl)-1H-indole from (53% yield).

3-Bromo-5-methyl-1-(toluene-4-sulfonyl)-1H-indole was prepared following the same procedure using 5-methyl-1-(toluene-4-sulfonyl)-1H-indole.

3-Bromo-6-methoxy-1-(toluene-4-sulfonyl)-1H-indole was prepared following the same procedure using 6-methoxy-1-(toluene-4-sulfonyl)-1H-indole (68% yield).

3-Bromo-6-methyl-1-(toluene-4-sulfonyl)-1H-indole was prepared following the same procedure using 5-methyl-1-(toluene-4-sulfonyl)-1H-indole from (86% yield).

Step 3—t-Butyllithium 1.7M in pentane (6.5 mL, 11.05 mmol) was added at −78° C. to a solution of 2 (2 g, 5.431 mmol) in 40 mL of THF. The resulting mixture was stirred at −78° C. for 15 minutes before adding 2-isopropoxy-4,4,5,5-tetramethyldioxaborolane (2.2 mL, 10.78 mmol). The reaction mixture was then stirred at −78° C. for 1 hour before being quenched with saturated aqueous ammonium chloride, warmed to RT, and partitioned between DCM and H$_2$O. The aqueous layer was back extracted once with DCM. Combined organic layers were dried over Na$_2$SO$_4$, filtered and evaporated. The residue was purified by SiO$_2$ chromatography (hexanes/EtOAc 0-15% EtOAc) to give 1.5 g of 3 (67% yield)

6-Fluoro-3-(4,4,5,5-tetramethyl-[1,3,2]dioxaborolan-2-yl)-1-(toluene-4-sulfonyl)-1H-indole was prepared following the same procedure but using 3-bromo-6-fluoro-1-(toluene-4-sulfonyl)-1H-indole as starting material. The product was used crude in the next reaction.

5-Cyano-3-(4,4,5,5-tetramethyl-[1,3,2]dioxaborolan-2-yl)-indole-1-carboxylic acid tert-butyl ester was prepared following the same procedure using 3-bromo-5-cyano-indole-1-carboxylic acid tert-butyl ester. The product was isolated by precipitation from EtOAc (42% yield)

5-methoxy-3-(4,4,5,5-tetramethyl-[1,3,2]dioxaborolan-2-yl)-1-(toluene-4-sulfonyl)-1H-indole was prepared following the same procedure using 3-bromo-5-methoxy-1-(toluene-4-sulfonyl)-1H-indole. It was used was used crude without purification in the next reaction.

5-Methyl-3-(4,4,5,5-tetramethyl-[1,3,2]dioxaborolan-2-yl)-1-(toluene-4-sulfonyl)-1H-indole was prepared following the same procedure using 3-bromo-5-methyl-1-(toluene- 4-sulfonyl)-1H-indole. It was used was used crude without purification in the next reaction.

6-Methoxy-3-(4,4,5,5-tetramethyl-[1,3,2]dioxaborolan-2-yl)-1-(toluene-4-sulfonyl)-1H-indole was prepared following the same procedure using 3-bromo-6-methoxy-1-(toluene-4-sulfonyl)-1H-indole. It was used was used crude without purification in the next reaction.

6-Methyl-3-(4,4,5,5-tetramethyl-[1,3,2]dioxaborolan-2-yl)-1-(toluene-4-sulfonyl)-1H-indole was prepared following the same procedure using 3-bromo-6-methyl-1-(toluene-4-sulfonyl)-1H-indole. It was used was used crude without purification in the next reaction.

Step 4—A mixture of 1-(2-bromo-5H-pyrrolo[2,3-b]pyrazin-7-yl)-2,2-dimethyl-propan-1-one (0.1 g, 0.354 mmol), 3 (0.16 g, 0.435 mol), K$_2$CO$_3$ (0.15 g, 1.085 mmol), and [1,1'-bis(diphenylphosphine)ferrocene]dichloridepalladium(II) DCM complex (0.03 g, 36.74 μmol) in 3.5 mL of a 4/1 mixture of 1,4-dioxane and H$_2$O was degassed for 10 minutes by bubbling argon though the mixture. The resulting mixture was stirred under microwave irradiation at 120° C. for 15 minutes before being cooled to RT. The 1,4-dioxane layer was filtered through a short pad of silica, the silica was rinsed with EtOAc, and the filtrate was evaporated. The residue was taken into DCM, the insoluble was filtered and rinsed with DCM and MeOH to give 0.125 g of 4 (84% yield)

1-[2-(1-Benzenesulfonyl-1H-indol-3-yl)-5H-pyrrolo[2,3-b]pyrazin-7-yl]-2,2-dimethyl-propan-1-one was prepared following a similar procedure but using 1-benzenesulfonyl-1H-indole-3-boronic acid as starting material. In this reaction tetrakis(triphenylphosphine)palladium(0) was used as catalyst and the reaction mixture was stirred at 150° C. for 30 minutes under microwave irradiation. The product was obtained in 68% yield after purification by SiO$_2$ chromatography (hexanes/EtOAc 0-40% EtOAc).

1-{2-[5-Fluoro-1-(toluene-4-sulfonyl)-1H-indol-3-yl]-5H-pyrrolo[2,3-b]pyrazin-7-yl}-2,2-dimethyl-propan-1-one was prepared following the same procedure but using 6-fluoro-3-(4,4,5,5-tetramethyl-[1,3,2]dioxaborolan-2-yl)-1-(toluene-4-sulfonyl)-1H-indole as starting material (19% over two steps).

5-Cyano-3-[7-(2,2-dimethyl-propionyl)-5H-pyrrolo[2,3-b]pyrazin-2-yl]-indole-1-carboxylic acid tert-butyl ester was prepared following the same procedure using 5-cyano-3-(4,4,5,5-tetramethyl-[1,3,2]dioxaborolan-2-yl)-indole-1-carboxylic acid tert-butyl ester.

1-{2-[5-Methoxy-1-(toluene-4-sulfonyl)-1H-indol-3-yl]-5H-pyrrolo[2,3-b]pyrazin-7-yl}-2,2-dimethyl-propan-1-one was prepared following the same procedure using 5-methoxy-3-(4,4,5,5-tetramethyl-[1,3,2]dioxaborolan-2-yl)-1-(toluene-4-sulfonyl)-1H-indole. The product was isolated in 75% yield over two steps by SiO$_2$ chromatography (toluene/EtOAc 0-50% EtOAc).

2,2-Dimethyl-1-{2-[5-methyl-1-(toluene-4-sulfonyl)-1H-indol-3-yl]-5H-pyrrolo[2,3-b]pyrazin-7-yl}-propan-1-one was prepared following the same procedure using 5-methyl-3-(4,4,5,5-tetramethyl-[1,3,2]dioxaborolan-2-yl)-1-(toluene-4-sulfonyl)-1H-indole. The product was isolated in 29% yield over two steps by SiO$_2$ chromatography (toluene/EtOAc (0-50% EtOAc).

1-{2-[6-Methoxy-1-(toluene-4-sulfonyl)-1H-indol-3-yl]-5H-pyrrolo[2,3-b]pyrazin-7-yl}-2,2-dimethyl-propan-1-one was prepared following the same procedure using 6-methoxy-3-(4,4,5,5-tetramethyl-[1,3,2]dioxaborolan-2-yl)-1-(toluene-4-sulfonyl)-1H-indole. The product was isolated in 45% yield over two steps by SiO$_2$ chromatography (toluene/EtOAc (0-50% EtOAc).

2,2-Dimethyl-1-{2-[6-methyl-1-(toluene-4-sulfonyl)-1H-indol-3-yl]-5H-pyrrolo[2,3-b]pyrazin-7-yl}-propan-1-one was prepared following the same procedure using 6-methyl-3-(4,4,5,5-tetramethyl-[1,3,2]dioxaborolan-2-yl)-1-(toluene-4-sulfonyl)-1H-indole. The product was isolated in 32% yield over two steps by SiO$_2$ chromatography (toluene/EtOAc (0-50% EtOAc).

1-(2-Imidazo[1,2-a]pyridin-3-yl-5H-pyrrolo[2,3-b]pyrazin-7-yl)-2,2-dimethyl-propan-1-one was prepared using the same procedure using the commercially available 3-(4,4,5,5-tetramethyl-[1,3,2]dioxaborolan-2-yl)-imidazo[1,2-a]pyridine. The product was isolated in 10% yield by SiO$_2$ chromatography (DCM/MeOH (0-5% MeOH).

Step 5—A suspension of 4 (0.12 g, 0.245 mmol) and NaOH (0.078 g, 1.957 mmol) in 15 mL of 4/1/1 mixture of 1,4-dioxane, H$_2$O, and MeOH was stirred at 70° C. for 3 hours before being cooled to RT and evaporated. The residue was taken into H$_2$O, the insoluble was filtered, the residue was rinsed with H$_2$O, and dried under vacuum. The residue was purified by SiO$_2$ chromatography (DCM/MeOH 9.5/0.5) to give 0.035 g of 5: 1-[2-(5-fluoro-1H-indol-3-yl)-5H-pyrrolo[2,3-b]pyrazin-7-yl]-2,2-dimethyl-propan-1-one (43% yield)

1-[2-(1H-Indol-3-yl)-5H-pyrrolo[2,3-b]pyrazin-7-yl]-2,2-dimethyl-propan-1-one was prepared following a similar procedure but using 1-[2-(1-benzenesulfonyl-1H-indol-3-yl)-5H-pyrrolo[2,3-b]pyrazin-7-yl]-2,2-dimethyl-propan-1-one as starting material. In this reaction, the reaction mixture was stirred at 50° C. for 4 hours. The product was obtained in 47% yield after purification by SiO$_2$ chromatography (DCM/MeOH 9.5/0.5).

1-[2-(5-Fluoro-1H-indol-3-yl)-5H-pyrrolo[2,3-b]pyrazin-7-yl]-2,2-dimethyl-propan-1-one was prepared following the same procedure but using 1-{2-[5-fluoro-1-(toluene-4-sulfonyl)-1H-indol-3-yl]-5H-pyrrolo[2,3-b]pyrazin-7-yl}-2,2-dimethyl-propan-1-one as starting material (24% yield).

1-[2-(5-Methoxy-1H-indol-3-yl)-5H-pyrrolo[2,3-b]pyrazin-7-yl]-2,2-dimethyl-propan-1-one was prepared following the same procedure using 1-{2-[5-Methoxy-1-(toluene-4-sulfonyl)-1H-indol-3-yl]-5H-pyrrolo[2,3-b]pyrazin-7-yl}-2,2-dimethyl-propan-1-one (59% yield).

2,2-Dimethyl-1-[2-(5-methyl-1H-indol-3-yl)-5H-pyrrolo[2,3-b]pyrazin-7-yl]-propan-1-one was prepared following the same procedure using 2,2-dimethyl-1-{2-[5-methyl-1-(toluene-4-sulfonyl)-1H-indol-3-yl]-5H-pyrrolo[2,3-b]pyrazin-7-yl}-propan-1-one (68% yield).

1-[2-(6-Methoxy-1H-indol-3-yl)-5H-pyrrolo[2,3-b]pyrazin-7-yl]-2,2-dimethyl-propan-1-one was prepared following the same procedure using 1-{2-[6-methoxy-1-(toluene-4-sulfonyl)-1H-indol-3-yl]-5H-pyrrolo[2,3-b]pyrazin-7-yl}-2,2-dimethyl-propan-1-one (42% yield).

2,2-Dimethyl-1-[2-(6-methyl-1H-indol-3-yl)-5H-pyrrolo[2,3-b]pyrazin-7-yl]-propan-1-one was prepared following the same procedure using 2,2-dimethyl-1-{2-[6-methyl-1-(toluene-4-sulfonyl)-1H-indol-3-yl]-5H-pyrrolo[2,3-b]pyrazin-7-yl}-propan-1-one (56% yield).

[2-(1H-Indol-3-yl)-5H-pyrrolo[2,3-b]pyrazin-7-yl]-(1-methyl-cyclohexyl)-methanone was prepared following the same procedure by using [2-(1-benzenesulfonyl-1H-indol-3-yl)-5H-pyrrolo[2,3-b]pyrazin-7-yl]-(1-methyl-cyclohexyl)-methanone as starting material. The product was obtained in 70% after SiO$_2$ chromatography (DCM/[DCM/MeOH 9.5/1] 10/0 to 0/10).

1-[2-(1H-Indol-3-yl)-5-methyl-5H-pyrrolo[2,3-b]pyrazin-7-yl]-2,2-dimethyl-propan-1-one was prepared following the same procedure but using 2,2-dimethyl-1-{5-methyl-2-[1-(toluene-4-sulfonyl)-1H-indol-3-yl]-5H-pyrrolo

[2,3-b]pyrazin-7-yl}-propan-1-one from as starting material. The product was obtained in 49% yield after purification by SiO$_2$ chromatography (hexanes/EtOAc 30% EtOAc).

2,2-Dimethyl-1-[2-(1H-pyrrolo[2,3-c]pyridin-3-yl)-5H-pyrrolo[2,3-b]pyrazin-7-yl]-propan-1-one was prepared following the same procedure but using 2,2-dimethyl-1-{2-[1-(toluene-4-sulfonyl)-1H-pyrrolo[2,3-c]pyridin-3-yl]-5H-pyrrolo[2,3-b]pyrazin-7-yl}-propan-1-one as starting material. The product was obtained in 18% after purification by SiO$_2$ chromatography (/MeOH 0-10% MeOH).

2,2-Dimethyl-1-[2-(1H-pyrrolo[2,3-b]pyridin-3-yl)-5H-pyrrolo[2,3-b]pyrazin-7-yl]-propan-1-one was prepared following the same procedure but using 2,2-dimethyl-1-{2-[1-(toluene-4-sulfonyl)-1H-pyrrolo[2,3-b]pyridin-3-yl]-5H-pyrrolo[2,3-b]pyrazin-7-yl}-propan-1-one (64% yield).

2,2-Dimethyl-1-[2-(1H-pyrrolo[3,2-c]pyridin-3-yl)-5H-pyrrolo[2,3-b]pyrazin-7-yl]-propan-1-one was prepared following the same procedure using 2,2-dimethyl-1-{2-[1-(toluene-4-sulfonyl)-1H-pyrrolo[3,2-c]pyridin-3-yl]-5H-pyrrolo[2,3-b]pyrazin-7-yl}-propan-1-one (17% yield).

Example 27

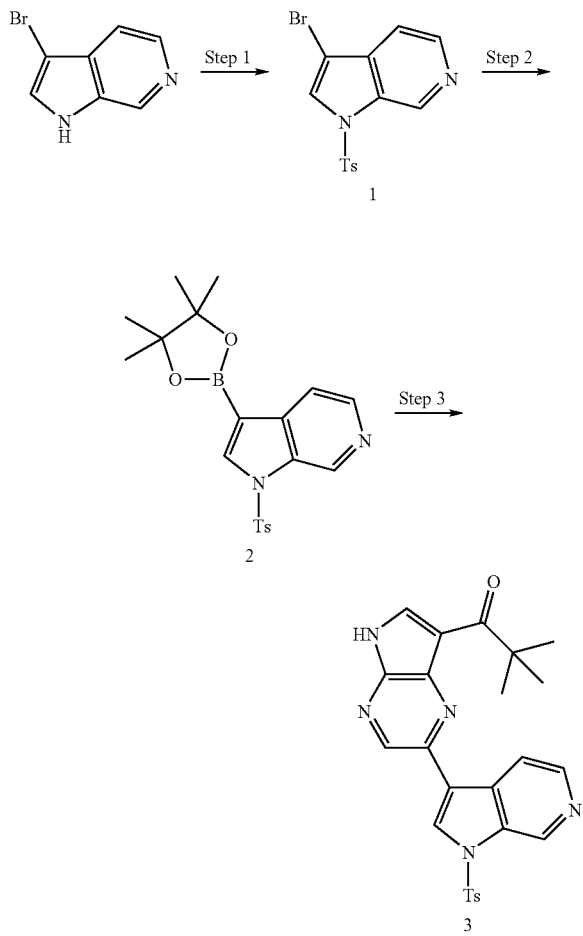

Step 1—3-Bromo-1H-pyrrolo[2,3-c]pyridine (0.5 g, 2.538 mmol) in 5 mL of DMF was added at 0° C. to a suspension of NaH 60% dispersion in oil in 5 mL of DMF. The resulting mixture was stirred at RT for 30 minutes before being cooled to 0° C. and then p-TsCl (0.508 g, 2.664 mmol) was added. The reaction mixture was stirred at RT overnight before being quenched by addition of H$_2$O and extracted three times with EtOAc. The combined organic layers were dried (MgSO$_4$), filtered and evaporated. The residue was purified by SiO$_2$ chromatography (hexanes/EtOAc 0-25% EtOAc) to give 0.535 g of 1 (60% yield).

3-Bromo-1-(toluene-4-sulfonyl)-1H-pyrrolo[2,3-b]pyridine was prepared following the same procedure starting from the commercially available 3-bromo-1H-pyrrolo[2,3-b] pyridine (59% yield).

Alternatively, 3-bromo-1-(toluene-4-sulfonyl)-1H-pyrrolo[3,2-c]pyridine was prepared according to the procedure described in WO2004 078756 (page 100) from 3-bromo-1H-pyrrolo[3,2-c]pyridine prepared from 1H-pyrrolo[3,2-c]pyridine using the procedure described in Synlett 2007, 2, 211-214.

Step 2—Method a: A mixture of 1 (0.25 g, 0.712 mmol), bis(pinacolato)diboron (0.208 g, 0.819 mmol), [1,1'-bis(diphenylphosphine)ferrocene]dichloridepalladium(II) DCM complex (0.058 g, 71 μmol), and KOAc (0.21 g, 2.135 mmol) in 4 mL of 1,4-dioxane was stirred at 70° C. overnight before being cooled to RT and filtered though celite. The filtrate was evaporated to give 2. The residue was used crude in the next step.

3-(4,4,5,5-Tetramethyl-[1,3,2]dioxaborolan-2-yl)-1-(toluene-4-sulfonyl)-1H-pyrrolo[2,3-b]pyridine was prepared following the same procedure using 3-bromo-1-(toluene-4-sulfonyl)-1H-pyrrolo[2,3-b]pyridine.

3-(4,4,5,5-tetramethyl-[1,3,2]dioxaborolan-2-yl)-1-(toluene-4-sulfonyl)-1H-pyrrolo[3,2-c]pyridine was prepared following the same procedure using 3-bromo-1-(toluene-4-sulfonyl)-1H-pyrrolo[3,2-c]pyridine.

Method b: tert-Butyllithium 1.7 M in pentane (0.75 mL, 1.278 mmol) was added at −78° C. to a solution of 3-bromo-1-methyl-1H-pyrrolo[2,3-b]pyridine (0.18 g, 0.853 mmol). The resulting mixture was stirred at −78° C. for 20 minutes before adding 2-isopropoxy-4,4,5,5-tetramethyl-1,3,2-dioxaborolane (0.26 mL, 1.278 mmol). The reaction mixture was stirred at −78° C. for 3 hours before being quenched by addition of a saturated aqueous solution of ammonium chloride and extracted twice with EtOAc. The combined organic layers were dried (MgSO$_4$), filtered, and evaporated. The residue was used crude in the next reaction.

Methyl-3-(4,4,5,5-tetramethyl-[1,3,2]dioxazolidin-2-yl)-1H-pyrrolo[2,3-b]pyridine was prepared following the same procedure but using 3-bromo-1-methyl-1H-pyrrolo[2,3-b] pyridine as starting material.

Methyl-3-(4,4,5,5-tetramethyl-[1,3,2]dioxazolidin-2-yl)-1H-indole was prepared following the same procedure but using 3-bromo-1-methyl-1H-indole as starting material.

Step 3—Method a: A mixture of 1-(2-bromo-5H-pyrrolo[2,3-b]pyrazin-7-yl)-2,2-dimethyl-propan-1-one (0.25 g, 0.367 mmol), 2 (theoretically 0.712 mmol), [1,1'-bis(diphenylphosphine)ferrocene]dichloridepalladium(II) DCM complex (0.030 g, 37 μmol) and 0.73 mL of 2M aqueous K$_2$CO$_3$ (1.47 mmol) in 4 mL of 1,4-dioxane was degassed by bubbling argon through the mixture for 10 minutes. The reaction mixture was stirred at 90° C. overnight before being cooled to RT and diluted with EtOAc. The organic layer was washed with a saturated aqueous solution of NaHCO$_3$ and H$_2$O. After back extraction of the aqueous layers with EtOAc, the combined organic layers were dried (MgSO$_4$), filtered, and evaporated. The residue was purified by SiO$_2$ chromatography (DCM/acetone 0-50% acetone) to give 0.032 g of 3: 2,2-dimethyl-1-{2-[1-(toluene-4-sulfonyl)-1H-pyrrolo[2,3-c]pyridin-3-yl]-5H-pyrrolo[2,3-b]pyrazin-7-yl}-propan-1-one (18% yield).

2,2-Dimethyl-1-{2-[1-(toluene-4-sulfonyl)-1H-pyrrolo[2,3-b]pyridin-3-yl]-5H-pyrrolo[2,3-b]pyrazin-7-yl}-propan-1-one was prepared using the same procedure from 3-(4,4,5,5-tetramethyl-[1,3,2]dioxaborolan-2-yl)-1-(toluene-4-sulfonyl)-1H-pyrrolo[2,3-b]pyridine (24% yield). In this reaction tetrakis(triphenylphosphine)palladium(0) was used instead of [1,1'-bis(diphenylphosphine)ferrocene]dichloridepalladium(II) DCM complex.

2,2-Dimethyl-1-{2-[1-(toluene-4-sulfonyl)-1H-pyrrolo[3,2-c]pyridin-3-yl]-5H-pyrrolo[2,3-b]pyrazin-7-yl}-propan-1-one was prepared the following the same procedure from 3-(4,4,5,5-tetramethyl-[1,3,2]dioxaborolan-2-yl)-1-(toluene-4-sulfonyl)-1H-pyrrolo[3,2-c]pyridine (67% yield). In this reaction tetrakis(triphenylphosphine)palladium(0) was used instead of [1,1'-bis(diphenylphosphine)ferrocene]dichloridepalladium(II) DCM complex.

2,2-Dimethyl-1-[2-(1-methyl-1H-pyrrolo[2,3-b]pyridin-3-yl)-5H-pyrrolo[2,3-b]pyrazin-7-yl]-propan-1-one was prepared following the same procedure using 1-methyl-3-(4,4,5,5-tetramethyl-[1,3,2]dioxazolidin-2-yl)-1H-pyrrolo[2,3-b]pyridine. In this reaction, the mixture was heated at 150° C. for an hour under microwave irradiation.

Example 28

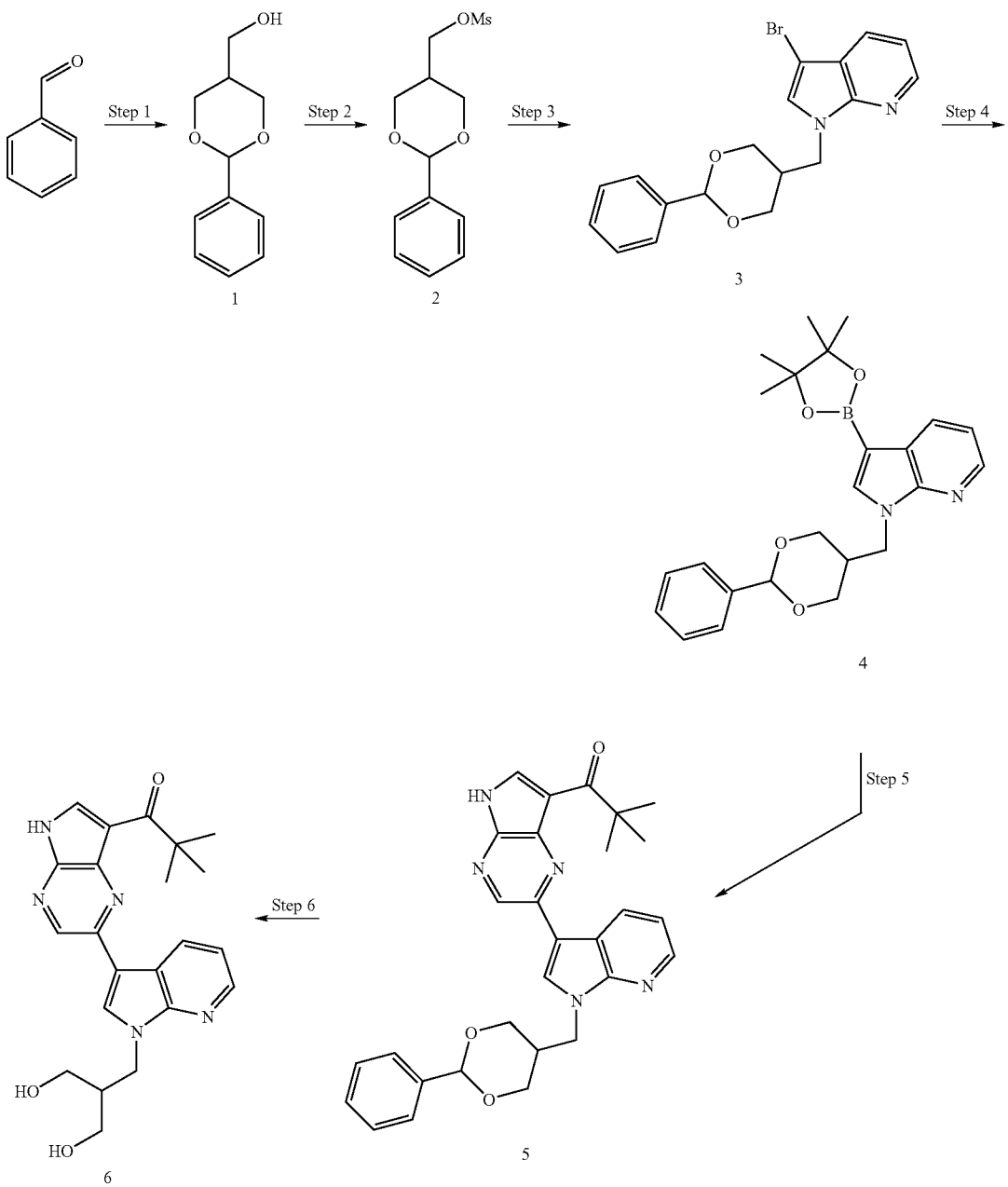

Step 1—A mixture of benzaldehyde (2.6 mL, 25.442 mmol), 2-hydroxymethyl-1,3-propanediol (2.97 g, 27.986 mmol) and p-TsOH.H₂O (0.484 g, 2.544 mmol) in 500 mL of toluene was stirred at reflux with a Dean Stark for 2 hours before being cooled to RT and evaporated. The residue was purified by SiO₂ chromatography (hexanes/EtOAc 0-40% EtOAc) to give 2.09 g of 1 as a mixture of cis and trans isomers (42% yield).

Step 2—MsCl (1 mL, 12.912 mmol) was added at 0° C. to a solution of 1 (2.09 g, 10.76 mmol) in 100 mL of pyridine. The resulting mixture was allowed to reach RT overnight. More MsCl (0.3 mL) was added and the reaction mixture was stirred 2 more hours at RT before being partitioned between saturated NH₄Cl and DCM. The aqueous layer was back extracted with DCM. The combined organic layers were washed with brine, dried (Na₂SO₄), filtered, and evaporated to give 2.74 g of 2 (94% yield). The product was used in the next step without purification.

Step 3—NaH 60% dispersion in oil (0.091 g, 2.284 mmol) was added at 0° C. to a solution of commercially available 3-bromo-1H-pyrrolo[2,3-b]pyridine (0.3 g, 1.523 mmol) in 12 mL of DMF. The resulting mixture was stirred at 0° C. for 20 minutes before adding 2 (0.829 g, 3.045 mmol) before being warmed to RT and then stirred at 50° C. overnight. The reaction mixture was cooled to RT and partitioned between ice-cold saturated NH₄Cl and Et₂O. The aqueous layer was extracted with Et₂O. The combined organic layers were washed with H₂O, dried (Na₂SO₄), filtered, and evaporated. The residue was purified by SiO₂ chromatography (hexanes/ EtOAc 0-15% EtOAc) to give 0.41 g of 3 (72% yield).

Step 4—-tert-Butyllithium 1.7 M in pentane (0.97 mL, 1.648 mmol) was added at −78° C. to a solution of 3 (0.41 g, 1.098 mmol). The resulting mixture was stirred at −78° C. for 20 minutes before adding 2-isopropoxy-4,4,5,5-tetramethyl-1,3,2-dioxaborolane (0.34 mL, 1.648 mmol). The reaction mixture was stirred at −78° C. for 2 hours before being quenched by addition of saturated aqueous NH₄Cl and extracted with EtOAc. The combined organic layers were dried (MgSO₄), filtered, and evaporated. The residue was used crude in the next reaction.

Step 5—A mixture of 1-(2-bromo-5H-pyrrolo[2,3-b] pyrazin-7-yl)-2,2-dimethyl-propan-1-one (0.15 g, 0.532 mmol), 4 (theoretically 1.098 mmol), [1,1'-bis(diphenylphosphine)ferrocene]dichloridepalladium(II) DCM complex (0.043 g, 53 µmol), and K₂CO₃ (0.22 g, 1.595 mmol) in 4 mL of 1,4-dioxane and 1 mL of H₂O was degassed by bubbling argon through the mixture. The reaction mixture was then stirred at 130° C. under microwave irradiation for 20 minutes before being cooled to RT and partitioned between H₂O and EtOAc. The aqueous layer was extracted with EtOAc. The combined organic layers were dried (Na₂SO₄), filtered, and evaporated. The residue was purified by SiO₂ chromatography (toluene/EtOAc 0-50% EtOAc) to give 0.058 g of 5 (22% yield).

Step 6—A suspension of 5 (0.055 g, 0.11 mmol) in 1 mL of 80% AcOH was stirred at 70° C. for 2.5 hours before being cooled to RT and partitioned between H₂O and EtOAc. The aqueous layer was extracted with EtOAc. The combined organic layers were dried (Na₂SO₄), filtered, and evaporated. The residue was purified by SiO₂ chromatography (DCM/ MeOH 0-7% MeOH) to give 0.036 g of 6: 1-{2-[1-(3-hydroxy-2-hydroxymethyl-propyl)-1H-pyrrolo[2,3-b]pyridin-3-yl]-5H-pyrrolo[2,3-b]pyrazin-7-yl}-2,2-dimethyl-propan-1-one (22% yield)

Example 29

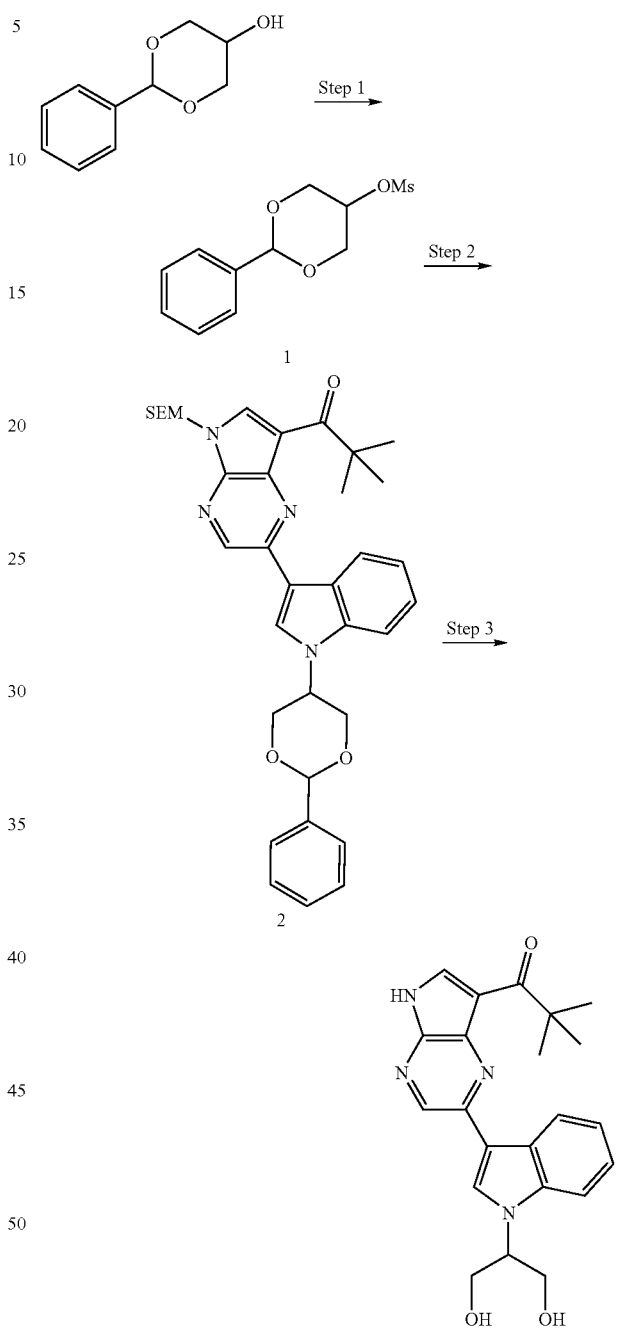

Step 1—Methanesulfonyl chloride (4 mL, 51.68 mmol) was added at 0° C. to a mixture of 2-phenyl-1,3-dioxan-5-ol (2 g, 11.10 mmol) in 20 mL of pyridine. The resulting mixture was stirred at 0° C. to RT overnight before being poured into 200 mL of ice H₂O. The precipitate that formed was filtered and thoroughly rinsed with ice H₂O before being dried to obtain 2.6 g of 1 (91% yield)

Step 2—A mixture of 1-[2-(1H-indol-3-yl)-5-(2-trimethylsilanyl-ethoxymethyl)-5H-pyrrolo[2,3-b]pyrazin-7-yl]-2, 2-dimethyl-propan-1-one (0.2 g, 0.446 mmol), 1 (0.23 g, 0.892 mmol), and cesium carbonate (0.29 g, 0.892 mmol) in 4 mL of acetonitrile was stirred at 80° C. overnight. TLC (hexanes/EtOAc 7/3) showed little conversion, so NaH 60% dispersion in oil (0.067 g, 1.672 mmol) was added and the after hydrogen evolution had stopped the reaction mixture was stirred at 130° C. under microwave irradiation for two hours before being cooled to RT. The reaction mixture was partitioned between EtOAc and saturated aqueous ammonium chloride, the aqueous layer was back extracted twice with EtOAc. Combined organic layers were dried over $Na_2SO_4$, filtered and evaporated. The residue was purified by $SiO_2$ chromatography (hexanes/EtOAc 0-20% EtOAc) and then a second time (toluene/acetone 0-10% acetone) to give 0.028 g of 2 (10% yield)

2,2-Dimethyl-1-[2-[1-(2-phenyl-[1,3]dioxan-5-ylmethyl)-1H-indol-3-yl]-5-(2-trimethylsilanyl-ethoxymethyl)-5H-pyrrolo[2,3-b]pyrazin-7-yl]-propan-1-one was prepared following a similar procedure but using methanesulfonic acid 2-phenyl-[1,3]

dioxan-5-ylmethyl ester as starting material (68% yield). In this reaction NaH 60% dispersion in oil was used and the reaction mixture was heated at 50° C. overnight. The product was obtained after purification by $SiO_2$ chromatography (hexanes/EtOAc 0-25% EtOAc).

2,2-Dimethyl-1-[2-[1-(2-methylsulfanyl-ethyl)-1H-indol-3-yl]-5-(2-trimethylsilanyl-ethoxymethyl)-5H-pyrrolo[2,3-b]pyrazin-7-yl]-propan-1-one was prepared following the same procedure but using 2-chloro methylsulfide as starting material (22% yield). In this reaction NaH 60% dispersion in oil was used, 1.5 equivalents of KI was added, and the reaction mixture was heated at 50° C. overnight. The product was obtained after purification by $SiO_2$ chromatography (hexanes/EtOAc 0-30% EtOAc).

Step 3—0.3 mL of trifluoroacetic acid was added at RT to a solution of 2 (0.028 g, 45.84 μmol) in 0.7 mL of DCM. The resulting dark orange/red mixture was stirred at RT overnight before being evaporated and coevaporated twice with toluene. The crude residue was taken into 0.5 mL of EtOH and sodium acetate (0.04 g, 0.488 mmol) was added. The resulting dark yellow mixture was stirred at RT for 2 hours before being evaporated. The residue was purified by flash The residue was purified by $SiO_2$ chromatography (DCM/[DCM/MeOH 5% MeOH] 10/0 to 0/10) and then by preparative TLC (DCM/MeOH 10% MeOH) to give 0.004 g of 3: 1-{2-[1-(2-hydroxy-1-hydroxymethyl-ethyl)-1H-indol-3-yl]-5H-pyrrolo[2,3-b]pyrazin-7-yl}-2,2-dimethyl-propan-1-one (22% yield)

1-{2-[1-(3-Hydroxy-2-hydroxymethyl-propyl)-1H-indol-3-yl]-5H-pyrrolo[2,3-b]pyrazin-7-yl}-2,2-dimethyl-propan-1-one was prepared following the same procedure but using 2,2-dimethyl-1-[2-[1-(2-phenyl-[1,3]dioxan-5-ylmethyl)-1H-indol-3-yl]-5-(2-trimethylsilanyl-ethoxymethyl)-5H-pyrrolo[2,3-b]pyrazin-7-yl]-propan-1-one as starting material (52% yield). In this reaction the product was purified by $SiO_2$ chromatography (DCM/MeOH 0-7% MeOH).

Example 30

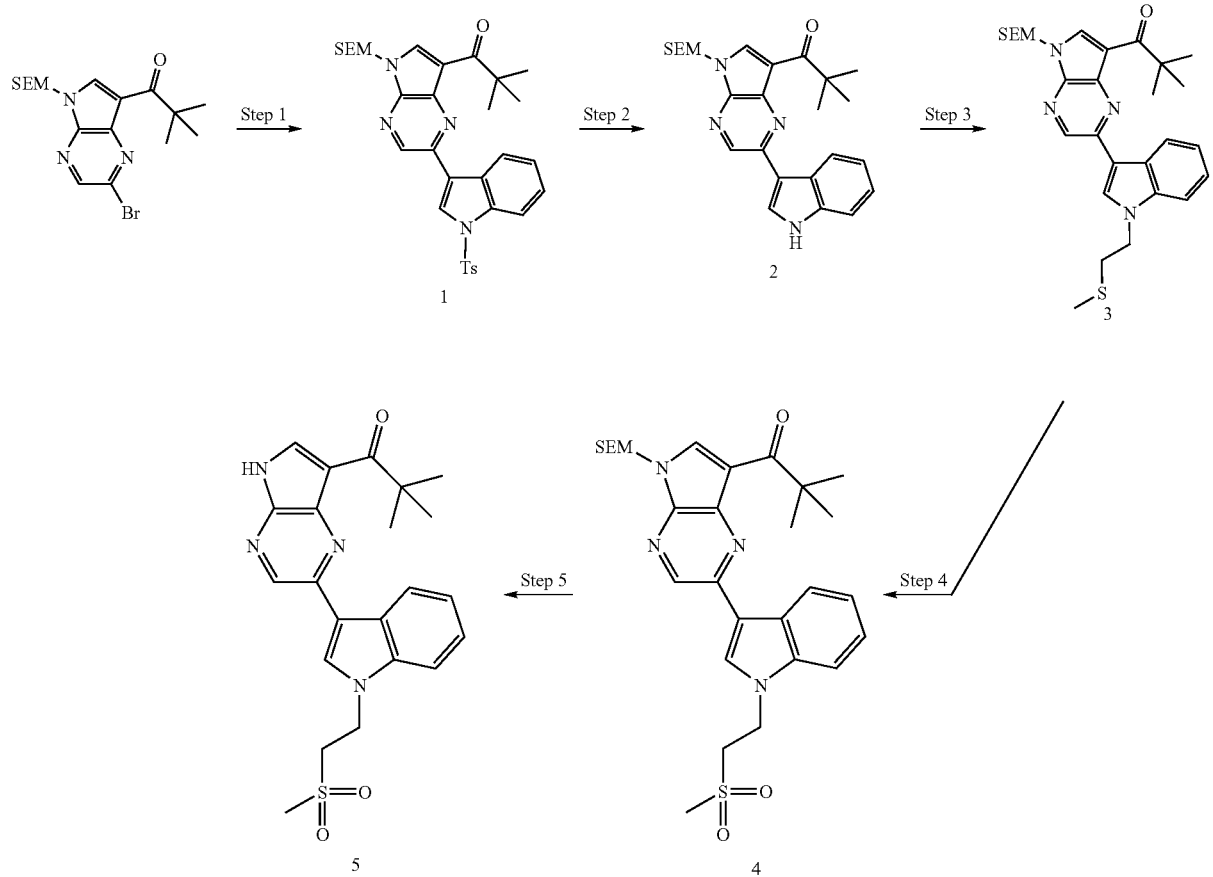

Step 1—A mixture of 1-[2-bromo-5-(2-trimethylsilanyl-ethoxymethyl)-5H-pyrrolo[2,3-b]pyrazin-7-yl]-2,2-dimethyl-propan-1-one (0.5 g, 1.212 mmol), commercially available 1-(phenylsulfonyl)-3-indoleboronic acid (0.452 g, 1.455 mmol) and tetrakis(triphenylphosphine)palladium(0) (0.14 g, 0.121 mmol) in 10 mL of degassed 1,4-dioxane and 1.8 mL of 2M aqueous $K_2CO_3$ (3.637 mmol) was stirred at 95° C. overnight before being cooled to RT and evaporated. The residue was purified by $SiO_2$ chromatography (hexanes/EtOAc 0-25% EtOAc) to give 0.67 g of 1 (94% yield).

Step 2—A mixture of 1 (0.665 g, 1.129 mmol) in 9 mL of 1,4-dioxane, 3 mL of MeOH, and 3 mL of 3M aqueous NaOH was stirred at 70° C. for 1 hour before being cooled to RT and evaporated. The residue was partitioned between $H_2O$ and EtOAc. The aqueous layer was extracted with EtOAc. The combined organic layers were dried ($Na_2SO_4$), filtered, and evaporated to give 0.504 of 2 quantitatively. The product was used in the next step without purification.

Step 3—NaH 60% dispersion in oil (0.021 g, 0.518 mmol) was added at 0° C. to a mixture of 2 (0.155 g, 0.345 mmol) and KI (0.086, 0.518 mmol) in 3 mL of DMF. The resulting mixture was stirred at RT for 15 minutes before adding commercially available 2-chloroethyl methylsulfide (0.05 mL, 0.518 mmol). The reaction mixture was allowed to reach RT and then was stirred at 50° C. overnight before being cooled to RT and partitioned between a saturated aqueous solution of $NH_4Cl$ and $Et_2O$. The aqueous layer was extracted with $Et_2O$. The combined organic layers were washed with brine, dried (Na2SO), filtered, and evaporated. The residue was purified by $SiO_2$ chromatography (hexanes/EtOAc 0-30% EtOAc) to give 0.039 g of 3 (22% yield).

2,2-Dimethyl-1-[2-(1-methyl-1H-indol-3-yl)-5-(2-trimethylsilanyl-ethoxymethyl)-5H-pyrrolo[2,3-b]pyrazin-7-yl]-propan-1-one was prepared following a similar procedure using iodomethane. In this reaction, KI was not used and the reaction mixture was stirred at RT for 5 hours before being worked up. The product was used in the next reaction without purification.

1-[2-{1-[2-(tert-Butyl-dimethyl-silanyloxy)-ethyl]-1H-indol-3-yl}-5-(2-trimethylsilanyl-ethoxymethyl)-5H-pyrrolo[2,3-b]pyrazin-7-yl]-2,2-dimethyl-propan-1-one was prepared following the same procedure using the commercially available 2-bromoethoxy-t-butylsilane as electrophile. In this reaction, KI was not used and the reaction mixture was stirred at RT overnight before being worked up. The product was obtained in 80% yield after purification by $SiO_2$ chromatography (hexanes/EtOAc 0-5% EtOAc).

Step 4—Oxone (0.069 g, 0.112 mmol) was added at RT to a solution of 3 (0.039 g, 75 µmol) in 0.6 mL of MeOH and 0.2 mL of $H_2O$. The resulting mixture was stirred at RT for four hours before being evaporated. The residue was partitioned between 3M NaOH and EtOAc. The organic layer was dried ($Na_2SO_4$), filtered, and evaporated. The residue was purified by $SiO_2$ chromatography (Toluene/EtOAc 0-50% EtOAc) to give 4 quantitatively.

Step 5—TFA (0.5 mL) was added at RT to a solution of 4 (0.05 g, 90 µmol) in 0.7 mL of DCM. The resulting mixture was stirred at RT for four hours before being evaporated and coevaporated twice with toluene. The residue was taken into 1 mL of EtOH and NaOAc (0.074 g, 0.9 mmol) was added. The reaction mixture was stirred at RT overnight before being evaporated. The residue was taken into $H_2O$, the suspension was sonicated and then filtered. The insoluble was rinsed with $H_2O$ and dried under vacuum to give 0.029 g of 5: 1-{2-[1-(2-methanesulfonyl-ethyl)-1-H-indol-3-yl]-5H-pyrrolo[2,3-b]pyrazin-7-yl}-2,2-dimethyl-propan-1-one (76% yield).

2,2-Dimethyl-1-[2-(1-methyl-1H-indol-3-yl)-5H-pyrrolo[2,3-b]pyrazin-7-yl]-propan-1-one was prepared following the same procedure but using 2,2-dimethyl-1-[2-(1-methyl-1H-indol-3-yl)-5-(2-trimethylsilanyl-ethoxymethyl)-5H-pyrrolo[2,3-b]pyrazin-7-yl]-propan-1-one as starting material. The product was obtained in 60% yield after purified by $SiO_2$ chromatography (Toluene/EtOAc 10-60% EtOAc).

1-{2-[1-(2-Hydroxy-ethyl)-1H-indol-3-yl]-5H-pyrrolo[2,3-b]pyrazin-7-yl}-2,2-dimethyl-propan-1-one was prepared following the same procedure but using 1-[2-{1-[2-(tert-butyl-dimethyl-silanyloxy)-ethyl]-1H-indol-3-yl}-5-(2-trimethylsilanyl-ethoxymethyl)-5H-pyrrolo[2,3-b]pyrazin-7-yl]-2,2-dimethyl-propan-1-one as starting material. The product was obtained in 67% by trituration in MeOH.

Example 31

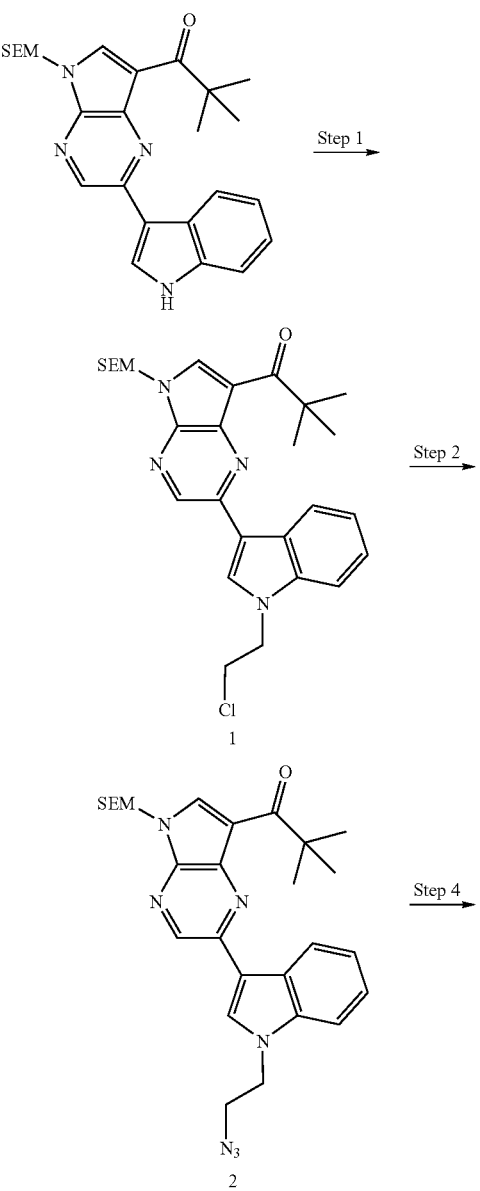

-continued

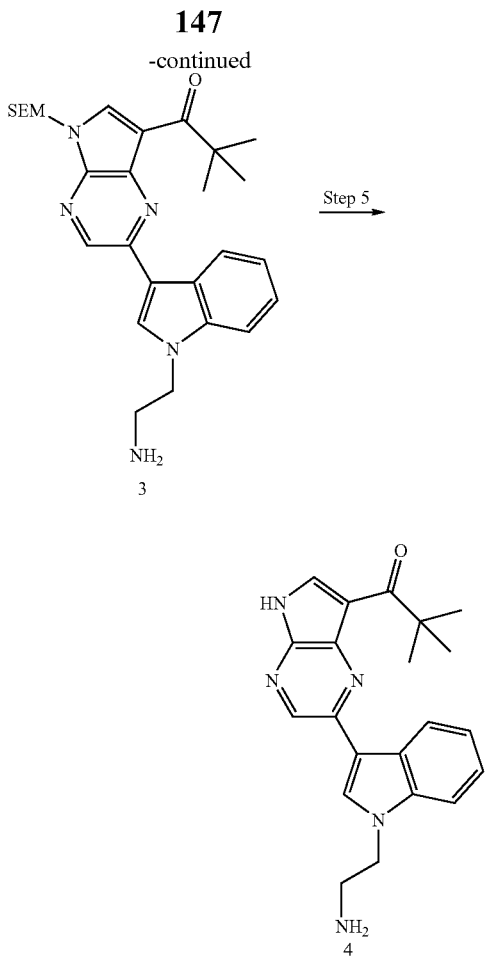

Step 1—Commercially available 2-chloroethyl p-toluenesulfonate (0.24 mL, 1.337 mmol) was added to a mixture of 1-[2-(1H-indol-3-yl)-5-(2-trimethylsilanyl-ethoxymethyl)-5H-pyrrolo[2,3-b]pyrazin-7-yl]-2,2-dimethyl-propan-1-one (0.5 g, 1.114 mmol) and $Cs_2CO_3$ (0.436 g, 1.337 mmol) in 10 mL of DMF. The resulting mixture was stirred at 50° C. overnight before adding 2 mL of $CH_3CN$. Stirring was continued at 70° C. for 4 hours before cooling the reaction mixture to RT. The mixture was partitioned between an ice cold saturated aqueous solution of $NH_4Cl$ and $Et_2O$. The aqueous layer was back extracted with $Et_2O$. The combined organic layers were dried ($Na_2SO_4$), filtered, and evaporated. The residue was purified by $SiO_2$ chromatography (hexanes/EtOAc 0-30% EtOAc) to give 0.378 g of 1 (66% yield).

2,2-Dimethyl-1-[5-(2-trimethylsilanyl-ethoxymethyl)-2-(1-vinyl-1H-indol-3-yl)-5H-pyrrolo[2,3-b]pyrazin-7-yl]-propan-1-one was prepared following a similar procedure. The product was isolated in 27% yield as the elimination product of 1.

Step 2—A mixture of 1 (0.2 g, 0.391 mmol), KI (0.078 g, 0.47 mmol), and $NaN_3$ (0.031 g, 0.47 mmol) in 3.5 mL of DMSO was stirred at 80° C. overnight before being cooled to RT and partitioned between $H_2O$ and EtOAc. The aqueous layer was back extracted with EtOAc. The combined organic layers were dried ($Na_2SO_4$), filtered, and evaporated. The residue was purified by $SiO_2$ chromatography (hexanes/EtOAc 0-20% EtOAc) to give 0.134 g of 2 (66% yield).

2,2-Dimethyl-1-[2-[1-(2-morpholin-4-yl-ethyl)-1H-indol-3-yl]-5-(2-trimethylsilanyl-ethoxymethyl)-5H-pyrrolo[2,3-b]pyrazin-7-yl]-propan-1-one was prepared following a similar procedure but using morpholine (2.6 equivalents) as starting material. In this reaction 1.3 equivalents of $Cs_2CO_3$ and KI were used. $CH_3CN$ was used as solvent and the reaction was stirred at RT for two days, at 50° C. overnight and finally at 80° C. for 24 hours. The product was obtained in 63% yield after purification by $SiO_2$ chromatography (DCM/MeOH 0-3% MeOH).

2,2-dimethyl-1-[2-{1-[2-(4-methyl-piperazin-1-yl)-ethyl]-1H-indol-3-yl}-5-(2-trimethylsilanyl-ethoxymethyl)-5H-pyrrolo[2,3-b]pyrazin-7-yl]-propan-1-one was prepared following a similar procedure but using 1-methylpiperazine (2.6 equivalents) as starting material. In this reaction 1.3 equivalents of $Cs_2CO_3$ and KI were used. $CH_3CN$ was used as solvent and the reaction was stirred at RT for two days, at 50° C. overnight and finally at 80° C. for 24 hours. The product was obtained in 71% yield after purification by $SiO_2$ chromatography (DCM/MeOH 0-7% MeOH).

Step 3—A mixture of 2 (0.13 g, 0.251 mmol) and Pd 10 wt % on carbon (0.02 g) in 1 mL of EtOH and 1 mL of EtOAc was stirred under an hydrogen atmosphere (1 atm) overnight at RT before being filtered. The filtrate was evaporated. The residue was purified twice by $SiO_2$ chromatography (DCM/MeOH 0-5% MeOH followed by DCM/MeOH 0-7% MeOH) to give 0.089 g of 3 (72% yield).

Step 4—TFA (0.7 mL) was added at RT to a solution of 3 (0.085 g, 0.173 mmol) in 1.3 mL of DCM. The resulting mixture was stirred at RT overnight before being evaporated and coevaporated twice with toluene. The residue was taken into 2 mL of EtOH and NaOAc (0.142 g, 1.729 mmol) was added. The reaction mixture was stirred at RT for 3 hours before being evaporated. The residue was purified twice by $SiO_2$ chromatography (DCM/[DCM/MeOH/$NH_4OH$ 60/10/1] 100% to 60% DCM, followed by 100% to 50% DCM), and then my preparative TLC (DCM/[DCM/MeOH/$NH_4OH$ 60/10/1] 80% DCM) to give 0.013 g of 4: 1-{2-[1-(2-aminoethyl)-1H-indol-3-yl]-5H-pyrrolo[2,3-b]pyrazin-7-yl}-2,2-dimethyl-propan-1-one (21% yield).

2,2-Dimethyl-1-{2-[1-(2-morpholin-4-yl-ethyl)-1H-indol-3-yl]-5H-pyrrolo[2,3-b]pyrazin-7-yl}-propan-1-one was prepared following the same procedure but using 2,2-dimethyl-1-[2-[1-(2-morpholin-4-yl-ethyl)-1H-indol-3-yl]-5-(2-trimethylsilanyl-ethoxymethyl)-5H-pyrrolo[2,3-b]pyrazin-7-yl]-propan-1-one as starting material. The product was isolated in 39% yield after two purification by $SiO_2$ chromatography (DCM/MeOH 0 to 4% MeOH, followed by hexanes/EtOAc 20 to 60% EtOAc for 20 minutes and DCM/MeOH 0 to 3% for 20 minutes).

2,2-Dimethyl-1-(2-{1-[2-(4-methyl-piperazin-1-yl)-ethyl]-1H-indol-3-yl}-5H-pyrrolo[2,3-b]pyrazin-7-yl)-propan-1-one was prepared following a similar procedure but using 2,2-dimethyl-1-[2-{1-[2-(4-methyl-piperazin-1-yl)-ethyl]-1H-indol-3-yl}-5-(2-trimethylsilanyl-ethoxymethyl)-5H-pyrrolo[2,3-b]pyrazin-7-yl]-propan-1-one as starting material. The product was isolated in 75% yield by $SiO_2$ chromatography (DCM/[DCM/MeOH/$NH_4OH$ 60/10/1] 100-75% DCM).

Example 32

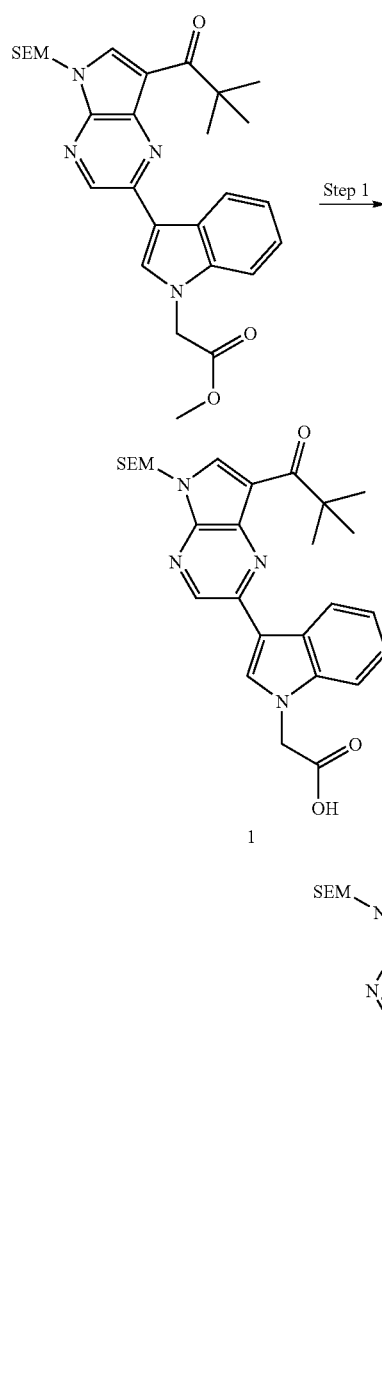

Step 1—A solution of LiOH.H₂O (0.093 g, 2.209 mmol) in 1 mL of H₂O was added to a solution of {3-[7-(2,2-dimethyl-propionyl)-5-(2-trimethylsilanyl-ethoxymethyl)-5H-pyrrolo[2,3-b]pyrazin-2-yl]-indol-1-yl}-acetic acid methyl ester (0.23 g, 0.442 mmol) in 3 mL of THF and 2 mL of MeOH. The resulting mixture was stirred at RT for 5 hours before being evaporated. The residue was partitioned between 1M HCl and EtOAc. The aqueous layer was back extracted with EtOAc. The combined organic layers were washed with brine, dried (MgSO₄), filtered, and evaporated to give 1 quantitatively. The product was used in the next reaction without purification.

Step 2—O-(7-Azabenzotriazole-1-yl)-N,N,N',N'tetramethyluroniumhexafluorophosphate (0.095 g, 0.25 mmol) was added to a mixture of 1 (0.115 g, 0.227 mmol), 1-methyl piperazine (0.027 g, 0.272 mmol) and DIPEA (0.4 mL, 0.227 mmol) in 3 mL of DMF. The resulting mixture was stirred at RT overnight before being evaporated. The residue was partitioned between 3M NaOH and DCM. The aqueous layer was back extracted twice with DCM. The combined organic layers were dried (MgSO₄), filtered, and evaporated. The residue was purified by SiO₂ chromatography (DCM/MeOH 0-8% MeOH) to give 0.075 g of 2: 2,2-dimethyl-1-[2-{1-[2-(4-methyl-piperazin-1-yl)-2-oxo-ethyl]-1H-indol-3-yl}-5-(2-trimethylsilanyl-ethoxymethyl)-5H-pyrrolo[2,3-b]pyrazin-7-yl]-propan-1-one (56% yield).

Example 33

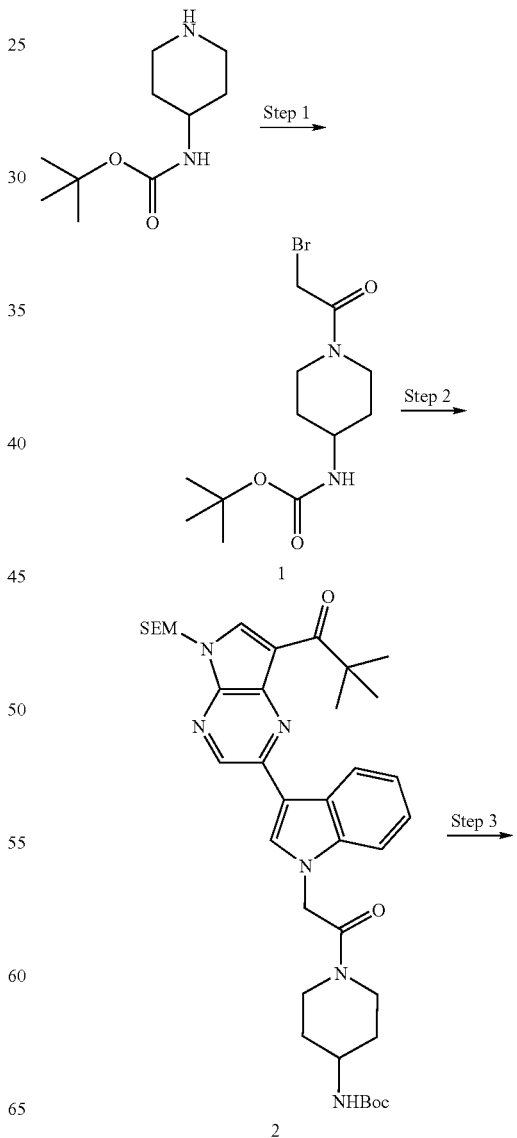

-continued

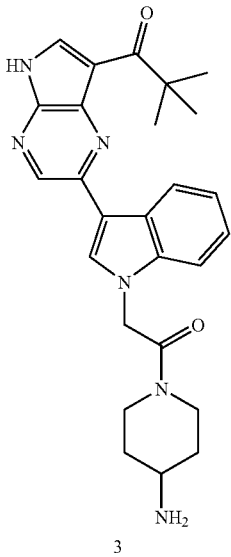

3

Step 1—Bromoacetyl bromide (1.3 mL, 14.979 mmol) was added dropwise at 0° C. to a solution of N,N-dimethylaniline (1.89 mL, 14.979 mmol) and piperidine-4-yl-carbamic acid tert-butyl ester (3 g, 14.979 mmol) in 50 mL of dimethylcarbonate. The resulting mixture was stirred at RT for 1 hour before being evaporated. The residue, taken into EtOAc was washed with 10% citric acid, 5% NaHCO$_3$ and brine. The organic layer was dried (MgSO$_4$), filtered, and evaporated to give 1 quantitatively. The residue was used in the next reaction without purification.

4-(2-Bromo-acetyl)-piperazine-1-carboxylic acid tert-butyl ester was prepared quantitatively following the same procedure but using piperazine-1-carboxylic acid tert-butyl ester as starting material.

Step 2—1-[2-(1H-Indol-3-yl)-5-(2-trimethylsilanyl-ethoxymethyl)-5H-pyrrolo[2,3-b]pyrazin-7-yl]-2,2-dimethyl-propan-1-one (0.1 g, 0.223 mmol) in 1 mL of DMF was added at 0° C. to a suspension of NaH 60% dispersion in oil (0.012 g, 0.312 mmol) in 2 mL of DMF. The resulting mixture was stirred at RT for 30 minutes before being cooled to 0° C. A solution of 1 (0.086 g, 0.267 mmol) in 2 mL of DMF was added and the reaction mixture was allowed to reach RT overnight before being quenched by addition of H$_2$O, and extracted 3 times with EtOAc. The combined organic layers were dried (MgSO$_4$), filtered, and evaporated. The residue was purified by SiO$_2$ chromatography (hexanes/EtOAc 0-40% EtOAc) to give 0.1 g of 2 (65% yield).

4-(2-{3-[7-(2,2-Dimethyl-propionyl)-5-(2-trimethylsilanyl-ethoxymethyl)-5H-pyrrolo[2,3-b]pyrazin-2-yl]-indol-1-yl}-acetyl)-piperazine-1-carboxylic acid tert-butyl ester was prepared following the same procedure but using 4-(2-bromo-acetyl)-piperazine-1-carboxylic acid tert-butyl ester as starting material (57% yield).

{3-[7-(2,2-Dimethyl-propionyl)-5-(2-trimethylsilanyl-ethoxymethyl)-5H-pyrrolo[2,3-b]pyrazin-2-yl]-indol-1-yl}-acetic acid methyl ester was prepared following the same procedure but using methyl bromoacetate as electrophile. In this reaction, the reaction mixture was stirred at RT for 2 hours before being worked up. The product was obtained quantitatively and was used in the next reaction without purification.

Step 3—0.7 mL of TFA was added at RT to a solution of 2 (0.1 g, 0.145 mmol) in 1.5 mL of DCM. The resulting dark orange/red mixture was stirred at RT for 2 hours before being evaporated and coevaporated twice with toluene. The crude residue was taken into 1.5 mL of EtOH and NaOAc (0.119 g, 1.451 mmol) was added. The resulting dark yellow mixture was stirred at RT overnight before being evaporated. The residue was partitioned between H$_2$O and EtOAc. The aqueous layer was back extracted twice with EtOAc. The combined organic layers were dried (MgSO$_4$), filtered, and evaporated. The residue was taken in H$_2$O, the insoluble was filtered, rinsed, and dried under vacuum to give 0.063 g of 3: 1-(2-{1-[2-(4-amino-piperidin-1-yl)-2-oxo-ethyl]-1H-indol-3-yl}-5H-pyrrolo[2,3-b]pyrazin-7-yl)-2,2-dimethyl-propan-1-one (95% yield).

2,2-Dimethyl-1-{2-[1-(2-oxo-2-piperazin-1-yl-ethyl)-1H-indol-3-yl]-5H-pyrrolo[2,3-b]pyrazin-7-yl}-propan-1-one was prepared following the same procedure but using 4-(2-{3-[7-(2,2-dimethyl-propionyl)-5-(2-trimethylsilanyl-ethoxymethyl)-5H-pyrrolo[2,3-b]pyrazin-2-yl]-indol-1-yl}-acetyl)-piperazine-1-carboxylic acid tert-butyl ester as starting material (71% yeild).

2,2-Dimethyl-1-(2-{1-[2-(4-methyl-piperazin-1-yl)-2-oxo-ethyl]-1H-indol-3-yl}-5H-pyrrolo[2,3-b]pyrazin-7-yl)-propan-1-one was prepared following the same procedure but using 2,2-dimethyl-1-[2-{1-[2-(4-methyl-piperazin-1-yl)-2-oxo-ethyl]-1H-indol-3-yl}-5-(2-trimethylsilanyl-ethoxymethyl)-5H-pyrrolo[2,3-b]pyrazin-7-yl]-propan-1-one as starting material. The product was isolated in 67% yield by SiO$_2$ chromatography (DCM/MeOH 0-10% MeOH).

Example 34

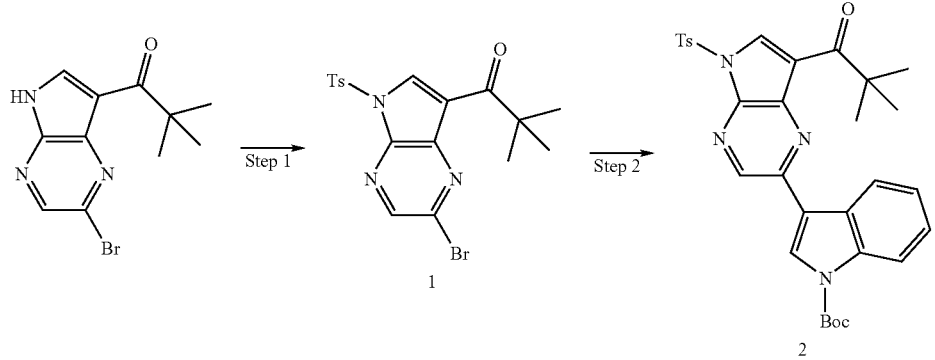

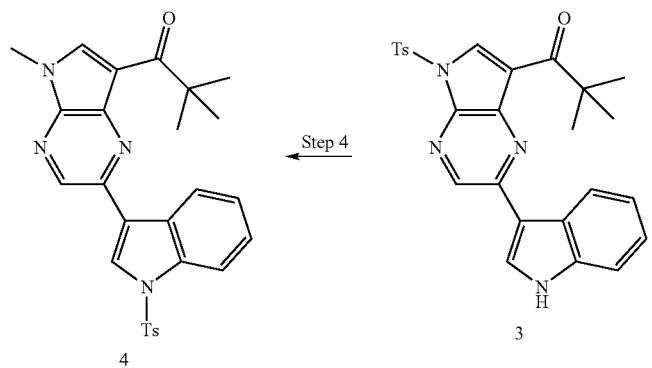

Step 1—A solution of 1-(2-bromo-5H-pyrrolo[2,3-b]pyrazin-7-yl)-2,2-dimethyl-propan-1-one (0.5 g, 1.772 mmol) in 3 mL of DMF was added at 0° C. to a suspension of NaH 60% dispersion in oil (0.078 g, 1.949 mmol) in 5 mL of DMF. The resulting mixture was stirred at 0° C. for 30 minutes before adding p-TsCl (0.375 g, 1.949 mmol) in 2 mL of DMF. The resulting mixture was allowed to reach RT and stirred at RT for 1 hour before adding 0.4 equivalents of p-TsCl. The reaction mixture was stirred at RT overnight before being quenched by addition of $H_2O$ and extracted with EtOAc. The aqueous layer was back extracted with EtOAc. The combined organic layers were dried ($Na_2SO_4$), filtered, and evaporated. The residue was purified by $SiO_2$ chromatography (hexanes/EtOAc 0-5% EtOAc) to give 0.51 g of 1 (66% yield).

Step 2—A mixture of 1 (0.23 g, 0.527 mmol), 3-(4,4,5,5-tetramethyl-[1,3,2]dioxaborolan-2-yl)-indole-1-carboxylic acid tert-butyl ester (0.199 g, 0.58 mmol), and tetrakis(triphenylphosphine)palladium(0) (0.061 g, 53 μmol) in 5 mL of degassed 1,4-dioxane and 0.53 mL of 2M $K_2CO_3$ (1.06 mmol) was stirred at 90° C. for 36 hours before being cooled to RT and evaporated. The residue was purifed by $SiO_2$ chromatography (hexanes/EtOAc 0-15% EtOAc) to give 0.12 g of 2 (40% yield).

Step 3—0.5 mL of 4M HCl in 1,4-dioxane were added at RT to a mixture of 2 (0.12 g, 0.21 mmol) in 1.6 mL of DCM and 0.4 mL of triethylsilane. The resulting mixture was stirred at reflux overnight before being cooled to RT and evaporated. The residue was taken into 1.6 mL of DCM and 8 equivalents of TFA were added. The reaction mixture was stirred at reflux overnight before being cooled to RT and washed with saturated $NaHCO_3$. The aqueous layer was back extracted twice with DCM. The combined organic layers were dried ($Na_2SO_4$), filtered, and evaporated to give 3 quantitatively. The product was used in the next step without purification.

Step 4—NaH 60% dispersion in oil (0.011 g, 0.273 mmol) was added at 0° C. to a solution of 3 (0.099 g, 0.21 mmol) in 1.5 mL of DMF. The resulting mixture was stirred at 0° C. for 30 minutes before adding iodomethane (0.02 mL, 0.273 mmol). The reaction mixture was stirred at 0° C. for 1 hour before being quenched by addition of saturated $NH_4Cl$ and extracted with EtOAc. The aqueous layer was back extracted with EtOAc. The combined organic layers were dried ($Na_2SO_4$), filtered, and evaporated. The residue was purified by $SiO_2$ chromatography (hexanes/EtOAc 0-30% EtOAc) to give 0.045 g of 4: 2,2-dimethyl-1-{5-methyl-2-[1-(toluene-4-sulfonyl)-1H-indol-3-yl]-5H-pyrrolo[2,3-b]pyrazin-7-yl}-propan-1-one (44% yield). The migration of the tosylate was accidental.

Example 35

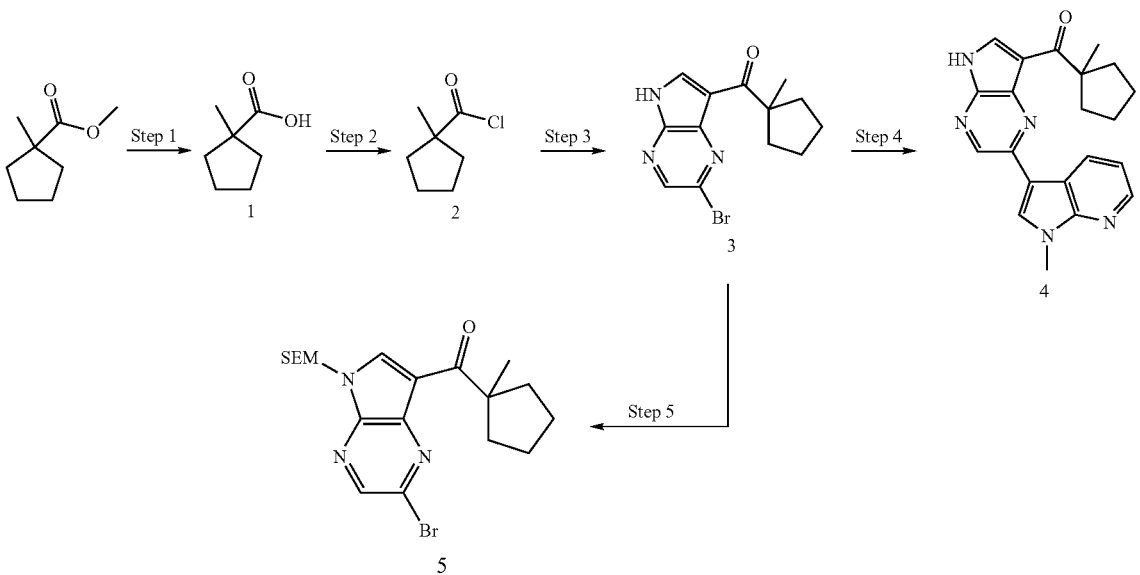

Step 1—A solution of LiOH.H$_2$O (3.423 g, 81.575 mmol) in 7 mL of H$_2$O was added at RT to solution of 1-methyl-cyclopentanecarboxylic acid methyl ester (2.9 g, 20.394 mmol) in 21 mL of THF and 14 mL of MeOH. The resulting mixture was stirred at RT overnight before being evaporated. The residue was partitioned between 2M HCl and EtOAc. The aqueous layer was back extracted twice with EtOAc. The combined organic layers were washed with brine, dried (MgSO$_4$), filtered, and evaporated to give 1 quantitatively. The product was used in the next step without purification.

Methyl-cyclopentanecarboxylic acid methyl ester was prepared according to the procedure in Tetrahedron 1985, 41(7), 1267-1275.

Step 2—Oxalyl chloride (0.93 mL, 10.65 mmol) was added dropwise to a solution of 1 (1.05 g, 8.192 mmol) in 5 mL of DCE+1 drop of DMF. The resulting mixture was stirred at RT for 3 hours before being evaporated and coevaporated three times with DCE to give 2 quantitatively. The product was used in the next step without purification.

Step 3—Diethylaluminium chloride 1 M in hexanes (1.67 mL, 1.67 mmol) was added dropwise at 0° C. to a suspension of 2-bromo-5H-pyrrolo[2,3-b]pyrazine (0.11 g, 0.555 mmol) in 4 mL of DCE. The resulting mixture was stirred at 0° C. for 30 minutes before adding 2 (0.652 g, 4.444 mol) in 2 mL of DCE. The resulting mixture was allowed to reach RT and was then stirred at 40° C. overnight before being cooled to RT and quenched by addition of saturated NaHCO$_3$. The bi-phasic mixture was evaporated until removal of DCE and the remaining aqueous layer was back extracted twice with EtOAc. The combined organic layers were dried (MgSO$_4$), filtered and evaporated. The residue was purified by SiO$_2$ chromatography (hexanes/EtOAc 0-20% EtOAc) to give 0.04 g of 3 (23% yield).

Step 4—A mixture of 3 (0.04 g, 0.13 mmol), 1-methyl-3-(4,4,5,5-tetramethyl-[1,3,2]dioxaborolan-2-yl)-1H-pyrrolo[2,3-b]pyridine (0.084 g, 0.324 mmol), and [1,1']-bis(diphenylphosphine)ferrocene]dichloridepalladium(II) DCM complex in 2 mL of 1,4-dioxane and 0.26 mL of 2 M K$_2$CO$_3$ (0.519 mmol) was degassed by bubbling argon through the mixture before being stirred for 1 hour at 150° C. under microwave irradiation, and cooled to RT. 2.5 equivalents of boronic ester, 2 equivalents of K$_2$CO$_3$, and 0.05 equivalents of catalyst were added, and the resulting mixture was stirred at 150° C. under microwave irradiation for another hour before being cooled to RT. The reaction mixture was evaporated. The residue was partitioned between H$_2$O and EtOAc. The aqueous layer was back extracted twice with EtOAc. The combined organic layers were filtered through celite, dried (MgSO$_4$), filtered, and evaporated. The residue was purified by SiO$_2$ preparative TLC (DCM/MeOH 0.5% MeOH) to give 0.005 g of 4: (1-methyl-cyclopentyl)-[2-(1-methyl-1H-pyrrolo[2,3-b]pyridin-3-yl)-5H-pyrrolo[2,3-b]pyrazin-7-yl]-methanone (11% yield).

Step 5—NaH 60% dispersion in oil (0.07 g, 1.73 mmol) was added at 0° C. to a solution of 3:(2-bromo-5H-pyrrolo[2,3-b]pyrazin-7-yl)-(1-methyl-cyclopentyl)-methanone (0.41 g, 1.33 mmol) in 8 mL of DMF. The resulting mixture was stirred at 0° C. for 30 minutes before adding SEM-Cl (0.28 mL, 1.596 mmol). The reaction mixture was allowed to reach RT overnight before being quenched by addition of ice-cold H$_2$O and extracted twice with EtOAc. The combined organic layers were washed with H$_2$O, dried (MgSO$_4$), filtered, and evaporated. The residue was purified by SiO$_2$ chromatography (hexanes/EtOAc 0-10% EtOAc) to give 0.512 g of 5: [2-bromo-5-(2-trimethylsilanyl-ethoxymethyl)-5H-pyrrolo[2,3-b]pyrazin-7-yl]-(1-methyl-cyclopentyl)-methanone (88% yield).

2-Bromo-5-(2-trimethylsilanyl-ethoxymethyl)-5H-pyrrolo[2,3-b]pyrazin-7-yl]-(1-methyl-cyclohexyl)-methanone was prepared following the same procedure but using (2-bromo-5H-pyrrolo[2,3-b]pyrazin-7-yl)-(1-methyl-cyclohexyl)-methanone as starting material (90% yield).

2-Bromo-7-(2-tert-butyl-[1,3]dioxolan-2-yl)-5-(2-trimethylsilanyl-ethoxymethyl)-5H-pyrrolo[2,3-b]pyrazine was prepared quantitatively following the same procedure but using 2-bromo-7-(2-tert-butyl-[1,3]dioxolan-2-yl)-5H-pyrrolo[2,3-b]pyrazine as starting material.

Example 36

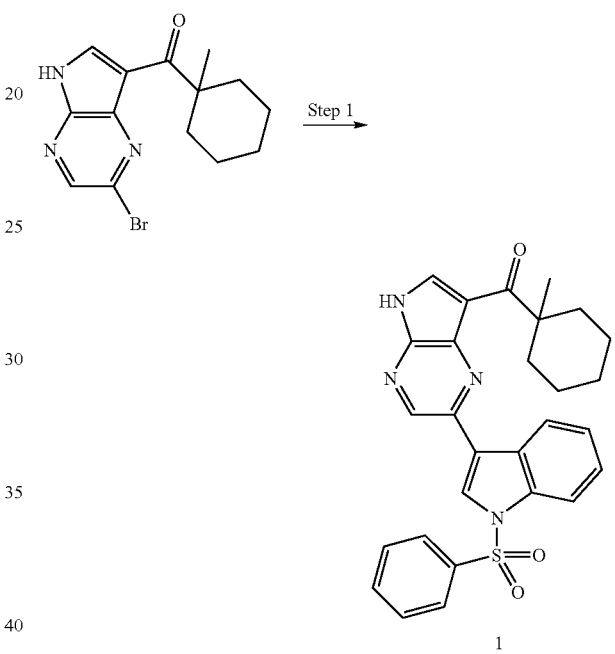

Step 1—A mixture of (2-bromo-5H-pyrrolo[2,3-b]pyrazin-7-yl)-(1-methyl-cyclohexyl)-methanone (0.1 g, 0.31 mmol), 1-phenylsulfonylindole-3-boronic acid (0.11 g, 0.365 mol), K$_2$CO$_3$ (0.13 g, 0.941 mmol), and [1,1']-bis(diphenylphosphine)ferrocene]dichloridepalladium(II) DCM complex (0.025 g, 31.01 μmol) in 3 mL of a 4/1 mixture of 1,4-dioxane and H$_2$O was degassed for 10 minutes by bubbling argon though the mixture. The resulting mixture was then stirred under microwave irradiation at 120° C. for 15 minutes before being cooled to RT. The residue was purified by SiO$_2$ chromatography (DCM/MeOH 5% MeOH) to give 0.04 g of 1: [2-(1-Benzenesulfonyl-1H-indol-3-yl)-5H-pyrrolo[2,3-b]pyrazin-7-yl]-(1-methyl-cyclohexyl)-methanone (26% yield)

(1-Methyl-cyclohexyl)-[2-(1-methyl-1H-indol-3-yl)-5H-pyrrolo[2,3-b]pyrazin-7-yl]-methanone was prepared following the same procedure but using 1-methyl-3-(4,4,5,5-tetramethyl-[1,3,2]dioxazolidin-2-yl)-1H-indole as starting material. In this instance, the reaction was stirred at 150° C. under microwave irradiation for 1 hour before adding 0.5 equivalents of boronic ester, 0.05 equivalent of fresh catalyst and 2 equivalents of K$_2$CO$_3$. The resulting mixture was stirred at 150° C. under microwave irration for another hour.

The product was obtained in 17% yield after purification by SiO$_2$ chromatography (DCM/MeOH 0-5% MeOH).

Example 37

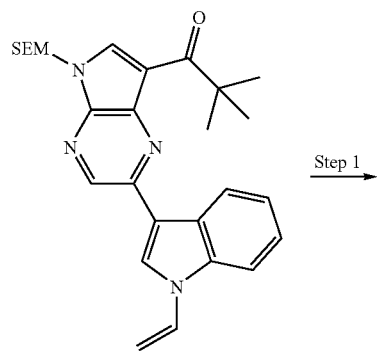

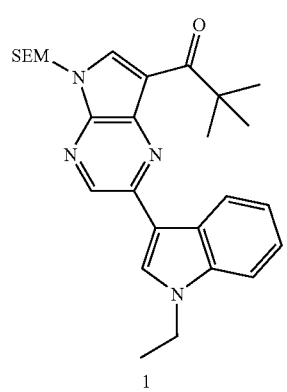

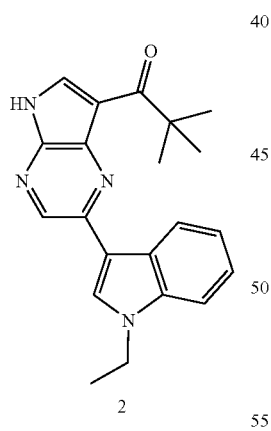

Step 1—A mixture of 2,2-dimethyl-1-[5-(2-trimethylsilanyl-ethoxymethyl)-2-(1-vinyl-1H-indol-3-yl)-5H-pyrrolo[2,3-b]pyrazin-7-yl]-propan-1-one (0.145 g, 0.305 mmol) and Pd/C 10 wt % (0.03 g) in 5 mL of EtOH was stirred under an atmosphere of hydrogen at RT for 1 hour before being filtered. The filtrate was evaporated to give 0.137 g of 1 (94% yield).

Step 2—TFA (1 mL) was added at RT to a solution of 1 (0.135 g, 0.283 mmol) in 2 mL of DCM. The resulting mixture was stirred at RT overnight before being evaporated and coevaporated twice with toluene. The residue was taken into 3 mL of EtOH and NaOAc (0.232 g, 2.832 mmol) was added. The reaction mixture was stirred at RT for 4 hours before being evaporated. The residue was taken into H$_2$O. After sonication, the insoluble was filtered and rinsed with H$_2$O before being adsorbed onto SiO$_2$ and purified by SiO$_2$ chromatography (Toluene/EtOAc 0-50% EtOAc). The fractions containing product were evaporated and the residue was taken into a minimal amount of DCM. The insoluble was filtered and dried to give 0.025 g of 2: 1-[2-(1-ethyl-1H-indol-3-yl)-5H-pyrrolo[2,3-b]pyrazin-7-yl]-2,2-dimethyl-propan-1-one (25% yield).

Example 38

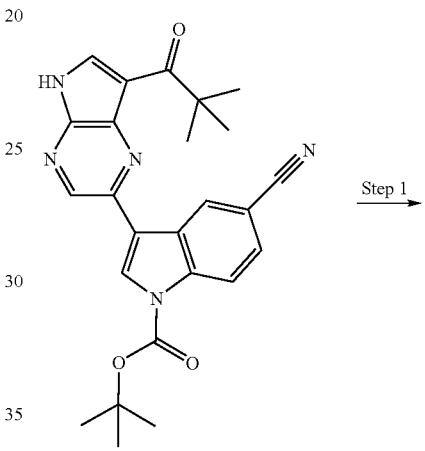

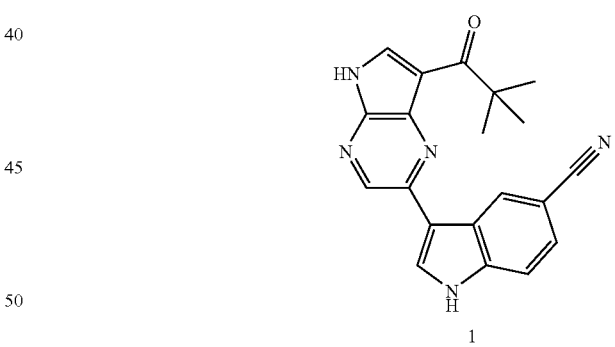

Step 1—A suspension of 5-cyano-3-[7-(2,2-dimethyl-propionyl)-5H-pyrrolo[2,3-b]pyrazin-2-yl]-indole-1-carboxylic acid tert-butyl ester (0.07 g, 0.158 mmol) in 10 mL of ethylene glycol was stirred at 190° C. for an hour before being cooled to RT. The mixture was partitioned between EtOAc and H$_2$O. The aqueous layer was back extracted twice with EtOAc. Combined organic layers were dried over Na$_2$SO$_4$, filtered and evaporated. The residue was taken into a minimal amount of acetone. The insoluble was filtered, rinsed with a minimal amount of MeOH and dried to give 0.035 g of 1: 3-[7-(2,2-dimethyl-propionyl)-5H-pyrrolo[2,3-b]pyrazin-2-yl]-1H-indole-5-carbonitrile (65% yield)

Example 39

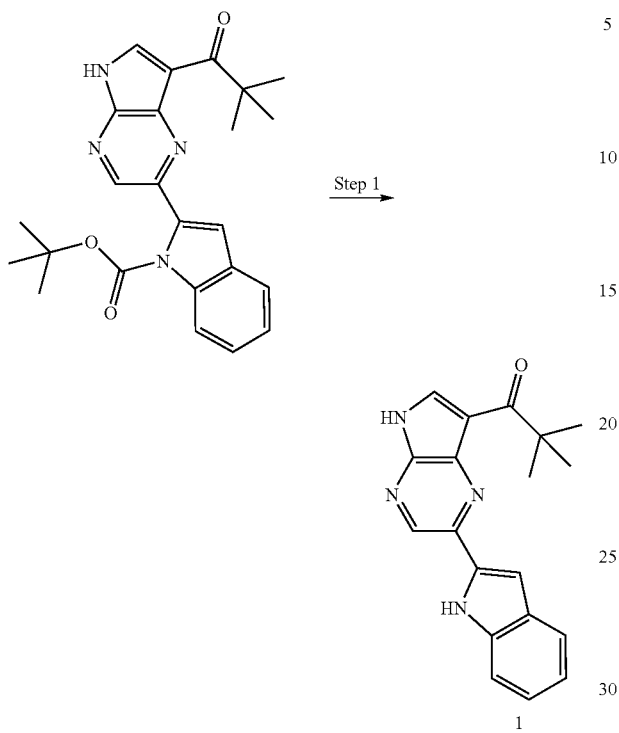

Step 1—0.39 mL of 2M K$_2$CO$_3$ (0.789 mmol) was added at RT to a solution of 2-[7-(2,2-dimethyl-propionyl)-5H-pyrrolo[2,3-b]pyrazin-2-yl]-indole-1-carboxylic acid tert-butyl ester (0.11 g, 0.263 mmol) in 2 mL of MeOH. The resulting mixture was stirred at reflux overnight before being cooled to RT and evaporated. The residue was taken into a minimal amount of Et$_2$O. After sonication, the insoluble was filtered, rinsed with H$_2$O, and dried under vacuum to give 0.049 g of 1: 1-[2-(1H-Indol-2-yl)-5H-pyrrolo[2,3-b]pyrazin-7-yl]-2,2-dimethyl-propan-1-one (59% yield).

Example 40

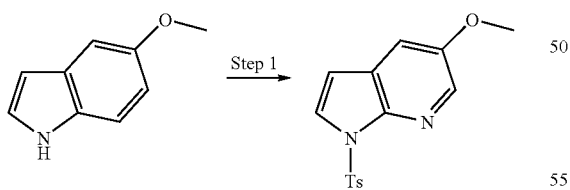

Step 1—NaH 60% dispersion in oil (0.326 g, 8.153 mmol) was added at 0° C. to a solution of commercially available 5-methoxyindole (1 g, 6.794 mmol) in 50 mL of DMF. The resulting mixture was stirred at 0° C. for 30 minutes before adding p-TsCl (1.943 g, 10.192 mmol). The reaction mixture was allowed to warm to RT overnight before being quenched by addition of saturated aqueous NH$_4$Cl. The precipitate was filtered, rinsed with H$_2$O and dried to give 1.93 g of 5-methoxy-1-(toluene-4-sulfonyl)-1H-indole (94% yield).

5-Methyl-1-(toluene-4-sulfonyl)-1H-indole was prepared following the same procedure but using the commercially available 5-methyl-1H-indole as starting material. In this reaction the product was obtained in 90% yield after purification by SiO$_2$ chromatography (hexanes/EtOAc 0 to 20% yield 6-Methoxy-1-(toluene-4-sulfonyl)-1H-indole was prepared following the same procedure but using the commercially available 6-methoxy-1H-indole as starting material (85% yield).

6-Methyl-1-(toluene-4-sulfonyl)-1H-indole was prepared following the same procedure but using the commercially available 6-methyl-1H-indole as starting material. In this reaction the product was obtained quantitatively after extraction with Et$_2$O of the quenched reaction mixture.

Example 41

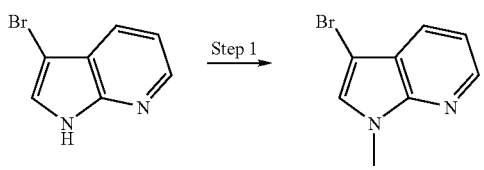

Step 1—A solution of commercially available 3-bromo-1H-pyrrolo[2,3-b]pyridine (0.53 g, 2.69 mmol) in 4 mL of DMF was added at 0° C. to a suspension of NaH 60% dispersion in oil (0.14 g, 3.497 mmol) in 4 mL of DMF. The resulting mixture was stirred at RT for 30 minutes before being cooled to 0° C. and adding iodomethane (0.67 mL, 10.759 mmol). The reaction mixture was allowed to reach RT overnight before being quenched by addition of H$_2$O and extracted three times with EtOAc. The combined organic layers were washed with brine, dried (MgSO$_4$), filtered, and evaporated. The residue was purified by SiO$_2$ chromatography (hexanes/EtOAc 0-20% EtOAc) to give 0.386 g of 3-bromo-1-methyl-1H-pyrrolo[2,3-b]pyridine (68% yield).

Example 42

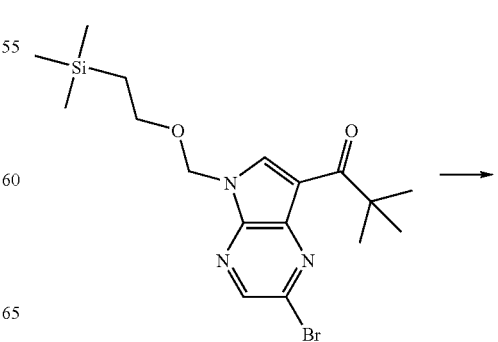

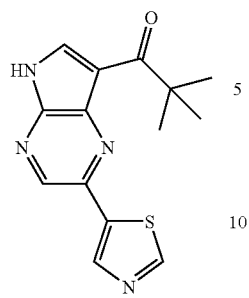

2,2-Dimethyl-1-(2-thiazol-5-yl-5H-pyrrolo[2,3-b]pyrazin-7-yl)-propan-1-one

To a microwave vial was added 1-[2-Bromo-5-(2-trimethylsilanyl-ethoxymethyl)-5H-pyrrolo[2,3-b]pyrazin-7-yl]-2,2-dimethyl-propan-1-one 0.075 gm (0.182 mM), tris(dibenzylideneacetone)dipalladium(0), 0.001 gm (0.002 mM), triphenylarsine 0.003 gm (0.01 mM) and 1 ml THF. The vial was sealed, evacuated and refilled three times with argon. After stirring a few minutes the purple color faded and 5-Tributylstannanyl-thiazole 0.10 gm (0.267 mM) was added by syringe. The vial was placed in a 70° C. oil bath for 19 hours then 20 hours at 80° C. The vial was cooled to room temperature, the mixture concentrated and purified by column chromatography to give the adduct 0.068 gm (0.163 mM, 89% yield). The SEM protecting group was removed with the procedure in JTB prep 1 and the product recrystallized from acetonitrile to give 2,2-Dimethyl-1-(2-thiazol-5-yl-5H-pyrrolo[2,3-b]pyrazin-7-yl)-propan-1-one 0.0118 gm, (0.041 mM) M+1 287, m.p. 281-282° C.

4-Amino-N-{5-[7-(2,2-dimethyl-propionyl)-5H-pyrrolo[2,3-b]pyrazin-2-yl]-2-methyl-phenyl}-benzenesulfonamide M+1 464, m.p. 264-266° C.

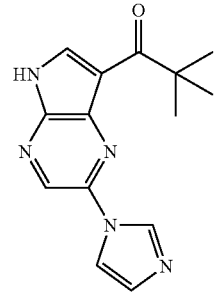

Preparation of B:

A mixture of A (0.20 g, 0.48 mmol), imidazole (0.049 g, 0.72 mmol), potassium carbonate (0.15 g, 1.1 mmol), cupurus iodide (0.014 g, 0.07 mmol) and DL-Proline (0.016 g, 0.14 mmol) in 3 ml. of DMSO was flushed with Argon for 5 minutes, then heated at 100 degree Celsius for 18 hrs. The cooled mixture was partitioned between water and ethyl acetate, the organic layer was washed with brine, dried over sodium sulphate, and concentrated in vacuo. The residual oil was loaded on silicagel column and eluted with 0.5% methanol-dichloromethane to afford the desired product B as an oil (0.13 g, 68% yield).

Preparation of 1-(2-Imidazol-1-yl-5H-pyrrolo[2,3-b]pyrazin-7-yl)-2,2-dimethyl-propan-1-one To a solution of B (0.125 g, 0.31 mmol) in THF (3 ml) was added a 1 Molar solution of TBAF in THF (1.75 ml) and the resulting rxn. Mixture was heated at 70 degree Celsius under reflux for 8 hrs. The cooled mixture was partitioned between water and ethyl acetate, the organic layer was washed with brine, dried over sodium sulphate, and concentrated in vacuo. The residual oil was loaded on silicagel column and eluted with 3% methanol-dichloromethane to afford the desired product, 1-(2-Imidazol-1-yl-5H-pyrrolo[2,3-b]pyrazin-7-yl)-2,2-dimethyl-propan-1-one as light yellow powder (0.023 g, 28% yield) mp 215-217° C.

Example 43

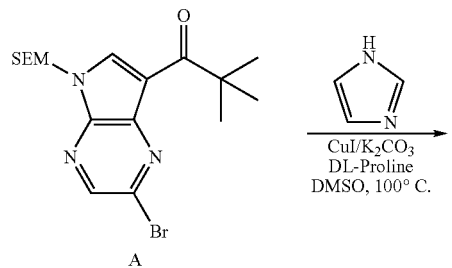

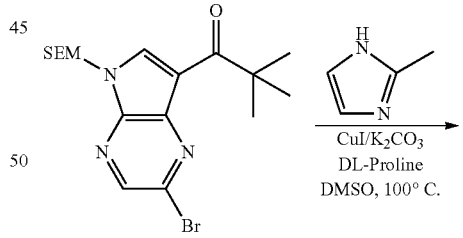

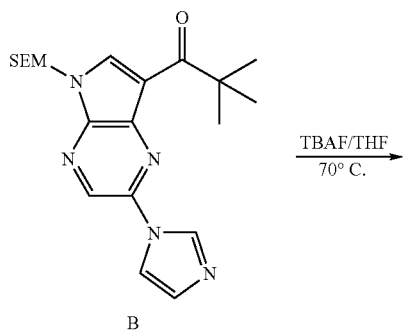

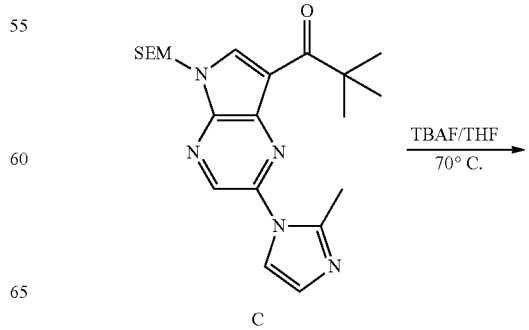

-continued

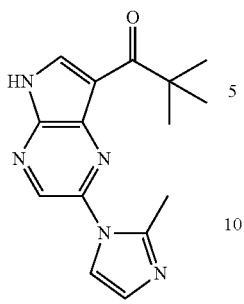

Preparation of C:

A mixture of A (0.20 g, 0.48 mmol), 2-methylimidazole (0.059 g, 0.72 mmol), potassium carbonate (0.15 g, 1.1 mmol), cupurus iodide (0.014 g, 0.07 mmol) and DL-Proline (0.016 g, 0.14 mmol) in 2.5 ml. of DMSO was flushed with Argon for 5 minutes, then heated at 100 degree Celsius for 18 hrs. The cooled mixture was partitioned between water and ethyl acetate, the organic layer was washed with brine, dried over sodium sulphate, and concentrated in vacuo. The residual oil was loaded on silicagel column and eluted with 2.5% methanol-dichloromethane to afford the desired product C as an oil (0.098 g, 48% yield).

Example 44

Preparation of 2,2-Dimethyl-1-[2-(2-methyl-imidazol-1-yl)-5H-pyrrolo[2,3-b]pyrazin-7-yl]-propan-1-one To a solution of C (0.098 g, 0.23 mmol) in THF (3 ml) was added a 1 Molar solution of TBAF in THF (1.5 ml) and the resulting rxn. Mixture was heated at 70 degree Celsius under reflux for 6 hrs. The cooled mixture was partitioned between water and ethyl acetate, the organic layer was washed with brine, dried over sodium sulphate, and concentrated in vacuo. The residual oil was loaded on silicagel column and eluted with 3% methanol-dichloromethane to afford the desired product, 2,2-Dimethyl-1-[2-(2-methyl-imidazol-1-yl)-5H-pyrrolo[2,3-b]pyrazin-7-yl]-propan-1-one as light brown powder (0.0118 g, 18% yield) mp 247-249° C.

Example 45

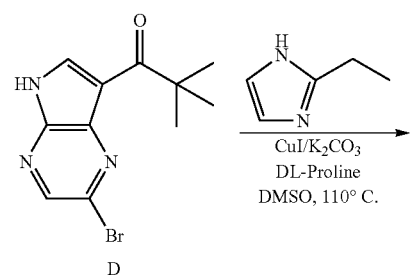

-continued

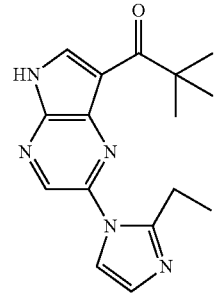

Preparation of 1-[2-(2-Ethyl-imidazol-1-yl)-5H-pyrrolo[2,3-b]pyrazin-7-yl]-2,2-dimethyl-propan-1-one A mixture of D (0.15 g, 0.53 mmol), 2-ethylimidazole (0.21 g, 2.12 mmol), potassium carbonate (0.16 g, 1.2 mmol), cupurus iodide (0.015 g, 0.08 mmol) and DL-Proline (0.018 g, 0.16 mmol) in 2.5 ml. of DMSO in a seal tube was purged with Argon for 2 minutes, then subjected to microwave irradiation at 110 degree Celsius for 10 hrs. The cooled mixture was partitioned between water and DCM, the organic layer was washed with brine, dried over sodium sulphate, and concentrated in vacuo. The residual oil was loaded on silicagel column and eluted with DCM: 1% $NH_4OH$-MeOH (9.5:0.5) to afford the desired product 1-[2-(2-Ethyl-imidazol-1-yl)-5H-pyrrolo[2,3-b]pyrazin-7-yl]-2,2-dimethyl-propan-1-oneas a light brown powder (0.055 g, 35%) mp 276-278° C.

Example 46

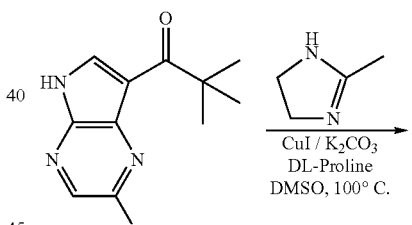

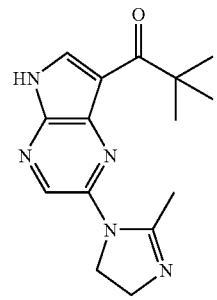

Preparation of 2,2-Dimethyl-1-[2-(2-methyl-4,5-dihydro-imidazol-1-yl)-5H-pyrrolo[2,3-b]pyrazin-7-yl]-propan-1-one A mixture of D (0.15 g, 0.53 mmol), 2-methyl-2-ethylimidazoline (0.17 g, 2.1 mmol), potassium carbonate (0.16 g, 1.2 mmol), cupurus iodide (0.015 g, 0.08 mmol) and DL-Proline (0.018 g, 0.16 mmol) in 2.5 ml. of DMSO in a seal tube was purged with Argon for 2 minutes, then subjected to microwave irradiation at 100 degree Celsius for 10 hrs. The cooled mixture was partitioned between water and DCM, the organic layer was washed with brine, dried over sodium sulphate, and concentrated in vacuo. The residual oil was loaded on silica-gel column and eluted with DCM: 1% $NH_4OH$-MeOH (9:1) to afford the desired product 2,2-Dimethyl-1-[2-(2-methyl-4,5-dihydro-imidazol-1-yl)-5H-pyrrolo[2,3-b]pyrazin-7-yl]-propan-1-one as a light brown powder (0.035 g, 23%) mp 235-236° C.

Example 47

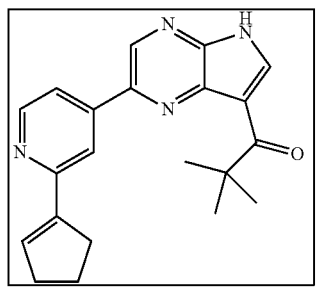

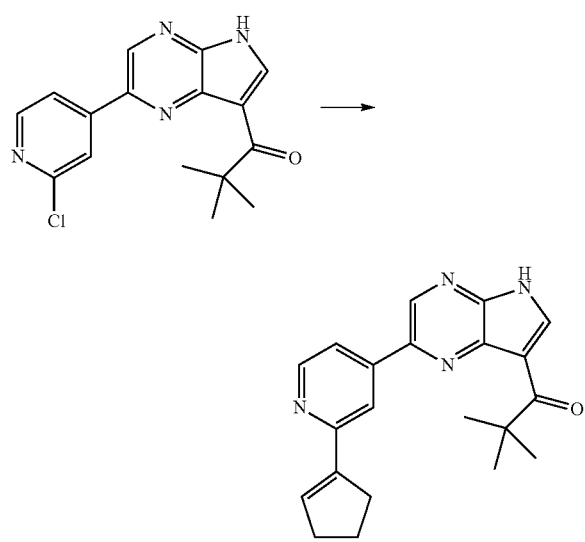

1-[2-(2-cyclopent-1-enyl-pyridin-4-yl)-5H-pyrrolo[2,3-b]pyrazin-7-yl]-2,2-dimethyl-propan-1-one A mixture of 1-[2-(2-chloro-pyridin-4-yl)-5H-pyrrolo[2,3-b]pyrazin-7-yl]-2,2-dimethyl-propan-1-one (0.060 g, 0.19 mmol), cyclopenten-1-yl boronic acid (0.032 g, 0.29 mmol), potassium carbonate (0.101 g, 0.73 mmol), and Pd(dppf)$Cl_2$.$CH_2Cl_2$ (0.012 g, 0.015 mmol) in 3 mL of 1,4-dioxane and 0.75 mL of water was stirred at 160° C. in a microwave for 30 min. The resulting black suspension was partitioned between 30 mL of ethyl acetate and 30 mL of water, and the aqueous layer was extracted with 30 mL of ethyl acetate. The combined organic layers were dried over $MgSO_4$, filtered and concentrated to a residue. Column chromatography (0->60% EtOAc/hexanes) afforded 0.016 g (25%) of 1-[2-(2-cyclopent-1-enyl-pyridin-4-yl)-5H-pyrrolo[2,3-b]pyrazin-7-yl]-2,2-dimethyl-propan-1-one as a pale yellow solid.

Example 48

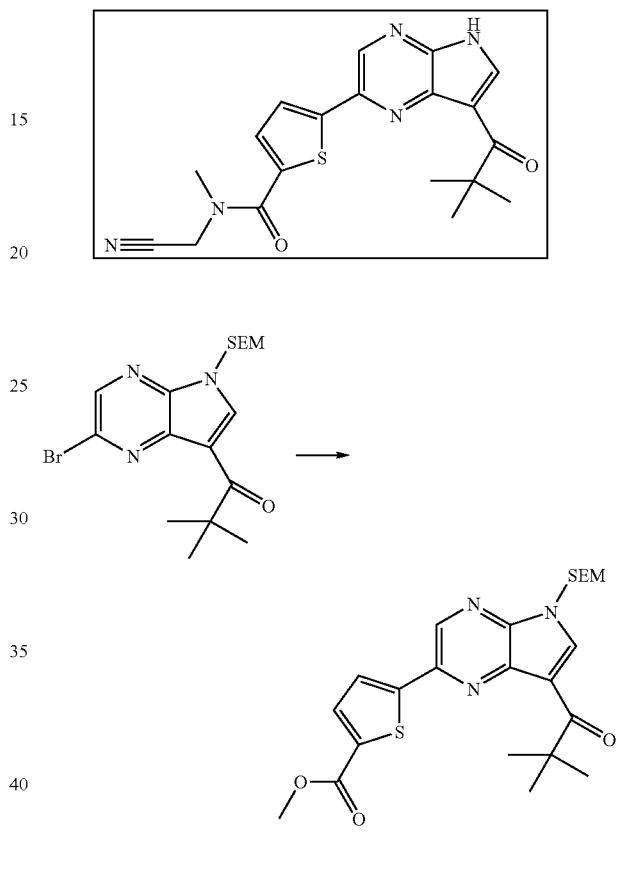

5-[7-(2,2-dimethyl-propionyl)-5H-pyrrolo[2,3-b]pyrazin-2-yl]-thiophene-2-carboxylic acid cyanomethyl-methyl-amide A mixture of thiophene-2-carboxylic acid methyl ester 5-boronic acid (0.350 g, 1.88 mmol), 1-[2-bromo-5-(2-trimethylsilanyl-ethoxymethyl)-5H-pyrrolo[2,3-b]pyrazin-7-yl]-2,2-dimethyl-propan-1-one (0.705 g, 1.71 mmol), potassium carbonate (0.898 g, 6.50 mmol), and Pd(dppf)$Cl_2$.$CH_2Cl_2$ (0.140 g, 0.171 mmol) in 12 mL of 1,4-dioxane and 3 mL of water was stirred at 160° C. in a microwave for 30 min. The resulting dark red suspension was partitioned between 50 ml of ethyl acetate and 100 mL of water, and the aqueous layer was extracted with two 50 mL portions of ethyl acetate. The combined organic layers were dried over $MgSO_4$, filtered and concentrated to a residue. Column chromatography (0->80 EtOAc/hexanes) afforded 0.620 g (77%) of 5-[7-(2,2-dimethyl-propionyl)-5-(2-trimethylsilanyl-ethoxymethyl)-5H-pyrrolo[2,3-b]pyrazin-2-yl]-thiophene-2-carboxylic acid methyl ester as a red solid.

Example 49

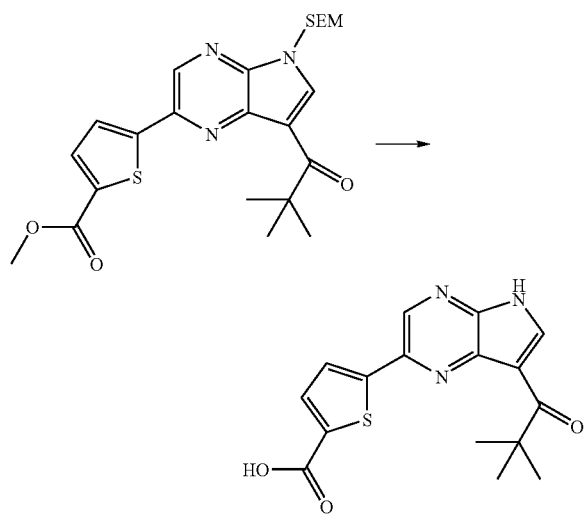

A solution of 5-[7-(2,2-dimethyl-propionyl)-5-(2-trimethylsilanyl-ethoxymethyl)-5H-pyrrolo[2,3-b]pyrazin-2-yl]-thiophene-2-carboxylic acid methyl ester (0.350 g, 0.739 mmol) in 8 mL of dichloromethane and 3 mL of trifluoroacetic acid was stirred for 2.5 h, then concentrated. The resulting residue was dissolved in 10 mL of ethanol and treated with lithium hydroxide (0.177 g, 7.39 mmol). The mixture was stirred overnight, then concentrated. The resulting residue was partitioned between 100 mL of ethyl acetate and 50 mL of a 10% acetic acid solution. The aqueous layer was extracted with 30 mL of ethyl acetate. The combined organic layers were dried over MgSO$_4$, filtered and concentrated to 0.232 g (95%) of slightly impure 5-[7-(2,2-dimethyl-propionyl)-5H-pyrrolo[2,3-b]pyrazin-2-yl]-thiophene-2-carboxylic acid as a brown solid, which was used without further purification.

Example 50

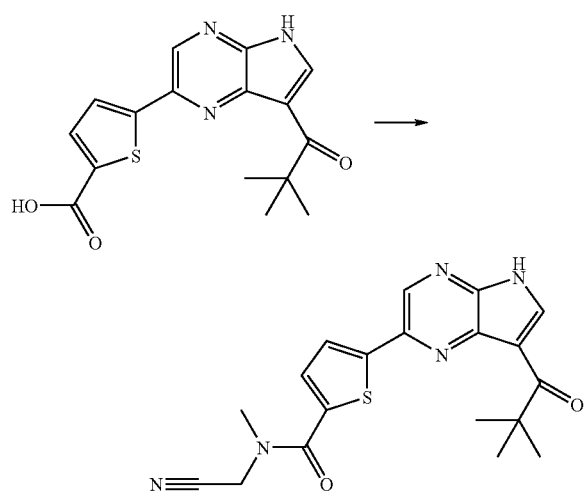

A solution of 5-[7-(2,2-dimethyl-propionyl)-5H-pyrrolo[2,3-b]pyrazin-2-yl]-thiophene-2-carboxylic acid (0.060 g, 0.18 mmol), methylaminoacetonitrile (0.200 mL, 1.64 mmol) and EDCI (0.315 g, 1.64 mmol) in 3 mL of ethanol and 3 mL of dichloromethane was stirred for 1 h, then concentrated. The resulting residue was partitioned between 30 ml of ethyl acetate and 30 mL of a 10% citric acid solution, and the aqueous layer was extracted 30 mL of ethyl acetate. The combined organic layers were dried over MgSO$_4$, filtered and concentrated to a residue. Column chromatography (0->40% EtOAc/hexanes) afforded 0.040 g (58%) of 5-[7-(2,2-dimethyl-propionyl)-5H-pyrrolo[2,3-b]pyrazin-2-yl]-thiophene-2-carboxylic acid cyanomethyl-methyl-amide as a pale yellow solid.

The following compounds were prepared in a similar fashion as 5-[7-(2,2-dimethyl-propionyl)-5H-pyrrolo[2,3-b]pyrazin-2-yl]-thiophene-2-carboxylic acid cyanomethyl-methyl-amide:

5-[7-(2,2-Dimethyl-propionyl)-5H-pyrrolo[2,3-b]pyrazin-2-yl]-thiophene-2-carboxylic acid bis-(2-hydroxy-ethyl)-amide 1-{2-[5-(4-Hydroxy-4-methyl-piperidine-1'-carbonyl)-thiophen-2-yl]-5H-pyrrolo[2,3-b]pyrazin-7-yl}-2,2-dimethyl-propan-1'-one 1-{2-[5-(Azetidine-1-carbonyl)-thiophen-2-yl]-5H-pyrrolo[2,3-b]pyrazin-7-yl}-2,2-dimethyl-propan-1-one 2,2-Dimethyl-1-{2-[5-(pyrrolidine-1-carbonyl)-thiophen-2-yl]-5H-pyrrolo[2,3-b]pyrazin-7-yl}-propan-1-one 2,2-Dimethyl-1-{2-[5-(piperidine-1-carbonyl)-thiophen-2-yl]-5H-pyrrolo[2,3-b]pyrazin-7-yl}-propan-1-one Methyl-cyclohexyl)-{2-[5-(4-methyl-piperazine-1-carbonyl)-thiophen-2-yl]-5H-pyrrolo[2,3-b]pyrazin-7-yl}-methanone; hydrochloride salt {2-[5-(4-Dimethylamino-piperidine-1-carbonyl)-thiophen-2-yl]-5H-pyrrolo[2,3-b]pyrazin-7-yl}-(1-methyl-cyclohexyl)-methanone; hydrochloride salt

Example 51

{2-[5-(4-hydroxy-piperidine-1-carbonyl)-thiophen-2-yl]-5H-pyrrolo[2,3-b]pyrazin-7-yl}-(1-methyl-cyclohexyl)-methanone

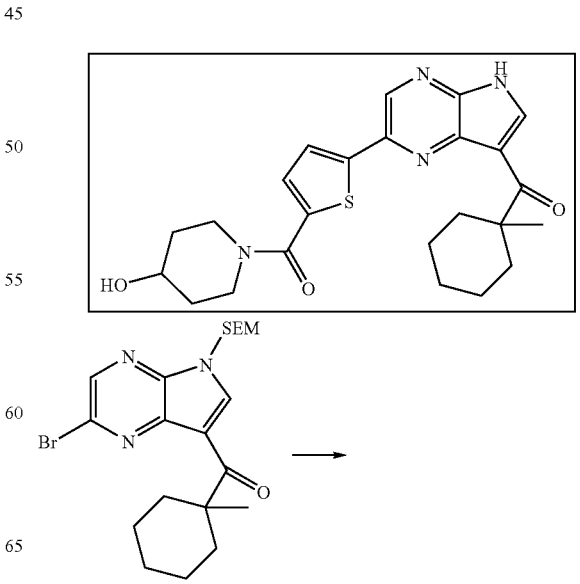

-continued

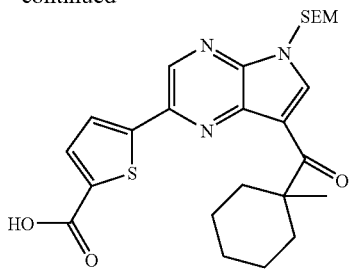

A mixture of 5-(dihydroxyboryl)-2-thiophene-carboxylic acid (1.0 g, 5.4 mmol), [2-bromo-5-(2-trimethylsilanyl-ethoxymethyl)-5H-pyrrolo[2,3-b]pyrazin-7-yl]-(1-methyl-cyclohexyl)-methanone (2.2 g, 4.9 mmol), potassium carbonate (2.0 g, 15 mmol), and Pd(dppf)Cl$_2$·CH$_2$Cl$_2$ (0.400 g, 0.489 mmol) in 12 mL of 1,4-dioxane and 3 mL of water was stirred at 120° C. in a microwave for 40 min. The resulting red suspension was partitioned between 60 mL of ethyl acetate and 100 mL of water, and the aqueous layer was extracted with three 60 mL portions of ethyl acetate. The combined organic layers were dried over MgSO$_4$, filtered and concentrated to a residue. Column chromatography (0->50% EtOAc/hexanes) afforded 1.24 g (46%) of 5-[7-(1-methyl-cyclohexanecarbonyl)-5-(2-trimethylsilanyl-ethoxymethyl)-5H-pyrrolo[2,3-b]pyrazin-2-yl]-thiophene-2-carboxylic acid as a brown solid.

Example 52

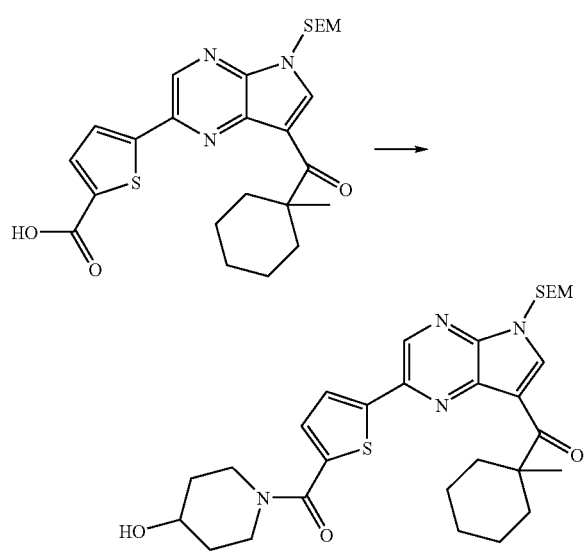

A solution of 5-[7-(1-methyl-cyclohexanecarbonyl)-5-(2-trimethylsilanyl-ethoxymethyl)-5H-pyrrolo[2,3-b]pyrazin-2-yl]-thiophene-2-carboxylic acid (0.080 g, 0.16 mmol), BOP (0.071 g, 0.16 mmol) and 4-hydroxypiperidine (0.162 g, 1.6 mmol) in 2 mL of N,N-dimethylformamide was stirred overnight. The resulting black mixture was taken up in 30 mL of ethyl acetate and washed with three 20 mL portions of a sat. aq. NH$_4$Cl solution, dried over MgSO$_4$, filtered and concentrated to a residue. Column chromatography (0->50% EtOAc/hexanes afforded 0.032 g (34%) of [2-[5-(4-hydroxy-piperidine-1-carbonyl)-thiophen-2-yl]-5-(2-trimethylsilanyl-ethoxymethyl)-5H-pyrrolo[2,3-b]pyrazin-7-yl]-(1-methyl-cyclohexyl)-methanone as a tan oil.

Example 53

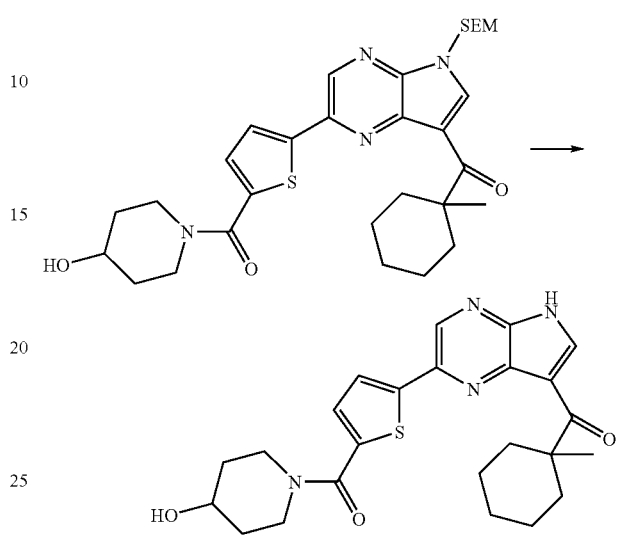

A solution of [2-[5-(4-hydroxy-piperidine-1-carbonyl)-thiophen-2-yl]-5-(2-trimethylsilanyl-ethoxymethyl)-5H-pyrrolo[2,3-b]pyrazin-7-yl]-(1-methyl-cyclohexyl)-methanone (0.032 g, 0.056 mmol) in 1 mL of dichloromethane and 1 mL of trifluoroacetic acid was stirred for 2 h, then concentrated. The residue was dissolved in 2 mL of ethanol and treated with sodium acetate trihydrate (0.076 g, 0.56 mmol). The mixture was stirred overnight, then concentrated to a residue. Column chromatography (0->50% EtOAc/hexanes) afforded 0.019 g (76%) of {2-[5-(4-hydroxy-piperidine-1-carbonyl)-thiophen-2-yl]-5H-pyrrolo[2,3-b]pyrazin-7-yl}-(1-methyl-cyclohexyl)-methanone as an off-white solid.

The following compounds were prepared in a similar fashion as {2-[5-(4-hydroxy-piperidine-1-carbonyl)-thiophen-2-yl]-5H-pyrrolo[2,3-b]pyrazin-7-yl}-(1-methyl-cyclohexyl)-methanone:

5-[7-(1-Methyl-cyclohexanecarbonyl)-5H-pyrrolo[2,3-b]pyrazin-2-yl]-thiophene-2-carboxylic acid (1-ethyl-propyl)-amide {2-[5-(3,3-Difluoro-azetidine-1-carbonyl)-thiophen-2-yl]-5H-pyrrolo[2,3-b]pyrazin-7-yl}-(1-methyl-cyclohexyl)-methanone {2-[5-(4-Hydroxy-piperidine-1-carbonyl)-thiophen-2-yl]-5H-pyrrolo[2,3-b]pyrazin-7-yl}-(1-methyl-cyclohexyl)-methanone {2-[5-(Azetidine-1-carbonyl)-thiophen-2-yl]-5H-pyrrolo[2,3-b]pyrazin-7-yl}-(1-methyl-cyclohexyl)-methanone {2-[5-(3-Hydroxy-azetidine-1-carbonyl)-thiophen-2-yl]-5H-pyrrolo[2,3-b]pyrazin-7-yl}-(1-methyl-cyclohexyl)-methanone Methyl-cyclohexyl)-{2-[5-(morpholine-4-carbonyl)-thiophen-2-yl]-5H-pyrrolo[2,3-b]pyrazin-7-yl}-methanone 5-[7-(1-Methyl-cyclohexanecarbonyl)-5H-pyrrolo[2,3-b]pyrazin-2-yl]-thiophene-2-carboxylic acid diethylamide 5-[7-(1-Methyl-cyclohexanecarbonyl)-5H-pyrrolo[2,3-b]pyrazin-2-yl]-thiophene-2-carboxylic acid cyclopentyl-methyl-amide {2-[5-(4-Hydroxy-4-methyl-piperidine-1-carbonyl)-thiophen-2-yl]-5H-pyrrolo[2,3-b]pyrazin-7-yl}-(1-methyl-cyclohexyl)-methanone 5-[7-(1-Methyl-cyclohexanecarbonyl)-5H-pyrrolo[2,3-b]pyrazin-2-yl]-thiophene-2-carboxylic acid bis-(2-hydroxy-ethyl)-amide 5-[7-(1-Methyl-cyclohexanecarbonyl)-5H-pyrrolo[2,3-b]pyrazin-2-yl]-thiophene-2-carboxylic acid (2-hydroxy-ethyl)-methyl-amide {2-[5-(3-Hydroxy-pyrrolidine-1-carbonyl)-thiophen-2-yl]-5H-pyrrolo[2,3-b]pyrazin-7-yl}-(1-methyl-cyclohexyl)-methanone Example 54

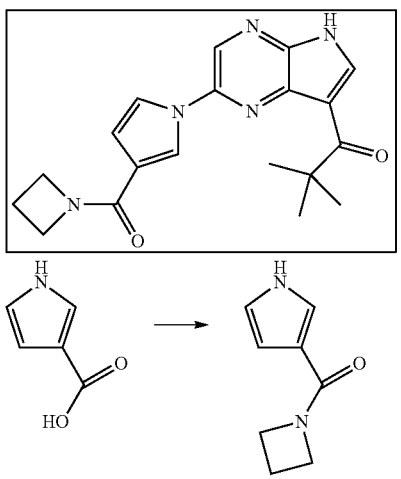

1-{2-[3-(azetidine-1-carbonyl)-pyrrol-1-yl]-5H-pyrrolo[2,3-b]pyrazin-7-yl}-2,2-dimethyl-propan-1-one Oxalyl chloride (0.13 mL, 1.5 mmol) was added to a mixture of 1H-pyrrole-3-carboxylic acid (0.111 g, 1.00 mmol) and 1 drop of N,N-dimethylformamide in 5 mL of dichloromethane. The mixture was stirred for 15 h, then concentrated, then redissolved in 5 mL of dichloromethane and cooled to 0-5° C. Azetidine (0.21 mL, 2.5 mmol) was added, and the mixture was stirred for 1 h at 0-5° C. then absorbed onto silica gel and concentrated. Column chromatography (2->10% MeOH/CH$_2$Cl$_2$) afforded 0.059 g (39%) of azetidin-1-yl-(1H-pyrrol-3-yl)-methanone as an off-white solid.

Example 55

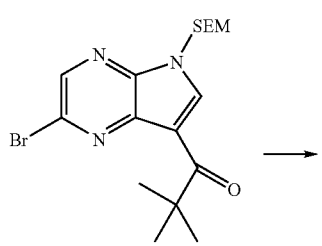

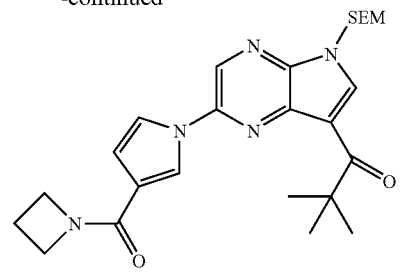

A mixture of 1-[2-bromo-5-(2-trimethylsilanyl-ethoxymethyl)-5H-pyrrolo[2,3-b]pyrazin-7-yl]-2,2-dimethyl-propan-1-one (0.578 g, 0.432 mmol), pyrrole y (0.059 g, 0.39 mmol), cesium carbonate (0.256 g, 0.786 mmol), copper (I) iodide (0.008 g, 0.04 mmol) and proline (0.009 g, 0.08 mmol) in 0.8 mL of dimethylsulfoxide was stirred at 90° C. for 64 h then allowed to cool. The mixture was partitioned between 50 mL of ethyl acetate and 25 mL of water, and the aqueous layer was extracted with 50 mL of ethyl acetate. The combined organic layers were dried over MgSO$_4$, filtered and concentrated to a residue. Column chromatography (0->3% MeOH/CH$_2$Cl$_2$) afforded 0.066 g (32%) of 1-[2-[3-(azetidine-1-carbonyl)-pyrrol-1-yl]-5-(2-trimethylsilanyl-ethoxymethyl)-5H-pyrrolo[2,3-b]pyrazin-7-yl]-2,2-dimethyl-propan-1-one as a yellow oil.

Example 56

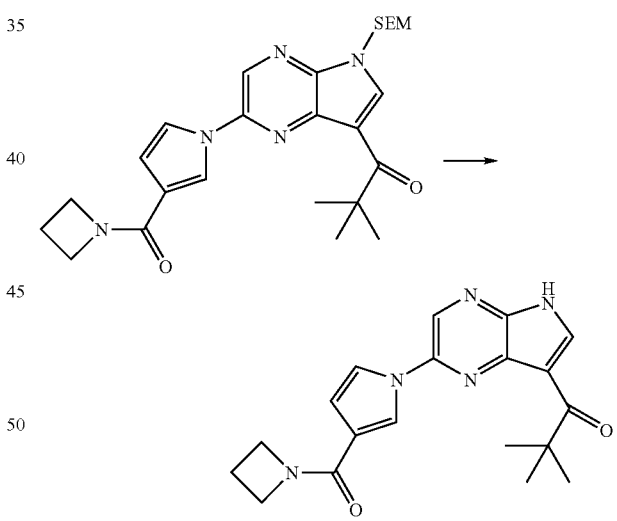

A solution of 1-[2-[3-(azetidine-1-carbonyl)-pyrrol-1-yl]-5-(2-trimethylsilanyl-ethoxymethyl)-5H-pyrrolo[2,3-b]pyrazin-7-yl]-2,2-dimethyl-propan-1-one (0.066 g, 0.137 mmol) in 2 mL of dichloromethane and 1 mL of trifluoroacetic acid was stirred for 5 h then concentrated. The resulting residue was dissolved in 1 mL of ethanol and treated with sodium acetate trihydrate (0.186 g, 1.37 mmol). The mixture was stirred for 17 h, then concentrated. Column chromatography (1->8% MeOH/CH$_2$Cl$_2$) afforded 0.015 g (31%) of 1-{2-[3-(azetidine-1-carbonyl)-pyrrol-1-yl]-5H-pyrrolo[2,3-b]pyrazin-7-yl}-2,2-dimethyl-propan-1-one as a yellow solid.

Compound prepared in similar fashion as 1-{2-[3-(azetidine-1-carbonyl)-pyrrol-1-yl]-5H-pyrrolo[2,3-b]pyrazin-7-yl}-2,2-dimethyl-propan-1-one:
2,2-Dimethyl-1-{2-[3-(pyrrolidine-1-carbonyl)-pyrrol-1-yl]-5H-pyrrolo[2,3-b]pyrazin-7-yl}-propan-1-one Example 57

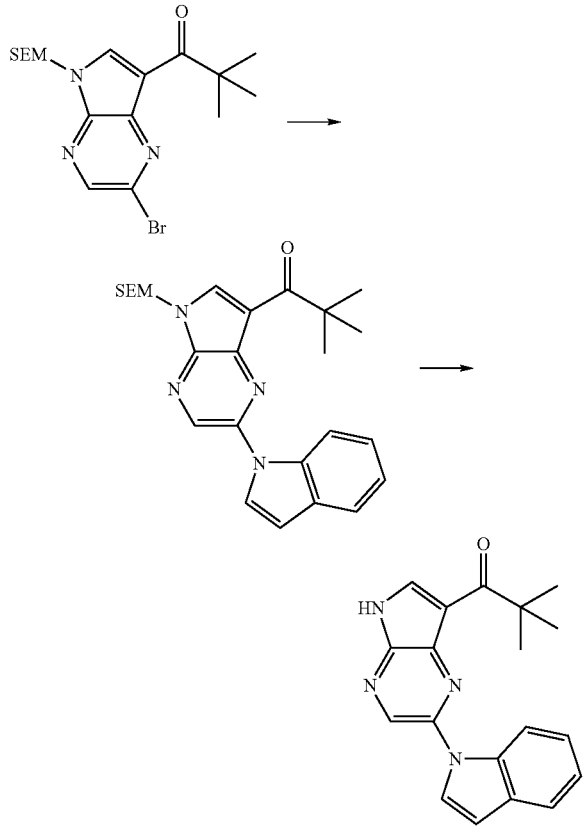

1-(2-Indol-1-yl-5H-pyrrolo[2,3-b]pyrazin-7-yl)-2,2-dimethyl-propan-1-one

DMSO (3 mL) was added to a mixture of copper iodide (10 mg; 0.05 mmol), d,l-proline (12 mg; 0.10 mmol), potassium carbonate (111 mg; 0.79 mmol), and 1-[2-bromo-5-(2-trimethylsilanyl-ethoxymethyl)-5H-pyrrolo[2,3-b]pyrazin-7-yl]-2,2-dimethyl-propan-1-one (150 mg; 0.36 mmol). Indole (327 mg; 2.91 mmol) was added and the resulting mixture was stirred at 100° C. (oil bath) for 24 hrs. TLC analysis (25% EtOAc/hexanes) shows a new more-polar product. The reaction mixture was poured into 50 mL of saturated sodium bicarbonate solution and extracted with EtOAc (2×30 mL). The organic layers were combined, washed with brine, dried over MgSO4, and concentrated to give a yellow oil. Chromatography (SiO$_2$; 0-15% EtOAc in hexanes) gives 1-[2-indol-1-yl-5-(2-trimethylsilanyl-ethoxymethyl)-5H-pyrrolo[2,3-b]pyrazin-7-yl]-2,2-dimethyl-propan-1-one (61%; ms=449 [M+H]) as a light brown oil. Following general procedures described in these Examples, the SEM group was removed to give 1-(2-Indol-1-yl-5H-pyrrolo[2,3-b]pyrazin-7-yl)-2,2-dimethyl-propan-1-one (53%; MS=319 [M+H]; $^1$H NMR (DMSO): δ 8.83 (s), 8.64 (s), 8.48 (d, br), 8.11 (d, br), 7.69 (d), 7.31 (t), 7.21 (t), 6.83 (d) ppm; MP: 205-207° C.).

Compounds prepared using the CuI/proline coupling and SEM removal route described herein:

N-{1-[7-(2,2-Dimethyl-propionyl)-5H-pyrrolo[2,3-b]pyrazin-2-yl]-pyrrolidin-3-yl}-acetamide: (M+H)$^+$=330; $^1$H NMR (DMSO): δ 8.12 (d), 7.71 (s), 4.4 (m), 3.7 (m), 2.2 (m), 3.32 (s), 1.42 (s) ppm;

2,2-Dimethyl-1-[2-(2-methyl-pyrrolidin-1-yl)-5H-pyrrolo[2,3-b]pyrazin-7-yl]-propan-1-one: (M+H)$^+$=287; MP=197-198° C.;

1-[2-(4-Acetyl-piperazin-1-yl)-5H-pyrrolo[2,3-b]pyrazin-7-yl]-2,2-dimethyl-propan-1-one: (M+H)$^+$=330; MP=213-214° C.;

2,2-Dimethyl-1-(2-morpholin-4-yl-5H-pyrrolo[2,3-b]pyrazin-7-yl)-propan-1-one: (M+H)$^+$=289; MP=238-239° C.;

1-[2-(5-Fluoro-indol-1-yl)-5H-pyrrolo[2,3-b]pyrazin-7-yl]-2,2-dimethyl-propan-1-one: (M+H)$^+$=337; $^1$H NMR (DMSO): δ 8.83 (s), 8.64 (s), 8.54 (dd), 8.2 (d), 7.47 (dd), 7.18 (dt), 6.82 (d), 1.45 (s) ppm;

1-[2-(5-Methoxy-indol-1-yl)-5H-pyrrolo[2,3-b]pyrazin-7-yl]-2,2-dimethyl-propan-1-one: (M+H)$^+$=349; $^1$H NMR (DMSO): δ 8.81 (s), 8.60 (s), 8.46 (d), 8.09 (d), 7.19 (d), 6.94 (dd), 6.74 (d), 3.81 (s), 1.46 (s) ppm;

1-(2-Indazol-1-yl-5H-pyrrolo[2,3-b]pyrazin-7-yl)-2,2-dimethyl-propan-1-one: (M+H)$^+$=320; $^1$H NMR (DMSO): δ 9.09 (s), 8.97 (d, br), 8.68 (s), 8.53 (s, br), 7.96 (d), 7.68 (t, br), 7.38 (t, br), 1.50 (s) ppm;

1-[2-(3,4-Dihydro-1H-isoquinolin-2-yl)-5H-pyrrolo[2,3-b]pyrazin-7-yl]-2,2-dimethyl-propan-1-one: (M+H)$^+$=335; MP=220-222° C.;

2,2-Dimethyl-1-[2-(1,3,4,9-tetrahydro-beta-carbolin-2-yl)-5H-pyrrolo[2,3-b]pyrazin-7-yl]-propan-1-one: (M+H)$^+$=374; MP=190-195° C.;

2,2-Dimethyl-1-[2-(1,3,4,5-tetrahydro-pyrido[4,3-b]indol-2-yl)-5H-pyrrolo[2,3-b]pyrazin-7-yl]-propan-1-one: (M+H)$^+$=374; MP=264-265° C.;

2,2-Dimethyl-1-[2-(3-phenyl-pyrrolidin-1-yl)-5H-pyrrolo[2,3-b]pyrazin-7-yl]-propan-1-one: (M+H)$^+$=349; MP=237-238° C.;

2-{1-[7-(2,2-Dimethyl-propionyl)-5H-pyrrolo[2,3-b]pyrazin-2-yl]-1H-indol-3-yl}-acetamide: (M+H)$^+$=376; $^1$H NMR (DMSO): δ 8.77 (s), 8.62 (s), 8.46 (d), 7.97 (s, br), 7.68 (d), 7.33 (t, br), 7.23 (t, br), 3.61 (s), 1.46 (s) ppm;

1-[2-(2-Benzyl-pyrrolidin-1-yl)-5H-pyrrolo[2,3-b]pyrazin-7-yl]-2,2-dimethyl-propan-1-one: (M+H)$^+$=363; MP=162-164° C.;

Additionally prepared following general procedures described in these Examples:

2,2-Dimethyl-1-(2-pyrazol-1-yl-5H-pyrrolo[2,3-b]pyrazin-7-yl)-propan-1-one (Prepare using 1-[2-Bromo-5-(2-trimethylsilanyl-ethoxymethyl)-5H-pyrrolo[2,3-b]pyrazin-7-yl]-2,2-dimethyl-propan-1-one instead of 1-(2-Bromo-5H-pyrrolo[2,3-b]pyrazin-7-yl)-2,2-dimethyl-propan-1-one and the SEM protecting group was removed following general procedures described in these Examples) M+1 269 m.p. 256-258° C.

2,2-Dimethyl-1-(2-pyrrol-1-yl-5H-pyrrolo[2,3-b]pyrazin-7-yl)-propan-1-one (Prepare using 1-[2-Bromo-5-(2-trimethylsilanyl-ethoxymethyl)-5H-pyrrolo[2,3-b]pyrazin-7-yl]-2,2-dimethyl-propan-1-one instead of 1-(2-Bromo-5H-pyrrolo[2,3-b]pyrazin-7-yl)-2,2-dimethyl-propan-1-one and the SEM protecting group was removed following general procedures described in these Examples) M+1 269.

Example 58

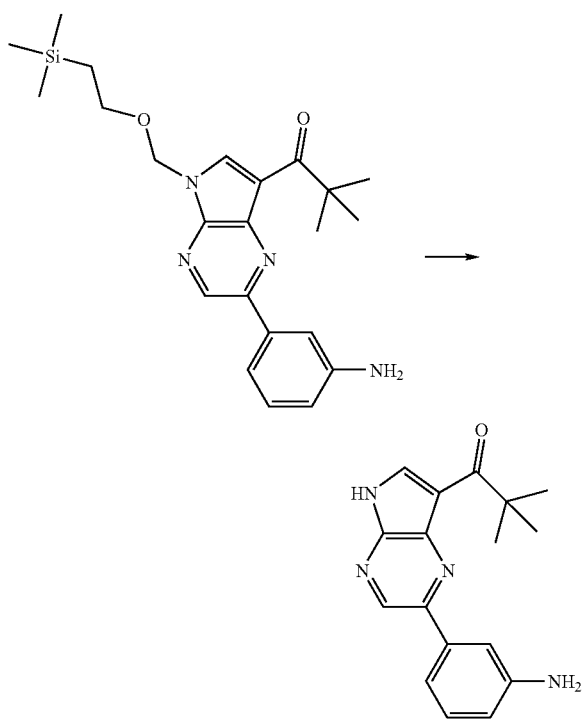

1-[2-(3-Amino-phenyl)-5H-pyrrolo[2,3-b]pyrazin-7-yl]-2,2-dimethyl-propan-1-one

To a microwave vial was added 0.032 gm (0.075 mM) 1-[2-(3-Amino-phenyl)-5-(2-trimethylsilanyl-ethoxymethyl)-5H-pyrrolo[2,3-b]pyrazin-7-yl]-2,2-dimethyl-propan-1-one followed by 0.75 ml of 1M tetrabutylammonium fluoride in THF. The vial was sealed and placed in a 80° C. oil bath for two hours then stirred at room temperature overnight. The mixture was diluted with 10 ml ethyl acetate, rinsed (3×50 ml) water, dried over magnesium sulfate, filtered and concentrated on a rotary evaporator. Purification on a preparative silica gel thin layer chromatography plate (5/95 MeOH/CH$_2$Cl$_2$) gave 0.014 gm (64% yield) of 1-[2-(3-Amino-phenyl)-5H-pyrrolo[2,3-b]pyrazin-7-yl]-2,2-dimethyl-propan-1-one, M+1 295, M.P. 239-241° C.

Example 59

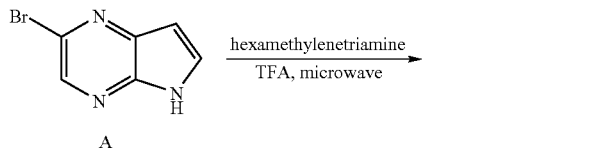

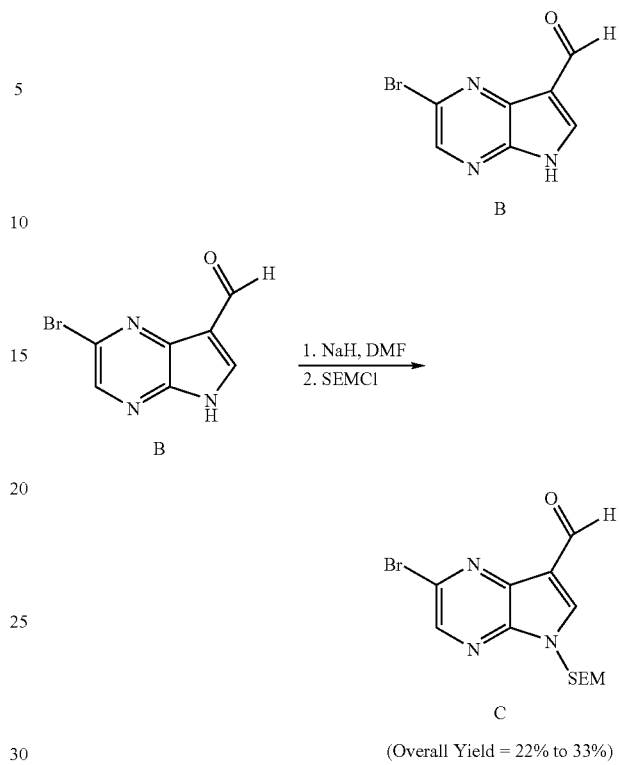

(Overall Yield = 22% to 33%)

Filled 5 microwave vials, each with 1.19 grams A, 0.88 grams hexamethylenetriamine (1.05 eq.) and 10 ml trifluoroacetic acid. Sealed and heated in the microwave apparatus at 80° C. for fifteen minutes. Combined the vials and rotovaped. Poured into aqueous sodium carbonate, stirred and the filtered. Dried, then chromatographed the 7.74 grams crude material on a silica column (5% to 10% methanol/dichloromethane with ammonium hydroxide) to yield 4.69 grams of impure material B which was used in the following step.

Stirred B in 40 ml DMF in an ice bath under argon. Added 1.16 grams 60% NaH in portions, then stirred cold for two hours. Next added 4.4 ml 2-(trimethylsilyl) ethoxymethyl chloride drop wise. Stirred two hours, then poured into ice water and extracted into ethyl acetate. Washed organics with water, then brine. Dried over sodium sulfate, filtered, then concentrated and pumped on to give 6.84 grams crude product. Chromatographed on a 50 gram Supelco Versaflash column (0% to 40% ethyl acetate/hexane) to give 3.24 grams (30%) of C, the bromo, sem-protected aldehyde.

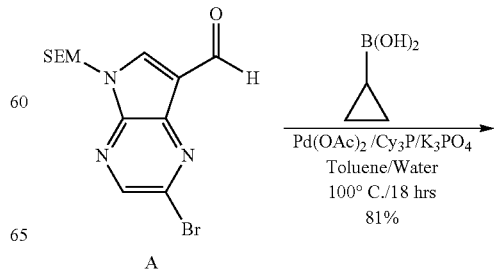

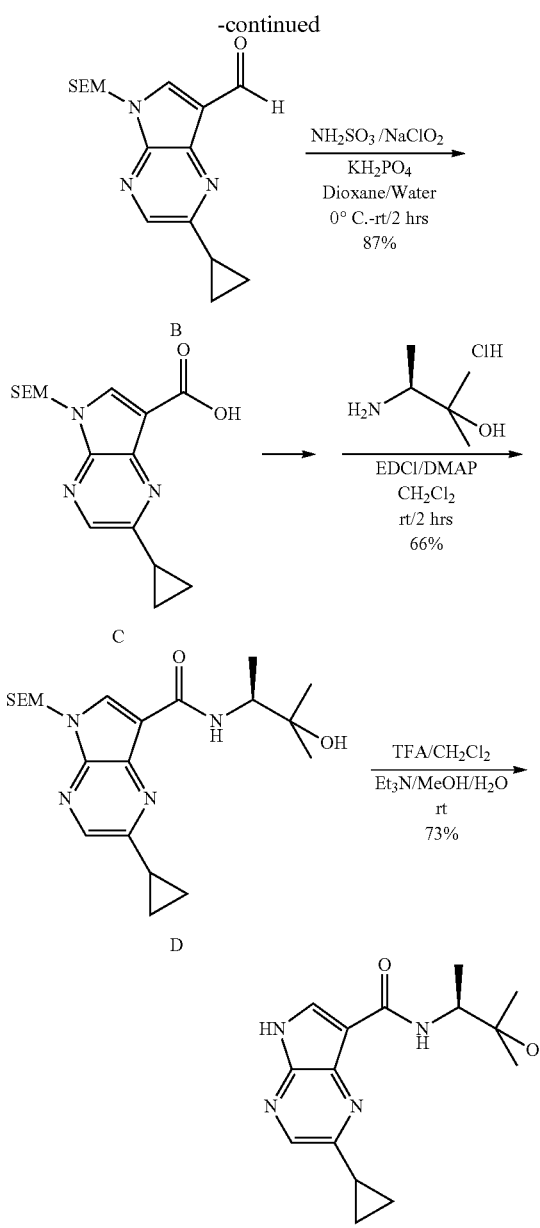

Preparation of B:

A mixture of A (0.33 g, 0.93 mmol), cyclopropyl boronic acid (0.12 g, 1.39 mmol), tricyclohexyl phosphine (0.026 g, 0.09 mmol), palladium(II) acetate (0.01 g, 0.046 mmol) and potassium phosphate tribasic (0.63 g, 2.97 mmol) in 4 ml. of toluene and 0.5 ml of water was flushed with Argon for 5 minutes, then heated at 100° C. for 18 hrs. The cooled mixture was filtered through a pad of SolkaFloc (Cellulose filter aid) washed with EtOAc, and concentrated in vacuo. The residual oil was loaded on silicagel column and eluted with 10% EtOAc-Hexane mixture to afford the desired product B as a yellow powder (0.24 g, 81% yield) mp 98-100° C.

Preparation of C:

To a solution of B (0.24 g, 0.75 mmol) in 1,4-Dioxane (10 ml) and water (2 ml) at 0° C. was added sulfamic acid (0.44 g, 4.54 mmol), followed by drop-wise addition of a solution of sodium chlorite (0.09 g, 0.98 mmol) and potassium dihydrogen phosphate (1.22 g, 9.0 mmol) in 6 ml of water. After addition, ice-bath removed and reaction mixture stirred at room temp. for 2 hrs. The reaction mixture was partitioned between water and ethyl acetate, the organic layer was washed with brine, dried over sodium sulphate, and concentrated in vacuo. The residual oil was triturated with hexane to obtain the desired product C as a light yellow powder (0.22 g, 87% yield) mp 92-94° C.

Preparation of D:

To a solution of C (0.22 g, 0.65 mmol) in 10 ml of dichloromethane at room temp. was added HCl salt of the amine (0.11 g, 0.79 mmol), EDCI (0.15 g, 0.79 mmol) and 4-dimethylaminopyridine (0.096 g, 0.79 mmol). The resulting reaction mixture was stirred at room temp. for 2 hrs. Solvent removed in vacuo, residue was diluted with EtOAc, washed with water, brine, dried over sodium sulphate, and concentrated in vacuo. The residual oil was loaded on a silicagel column and eluted with 1.5% methanol-dichloromethane to afford the desired product D as an oil (0.18 g, 66%).

To a solution of D (0.18 g, 0.43 mmol) in 3.0 ml of dichloromethane at room temp. under nitrogen was added 1.0 ml of trifluoroacetic acid and stirred for 4 hrs. Solvent removed in vacuo. The residual oil was dissolved in methanol (10.0 ml) while stirring at room temp. water (2 ml) followed by triehyl amine (2.0 ml) was added and the resulting reaction mixture was stirred at room temperature for 3 hrs. Solvent removed in vacuo, co-evaporated with toluene to remove water, residue was treated with 50% EtOAc-Hexane, the off-white solid formed was filtered, washed with ether, dried to obtain 2-Cyclopropyl-5H-pyrrolo[2,3-b]pyrazine-7-carboxylic acid ((S)-2-hydroxy-1,2-dimethyl-propyl)-amide as a off-white powder (0.091 g, 73%) mp 272-274° C.

JAK Assay Information

Determination of $IC_{50}$ of Janus Kinase (JAK) Inhibition

Enzymes and peptide substrate used are described below:
JAK1: Recombinant human kinase domain from Invitrogen (Cat # PV4774)
JAK3: Recombinant human kinase domain from Millipore (Cat # 14-629) or prepared.
JAK2: Recombinant human kinase domain from Millipore (Cat # 14-640)
Substrate: N-terminally biotinylated 14-mer peptide derived from activation loop of JAK1 with sequence of the peptide substrate: Biotin-KAIETDKEYYTVKD
Assay conditions used are described below:
Assay Buffer: JAK Kinase Buffer: 50 mM Hepes [pH 7.2], 10 mM $MgCl_2$, 1 mM DTT, 1 mg/ml BSA. The assay is carried out in this buffer.
Assay Format The kinase activity of all three JAK kinases is measured using a radioactive, end-point assay and with trace amounts of $^{33}$P-ATP. The assays are carried out in 96-well polypropylene plates.

Experimental Method

All concentrations are final in the reaction mixture and all incubations are carried at room temperature. Assay steps are described below:
1) Compounds are serially diluted in 100% DMSO typically at a 10× starting concentration of 1 mM. Final concentration of DMSO in the reaction is 10%.
2) Compounds are preincubated with enzyme (0.5 nM JAK3 (commercially available), 0.2 nM JAK3 (prepared), 1 nM JAK2, 5 nM JAK1) for 10 minutes.
3) Reactions are initiated by the addition of a cocktail of the two substrates (ATP and peptide premixed in the JAK Kinase Buffer). In the JAK2/JAK3 assays, ATP and the peptide are used at concentrations of 1.5 uM and 50 uM, respectively. JAK1 assay is carried out at an ATP concentration of 10 uM and a peptide concentration of 50 uM.

4) The duration of the assay for JAK2 and JAK3 is 20 minutes. JAK1 assay is carried out for 40 minutes. With all three enzymes, reactions are terminated by the addition of 0.5M EDTA to a final concentration of 100 mM.
5) 25 ul of terminated reactions are transferred to 150 ul of a 7.5% (v/v) slurry of streptavidin-coated sepharose beads in $MgCl_2$- and $CaCl_2$-free 1× Phosphate Buffered Saline containing 50 mM of EDTA in 96-well, 1.2 um MultiScreen-BV filter plates.
6) After a 30-minute incubation, the beads are washed under vacuum with the following buffers:
   a. 3 to 4 washes with 200 ul of 2M NaCl.
   b. 3 to 4 washes with 200 ul of 2M NaCl plus 1% (v/v) phosphoric acid.
   c. 1 wash with water.
7) Washed plates are dried in a 60° C. oven for between 1 to 2 hours.
8) 70 ul of Microscint 20 scintillation fluid is added to each well of filter plates and after at least 30 minutes of incubation, radioactive counts are measured in a Perkinelmer microplate scintillation counter.

Representative $IC_{50}$ results are in Table II below:

TABLE II

| Compound | $IC_{50}$ h-jak3-sf21-c |
|---|---|
| I-40 | 0.04474 |
| I-41 | 0.03524 |
| I-73 | 0.01799 |
| I-74 | 0.02834 |

SYK Assay Information

Determination of $IC_{50}$ of Spleen Tyrosine Kinase (SYK) Inhibition

SYK kinase assay is a standard kinase assay adapted to a 96 well plate format. This assay is performed in 96-well format for $IC_{50}$ determination with 8 samples which represented 10 half log dilutions and a 40 μL reaction volume. The assay measures the incorporation of radiolabeled $^{33}P$ γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB10)
Streptavidin coated beads: Streptavidin Sepharose™, suspension 5.0 mL, in 50 mM EDTA/PBS diluted (1:100), (Amersham, Cat. No.: 17-5113-01)
Compounds: 10 mM in 100% dimethylsulfoxide (DMSO), final conc.: compound 0.003-100 uM in 10% DMSO
Enzyme: SYK RPA purified, truncated construct of Spleen Tyrosine Kinase aa 360-635, stock solution 1 mg/mL, MW: 31.2 KDa, final conc.: 0.0005 μM.
Peptide 1: biotinylated peptide is derived from a naturally occurring phosphor-acceptor consensus sequence (Biotin-EPEGDYEEVLE), special order from QCB, stock solution 20 mM, final conc.: 5.0 μM.
ATP: Adenosine-5'-triphosphate 20 mM, (ROCHE Cat. No.: 93202720), final concentration: 20 μM
Buffer: HEPES: 2-Hydroxyethyl piperazine-2-ethane-sulfonic acid (Sigma, Cat. No.: H-3375) final concentration: 50 mM HEPES pH7.5
BSA: Bovine Serum Albumin Fraction V, fatty acid free (Roche Diagnostics GmbH, Cat. No. 9100221) diluted to a final concentration of 0.1%
EDTA: EDTA stock solution 500 mM, (GIBCO, Cat. No.: 15575-038) final concentration: 0.1 mM
DTT: 1,4-Dithiothreitol (Roche Diagnostics GmbH, Cat. No.: 197777), final conc.: 1 mM
$MgCl_2×6H_2O$: MERCK, Cat. No.: 105833.1000, final concentration: 10 mM
Assay Dilution Buffer (ADB): 50 mM HEPES, 0.1 mM EGTA, 0.1 mM Na Vanadate, 0.1 mM β-glycerophosphate, 10 mM $MgCl_2$, 1 mM DTT, 0.1% BSA, pH 7.5
Bead wash buffer: 10 g/L PBS (Phosphate buffered saline) with 2M NaCl+1% phosphoric acid.

Experimental Method

In 40 μL volume, 26 μL of ADB diluted, purified recombinant human SYK360-635 [0.5 nM] was mixed with 4 μL of 10× concentrations of the test compounds, [usually 100 μM-0.003 μM] in [10%] DMSO and the mixture was incubated for 10 min at RT.

The kinase reaction was initiated by the addition of 10 μL 4× substrate cocktail containing the DYE peptide substrate [0 or 5 μM], ATP [20 μM] and $^{33}$ PγATP [2 μCi/rxn]. After incubation at 30° C. for 15 min, the reaction was terminated by the transfer of 25 μL of the reaction sample to a 96 well 0.65 μm Millipore MADVNOB membrane/plate containing 200 μL 5 mM EDTA and 20% Streptavidine coated beads in PBS.

The unbound radionucleotides were washed under vacuum with 3×250 μL 2M NaCl; 2×250 μL 2M NaCl+1% phosphoric acid; 1×250 μL $H_2O$. After the last wash membrane/plates were transferred to an adaptor plate, heat dried for 15 min at 60° C., and 50 μL scintillation cocktail was added to each well and 4 h later the amount of radioactivity was counted in a top counter.

The percent inhibition was calculated based on the uninhibited enzyme rate:

$$\% \text{ Inhibition} = 100/(1+(IC_{50}/\text{Inhibitor } conc)^n)$$

The $IC_{50}$ was calculated using a non-linear curve fit with XLfit software (ID Business Solution Ltd., Guilford, SurTey, UK).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound of Formula I $$\text{[structure: pyrrolo[2,3-b]pyrazine with Q}^2\text{ substituent and C(=O)R group]}$$

wherein:

R is $R^1$, $R^2$, $R^3$, or $R^4$;
  $R^1$ is lower alkyl, lower alkoxy, phenyl, benzyl, heteroaryl, cycloalkyl, heterocycloalkyl, or cycloalkylalkyl, optionally substituted with one or more $R^{1a}$;
  $R^{1a}$ is $R^{1b}$ or $R^{1c}$;
    $R^{1b}$ is halogen, oxo, hydroxy, or —CN;
    $R^{1c}$ is —C(=O)O($R^{1f}$), —C(=O)CH$_2$($R^{1e}$), —S($R^{1f}$), —S(O)$_2$($R^{1f}$), or —S(=O) ($R^{1f}$), lower alkyl, lower alkoxy, amino, amido, lower haloalkyl, phenyl, heteroaryl, cycloalkyl, heterocycloalkyl, cycloalkyloxy, or heterocycloalkyloxy optionally substituted with one or more $R^{1d}$;
    $R^{1d}$ is H, halogen, hydroxy, lower alkyl, lower alkoxy, or lower haloalkyl;
    $R^{1e}$ is H, lower alkyl, lower alkoxy, —CN, lower haloalkyl, phenyl, heteroaryl, cycloalkyl, or heterocycloalkyl;
    $R^{1f}$ is H, lower alkyl, lower haloalkyl, phenyl, heteroaryl, cycloalkyl, or heterocycloalkyl;
  $R^2$ is N($R^{2a}$)$_2$;
  each $R^{2a}$ is independently H or $R^{2b}$;
    each $R^{2b}$ is independently lower alkyl, phenyl, heteroaryl, cycloalkyl, heterocycloalkyl, or heterocycloalkyl alkylene, optionally substituted with one or more $R^{2c}$;
    $R^{2c}$ is $R^{2d}$ or $R^{2e}$;
      $R^{2d}$ is halogen, oxo, or hydroxy;
      $R^{2e}$ is —N($R^{2g}$)$_2$, —C(=O)($R^{2g}$), —C(=O)O ($R^{2g}$), —C(=O)N($R^{2g}$)$_2$, —N($R^{2g}$)C(=O)($R^{2g}$), —S(=O)$_2$($R^{2g}$), —S(O)$_2$N($R^{2g}$)$_2$, lower alkyl, lower alkoxy, lower haloalkyl, phenyl, heteroaryl, heteroaryloxy, cycloalkyl, or heterocycloalkyl, optionally substituted with one or more $R^{2f}$;
      each $R^{2f}$ is independently H, halogen, lower alkyl, lower alkoxy, or lower haloalkyl;
      each $R^{2g}$ is independently H, lower alkyl, Lower alkoxy, lower haloalkyl, or phenyl;
  $R^3$ is —C(=O)$R^{3a}$;
    $R^{3a}$ is lower alkyl, lower alkoxy, phenyl, or N($R^{3b}$)$_2$;
      each $R^{3b}$ is independently H or lower alkyl;
  $R^4$ is —O($R^{4a}$);
  $R^{4a}$ is H or $R^{4b}$;
    $R^{4b}$ is lower alkyl, phenyl, benzyl, lower haloalkyl, cycloalkyl, heterocycloalkyl, heteroaryl, optionally substituted with one or more $R^{4c}$;
    $R^{4c}$ is halogen, hydroxy, lower alkyl, lower haloalkyl, or lower alkoxy;
  $Q^2$ is cycloalkyl, cycloalkenyl, heterocycloalkyl, or heteroaryl, optionally substituted with one or more $Q^{2a}$;
  $Q^{2a}$ is $Q^{2b}$ or $Q^{2c}$;
    $Q^{2b}$ is halogen, oxo, hydroxy, —CN, —SCH$_3$, —S(O)$_2$ CH$_3$, or —S(=O)CH$_3$;
    $Q^{2c}$ is $Q^{2d}$ or $Q^{2e}$;
  or two $Q^{2a}$ come together to form a bicyclic ring system, optionally Substituted with one or more $Q^{2b}$ or $Q^{2c}$;
    $Q^{2d}$ is —O($Q^{2e}$), —S(=O)$_2$($Q^{2e}$), —C(=O)N ($Q^{2e}$)$_2$, —S(O)$_2$($Q^{2e}$), —C(=O)($Q^{2e}$), —C(=O)O ($Q^{2e}$), —N($Q^{2e}$)$_2$; —N($Q^{2e}$)C(=O)($Q^{2e}$), —N($Q^{2e}$)C(=O)O($Q^{2e}$), or —N($Q^{2e}$)C(=O)N($Q^{2e}$)$_2$;
    each $Q^{2e}$ is independently H or $Q^{2e'}$;
      each $Q^{2e'}$ is independently lower alkyl, phenyl, benzyl, lower haloalkyl, cycloalkyl, cycloalkenyl, heterocycloalkyl, or heteroaryl, optionally substituted with one or more $Q^{2f}$;
    $Q^{2f}$ is $Q^{2g}$ or $Q^{2h}$;
      $Q^{2g}$ is halogen, hydroxy, cyano, oxo, or —C(=O) ($Q^{2h}$);
      $Q^{2h}$ is lower alkyl, lower haloalkyl, lower alkoxy, amino, phenyl, benzyl, cycloalkyl, heterocycloalkyl, or heteroaryl, optionally substituted with one or more $Q^{2i}$; and
      $Q^{2i}$ is halogen, hydroxy, cyano, lower alkyl, lower haloalkyl, or lower alkoxy;

or a pharmaceutically acceptable salt thereof.

2. The compound of claim 1, wherein R is $R^1$.
3. The compound of claim 2, wherein $R^1$ is lower alkyl.
4. The compound of claim 3, wherein $R^1$ is tert-butyl.
5. The compound of claim 3, wherein $R^1$ is —CHC(CH$_3$)$_3$.
6. The compound of claim 3, wherein $R^1$ is iso-butyl.
7. The compound of claim 3, wherein $R^1$ is iso-propyl.
8. The compound of claim 2, wherein $R^1$ is cycloalkyl.
9. The compound of claim 2, wherein $R^1$ is heterocycloalkyl.
10. The compound of claim 2, wherein $R^1$ is benzyl.
11. The compound of claim 2, wherein $R^1$ is phenyl.
12. The compound of claim 1, wherein R is $R^2$ and $R^2$ is NH($R^{2a}$).
13. The compound of claim 12, wherein $R^{2a}$ is $R^{2b}$.
14. The compound of claim 13, wherein $R^{2b}$ is lower alkyl.
15. The compound of claim 14, wherein $R^{2b}$ is iso-propyl.
16. The compound of claim 13, wherein $R^{2b}$ is heterocycloalkyl.
17. The compound of claim 13, wherein $R^{2b}$ is cycloalkyl.
18. The compound of claim 13, wherein $R^{2b}$ is heterocycloalkyl alkylene.
19. The compound of claim 18, wherein $R^{2b}$ is pyrrolidinyl alkylene.
20. The compound of claim 18, wherein $R^{2b}$ pyrrolidinyl methylene.
21. The compound of claim 1, wherein $Q^2$ is heterocycloalkyl, optionally substituted with one or more $Q^{2a}$.
22. The compound of claim 21, wherein $Q^2$ is pyrrolidine.
23. The compound of claim 21, wherein $Q^2$ is piperidine.
24. The compound of claim 1, wherein $Q^2$ is heteroaryl, optionally substituted with one or more $Q^{2a}$.
25. The compound of claim 24, wherein $Q^2$ is pyridine.
26. The compound of claim 25, wherein $Q^{2a}$ is $Q^{2c}$ and $Q^{2C}$ is heterocycloalkyl.
27. The compound of claim 26, wherein $Q^{2c}$ is piperazine.
28. The compound of claim 26, wherein $Q^{2c}$ is pyrrolidine.
29. The compound of claim 26, wherein $Q^{2c}$ is piperidine.
30. The compound of claim 1, wherein $Q^2$ is cycloalkyl.
31. A compound selected from the group consisting of:
  1-[2-(1-Benzenesulfonyl-1H-indol-3-yl)-5H-pyrrolo[2,3-b]pyrazin-7-yl]-2,2-dimethyl-propan-1-one;
  1-[2-(1H-Indol-3-yl)-5H-pyrrolo[2,3-b]pyrazin-7-yl]-2,2-dimethyl-propan-1-one;
  2-Cyclohex-1-enyl-5H-pyrrolo[2,3-b]pyrazine-7-carboxylic acid isopropylamide;

2-Cyclohexyl-5H-pyrrolo[2,3-b]pyrazine-7-carboxylic acid isopropylamide;
1-{2-[2-(4-Acetyl-piperazin-1-yl)-pyridin-4-yl]-5H-pyrrolo[2,3-b]pyrazin-7-yl}-2,2-dimethyl-propan-1-one;
1-[2-(5-Methoxy-pyridin-3-yl)-5H-pyrrolo[2,3-b]pyrazin-7-yl]-2,2-dimethyl-propan-1-one;
[1-(7-Isopropylcarbamoyl-5H-pyrrolo[2,3-b]pyrazin-2-yl)-piperidin-3-yl]-methyl-carbamic acid tert-butyl ester;
2-(3-Methylamino-piperidin-1-yl)-5H-pyrrolo[2,3-b]pyrazine-7-carboxylic acid isopropylamide;
2,2-Dimethyl-1-(2-pyrrolidin-1-yl-5H-pyrrolo[2,3-b]pyrazin-7-yl)-propan-1-one;
1-[7-(2,2-Dimethyl-propionyl)-2'-pyrrolidin-1-yl-5H-[2,5']bi[pyrrolo[2,3-b]pyrazinyl]-7'-yl]-2,2-dimethyl-propan-1-one;
2,2-Dimethyl-1-[2-(2-pyrrolidin-1-yl-pyridin-4-yl)-5H-pyrrolo[2,3-b]pyrazin-7-yl]-propan-1-one;
1-[2-(1-Cyclopentyl-1H-[1,2,3]triazol-4-yl)-5H-pyrrolo[2,3-b]pyrazin-7-yl]-2,2-dimethyl-propan-1-one;
2,2-Dimethyl-1-[2-(3,4,5,6-tetrahydro-2H-[1,2']bipyridinyl-4'-yl)-5H-pyrrolo[2,3-b]pyrazin-7-yl]-propan-1-one;
1-{2-[2-(3-Dimethylamino-pyrrolidin-1-yl)-pyridin-4-yl]-5H-pyrrolo[2,3-b]pyrazin-7-yl}-2,2-dimethyl-propan-1-one;
2,2-Dimethyl-1-[2-(2-thiomorpholin-4-yl-pyridin-4-yl)-5H-pyrrolo[2,3-b]pyrazin-7-yl]-propan-1-one;
2,2-Dimethyl-1-{2-[2-(2-methyl-pyrrolidin-1-yl)-pyridin-4-yl]-5H-pyrrolo[2,3-b]pyrazin-7-yl}-propan-1-one;
1-[2-(1,3-Dihydro-isoindol-2-yl)-5H-pyrrolo[2,3-b]pyrazin-7-yl]-2,2-dimethyl-propan-1-one;
1-[2-(2,3-Dihydro-indol-1-yl)-5H-pyrrolo[2,3-b]pyrazin-7-yl]-2,2-dimethyl-propan-1-one;
2-[7-(2,2-Dimethyl-propionyl)-5H-pyrrolo[2,3-b]pyrazin-2-yl]-3,4-dihydro-2H-isoquinolin-1-one;
1-[7-(2,2-Dimethyl-propionyl)-5H-pyrrolo[2,3-b]pyrazin-2-yl]-3,4-dihydro-1H-quinolin-2-one;
2-[7-(2,2-Dimethyl-propionyl)-5H-pyrrolo[2,3-b]pyrazin-2-yl]-2,3-dihydro-isoindol-1-one;
1-[7-(2,2-Dimethyl-propionyl)-5H-pyrrolo[2,3-b]pyrazin-2-yl]-piperidin-2-one;
1-[7-(2,2-Dimethyl-propionyl)-5H-pyrrolo[2,3-b]pyrazin-2-yl]-pyrrolidin-2-one;
1-[2-(1H-Indol-3-yl)-5H-pyrrolo[2,3-b]pyrazin-7-yl]-2,2-dimethyl-propan-1-one;
2,2-Dimethyl-1-[2-(6-pyrrolidin-1-yl-pyridin-2-yl)-5H-pyrrolo[2,3-b]pyrazin-7-yl]-propan-1-one;
2,2-Dimethyl-1-[2-(4-pyrrolidin-1-yl-pyridin-2-yl)-5H-pyrrolo[2,3-b]pyrazin-7-yl]-propan-1-one;
2,2-Dimethyl-1-(2-pyridin-2-yl-5H-pyrrolo[2,3-b]pyrazin-7-yl)-propan-1-one;
[1-(7-Isopropylcarbamoyl-5H-pyrrolo[2,3-b]pyrazin-2-yl)-piperidin-3-yl]-methyl-carbamic acid tert-butyl ester;
2-(3-Methylamino-piperidin-1-yl)-5H-pyrrolo[2,3-b]pyrazine-7-carboxylic acid; isopropylamide;
5-[7-(2,2-Dimethyl-propionyl)-5H-pyrrolo[2,3-b]pyrazin-2-yl]-thiophene-3-carboxylic acid (tetrahydro-pyran-4-yl)-amide;
5-[7-(2,2-Dimethyl-propionyl)-5H-pyrrolo[2,3-b]pyrazin-2-yl]-thiophene-2-carboxylic acid cyclopentylamide;
5-[7-(2,2-Dimethyl-propionyl)-5H-pyrrolo[2,3-b]pyrazin-2-yl]-thiophene-2-carboxylic acid (tetrahydro-pyran-4-yl)-amide;
1-(2-Cyclopropyl-5H-pyrrolo[2,3-b]pyrazin-7-yl)-2,2-dimethyl-propan-1-one;
5-[7-(2,2-Dimethyl-propionyl)-5H-pyrrolo[2,3-b]pyrazin-2-yl]-thiophene-3-carboxylic acid;
5-[7-(2,2-Dimethyl-propionyl)-5H-pyrrolo[2,3-b]pyrazin-2-yl]-thiophene-3-carboxylic acid (2-dimethylamino-ethyl)-amide;
1-{2-[2-(3-Methoxy-phenyl)-cyclopent-1-enyl]-5H-pyrrolo[2,3-b]pyrazin-7-yl}-2,2-dimethyl-propan-1-one;
6-{2-[7-(2,2-Dimethyl-propionyl)-5H-pyrrolo[2,3-b]pyrazin-2-yl]-cyclopent-1-enyl}-pyridine-2-carboxylic acid ethyl ester;
2,2-Dimethyl-1-[2-(2-phenyl-cyclopent-1-enyl)-5H-pyrrolo[2,3-b]pyrazin-7-yl]-propan-1-one;
5-{2-[7-(2,2-Dimethyl-propionyl)-5H-pyrrolo[2,3-b]pyrazin-2-yl]-cyclopent-1-enyl}-1H-indole-2-carboxylic acid ethyl ester;
4-[7-(1-Methyl-cyclohexanecarbonyl)-5H-pyrrolo[2,3-b]pyrazin-2-yl]-thiophene-2-carboxylic acid cyanomethyl-methyl-amide;
(1-Methyl-cyclohexyl)-{2-[5-(morpholine-4-carbonyl)-thiophen-3-yl]-5H-pyrrolo[2,3-b]pyrazin-7-yl}-methanone;
1-(2-Furan-3-yl-5H-pyrrolo[2,3-b]pyrazin-7-yl)-2,2-dimethyl-propan-1-one;
4-[7-(1-Methyl-cyclohexanecarbonyl)-5H-pyrolo[2,3-b]pyrazin-2-yl]-thiophene-2-carboxylic acid (1-ethyl-propyl)-amide;
{2-[5-(4-Hydroxy-4-methyl-piperidine-1-carbonyl)-thiophen-3-yl]-5H-pyrrolo[2,3-b]pyrazin-7-yl}-(1-methyl-cyclohexyl)-methanone;
2,2-Dimethyl-1-[2-(2-pyrrolidin-1-yl-pyridin-4-yl)-5H-pyrrolo[2,3-b]pyrazin-7-yl]-propan-1-one;
2,2-Dimethyl-1-[2-(3,4,5,6-tetrahydro-2H-[1,2']bipyridinyl-4'-yl)-5H-pyrrolo[2,3-b]pyrazin-7-yl]-propan-1-one;
1-{2-[2-(3-Dimethylamino-pyrrolidin-1-yl)-pyridin-4-yl]-5H-pyrrolo[2,3-b]pyrazin-7-yl}-2,2-dimethyl-propan-1-one;
2,2-Dimethyl-1-[2-(2-thiomorpholin-4-yl-pyridin-4-yl)-5H-pyrrolo[2,3-b]pyrazin-7-yl]-propan-1-one;
2,2-Dimethyl-1-{2-[2-(2-methyl-pyrrolidin-1-yl)-pyridin-4-yl]-5H-pyrrolo[2,3-b]pyrazin-7-yl}-propan-1-one;
1-{2-[2-(3-Hydroxy-pyrrolidin-1-yl)-pyridin-4-yl]-5H-pyrrolo[2,3-b]pyrazin-7-yl}-2,2-dimethyl-propan-1-one;
1-{2-[2-(3,3-Difluoro-pyrrolidin-1-yl)-pyridin-4-yl]-5H-pyrrolo[2,3-b]pyrazin-7-yl}-2,2-dimethyl-propan-1-one;
1-[2-(2-Azepan-1-yl-pyridin-4-yl)-5H-pyrrolo[2,3-b]pyrazin-7-yl]-2,2-dimethyl-propan-1-one;
1-{2-[2-((S)-3-Fluoro-pyrrolidin-1-yl)-pyridin-4-yl]-5H-pyrrolo[2,3-b]pyrazin-7-yl}-2,2-dimethyl-propan-1-one;
1-{2-[2-((R)-3-Fluoro-pyrrolidin-1-yl)-pyridin-4-yl]-5H-pyrrolo[2,3-b]pyrazin-7-yl}-2,2-dimethyl-propan-1-one;
1-{2-[2-(1,1-Dioxo-1$\lambda^6$-thiomorpholin-4-yl)-pyridin-4-yl]-5H-pyrrolo[2,3-b]pyrazin-7-yl}-2,2-dimethyl-propan-1-one;
1-[2-(2-Chloro-pyridin-4-yl)-5H-pyrrolo[2,3-b]pyrazin-7-yl]-2,2-dimethyl-propan-1-one
2,2-Dimethyl-1-{2-[2-(1-oxo-1$\lambda^4$-thiomorpholin-4-yl)-pyridin-4-yl]-5H-pyrrolo[2,3-b]pyrazin-7-yl}-propan-1-one;

1-[2-(2-Cyclopent-1-enyl-pyridin-4-yl)-5H-pyrrolo[2,3-b]pyrazin-7-yl]-2,2-dimethyl-propan-1-one;
(1-Methyl-cyclohexyl)-[2-(2-pyrrolidin-1-yl-pyridin-4-yl)-5H-pyrrolo[2,3-b]pyrazin-7-yl]-methanone;
1-[2-(4-Hydroxy-3,4,5,6-tetrahydro-2H-[1,2']bipyridinyl-4'-yl)-5H-pyrrolo[2,3-b]pyrazin-7-yl]-2,2-dimethyl-propan-1-one;
5-[7-(1-Methyl-cyclohexanecarbonyl)-5H-pyrrolo[2,3-b]pyrazin-2-yl]-thiophene-2-carboxylic acid (1-ethyl-propyl)-amide;
{2-[5-(3,3-Difluoro-azetidine-1-carbonyl)-thiophen-2-yl]-5H-pyrrolo[2,3-b]pyrazin-7-yl}-(1-methyl-cyclohexyl)-methanone;
{2-[5-(4-Hydroxy-piperidine-1-carbonyl)-thiophen-2-yl]-5H-pyrrolo[2,3-b]pyrazin-7-yl}-(1-methyl-cyclohexyl)-methanone;
(1-Methyl-cyclohexyl)-{2-[2-(1-oxo-1$\lambda^4$-thiomorpholin-4-yl)-pyridin-4-yl]-5H-pyrrolo[2,3-b]pyrazin-7-yl}-methanone;
{2-[5-(Azetidine-1-carbonyl)-thiophen-2-yl]-5H-pyrrolo[2,3-b]pyrazin-7-yl}-(1-methyl-cyclohexyl)-methanone;
{2-[5-(3-Hydroxy-azetidine-1-carbonyl)-thiophen-2-yl]-5H-pyrrolo[2,3-b]pyrazin-7-yl}-(1-methyl-cyclohexyl)-methanone;
1-{2-[2-((1S,5R,6R)-6-Hydroxymethyl-3-aza-bicyclo[3.1.0]hex-3-yl)-pyridin-4-yl]-5H-pyrrolo[2,3-b]pyrazin-7-yl}-2,2-dimethyl-propan-1-one;
(1-Methyl-cyclohexyl)-{2-[5-(morpholine-4-carbonyl)-thiophen-2-yl]-5H-pyrrolo[2,3-b]pyrazin-7-yl}-methanone;
5-[7-(1-Methyl-cyclohexanecarbonyl)-5H-pyrrolo[2,3-b]pyrazin-2-yl]-thiophene-2-carboxylic acid diethylamide;
5-[7-(1-Methyl-cyclohexanecarbonyl)-5H-pyrrolo[2,3-b]pyrazin-2-yl]-thiophene-2-carboxylic acid cyclopentylmethyl-amide;
{2-[5-(4-Hydroxy-4-methyl-piperidine-1-carbonyl)-thiophen-2-yl]-5H-pyrrolo[2,3-b]pyrazin-7-yl}-(1-methyl-cyclohexyl)-methanone;
5-[7-(1-Methyl-cyclohexanecarbonyl)-5H-pyrrolo[2,3-b]pyrazin-2-yl]-thiophene-2-carboxylic acid bis-(2-hydroxy-ethyl)-amide;
5-[7-(1-Methyl-cyclohexanecarbonyl)-5H-pyrrolo[2,3-b]pyrazin-2-yl]-thiophene-2-carboxylic acid (2-hydroxy-ethyl)-methyl-amide;
{2-[5-(3-Hydroxy-pyrrolidine-1-carbonyl)-thiophen-2-yl]-5H-pyrrolo[2,3-b]pyrazin-7-yl}-(1-methyl-cyclohexyl)-methanone;
5-[7-(2,2-Dimethyl-propionyl)-5H-pyrrolo[2,3-b]pyrazin-2-yl]-thiophene-2-carboxylic acid cyanomethyl-methyl-amide;
5-[7-(2,2-Dimethyl-propionyl)-5H-pyrrolo[2,3-b]pyrazin-2-yl]-thiophene-2-carboxylic acid bis-(2-hydroxy-ethyl)-amide;
1-{2-[5-(4-Hydroxy-4-methyl-piperidine-1-carbonyl)-thiophen-2-yl]-5H-pyrrolo[2,3-b]pyrazin-7-yl}-2,2-dimethyl-propan-1-one;
1-{2-[5-(Azetidine-1-carbonyl)-thiophen-2-yl]-5H-pyrrolo[2,3-b]pyrazin-7-yl}-2,2-dimethyl-propan-1-one;
2,2-Dimethyl-1-{2-[5-(pyrrolidine-1-carbonyl)-thiophen-2-yl]-5H-pyrrolo[2,3-b]pyrazin-7-yl}-propan-1-one;
2,2-Dimethyl-1-{2-[5-(piperidine-1-carbonyl)-thiophen-2-yl]-5H-pyrrolo[2,3-b]pyrazin-7-yl}-propan-1-one;
3-Dimethylamino-1-{5-[7-(2,2-dimethyl-propionyl)-5H-pyrrolo[2,3-b]pyrazin-2-yl]-thiophene-2-carbonyl}-azetidine-3-carbonitrile;
1-{2-[5-(4-Hydroxy-piperidine-1-carbonyl)-thiophen-2-yl]-5H-pyrrolo[2,3-b]pyrazin-7-yl}-2,2-dimethyl-propan-1-one;
1-{2-[4-(Azetidine-1-carbonyl)-thiophen-2-yl]-5H-pyrrolo[2,3-b]pyrazin-7-yl}-2,2-dimethyl-propan-1-one;
2,2-Dimethyl-1-{2-[4-(pyrrolidine-1-carbonyl)-thiophen-2-yl]-5H-pyrrolo[2,3-b]pyrazin-7-yl}-propan-1-one;
2,2-Dimethyl-1-{2-[4-(piperidine-1-carbonyl)-thiophen-2-yl]-5H-pyrrolo[2,3-b]pyrazin-7-yl}-propan-1-one;
(1-Methyl-cyclohexyl)-{2-[5-(4-methyl-piperazine-1-carbonyl)-thiophen-2-yl]-5H-pyrrolo[2,3-b]pyrazin-7-yl}-methanone;
{2-[5-(4-Dimethylamino-piperidine-1-carbonyl)-thiophen-2-yl]-5H-pyrrolo[2,3-b]pyrazin-7-yl}-(1-methyl-cyclohexyl)-methanone;
1-(2-Cyclopent-1-enyl-5H-pyrrolo[2,3-b]pyrazin-7-yl)-2,2-dimethyl-propan-1-one;
2,2-Dimethyl-1-(2-pyrrolidin-1-yl-5H-pyrrolo[2,3-b]pyrazin-7-yl)-propan-1-one;
1-[7-(2,2-Dimethyl-propionyl)-2'-pyrrolidin-1-yl-5H-[2,5']bi[pyrrolo[2,3-b]pyrazinyl]-7'-yl]-2,2-dimethyl-propan-1-one;
N-{1-[7-(2,2-Dimethyl-propionyl)-5H-pyrrolo[2,3-b]pyrazin-2-yl]-pyrrolidin-3-yl}-acetamide;
2,2-Dimethyl-1-[2-(2-methyl-pyrrolidin-1-yl)-5H-pyrrolo[2,3-b]pyrazin-7-yl]-propan-1-one;
1-[2-(4-Acetyl-piperazin-1-yl)-5H-pyrrolo[2,3-b]pyrazin-7-yl]-2,2-dimethyl-propan-1-one;
2,2-Dimethyl-1-(2-morpholin-4-yl-5H-pyrrolo[2,3-b]pyrazin-7-yl)-propan-1-one;
1-[2-(5-Fluoro-indol-1-yl)-5H-pyrrolo[2,3-b]pyrazin-7-yl]-2,2-dimethyl-propan-1-one;
1-[2-(5-Methoxy-indol-1-yl)-5H-pyrrolo[2,3-b]pyrazin-7-yl]-2,2-dimethyl-propan-1-one;
1-(2-Indol-1-yl-5H-pyrrolo[2,3-b]pyrazin-7-yl)-2,2-dimethyl-propan-1-one;
1-(2-Indazol-1-yl-5H-pyrrolo[2,3-b]pyrazin-7-yl)-2,2-dimethyl-propan-1-one;
1-[2-(3,4-Dihydro-1H-isoquinolin-2-yl)-5H-pyrrolo[2,3-b]pyrazin-7-yl]-2,2-dimethyl-propan-1-one;
2,2-Dimethyl-1-[2-(1,3,4,9-tetrahydro-β-carbolin-2-yl)-5H-pyrrolo[2,3-b]pyrazin-7-yl]-propan-1-one;
2-{1-[7-(2,2-Dimethyl-propionyl)-5H-pyrrolo[2,3-b]pyrazin-2-yl]-1H-indol-3-yl}-acetamide;
2,2-Dimethyl-1-[2-(1,3,4,5-tetrahydro-pyrido[4,3-b]indol-2-yl)-5H-pyrrolo[2,3-b]pyrazin-7-yl]-propan-1-one;
2,2-Dimethyl-1-[2-(3-phenyl-pyrrolidin-1-yl)-5H-pyrrolo[2,3-b]pyrazin-7-yl]-propan-1-one;
1-(2-Imidazol-1-yl-5H-pyrrolo[2,3-b]pyrazin-7-yl)-2,2-dimethyl-propan-1-one;
2,2-Dimethyl-1-[2-(2-methyl-imidazol-1-yl)-5H-pyrrolo[2,3-b]pyrazin-7-yl]-propan-1-one;
2,2-Dimethyl-1-[2-(2-methyl-4,5-dihydro-imidazol-1-yl)-5H-pyrrolo[2,3-b]pyrazin-7-yl]-propan-1-one;
1-[2-(2-Ethyl-imidazol-1-yl)-5H-pyrrolo[2,3-b]pyrazin-7-yl]-2,2-dimethyl-propan-1-one;
2,2-Dimethyl-1-(2-thiophen-2-yl-5H-pyrrolo[2,3-b]pyrazin-7-yl)-propan-1-one;
2,2-Dimethyl-1-[2-(1H-pyrrol-2-yl)-5H-pyrrolo[2,3-b]pyrazin-7-yl]-propan-1-one;
2,2-Dimethyl-1-(2-thiophen-3-yl-5H-pyrrolo[2,3-b]pyrazin-7-yl)-propan-1-one;
2,2-Dimethyl-1-(2-oxazol-5-yl-5H-pyrrolo[2,3-b]pyrazin-7-yl)-propan-1-one;
2,2-Dimethyl-1-[2-(1H-pyrazol-4-yl)-5H-pyrrolo[2,3-b]pyrazin-7-yl]-propan-1-one;

4-[7-(2,2-Dimethyl-propionyl)-5H-pyrrolo[2,3-b]pyrazin-2-yl]-pyrazole-1-carboxylic acid tert-butyl ester;
2,2-Dimethyl-1-(2-pyrazol-1-yl-5H-pyrrolo[2,3-b]pyrazin-7-yl)-propan-1-one;
2,2-Dimethyl-1-[2-(2H-pyrazol-3-yl)-5H-pyrrolo[2,3-b]pyrazin-7-yl]-propan-1-one;
2,2-Dimethyl-1-(2-pyrrol-1-yl-5H-pyrrolo[2,3-b]pyrazin-7-yl)-propan-1-one;
2,2-Dimethyl-1-[2-(1H-pyrrol-3-yl)-5H-pyrrolo[2,3-b]pyrazin-7-yl]-propan-1-one;
2,2-Dimethyl-1-(2-thiazol-5-yl-5H-pyrrolo[2,3-b]pyrazin-7-yl)-propan-1-one;
3-[7-(2,2-Dimethyl-propionyl)-5H-pyrrolo[2,3-b]pyrazin-2-yl]-1H-indole-5-carbonitrile;
1-[2-(5-Fluoro-1H-indol-3-yl)-5H-pyrrolo[2,3-b]pyrazin-7-yl]-2,2-dimethyl-propan-1-one;
[2-(1H-Indol-3-yl)-5H-pyrrolo[2,3-b]pyrazin-7-yl]-(1-methyl-cyclohexyl)-methanone;
1-{2-[1-(2-Hydroxy-1-hydroxymethyl-ethyl)-1H-indol-3-yl]-5H-pyrrolo[2,3-b]pyrazin-7-yl}-2,2-dimethyl-propan-1-one;
1-[2-(1H-Indol-3-yl)-5H-pyrrolo[2,3-b]pyrazin-7-yl]-2,2-dimethyl-propan-1-one;
1-(2-Benzo[b]thiophen-2-yl-5H-pyrrolo[2,3-b]pyrazin-7-yl)-2,2-dimethyl-propan-1-one;
2,2-Dimethyl-1-[2-(5-phenyl-thiophen-2-yl)-5H-pyrrolo[2,3-b]pyrazin-7-yl]-propan-1-one;
2,2-Dimethyl-1-[2-(1-methyl-1H-indol-2-yl)-5H-pyrrolo[2,3-b]pyrazin-7-yl]-propan-1-one;
1-[2-(1H-Indol-2-yl)-5H-pyrrolo[2,3-b]pyrazin-7-yl]-2,2-dimethyl-propan-1-one;
1-[2-(1H-Indol-3-yl)-5-methyl-5H-pyrrolo[2,3-b]pyrazin-7-yl]-2,2-dimethyl-propan-1-one;
2,2-Dimethyl-1-[2-(1-methyl-1H-indol-3-yl)-5H-pyrrolo[2,3-b]pyrazin-7-yl]-propan-1-one;
2,2-Dimethyl-1-[2-(5-phenyl-1H-pyrrol-3-yl)-5H-pyrrolo[2,3-b]pyrazin-7-yl]-propan-1-one;
1-{2-[1-(2-Hydroxy-ethyl)-1H-indol-3-yl]-5H-pyrrolo[2,3-b]pyrazin-7-yl}-2,2-dimethyl-propan-1-one;
1-[2-(6-Fluoro-1H-indol-3-yl)-5H-pyrrolo[2,3-b]pyrazin-7-yl]-2,2-dimethyl-propan-1-one;
1-{2-[1-(2-Methanesulfonyl-ethyl)-1H-indol-3-yl]-5H-pyrrolo[2,3-b]pyrazin-7-yl}-2,2-dimethyl-propan-1-one;
1-[2-(5-Methoxy-1H-indol-3-yl)-5H-pyrrolo[2,3-b]pyrazin-7-yl]-2,2-dimethyl-propan-1-one;
1-[2-(1-Ethyl-1H-indol-3-yl)-5H-pyrrolo[2,3-b]pyrazin-7-yl]-2,2-dimethyl-propan-1-one;
2,2-Dimethyl-1-[2-(5-methyl-1H-indol-3-yl)-5H-pyrrolo[2,3-b]pyrazin-7-yl]-propan-1-one;
2,2-Dimethyl-1-(2-{1-[2-(4-methyl-piperazin-1-yl)-ethyl]-1H-indol-3-yl}-5H-pyrrolo[2,3-b]pyrazin-7-yl)-propan-1-one;
2,2-Dimethyl-1-{2-[1-(2-morpholin-4-yl-ethyl)-1H-indol-3-yl]-5H-pyrrolo[2,3-b]pyrazin-7-yl}-propan-1-one;
1-{2-[1-(3-Hydroxy-2-hydroxymethyl-propyl)-1H-indol-3-yl]-5H-pyrrolo[2,3-b]pyrazin-7-yl}-2,2-dimethyl-propan-1-one;
1-{2-[1-(3-Hydroxy-2-hydroxymethyl-propyl)-1H-pyrrolo[2,3-b]pyridin-3-yl]-5H-pyrrolo[2,3-b]pyrazin-7-yl}-2,2-dimethyl-propan-1-one;
2,2-Dimethyl-1-[2-(6-methyl-1H-indol-3-yl)-5H-pyrrolo[2,3-b]pyrazin-7-yl]-propan-1-one;
1-[2-(6-Methoxy-1H-indol-3-yl)-5H-pyrrolo[2,3-b]pyrazin-7-yl]-2,2-dimethyl-propan-1-one;
1-{2-[1-(2-Amino-ethyl)-1H-indol-3-yl]-5H-pyrrolo[2,3-b]pyrazin-7-yl}-2,2-dimethyl-propan-1-one;
2,2-Dimethyl-1-[2-(6-morpholin-4-yl-pyridin-3-yl)-5H-pyrrolo[2,3-b]pyrazin-7-yl]-propan-1-one;
(1-Methyl-cyclohexyl)-[2-(6-morpholin-4-yl-pyridin-3-yl)-5H-pyrrolo[2,3-b]pyrazin-7-yl]-methanone;
1-[2-(1H-Indol-3-yl)-5H-pyrrolo[2,3-b]pyrazin-7-yl]-2,2-dimethyl-propan-1-one;
1-(2-Imidazo[1,2-a]pyridin-3-yl-5H-pyrrolo[2,3-b]pyrazin-7-yl)-2,2-dimethyl-propan-1-one;
2,2-Dimethyl-1-[2-(1H-pyrrolo[2,3-b]pyridin-3-yl)-5H-pyrrolo[2,3-b]pyrazin-7-yl]-propan-1-one;
2,2-Dimethyl-1-[2-(1H-pyrrolo[3,2-c]pyridin-3-yl)-5H-pyrrolo[2,3-b]pyrazin-7-yl]-propan-1-one;
2,2-Dimethyl-1-[2-(1H-pyrrolo[2,3-c]pyridin-3-yl)-5H-pyrrolo[2,3-b]pyrazin-7-yl]-propan-1-one;
2,2-Dimethyl-1-[2-(1-methyl-1H-pyrrolo[2,3-b]pyridin-3-yl)-5H-pyrrolo[2,3-b]pyrazin-7-yl]-propan-1-one;
2,2-Dimethyl-1-{2-[1-(2-oxo-2-piperazin-1-yl-ethyl)-1H-indol-3-yl]-5H-pyrrolo[2,3-b]pyrazin-7-yl}-propan-1-one;
1-(2-{1-[2-(4-Amino-piperidin-1-yl)-2-oxo-ethyl]-1H-indol-3-yl}-5H-pyrrolo[2,3-b]pyrazin-7-yl)-2,2-dimethyl-propan-1-one;
(1-Methyl-cyclohexyl)-[2-(1-methyl-1H-pyrrolo[2,3-b]pyridin-3-yl)-5H-pyrrolo[2,3-b]pyrazin-7-yl]-methanone;
2,2-Dimethyl-1-(2-{1-[2-(4-methyl-piperazin-1-yl)-2-oxo-ethyl]-1H-indol-3-yl}-5H-pyrrolo[2,3-b]pyrazin-7-yl)-propan-1-one;
(1-Methyl-cyclopentyl)-[2-(1-methyl-1H-pyrrolo[2,3-b]pyridin-3-yl)-5H-pyrrolo[2,3-b]pyrazin-7-yl]-methanone;
1-[2-(5-Methoxy-pyridin-3-yl)-5H-pyrrolo[2,3-b]pyrazin-7-yl]-2,2-dimethyl-propan-1-one;
4-[7-(1-Methyl-cyclohexanecarbonyl)-5H-pyrrolo[2,3-b]pyrazin-2-yl]-thiophene-2-carboxylic acid (1-ethyl-propyl)-amide;
{2-[5-(4-Hydroxy-4-methyl-piperidine-1-carbonyl)-thiophen-3-yl]-5H-pyrrolo[2,3-b]pyrazin-7-yl}-(1-methyl-cyclohexyl)-methanone;
5-[7-(2,2-Dimethyl-propionyl)-5H-pyrrolo[2,3-b]pyrazin-2-yl]-thiophene-2-carboxylic acid (2-hydroxy-ethyl)-methyl-amide;
2-Cyclopropyl-5H-pyrrolo[2,3-b]pyrazine-7-carboxylic acid ((S)-2-hydroxy-1,2-dimethyl-propyl)-amide;
4-[7-(1-Methyl-cyclohexanecarbonyl)-5H-pyrrolo[2,3-b]pyrazin-2-yl]-thiophene-2-carboxylic acid;
4-[7-(1-Methyl-cyclohexanecarbonyl)-5H-pyrrolo[2,3-b]pyrazin-2-yl]-thiophene-2-carboxylic acid (2-amino-2-methyl-propyl)-amide;
{2-[5-(4-Dimethylamino-piperidine-1-carbonyl)-thiophen-3-yl]-5H-pyrrolo[2,3-b]pyrazin-7-yl}-(1-methyl-cyclohexyl)-methanone;
2-Cyclopropyl-5H-pyrrolo[2,3-b]pyrazine-7-carboxylic acid (3-hydroxy-2,2-dimethyl-propyl)-amide;
2-Cyclopropyl-5H-pyrrolo[2,3-b]pyrazine-7-carboxylic acid tert-butylamide;
2-[7-(2,2-Dimethyl-propionyl)-5H-pyrrolo[2,3-b]pyrazin-2-yl]-pyrrole-1-carboxylic acid tert-butyl ester; and
2-Thiophen-2-yl-5H-pyrrolo[2,3-b]pyrazine-7-carboxylic acid (3-hydroxy-2,2-dimethyl-propyl)-amide.

32. A pharmaceutical composition comprising the compound of claim 1, admixed with at least one pharmaceutically acceptable carrier, excipient or diluent.

* * * * *

UNITED STATES PATENT AND TRADEMARK OFFICE
CERTIFICATE OF CORRECTION

| | | |
|---|---|---|
| PATENT NO. | : 7,939,531 B2 | |
| APPLICATION NO. | : 12/378978 | |
| DATED | : May 10, 2011 | |
| INVENTOR(S) | : Joe Timothy Bamberg et al. | |

It is certified that error appears in the above-identified patent and that said Letters Patent is hereby corrected as shown below:

Claim 1, column 181, line 50, end of line delete "Lower" and insert -- lower --

Claim 1, column 182, line 2, delete "Substituted" and insert -- substituted --

Signed and Sealed this
Twenty-third Day of August, 2011

David J. Kappos
*Director of the United States Patent and Trademark Office*